United States Patent
Alexander et al.

(10) Patent No.: US 11,116,959 B2
(45) Date of Patent: Sep. 14, 2021

(54) REMOVABLE MECHANICAL CIRCULATORY SUPPORT FOR SHORT TERM USE

(71) Applicants: Theodosios Alexander, Venice, FL (US); Martin T. Rothman, Santa Rosa, CA (US)

(72) Inventors: Theodosios Alexander, Venice, FL (US); Martin T. Rothman, Santa Rosa, CA (US)

(*) Notice: Subject to any disclaimer, the term of this patent is extended or adjusted under 35 U.S.C. 154(b) by 0 days.

(21) Appl. No.: 16/374,624

(22) Filed: Apr. 3, 2019

(65) Prior Publication Data

US 2019/0321529 A1    Oct. 24, 2019

Related U.S. Application Data

(60) Provisional application No. 62/652,820, filed on Apr. 4, 2018, provisional application No. 62/680,954, filed on Jun. 5, 2018.

(51) Int. Cl.
*A61M 60/148* (2021.01)
*A61M 60/205* (2021.01)
(Continued)

(52) U.S. Cl.
CPC ........ *A61M 60/205* (2021.01); *A61M 60/148* (2021.01); *A61M 60/40* (2021.01);
(Continued)

(58) Field of Classification Search
CPC .. A61M 1/1024; A61M 1/1029; A61M 1/122; A61M 1/1015; A61M 1/1086; A61M 2205/04
See application file for complete search history.

(56) References Cited

U.S. PATENT DOCUMENTS 5,267,940 A    12/1993   Moulder
6,171,078 B1    1/2001   Schob
(Continued)

FOREIGN PATENT DOCUMENTS

EP    3519008    8/2019
EP    3630218    4/2020
(Continued)

OTHER PUBLICATIONS

Search Report and Written Opinion for International Application No. PCT/US19/25667 dated Jul. 29, 2019 in 19 pages.
(Continued)

*Primary Examiner* — Ankit D Tejani
*Assistant Examiner* — Joshua Brendon Solomon
(74) *Attorney, Agent, or Firm* — Knobbe, Martens, Olson & Bear, LLP

(57) ABSTRACT

Mechanical circulatory supports configured to operate in series with the native heart are disclosed. In an embodiment, an intravascular propeller is installed into the descending aorta and anchored within via an expandable anchoring mechanism. The propeller and anchoring mechanism may be foldable so as to be percutaneously deliverable to the aorta. The propeller may have foldable blades. The blades may be magnetic and may be driven by a concentric electromagnetic stator circumferentially outside the magnetic blades. The stator may be intravascular or may be configured to be installed around the outer circumference of the blood vessel. The support may create a pressure rise between about 20-50 mmHg, and maintain a flow rate of about 5 L/min. The support may have one or more pairs of contra-rotating propellers to modulate the tangential velocity of the blood flow. The support may have static pre-swirlers and or de-swirlers. The support may be optimized to replicate
(Continued)

naturally occurring vortex formation within the descending aorta.

20 Claims, 132 Drawing Sheets

(51) Int. Cl.
    *A61M 60/40* (2021.01)
    *A61M 60/50* (2021.01)
    *A61M 60/82* (2021.01)
(52) U.S. Cl.
    CPC ............. *A61M 60/50* (2021.01); *A61M 60/82* (2021.01); *A61M 2205/04* (2013.01)

(56) References Cited

U.S. PATENT DOCUMENTS

| | | | |
|---|---|---|---|
| 6,575,717 B2 | 6/2003 | Ozaki et al. | |
| 6,716,157 B2 | 4/2004 | Goldowsky | |
| 7,841,976 B2 | 11/2010 | McBride et al. | |
| 7,976,271 B2 | 7/2011 | Larose et al. | |
| 8,177,703 B2 | 5/2012 | Smith et al. | |
| 8,690,749 B1 | 4/2014 | Nunez | |
| 9,638,202 B2 | 5/2017 | Ozaki et al. | |
| 2002/0094281 A1 | 7/2002 | Khanvilkar et al. | |
| 2003/0228214 A1* | 12/2003 | McBride | B63H 11/08 415/191 |
| 2003/0233143 A1 | 12/2003 | Gharib et al. | |
| 2006/0245959 A1 | 11/2006 | LaRose et al. | |
| 2008/0058146 A1* | 3/2008 | Pizzichil | F04D 13/022 475/72 |
| 2010/0076247 A1 | 3/2010 | Zilbershlag et al. | |
| 2011/0034874 A1 | 2/2011 | Reitan et al. | |
| 2011/0200451 A1* | 8/2011 | Lehmann | F04D 15/0088 417/42 |
| 2011/0238172 A1 | 9/2011 | Akdis | |
| 2011/0239693 A1* | 10/2011 | Fujisaku | F04D 29/053 62/498 |
| 2012/0253103 A1 | 10/2012 | Robert | |
| 2012/0277520 A1 | 11/2012 | Duncan | |
| 2013/0281762 A1 | 10/2013 | Mi-Vad | |
| 2014/0051908 A1 | 2/2014 | Hridaya | |
| 2014/0275726 A1* | 9/2014 | Zeng | A61M 1/1012 600/16 |
| 2015/0297813 A1 | 10/2015 | Korakianitis et al. | |
| 2016/0089482 A1* | 3/2016 | Siegenthaler | A61N 1/057 600/16 |
| 2016/0271309 A1 | 9/2016 | Throckmorton et al. | |
| 2017/0274128 A1 | 9/2017 | Tamburino et al. | |
| 2017/0340788 A1 | 11/2017 | Korakianitis et al. | |
| 2018/0169313 A1* | 6/2018 | Schwammenthal | A61M 1/1012 |
| 2019/0321529 A1 | 10/2019 | Korakianitis et al. | |

FOREIGN PATENT DOCUMENTS

| | | | |
|---|---|---|---|
| WO | WO 2016/097976 | 6/2016 | |
| WO | WO 2016/185473 | 11/2016 | |
| WO | WO-2016185473 A1 * | 11/2016 | .......... A61M 1/1012 |
| WO | WO 2018/067410 | 4/2018 | |
| WO | WO 2018/209191 | 11/2018 | |
| WO | WO 2018/223060 | 12/2018 | |
| WO | WO 2019/195480 | 10/2019 | |

OTHER PUBLICATIONS

U.S. Appl. No. 16/338,961, filed Apr. 2, 2019, Korakianitis et al.
Search Report and Written Opinion for PCT/US2017/054573 dated Dec. 15, 2017 in 14 pages.
Extended European Search Report for EP 17858942.0 dated Jul. 23, 2020 in 14 pages.
Partial Supplementary European Search Report for EP 17858942.0 dated Apr. 22, 2020 in 18 pages.
Search Report and Written Opinion for PCT/US2018/035694 dated Nov. 5, 2018 in 12 pages.
U.S. Appl. No. 15/720,592, filed Sep. 29, 2017, Korakianitis et al.
U.S. Appl. No. 16/914,019, filed Jun. 26, 2020, Korakianitis et al.
Search Report and Written Opinion for PCT/US2020/039978 dated Nov. 20, 2020 in 25 pages.
Invitation to Pay Additional Fees for PCT/US20/39978 dated Sep. 15, 2020.
Partial Supplementary European Search Report for EP 18809622.6 dated Jan. 12, 2021 in 22 pages.
Extended European Search Report for EP 18809622.6 dated Apr. 14, 2021 in 18 pages.

\* cited by examiner

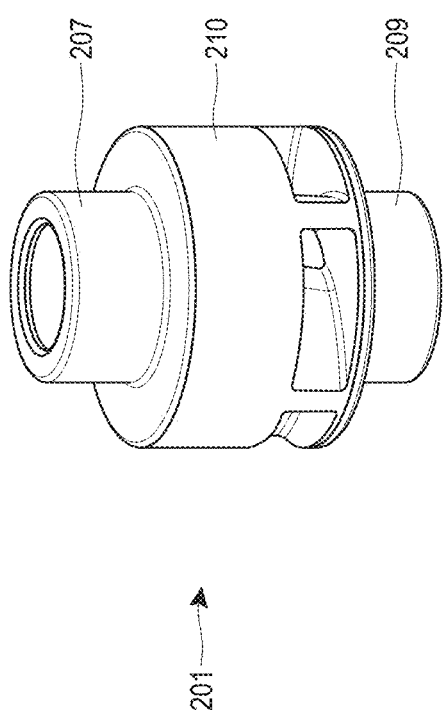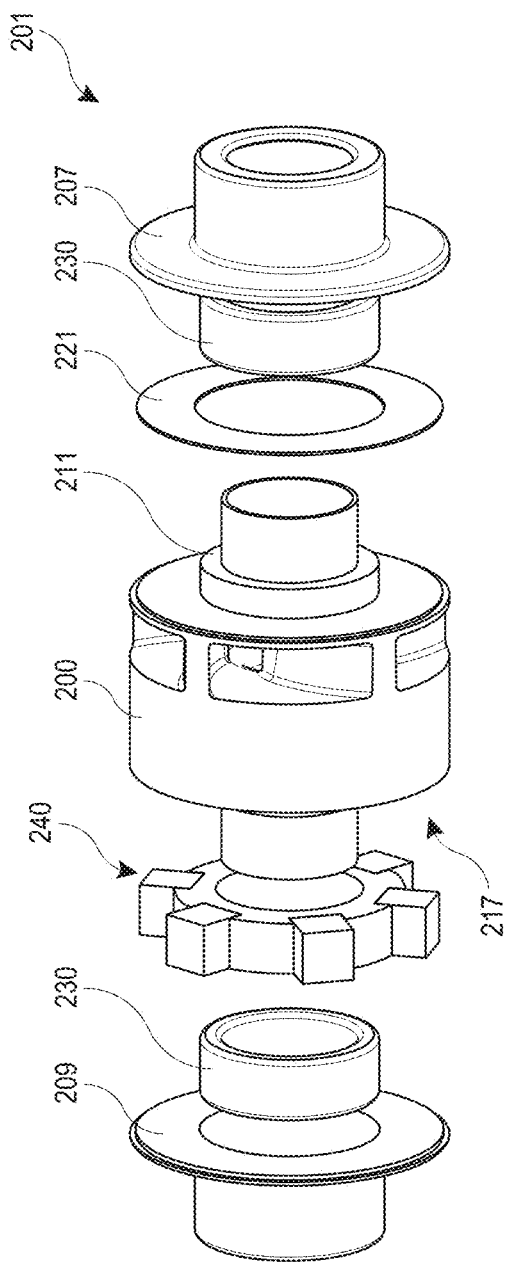

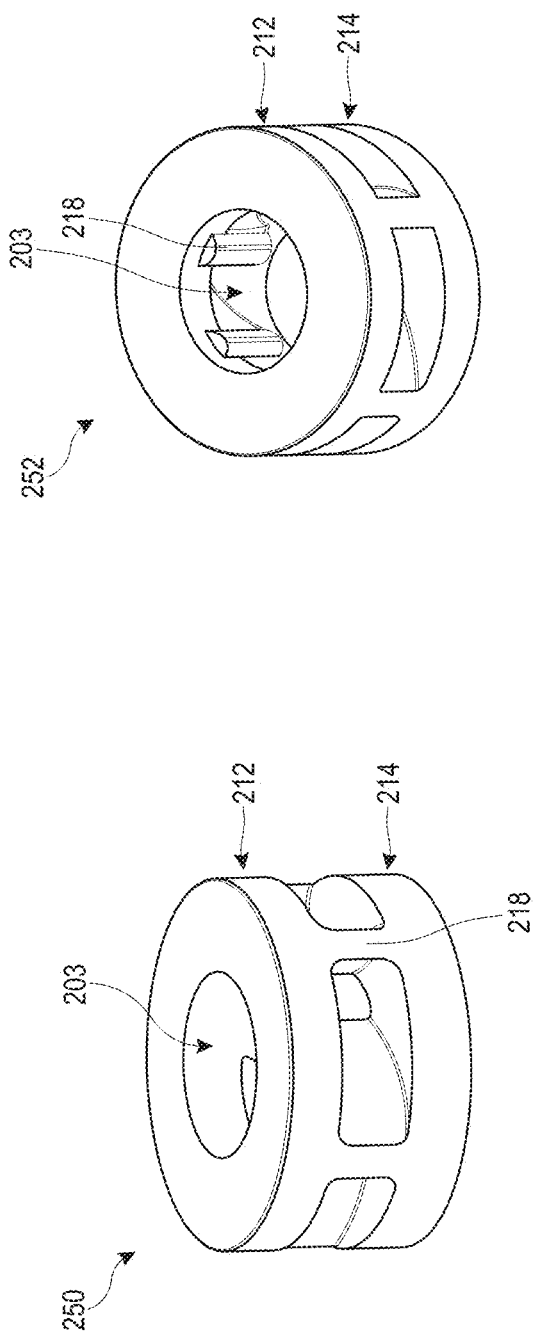
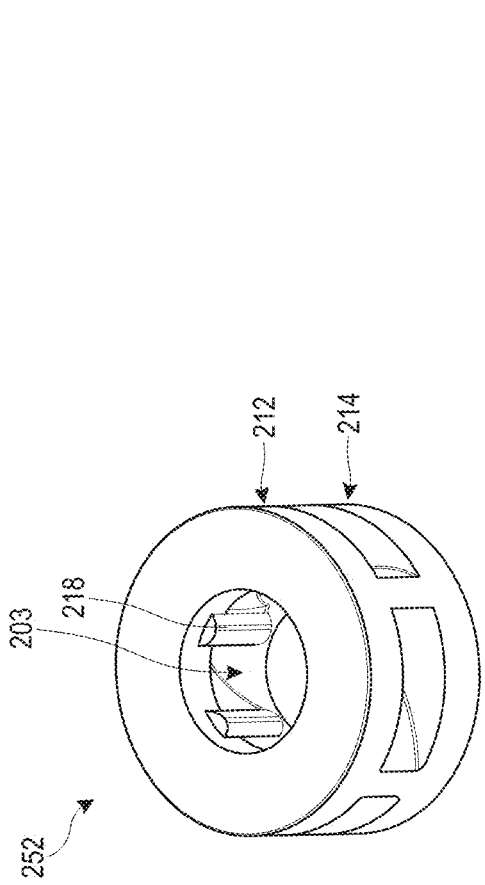
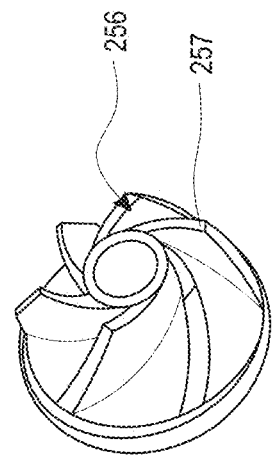
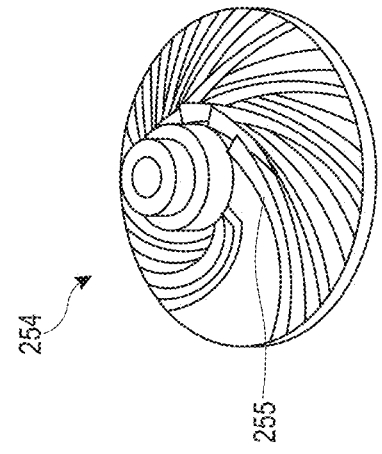
FIG. 7A
FIG. 7B
FIG. 7C
FIG. 7D

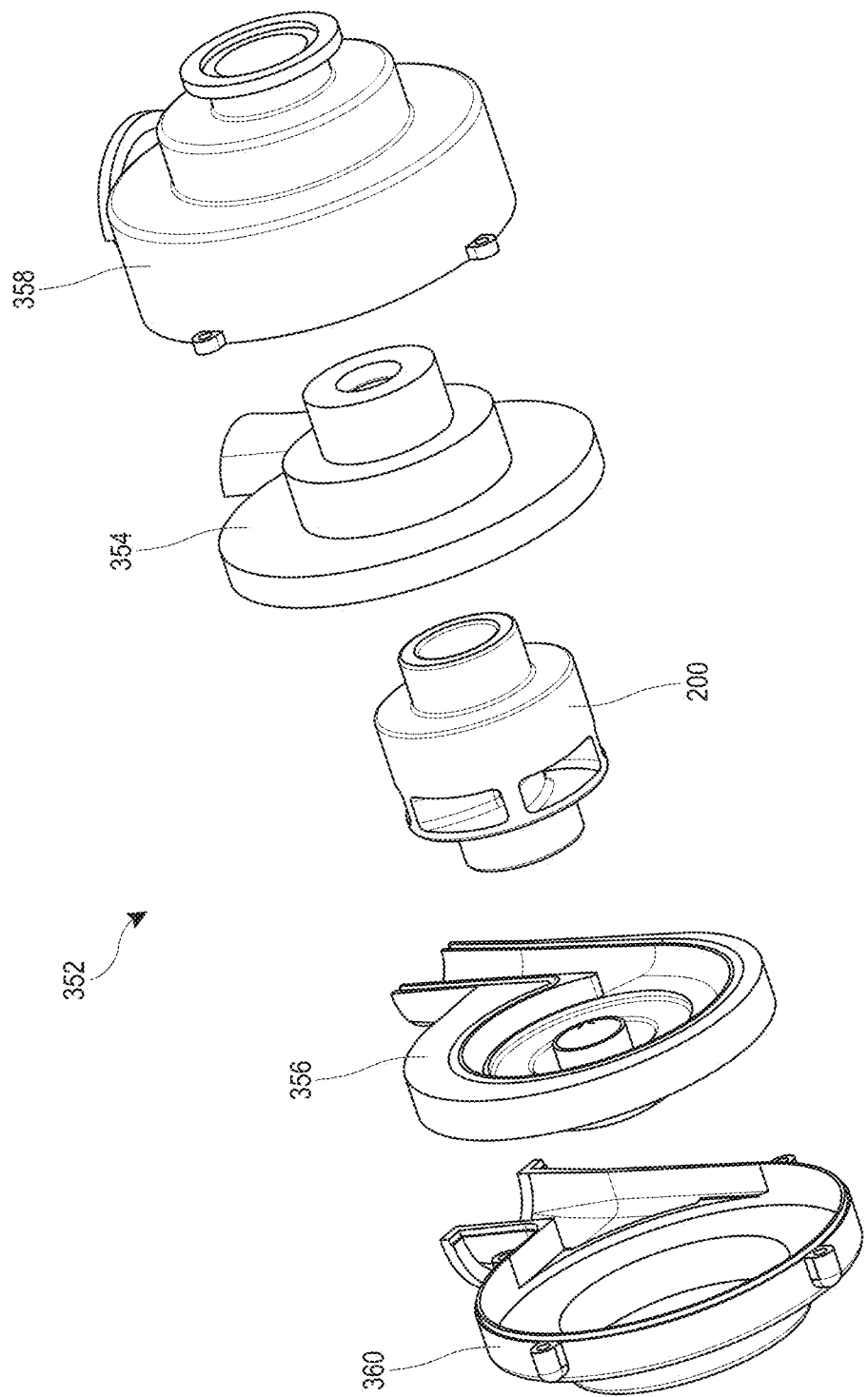

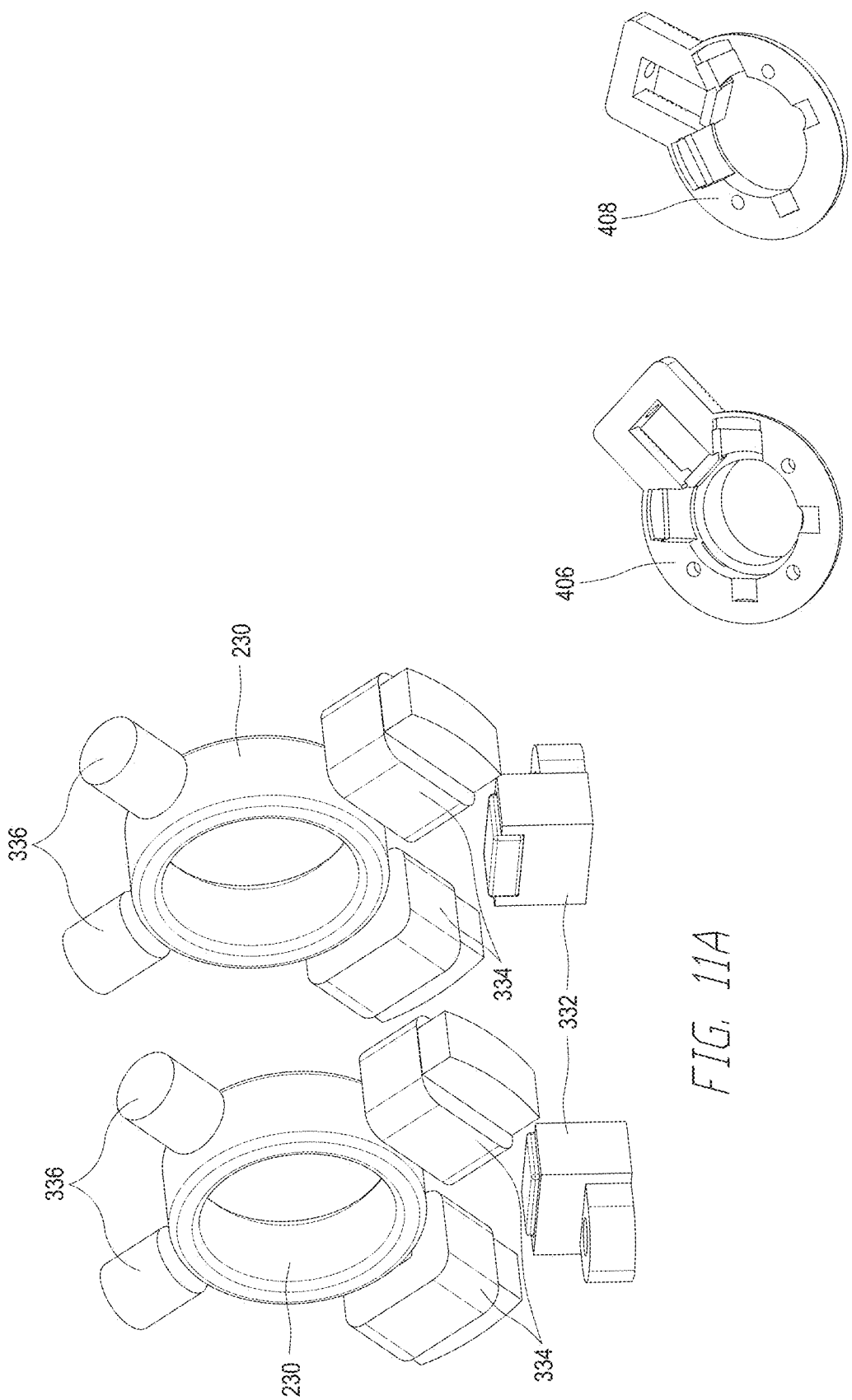

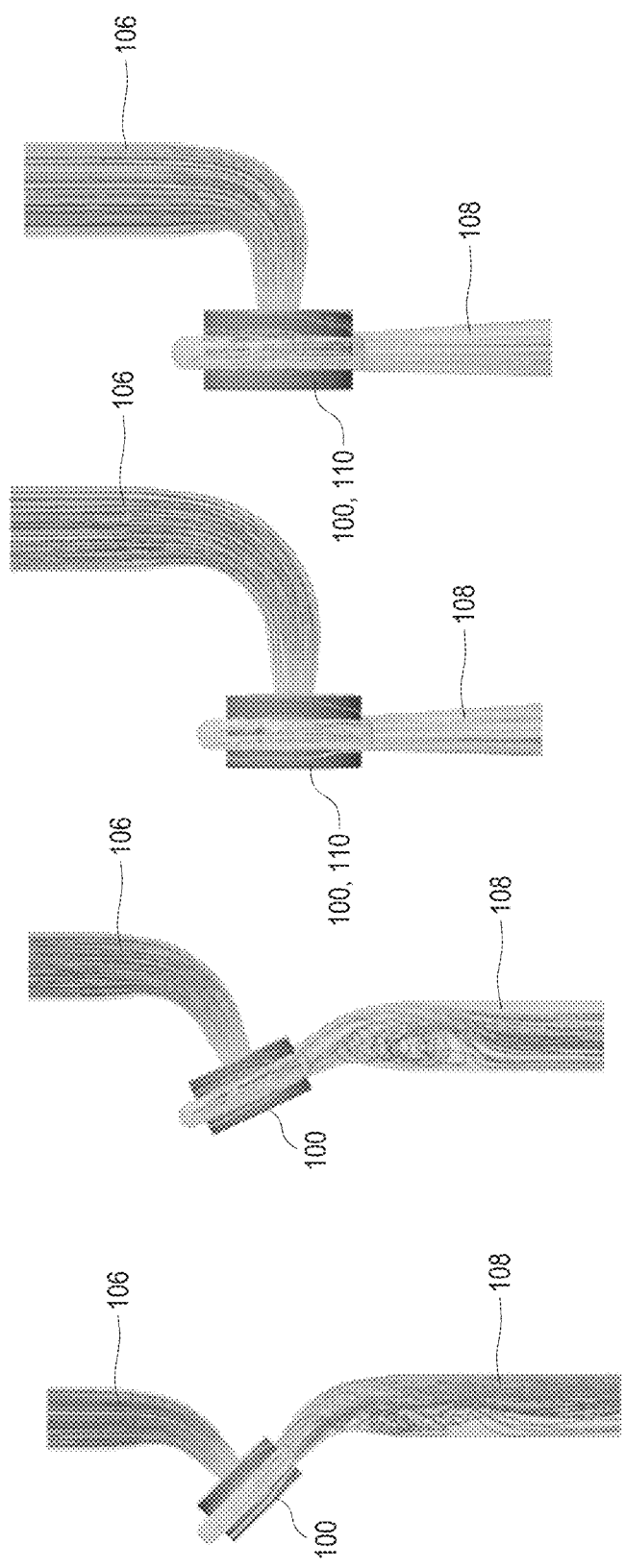

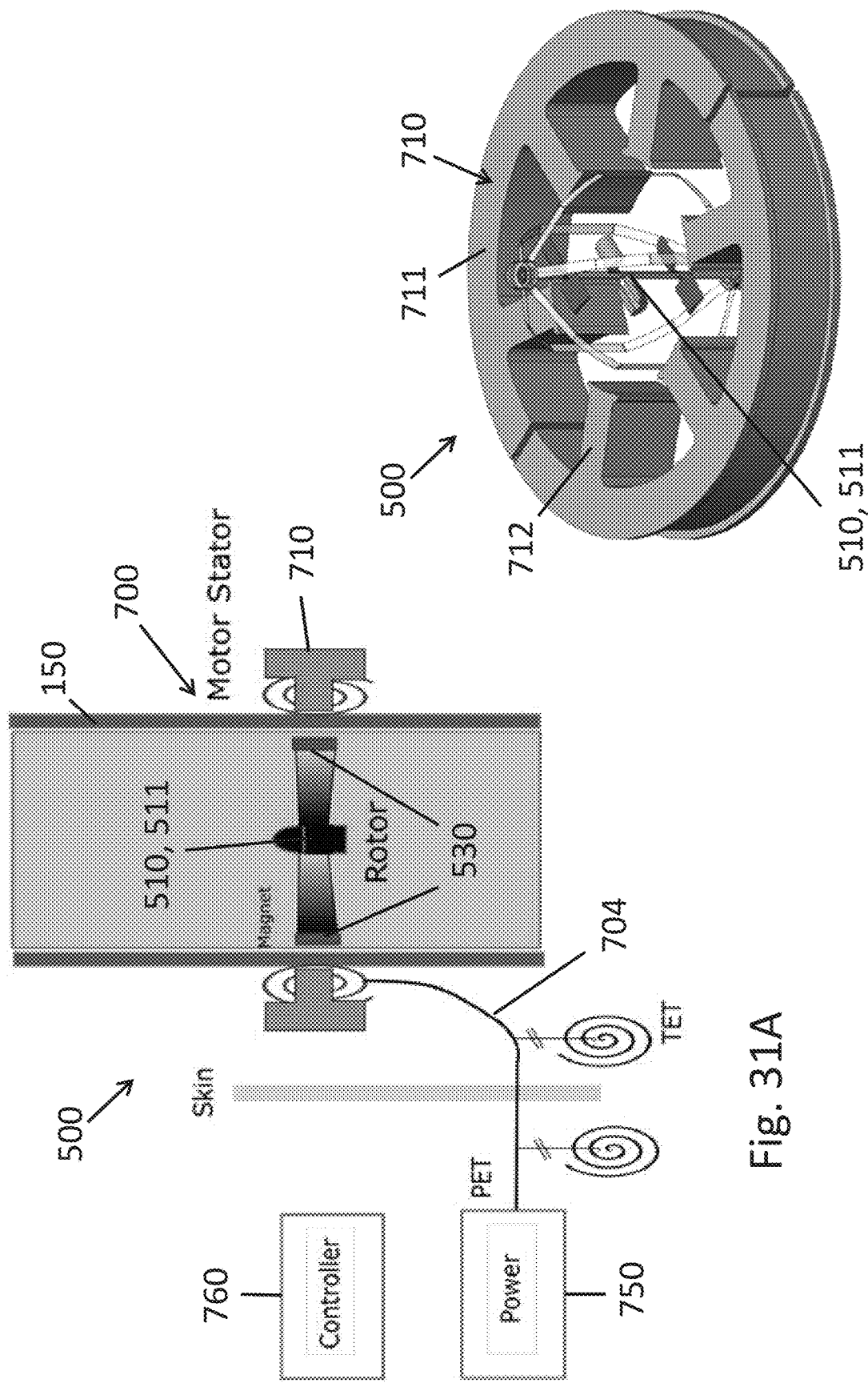

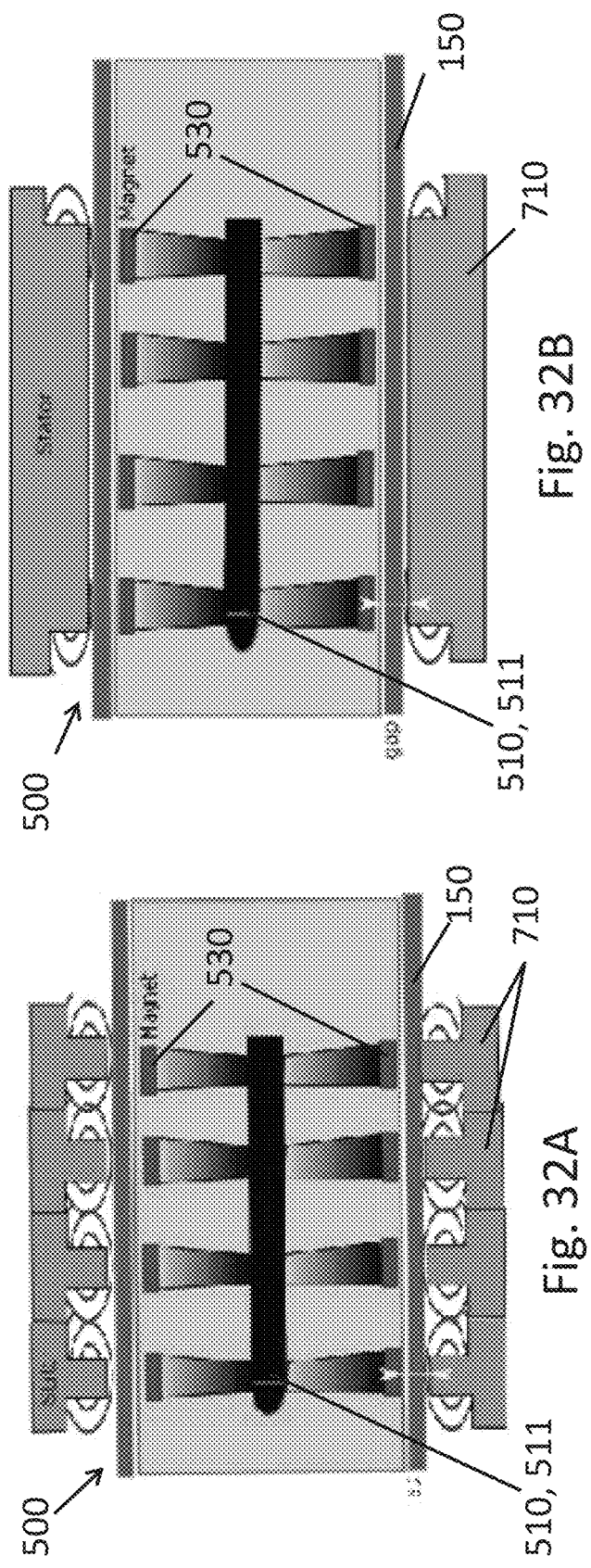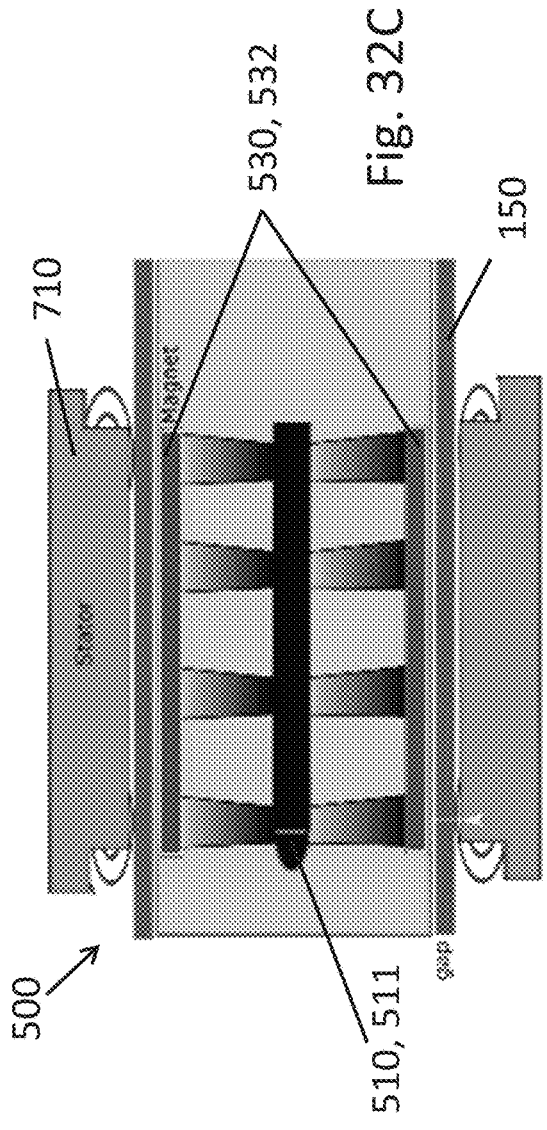
Fig. 32A  Fig. 32B  Fig. 32C

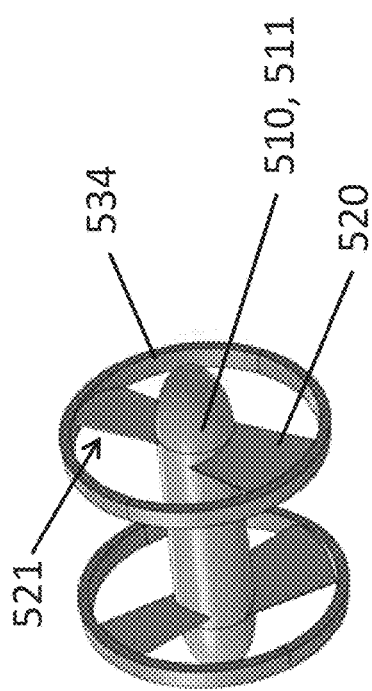
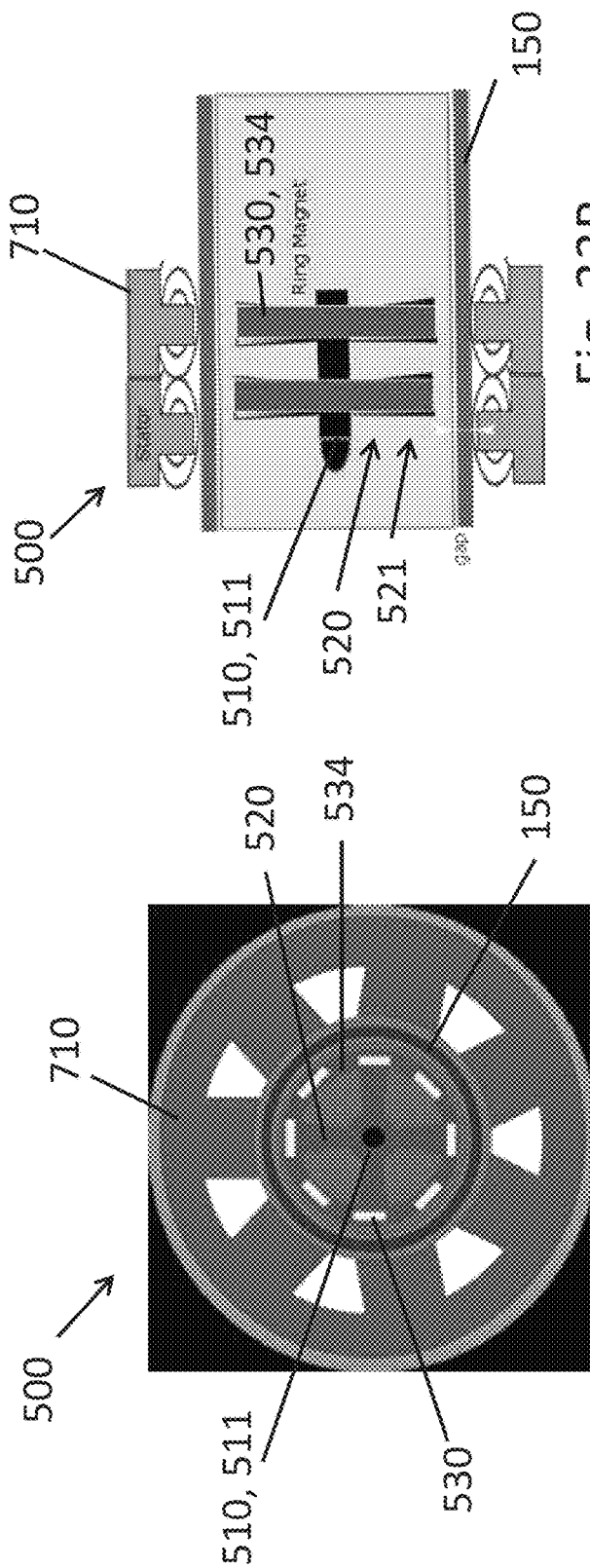

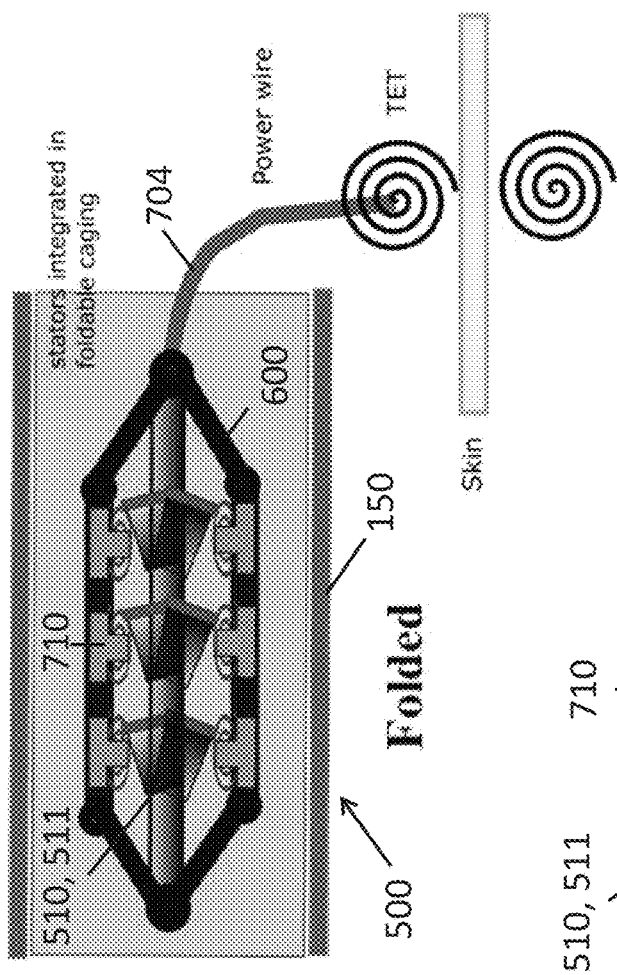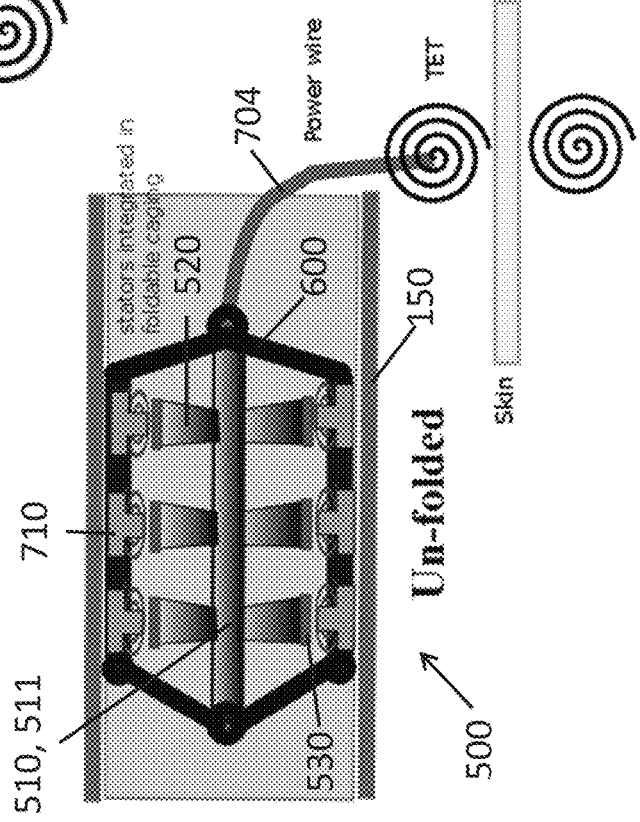
Fig. 38A Folded
Fig. 38B Un-folded

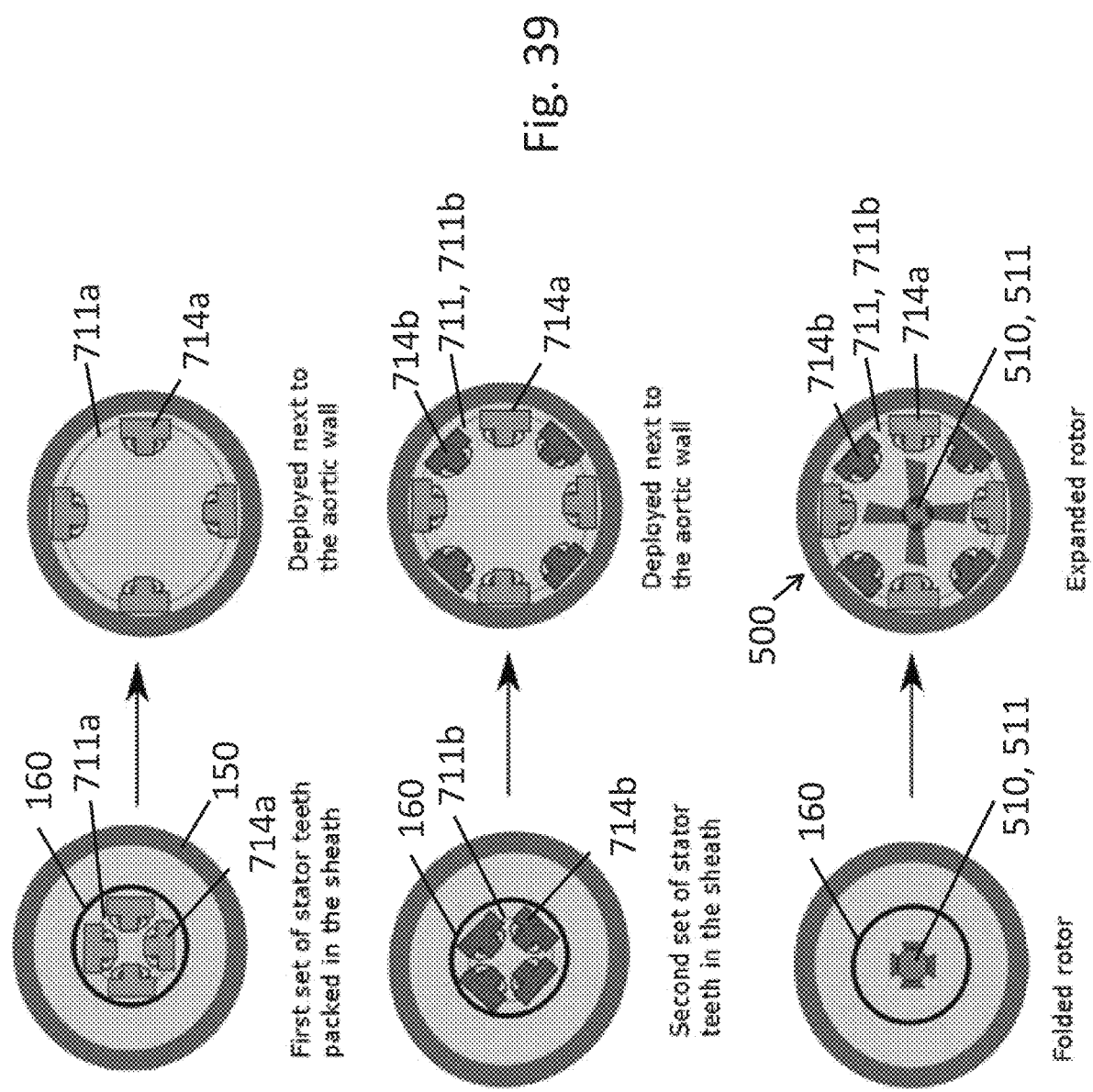

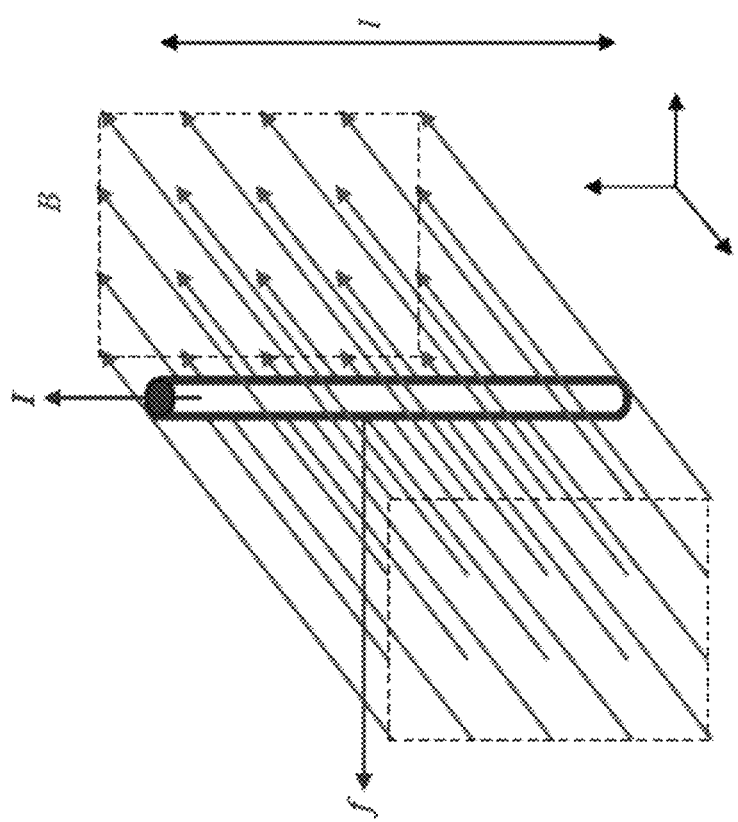

|  | BLDC | PMSM |
| --- | --- | --- |
| Desired back-emf shape | Trapezoidal | Sinusoidal |
| Applied current shape | Rectangular | Sinusoidal |
| Position sensing | Discrete (e.g. Hall effect) | Continuous (e.g. resolver or shaft encoder) |
| Torque ripple | Higher | Lower |
| Motor constant (for the same back-emf amplitude) | Higher | Lower |
| Cost | Lower | Higher |

Fig. 42C

|  | Radial flux | Axial flux |
| --- | --- | --- |
| Power density | Lower | Higher |
| Stator manufacturing cost | Lower | Higher |
| Maximum allowable number of poles | Lower | Higher |
| Ventilation |  | Better |
| Size characteristics | Larger length to diameter | Larger diameter to length |
| High power motor | Commonly used | Cannot be used |

Fig. 42E

| | Internal rotor | External rotor |
|---|---|---|
| Heat removal | Better | Worse |
| Air gap radius | Lower | Higher |
| Developed torque | Lower | Higher |
| Torque/inertial ratio | Higher | Lower |
| Winding | More difficult | Easier |
| Robustness for surface mounted PM | Lower | Higher |
| Applications | Rapid acceleration and deceleration (Servo systems) | Constant speed (fans and blowers) |

Fig. 42F

| | Slotted | Slotless |
|---|---|---|
| Cogging torque | exists | Almost nothing |
| Cost of winding | Higher | Lower |
| Magnetic air gap | Smaller | Larger |
| Air gap flux density | Higher | Lower |
| Inductance | Higher | Lower |
| Heat removal | Better | worse |
| Winding space | Lower | Higher |
| Electric per magnetic loadings | Lower | Higher |

Fig. 42G

|  | Typical at 20 °C | | | Relative material cost | Resistance to corrosion | Temperature performance | Shape complexity |
|---|---|---|---|---|---|---|---|
|  | $B_r$ (T) | $H_c$ (kA/m) | $H_{ci}$ (kA/m) | $(BH)_{max}$ (kJ/m³) | | | | |
| NdFeB[1] | 1.18 | 840 | 1040 | 256 | High | Poor (coating is vital) | Poor | Very simple |
| NdFeB[2] | 0.56 | 400 | 800 | 60 | | | | Complex |
| NdFeB[3] | 0.70 | 480 | 840 | 84 | | | | Simple |
| Sm$_2$Co$_{17}$[1] | 1.00 | 480 | 558 | 192 | Very high | Good | Very good | Very simple |
| SmCo$_5$[1] | 0.83 | 600 | 1440 | 128 | | | | Very simple |
| SmCo$_5$[2] | 0.65 | 460 | 620 | 80 | | | | Complex |
| Sm$_2$Co$_{17}$[3] | 0.86 | 497 | 800 | 130 | | | | Simple |
| Alnico-5[1] | 1.05 | 48 | 50 | 24 | Low | Good | Excellent | Very simple |
| Alnico-5[4] | 1.24 | 51 | 51 | 44 | | | | Complex |
| Ferrite[1] | 0.41 | 223 | 231 | 32 | Very low | Excellent | Good | Very simple |
| Ferrite[2] | 0.30 | 191 | 223 | 16 | | | | Complex |

[1] Sintering [2] Injection moulding [3] Compression bonding [4] Casting

Fig. 42H

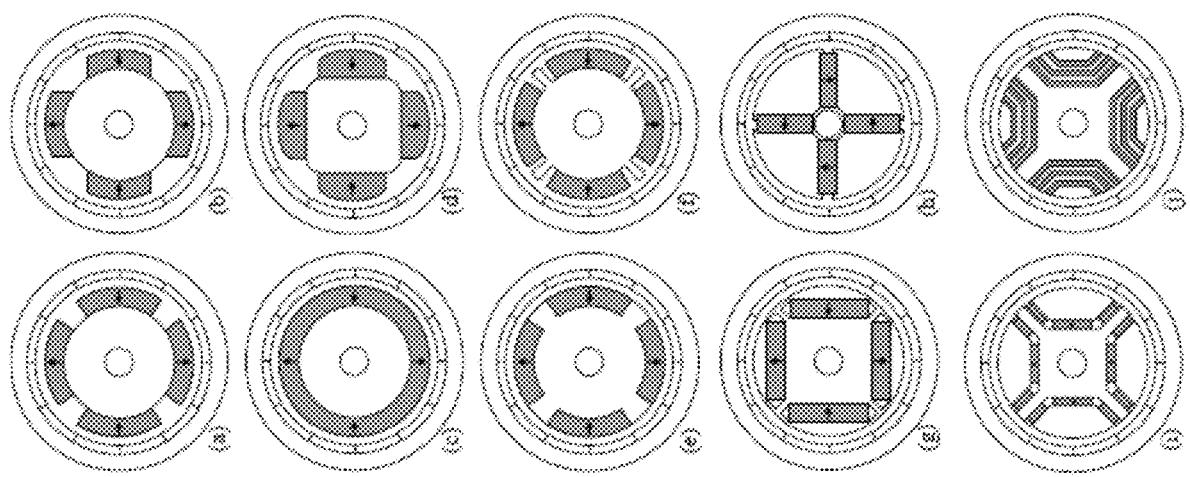

|  | Surface mounted PM (Fig. 2.4 (c), (d)) | Surface inset PM (Fig. 2.4 (e), (f)) | Buried PM (Fig. 2.4 (g), (i), (j)) | Spoke PM (Fig. 2.4 (h)) |
|---|---|---|---|---|
| Cost | Low | Low | High | Medium |
| Robustness | Low | Medium | Very high | High |
| Maximum speed | Low | Medium | High | High |
| D/Q axis reluctance | ≈1 | >1 | >1 | <1 |
| Magnet Eddy current loss | High | Medium | Low | Low |
| Harmonics in PM due to stator MMF | High | Medium | Low | Low |
| Power extension capability | Lower | Higher | | |

Fig. 42J

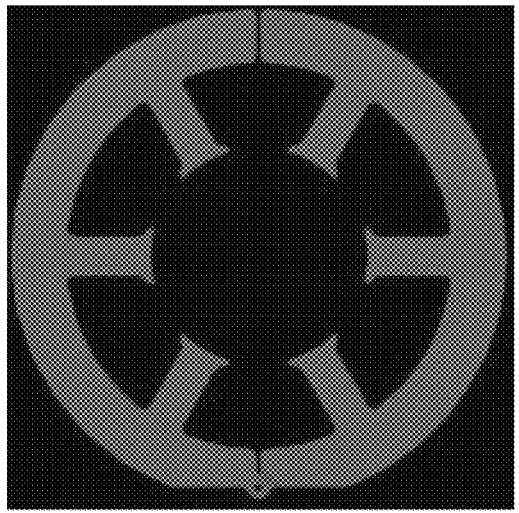
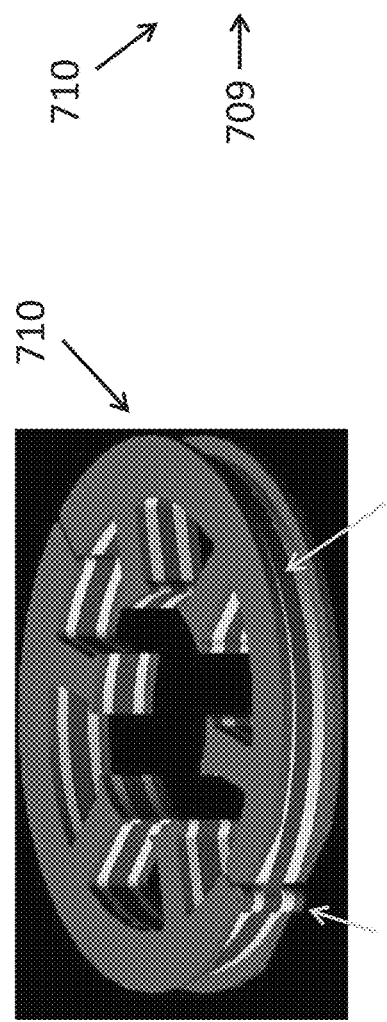
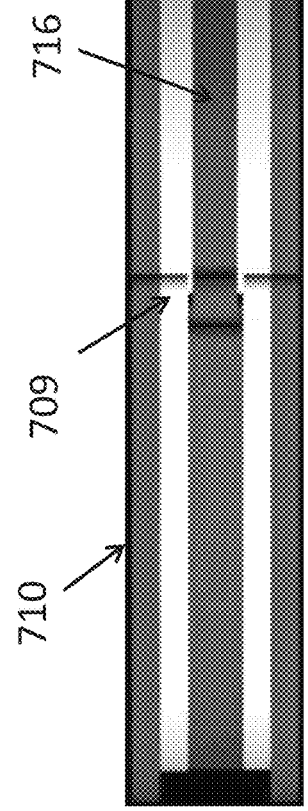
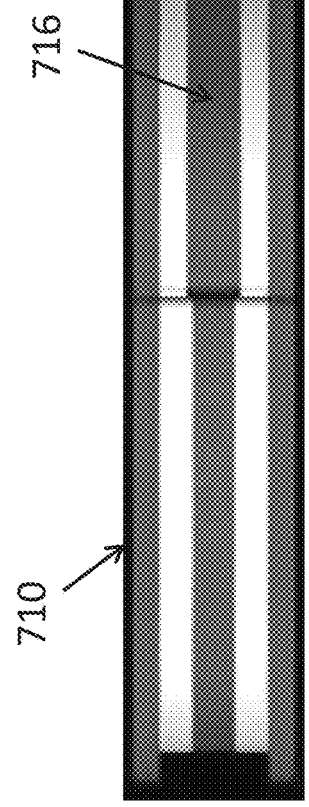
Fig. 43C
Fig. 43D
Fig. 43E
Fig. 43B

| AWG gauge | Conductor Diameter (Inches) | Conductor Diameter (mm) | Ohms per 1000 ft | Ohms per km | Maximum amps for chassis wiring (A) | Maximum amps for power transmission (A) |
|---|---|---|---|---|---|---|
| 18 | 0.0403 | 1.02362 | 6.385 | 20.9428 | 16 | 2.3 |

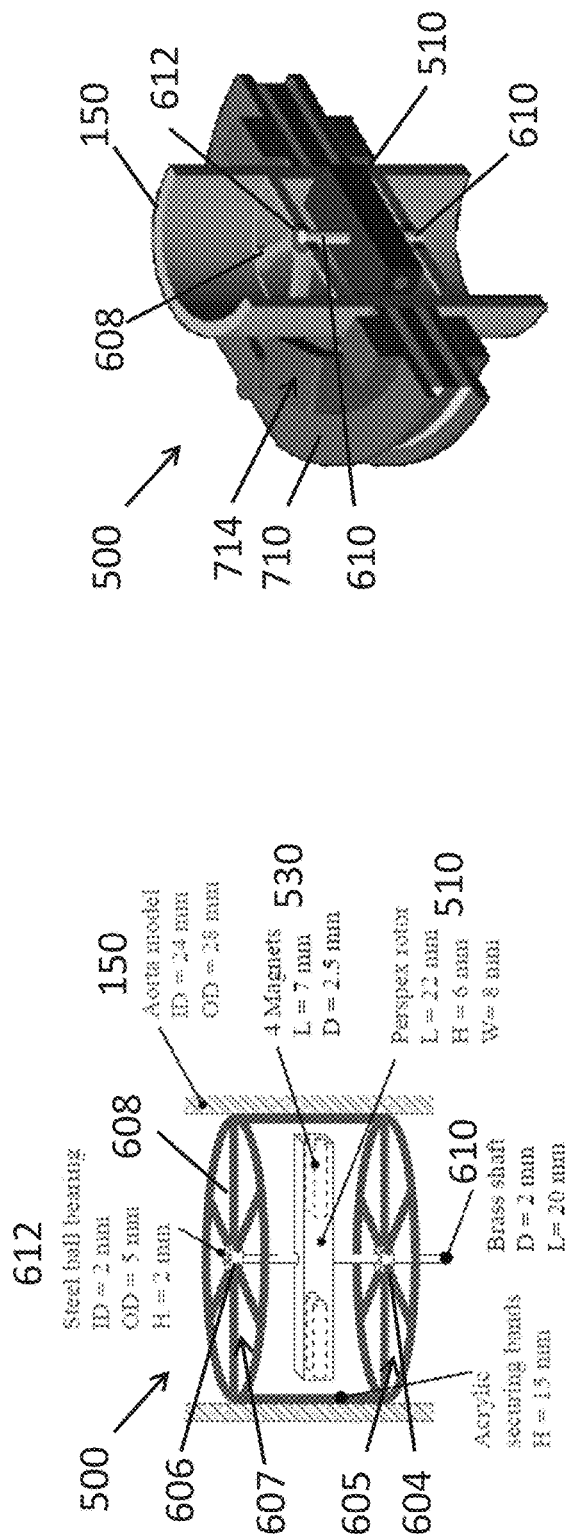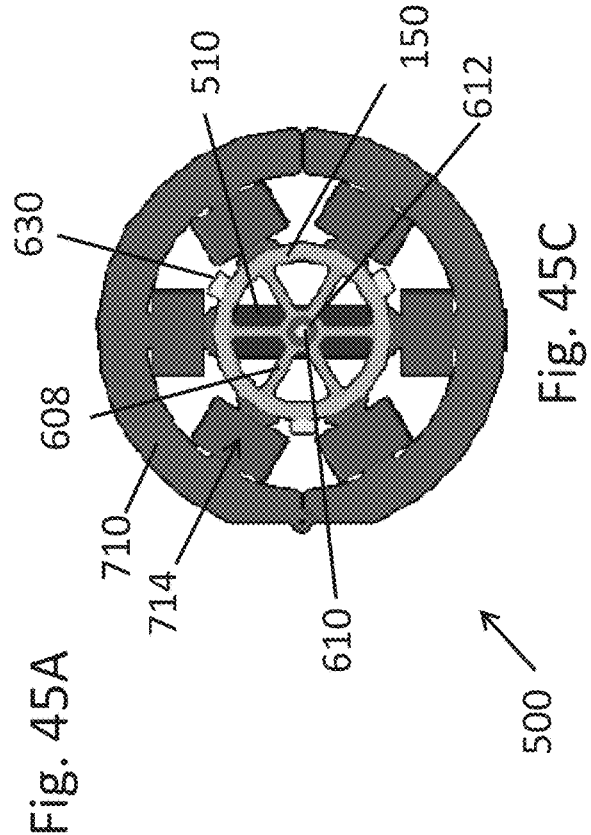
Fig. 45A
Fig. 45B
Fig. 45C

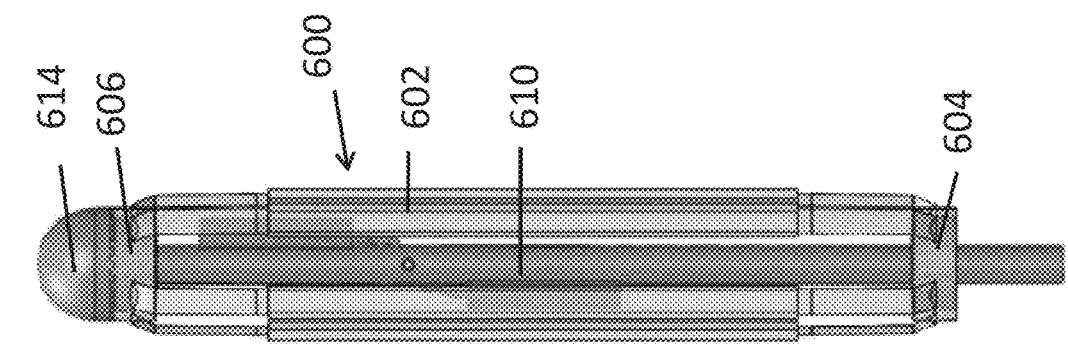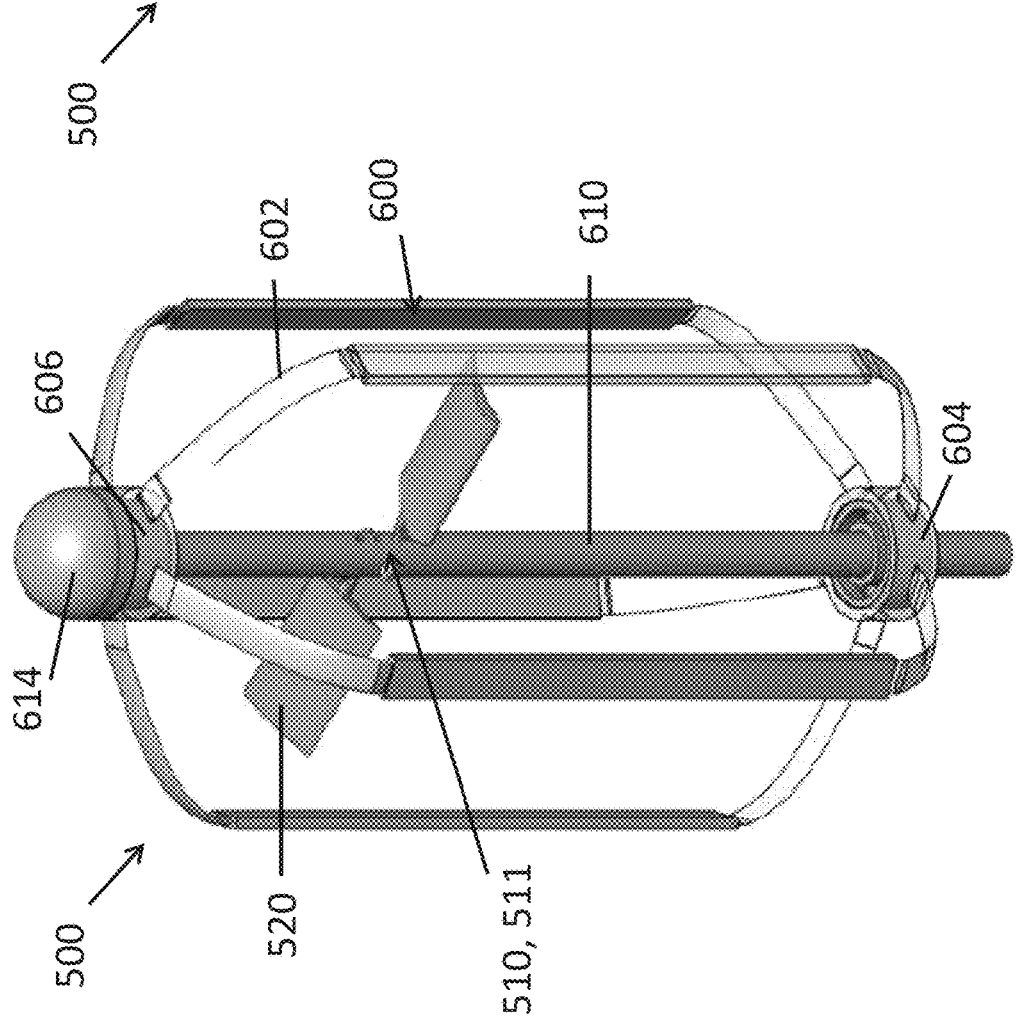

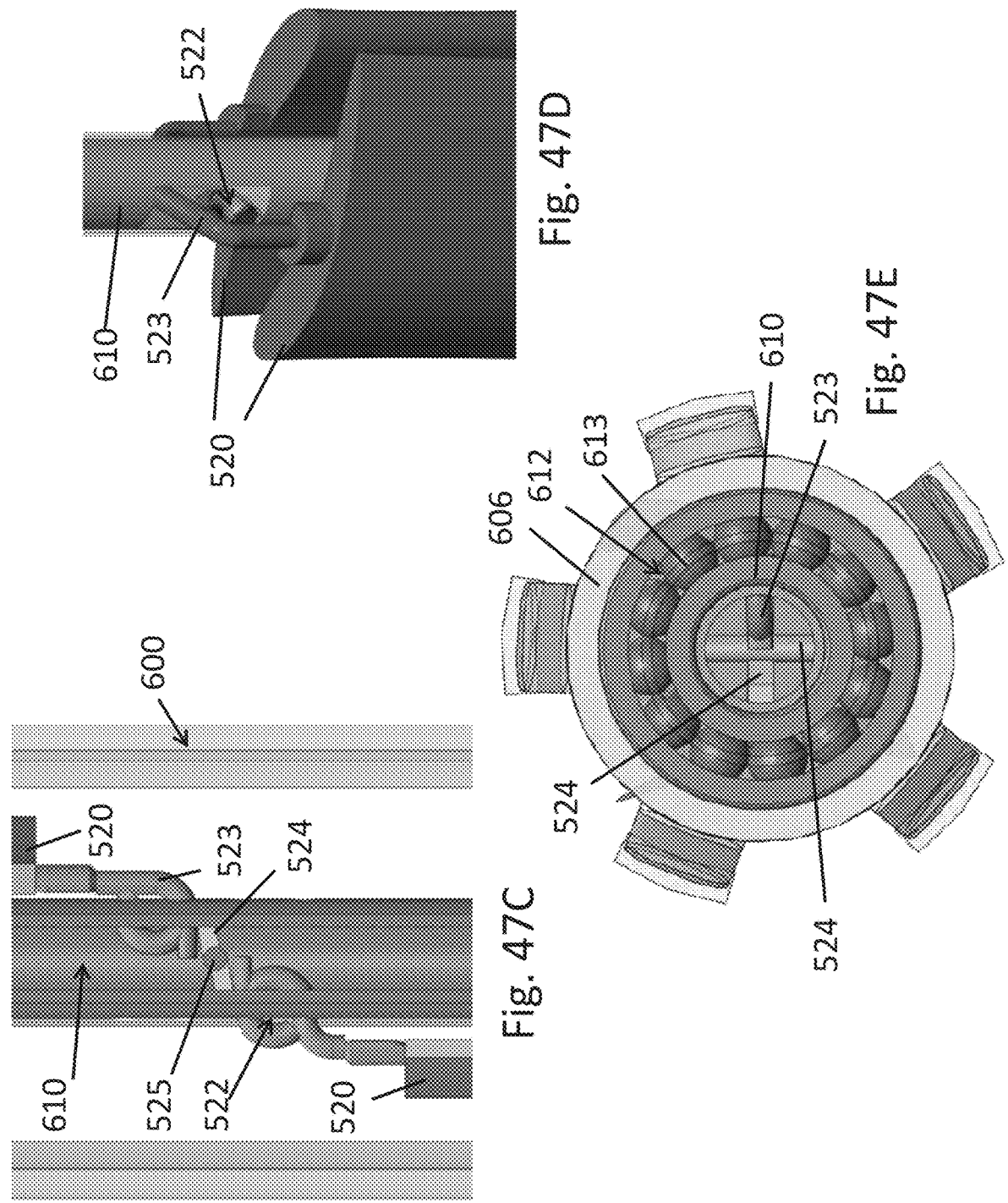

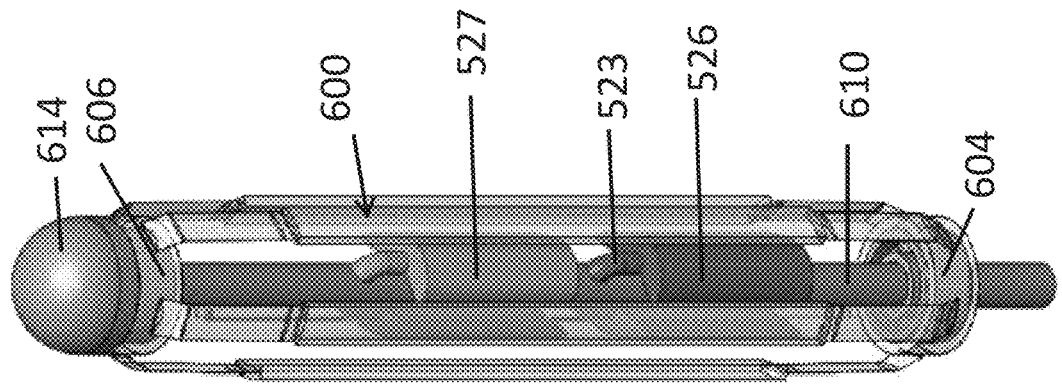
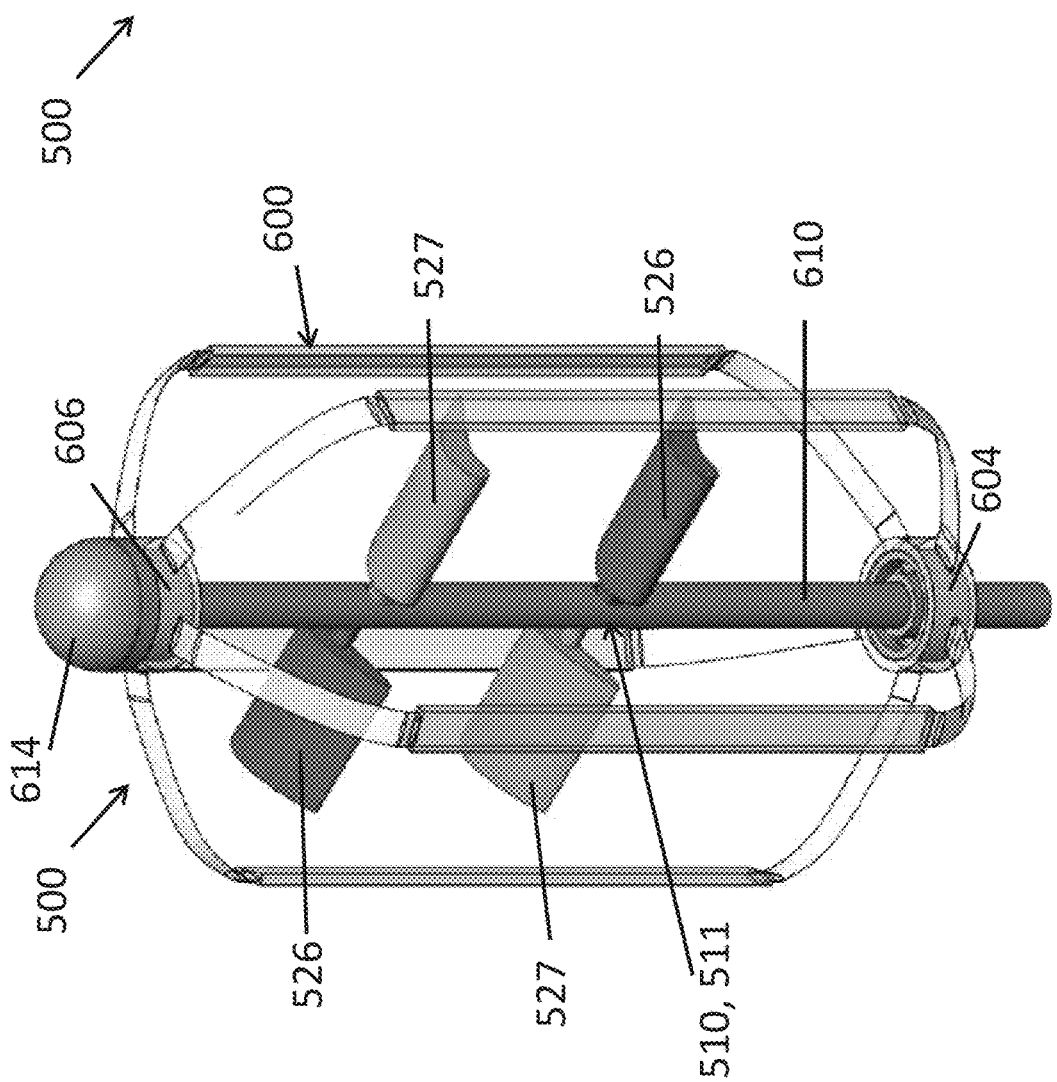
Fig. 48B
Fig. 48A

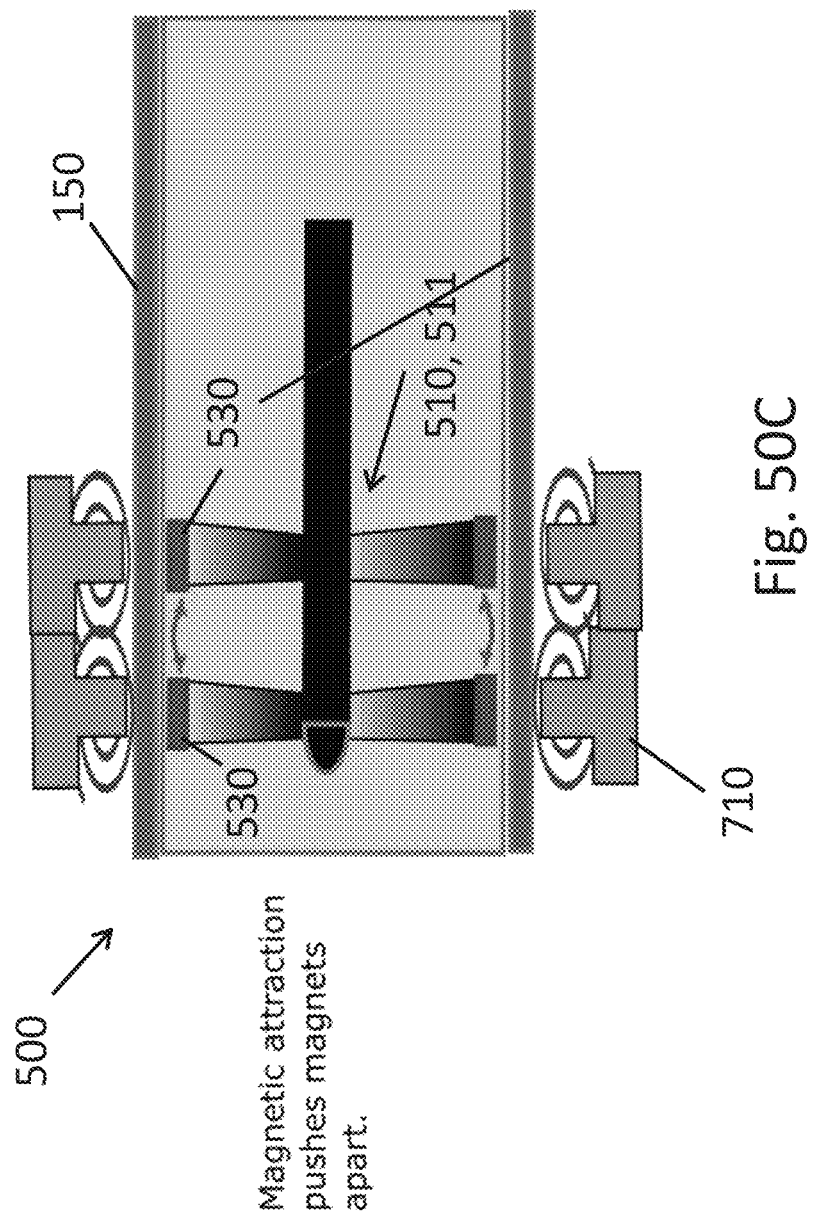

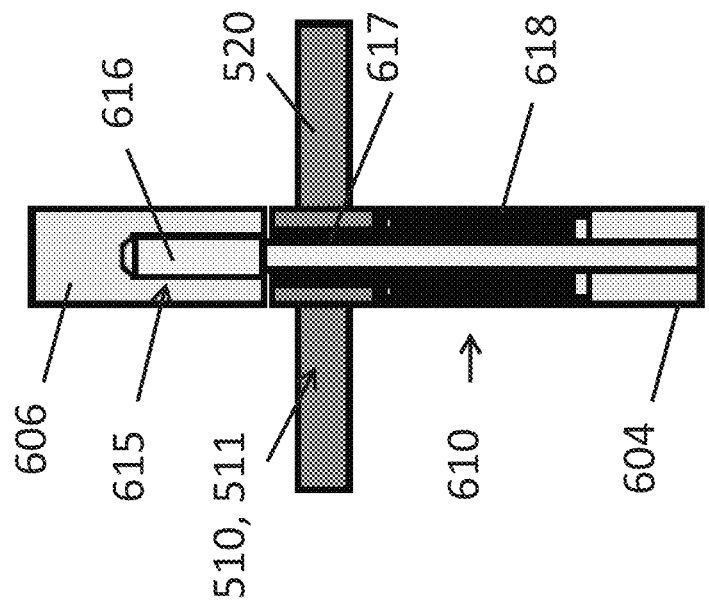
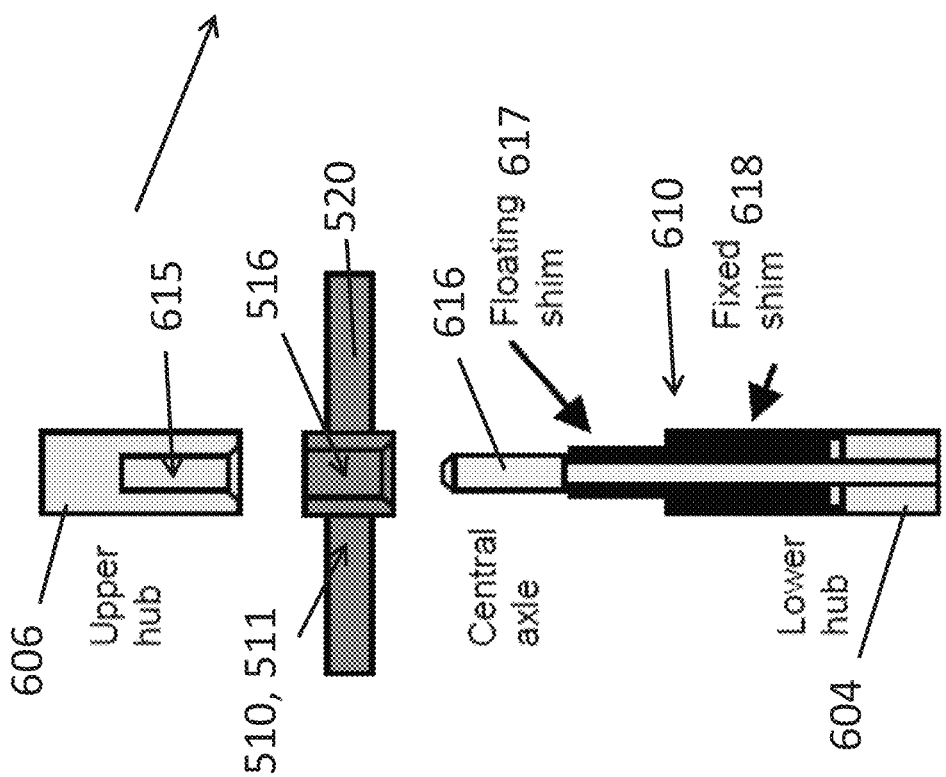
Fig. 51B
Fig. 51A

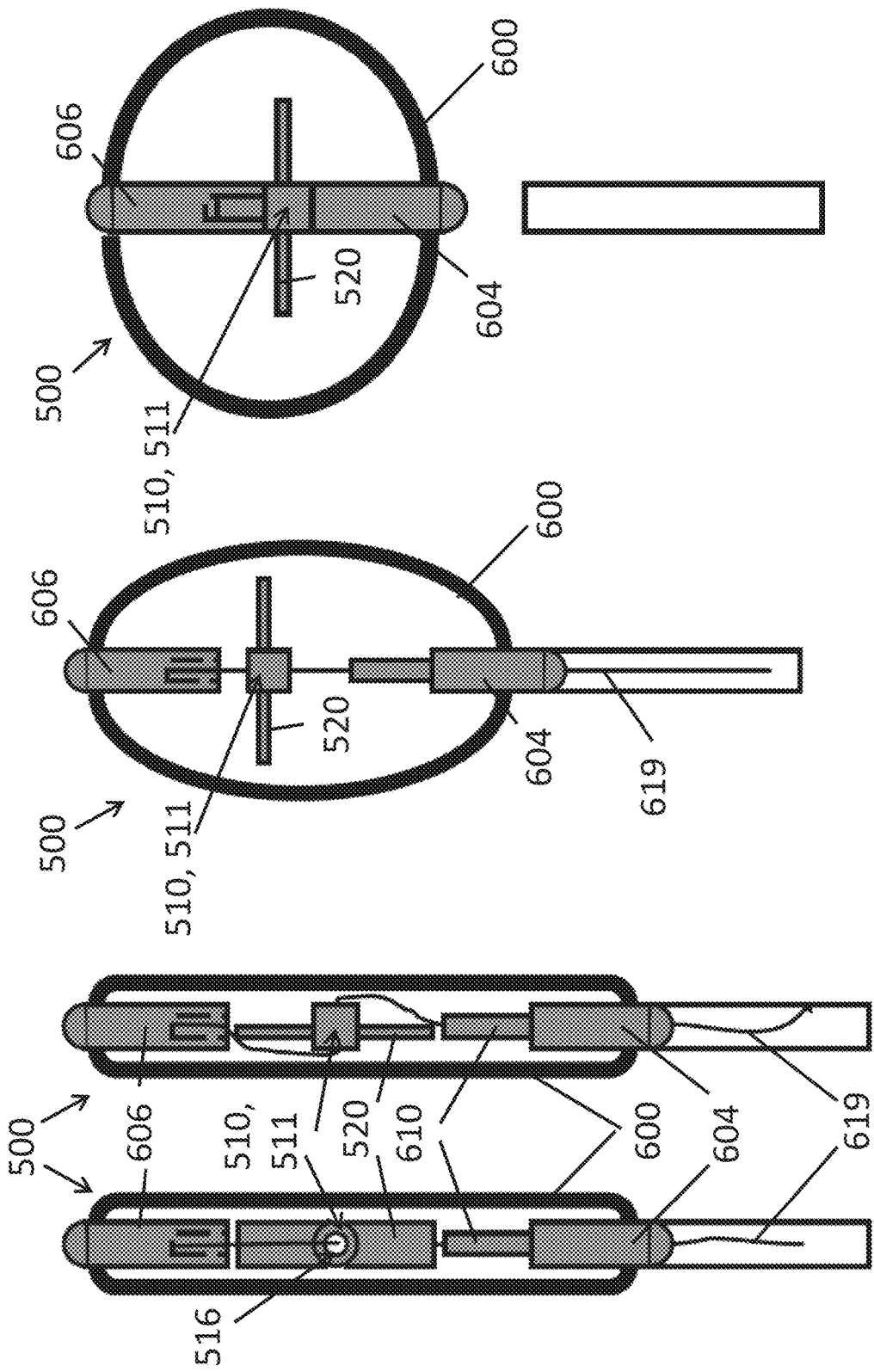

Expanded spring support

Closed spring support

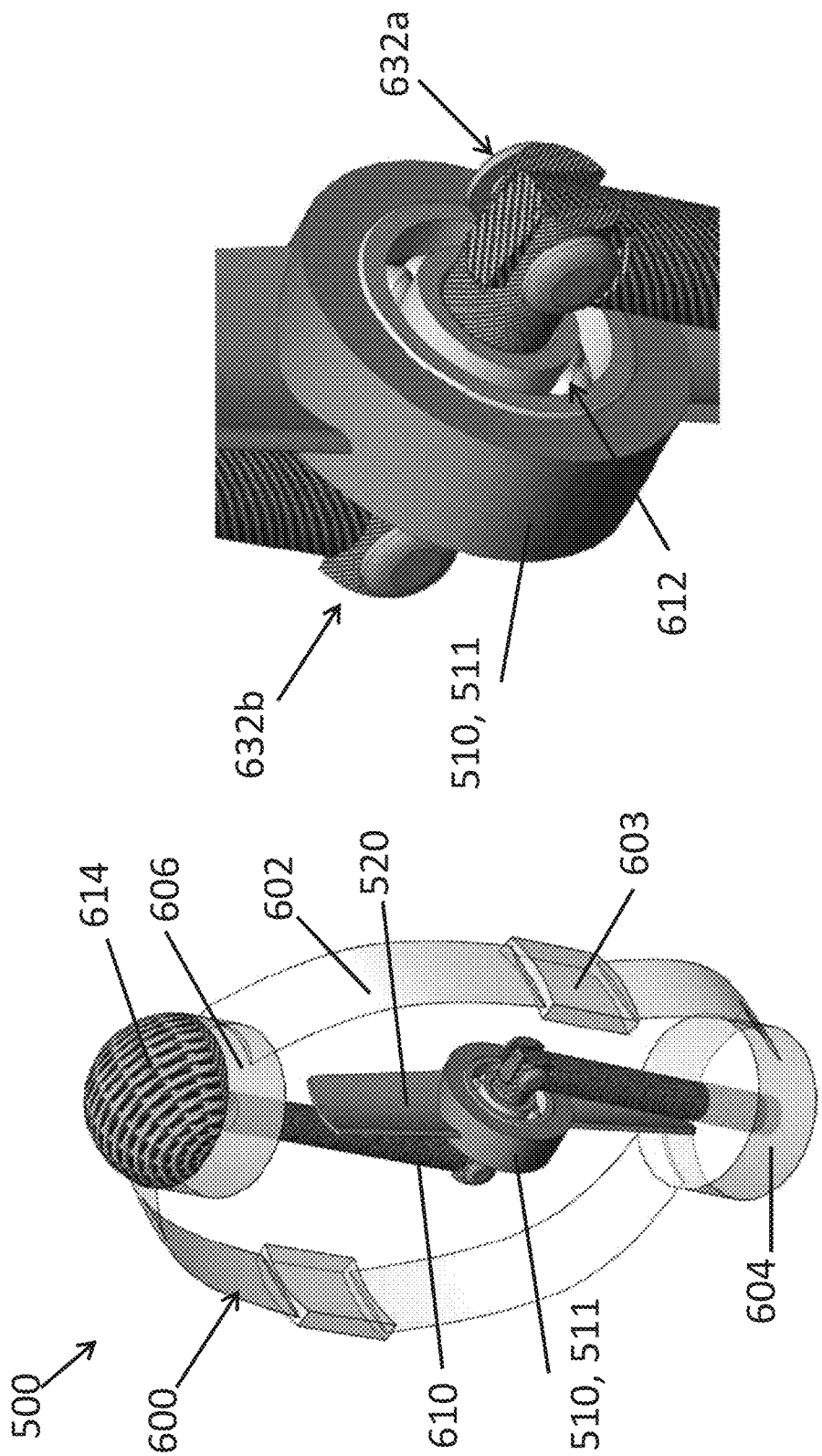

| | | |
|---|---|---|
| $Q_a$ | ~8 | lt/min | Volume flow rate |
| $\rho$ | 1060 | kg/m³ | Blood density |
| $\Delta p$ | ~20 | mmHg | Pressure difference |
| $\omega$ | ~12000 | rpm | Rotational speed |
| $D_{aorta}$ | 0.024 | m | Diameter of aorta |
| $D_{prop,tip}$ | 0.022 | m | Tip diameter of propeller |
| $D_{prop,hub}$ | 0.005 | m | Hub diameter of propeller |
| $N_{sections}$ | 11 | | Number of sections for each side of propeller |
| $\eta$ | 0.8 | | Efficiency |

Fig. 57A

| | | |
|---|---|---|
| $Q_a$ | 0.000133 | m³/s |
| $m$ | 0.141333 | kg/s |
| $\Delta p$ | 2666.4 | Pa=kg/(ms²) |
| $\omega$ | 1256.637 | rad/s |
| $A_{aorta}$ | 0.0004452 | m² |
| $\Delta r$ | 0.00085 | m |
| $W_{ideal}$ | 0.35552 | W=kgm²/s³ |
| $W_{actual}$ | 0.4444 | W |
| $C_x$ | 0.294731 | m/s |
| $C_1$ | 0.294731 | m/s |

Fig. 57B

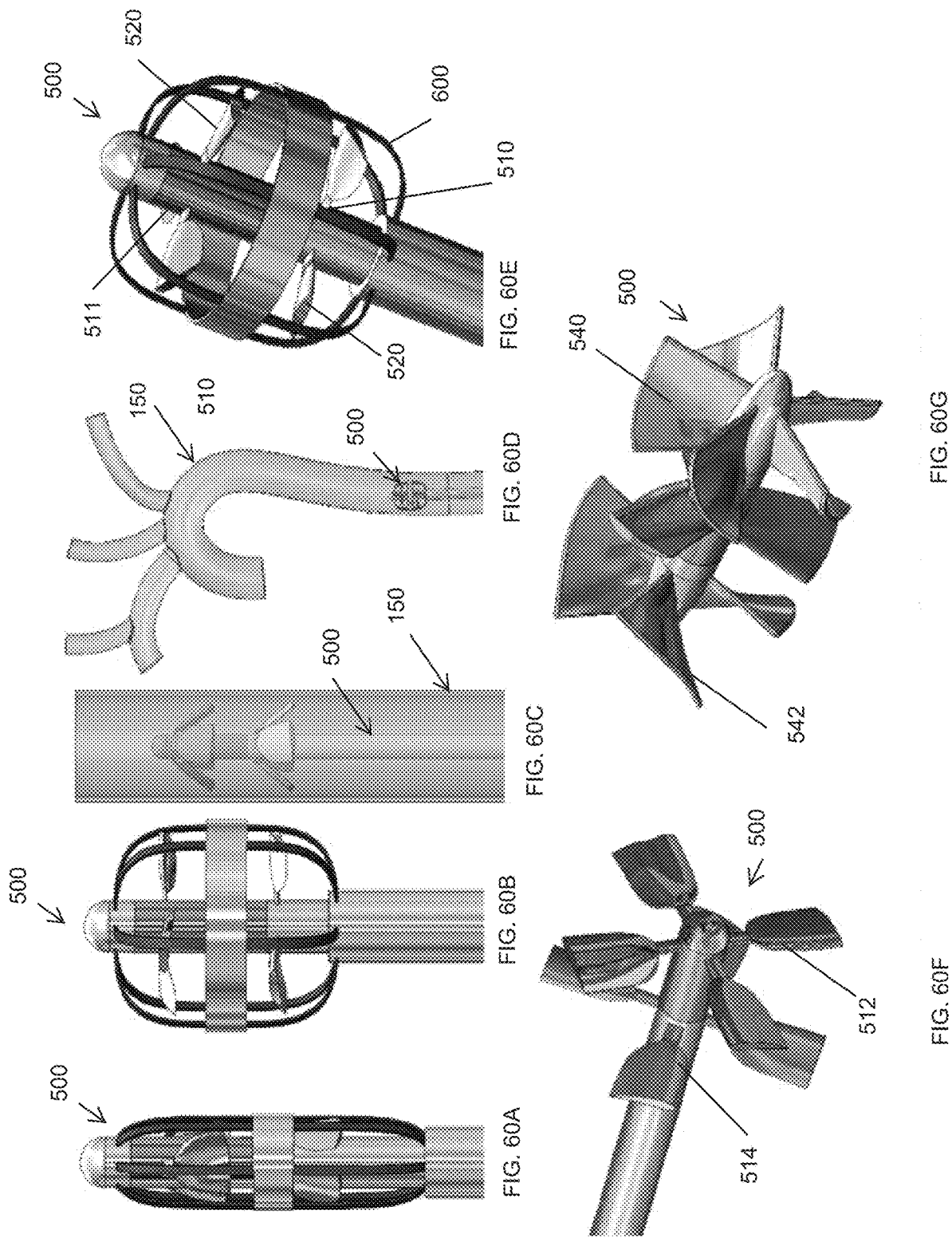

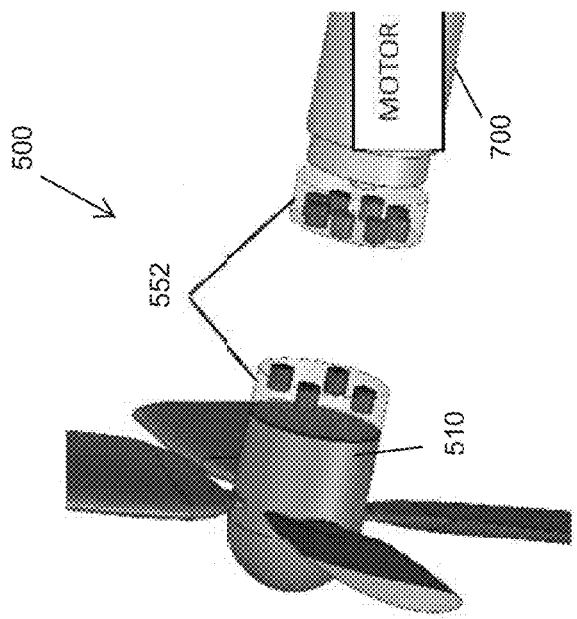
FIG. 62C
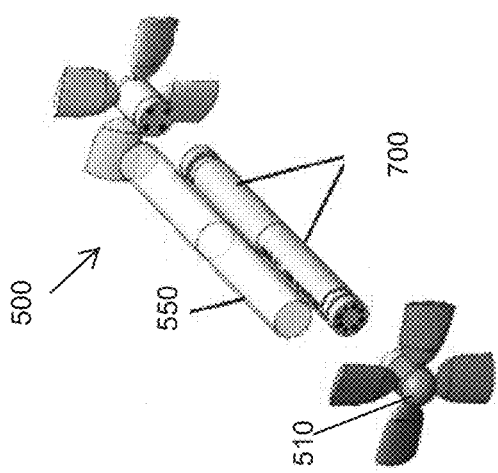
FIG. 62B
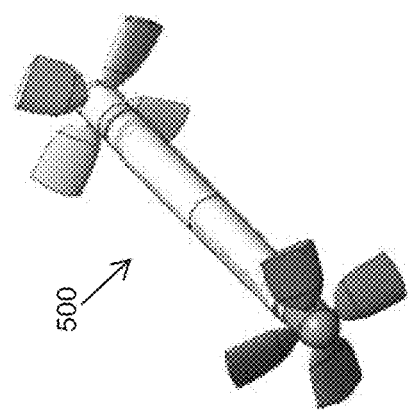
FIG. 62A
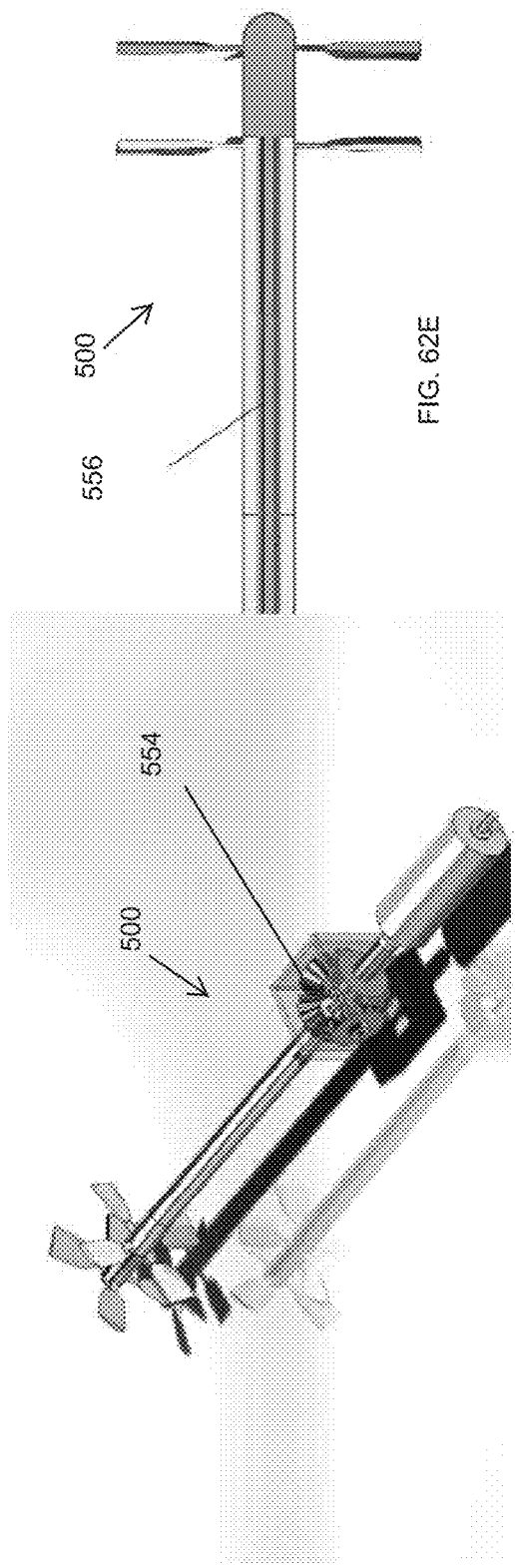
FIG. 62E
FIG. 62D

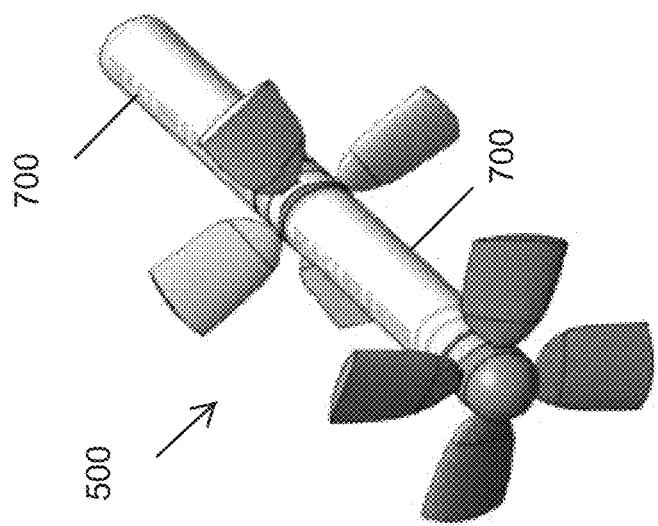
FIG. 64C
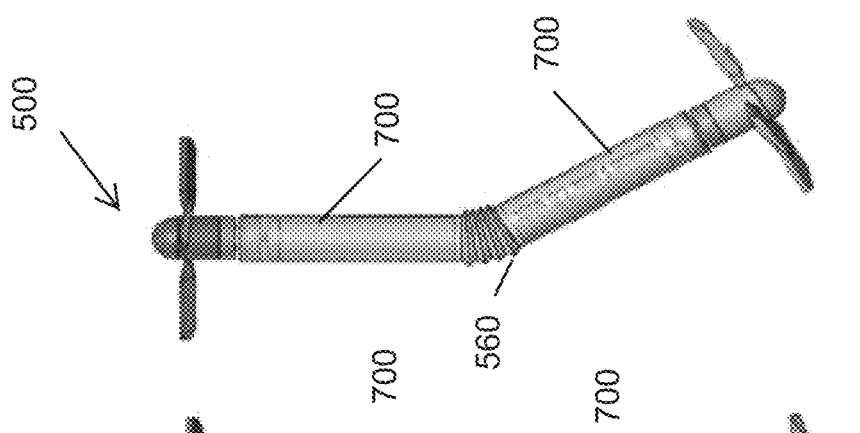
FIG. 64B
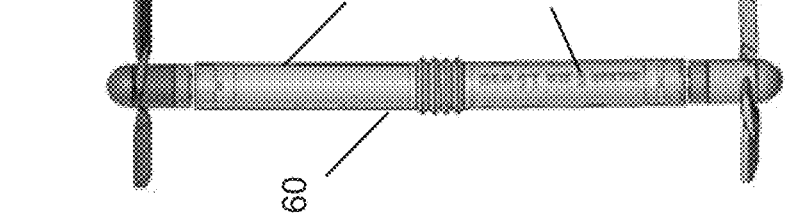
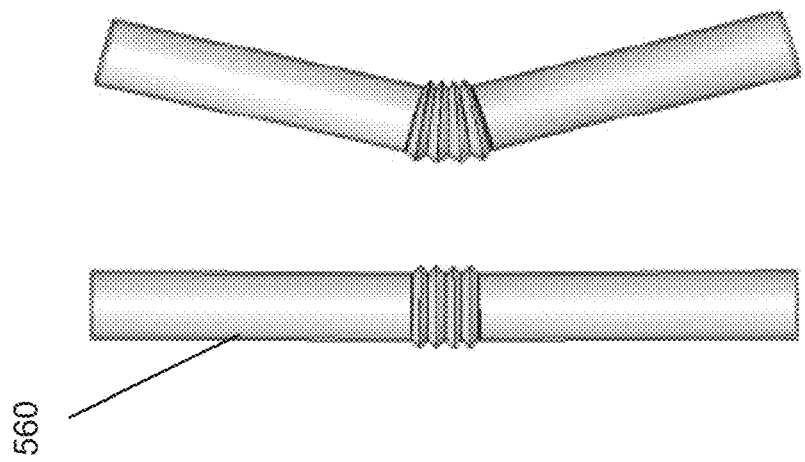
FIG. 64A

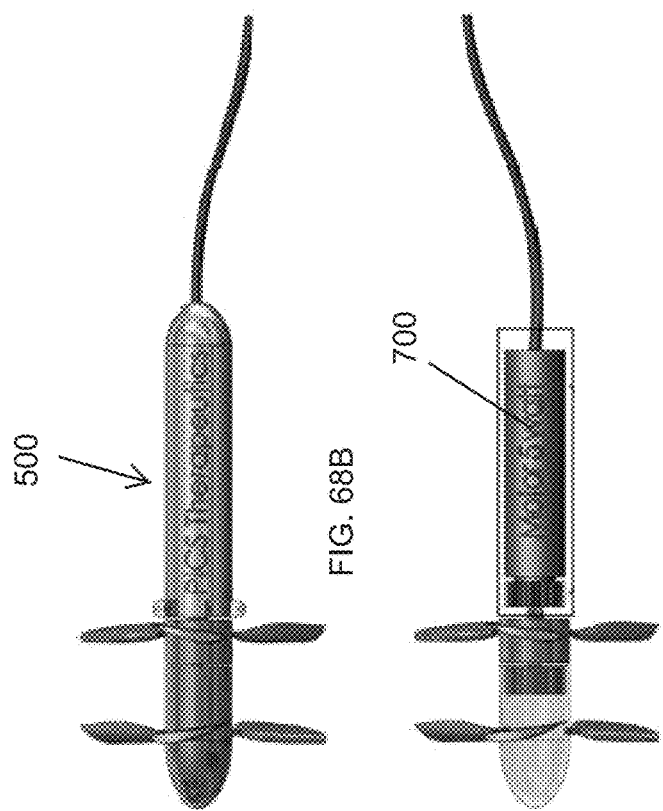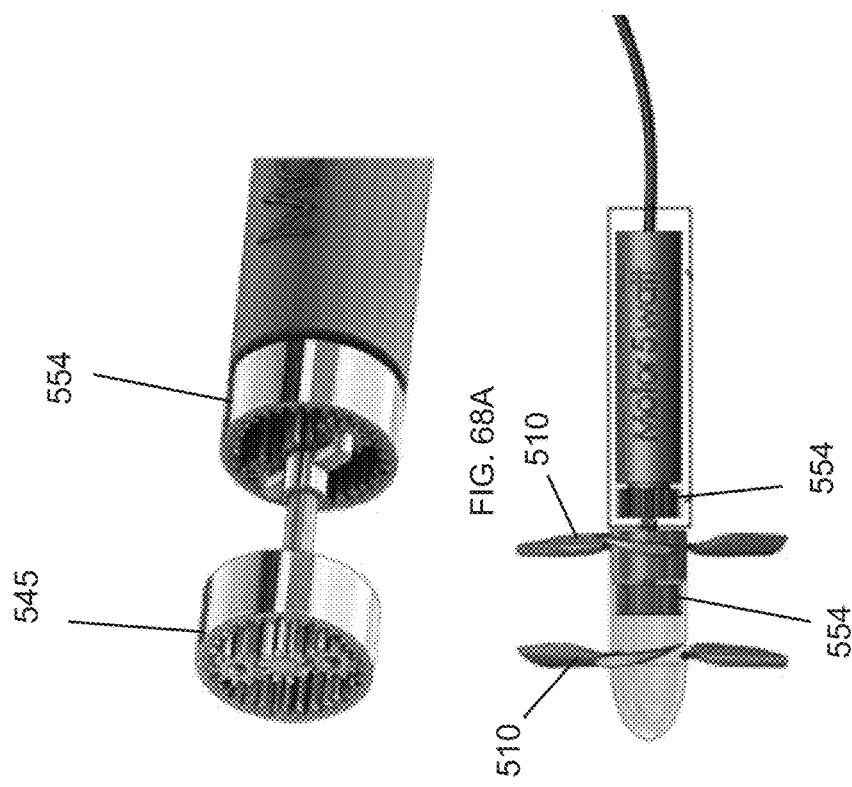

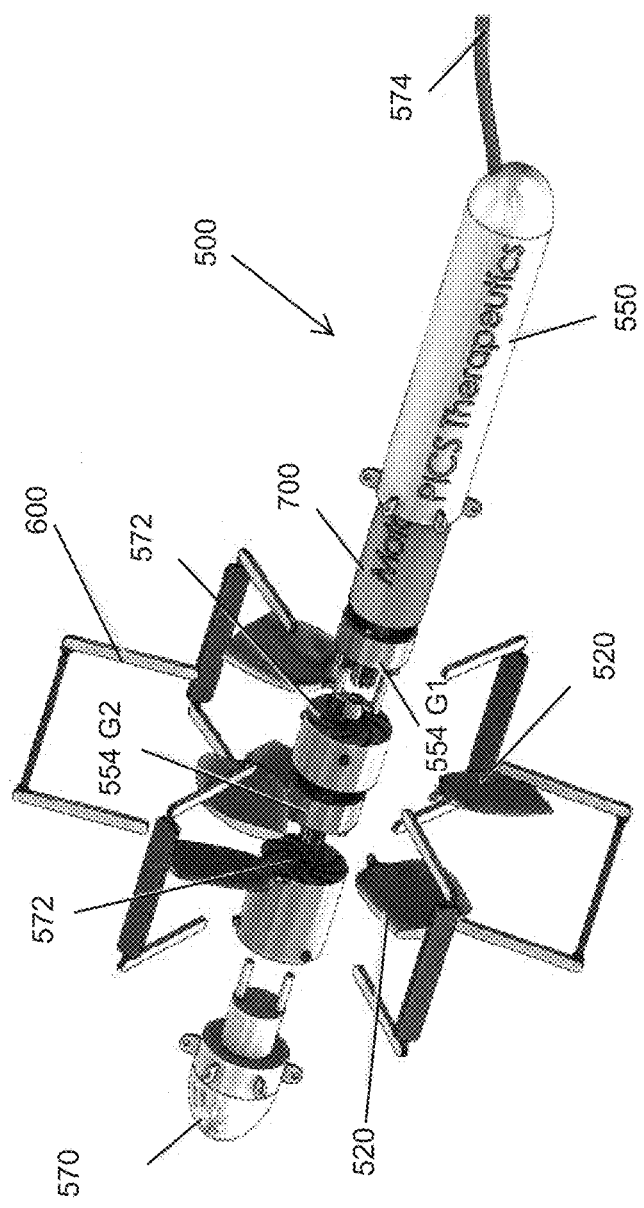
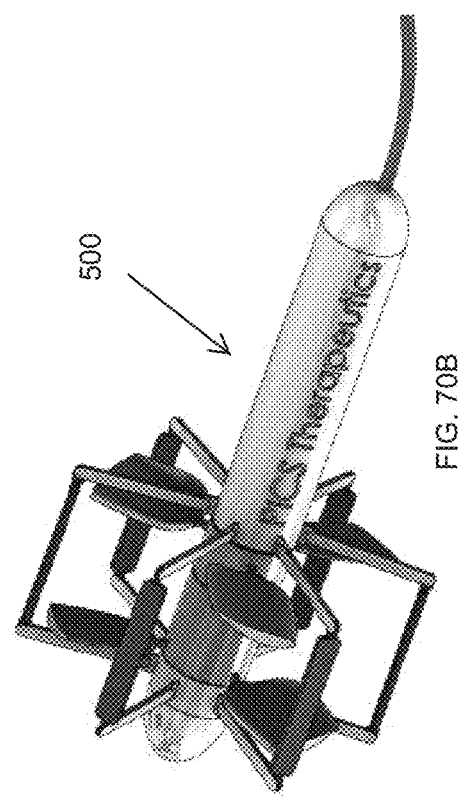
FIG. 70A
FIG. 70B

REMOVABLE MECHANICAL CIRCULATORY SUPPORT FOR SHORT TERM USE

INCORPORATION BY REFERENCE

This application claims priority benefit of U.S. Provisional Patent Application No. 62/652,820 filed Apr. 4, 2018, and U.S. Provisional Patent Application No. 62/680,954, filed Jun. 5, 2018, each of which is incorporated herein by reference in its entirety for all purposes. Any and all applications related thereto by way of priority thereto or therefrom are hereby incorporated by reference in their entirety.

BACKGROUND

The present invention relates to a mechanical circulatory support (MCS), otherwise known as a mechanical circulatory support device (MCSD), for assisting or replacing native heart function in cases of congestive heart failure (CHF). The present invention also relates to percutaneously implantable cardiovascular support (PICS) and percutaneously implantable temporary mechanical circulatory support device (TAD).

Patients with CHF usually have a low cardiac output state as the native heart functions (pumps) poorly. This in turn leads to poor organ perfusion and the symptoms of heart failure including fatigue, breathlessness and feeling generally unwell. In heart failure the kidneys also suffer with poor perfusion and their function often deteriorates considerably (a condition called "the cardio-renal syndrome"). Poor kidney function means that patients feel more unwell, and important drugs have to be withdrawn as they can further adversely affect kidney function.

CHF is common and is a significant health care burden. It is graded from stage I-IV in severity. Once diagnosed a patient has 4-5 years of progression from stage I to IV and death. Stage IV patients are breathless at rest, candidates for heart transplantation, and medication is considered palliative. Congestive heart failure (CHF) is the main cause of mortality for men and women alike in the western world, affecting about 2% of the population. In the USA alone there are 5.7 million patients suffering from CHF and costs to treat this exceed $37.2 billion/year. In the Western world current supply of donor hearts only meets about 12% of demand. This percentage is higher than the actual number because most potential recipients are not included in the calculation; they are considered not suitable for a transplant because of co-morbidities or lack of a matched donor. This shortfall has resulted in the development of MCS devices as a transplant alternative. MCS devices are expensive and require invasive cardiac surgery (sternotomy or thoracotomy). Implantation carries a significant risk. Not all candidates are suitable for MCS because of co-morbidities.

Most permanent MCS devices assist the ventricle and are attached to it in use. These are called Ventricular Assist Devices (VADs), and are designed to drive a flow of blood that is in parallel with flow within the native heart, between the ventricle and the aorta. In other words, they are designed as left (or right) ventricular assist devices (LVADs or RVADs), pumping devices that directly unload the respective ventricle. Such "in-parallel" configurations involve the device and heart sharing, and therefore competing, for inlet flow, which can disrupt normal functioning of the heart. Regeneration of heart muscle may be impeded and the heart is not able to pump to its best capacity. The inlet of most of these VADs is anastomosed to the apex of the left ventricle of the heart, and therefore their installation requires major sternotomy or thoracotomy and cardiopulmonary bypass (CPB), i.e. stopping of the heart during a prolonged surgical operation, for permanent installation. Survival rates of patients on VADs have been poor.

Due to inefficiencies, existing MCS/VAD devices typically require significantly more input power than is necessary from a theoretical point of view purely to impart the desired momentum to the blood. The excess power is used to overcome the losses. The portion of the power that is used to overcome flow losses is imparted as unnecessary damage to the blood, leading to increased levels of haemolysis and/or thrombus formation that would be avoided with devices having higher fluid dynamic efficiency.

VADs entered clinical use as displacement (or pulsatile flow) devices, which mimic the native left ventricle by providing pulsatile flow taking over the function of the patient's own left ventricle. Most widely used displacement, pulsatile, devices have been extracorporeal devices such as the BVS® 5000 VAD of Abiomed, Inc. (Danvers, Mass., USA) and the Thoratec VAD of Thoratec Corporation (Pleasanton, Calif., USA), and intracorporeal devices such as the Novacor® LVA System of WorldHeart, Inc. (Oakland, Calif., USA), the HeartMate IP and VE/XVE of Thoratec Corporation. Although the large external pneumatic consoles of the first-generation displacement VADs have been replaced by implantable electric systems with a portable controller and power source, the serious problems of device weight (e.g., approximately 1.5 kg for the HeartMate XVE), size, noise, driveline infection and thromboembolism persist. Consequently, newer displacement devices are totally implantable, such as the LionHeart™ VAD of Arrow International, Inc. (Reading, Pa., USA), and the Novacor® LVA System of WorldHeart, Inc. (Oakland, Calif., USA).

Rotary (or continuous flow) devices (second-generation VADs) have been developed to overcome the shortcomings of pulsatile devices. Initial concerns with their pulseless flow are now overcome, provided that the patient's native system still provides some pulsatility, and they have their own relative advantages (e.g., fewer moving parts, lower power required, absence of bioprosthetic valves) and disadvantages (e.g., complex control, high afterload and low preload sensitivity, and haemolysis and thrombosis from unnatural flow patterns). Examples of axial rotary pumps (which operate at 10,000-20,000 rpm) are the DeBakey VAD® of MicroMed Cardiovascular, Inc. (Houston, Tex., USA), the FlowMaker® of Jarvik Heart, Inc. (New York, N.Y., USA), formerly known as Jarvik 2000, the HeartMate II of Thoratec Corporation (Pleasanton, Calif., USA), and the Impella Recover® system of Impella CardioSystems AG (Aachen, Germany) intended for short-term circulatory support for up to seven days. These existing devices attempt to provide total flow and pressure capacity, forcing the pump to operate in inefficient flow regimes.

Centrifugal or radial flow blood pumps are generally somewhat larger than axial flow devices and provide non-pulsatile flow, but the rotational speeds are generally much slower (2,000-10,000 rpm) than axial flow blood pumps. While axial flow blood pumps are the smallest VAD, they are higher speed lower pressure rise devices, while centrifugal VADs are better suited to take over heart function and to provide total pressure rise and flow (about 120 mmHg and 5 L/min). Examples are the Gyro C1E3 of Kyocera Corporation (Kyoto, Japan) which evolved into the NEDO PI-601 pump (animal studies).

Third-generation VADs are those that have replaced the mechanical bearings of second generation ones with hydrodynamic or magnetic-suspension bearings. Examples of axial flow VADS are: the INCOR® LVAD of Berlin Heart AG (Berlin, Germany); the MicroVad currently under development at Helmholtz-Institute for Biomedical Engineering (Aachen, Germany); and the MagneVAD I and II of Gold Medical Technologies, Inc. (Valhalla, N.Y., USA). Examples of centrifugal flow VADs are: the HVAD of HeartWare Ltd (Sydney, NSW, Australia); the EVAHEART™ of Evaheart Medical USA, Inc. (Pittsburgh, Pa., USA); the VentrAssist LVAD of Ventracor Ltd (Chatswood, NSW, Australia); the CorAide™ LVAD of Arrow International (Reading, Pa., USA); the DuraHeart of Terumo Heart, Inc. (Ann Arbor, Mich., USA); the HeartQuest VAD of WorldHeart, Inc. (Oakland, Calif., USA); the HeartMate III of Thoratec Corporation (Pleasanton, Calif., USA); and the MiTiHeart™ LVAD of Mohawk Innovative Technology, Inc. (Albany, N.Y., USA). All the above devices require major sternotomy or otherwise invasive surgery and CPB.

Other examples of previous devices can be found in the following patents, each of which is hereby incorporated by reference: U.S. Pat. Nos. 4,625,712; 4,779,614; 4,846,152; 5,267,940; 6,632,169, 6,866,625; 7,238,151; 7,485,104; 8,075,472; 8,371,997; 8,545,380; 8,562,509; 8,585,572; 8,597,170; 8,684,904; 8,690,749; 8,727,959; 8,734,508; 8,814,933; 8,870,552; 8,900,115; 8,961,389; 9,028,392; 9,107,992; 9,138,518; 9,162,018; 9,211,368; 9,295,550; 9,339,597; 9,364,593; 9,370,613; 9,387,285; 9,474,840; 9,555,175; 9,572,915; 9,579,433; 9,597,437; 8,376,707; 2,308,422; 8,814,933; 9,572,915; and 5,749,855.

SUMMARY

It is an object of the invention to provide a device that can be installed with less risk to the patient, which reduces disruption to normal functioning of the heart and/or which minimizes damage to the blood.

According to an aspect of the invention, there is provided a mechanical circulatory support, comprising: a body portion defining an internal lumen; an inlet port in fluid communication with the lumen; an outlet port in fluid communication with the lumen; and a pump for driving fluid flow from the inlet port towards the outlet port, wherein: the inlet port is arranged to provide a connection, or is in a state of connection, into the aorta of a human body.

This arrangement does not require any connections to be made directly to the heart and can be installed using minimally invasive surgery, greatly reducing the risks associated with installation relative to arrangements that need to be connected directly to the heart. There is no need to perform a cardiopulmonary bypass for example. The reduced installation risk makes the device more suitable for treatment of earlier stage CHF than existing MCS/VAD devices, for example early stage IV CHF. In some embodiments, the device may be suitable for treating stage III or stage IV CHF. The device may be particularly suited to treat late stage III CHF or early stage IV CHF.

The outlet port may be connected to a downstream position in the aorta so as to be connected in series with the native heart. This type of connection is less disruptive to the normal functioning of the heart than systems which work in parallel with the heart and may help to promote regeneration of the heart muscle. Additionally or alternatively, by allowing the native heart to pump to its best capacity the additional pumping power required by the support may be reduced.

In an embodiment, the series connection is implemented by connecting the support in parallel with a small section of the descending aorta. In an alternative embodiment, the descending aorta is interrupted so that all of the blood flow passes through the support.

In other embodiments, the outlet port is connected at other positions in the vasculature, for example in the ascending aorta. In an embodiment, the support comprises one outlet port in the descending aorta and one outlet port in the ascending aorta. In this way, a proportion of the outflow is provided to the ascending aorta to support coronary flow more directly. In an embodiment, the inlet port is connected to one or more other strategic locations such as the ascending aorta, and the outlet port(s) connected as previously described into the descending aorta, the ascending aorta, or both. The descending aorta outlet has additional advantages for renal, splanchnic, and other organ perfusion without affecting brain flow.

In an embodiment, the pump is a centrifugal pump. The inventors have discovered that such pumps can provide particularly effective impetus to the circulating blood. In particular, unnecessary blood shear and fluid-dynamic diffusion (the effect of pressure rise as flow decelerates along the device passage) and turbulence can be minimized, which in turn minimizes the imposed shear stress to blood cells, thus minimizing blood cell lysis (haemolysis) and thrombus formation. The improved pumping efficiency reduces power requirements, enabling the power supply to be made smaller and more comfortable to carry. In addition, the pump itself can be made more compact. In an alternative embodiment, the pump is a mixed flow pump (e.g. a pump having characteristics intermediate between a centrifugal pump and an axial pump). In a still further embodiment, the pump is a helical pump. In a still further embodiment, the pump is an axial pump.

In an embodiment, the pump is configured to provide a continuous, rather than pulsatile flow. The inventors have realized that it is not necessary for the pump to mimic the pulsatile flow imparted by the native heart, particularly when installed so as to work in series with the heart. The pump can thus interact more smoothly with the blood flow, further minimizing damage to the blood. Additionally, the efficiency of a continuous pump can be optimized further than a pulsatile pump. Acceleration and deceleration of the blood is reduced, which reduces the stresses that need to be applied to the blood as well as the needed power input to the pump. In alternative embodiments the pump is configured to provide a pulsatile flow (synchronous or asynchronous or different fixed phase or variable phase with the heart).

In an embodiment, the support comprises a power receiving member that is configured to receive power for driving the pump transcutaneously, for example by electromagnetic induction. Alternatively or additionally, power can be supplied percutaneously.

According to an aspect of the invention, there is provided a mechanical circulatory support, comprising: a pump configured to be installed, or in a state of installation, in a human body and configured to operate in series with the native heart; and a device for electromagnetically driving the pump that is configured to be mounted to the body. Thus, a support is provided that is suitable for "permanent" installation (e.g. so that the patient can leave the hospital with the support installed and operational) and which provides a pumping action that is in series, rather than in parallel, with the native heart.

MCSs which generate full physiological pressure rises (about 120 mmHg), such as VADs in-parallel with the heart, may impart tremendous damage to the blood (e.g., haemolysis), especially in later stages of CHF. MCSs which are installed in-series with the heart (i.e. the left ventricle) may exploit the existing pressure rise of the native heart and provide an additive pressure rise. Disclosed herein are embodiments of MCSs configured for in-series installation in the aorta, particularly the descending aorta. Installation within the descending aorta advantageously is conducive to installation via minimally invasive surgery (e.g., percutaneous installation or thoracoscopy), which produces better outcomes (e.g., reduced morbidity) and shorter recovery periods for patients, especially those suffering CHF. Additionally, minimally invasive surgical procedures may generally be performed at district hospitals by vascular surgeons, unlike the sternoscopy procedures that are generally necessary for installation of VADs, which usually must be performed by cardiothoracic surgeons in critical care units. Installation within the descending aorta is further advantageous because the MCS intercept location is downstream of the cerebral blood flow, fed by the carotid arteries, reducing the risk of cerebral thromboembolism or stroke. Any blood damaged by an MCS installed in the descending aorta is pumped to the renal inflow arteries and remaining systemic and pulmonary perfusion system prior to reaching the cerebral blood flow. MCSs which are installed in the descending aorta must be careful not to establish such a large pressure rise that upstream blood perfusion to the cerebral blood flow is not suppressed, or stolen, by the suction of the MCS.

MCSs may be designed with operating conditions specifically configured for particular stages of CHF. For instance, a MCS designed for late stage II or early stage III CHF may provide a 20-50 mmHg pressure rise, while a MCS designed for late stage III or early stage IV CHF may provide a 40-80 mmHg pressure rise, to better supplant the failing heart. The reduced pressure requirements of MCSs that are installed in-series with the heart may effectively reduce the load on the heart (afterload reduction) by lowering the resistance to blood flow, which can advantageously provide the heart increased potential for regeneration of diseased tissue. MCSs with less than full physiological pressure rises generally will require less power and will be smaller and lighter weight than MCSs such as VADs which generate larger pressure rises. MCSs installed in series may be configured to maintain the physiological flow rate of a healthy individual of about 5 L/min. The MCSs may pump blood at a continuous flow, while the native heart may maintain pulsatility in total perfusion. In alternative embodiments, the MCS may provide a pulsatile flow. Such pulsatile flow may be established, for example, by axially oscillating the impeller within the MCS casing.

Turbomachines operate efficiently over only a very narrow regime of pressure rise, flow rate and rotational speed specifications, all of which translate into a narrow regime of optimal angles of attack (angle of incoming flow) to turbomachinery airfoils. Therefore, a turbomachine configured, for example, to generate a 120 mmHg pressure rise, such as a VAD designed for in-parallel implantation with the left ventricle, will operate substantially less efficient if instead installed in the descending aorta and operated at a much lower pressure differential (e.g., 70 mm Hg). For instance, operating a turbomachine below its configured pressure differential will: operate at a much different than as-designed pressure rise, flow rate, and rotational speed; operate away from the as-designed optimal condition for angles of attack to turbomachine blades; will not work efficiently; and will create unnecessary blood shear, turbulence, stall and losses. These deviations from optimal as-designed operating conditions will increase blood trauma and reduce device efficiency and efficacy for use in this location.

Disclosed herein are embodiments of MCS devices and systems along with methods of installing and/or using MCS devices to treat CHF. In various embodiments, the MCS is a centrifugal pump, comprising an impeller suspended in a casing, an inlet introducing blood flow from the native vasculature to the impeller in an axial direction, and a diffuser with an entrance positioned along the circumference of the impeller and an outlet returning blood flow to the native vasculature. The impeller may be magnetically suspended in a contactless manner within the casing and rotated using an electromagnetic motor. An external controller implanted within the body may provide power to the MCS and control the electrical operations. The MCS may be powered by internal and/or external batteries. The internal batteries may be recharged and/or power may be delivered from external batteries through transcutaneous or percutaneous energy transfer systems. In various embodiments, the MCS is specifically suited for late stage III and/or early stage IV CHF and generates pressures rises between about 40 to about 80 mmHg and maintains a flow rate of approximately 5 L/min.

In some embodiments, a mechanical circulatory support for assisting the heart support comprises a casing comprising a main body, an inlet configured to introduce blood flow from an upstream portion of a human aorta into the main body, and an outlet configured to return the blood flow from the main body to a downstream portion of the human aorta. The support further comprises an impeller positioned within an internal volume of the main body of the casing so as to receive blood flow from the inlet, the direction of the received blood flow defining a longitudinal axis, wherein the impeller comprises a plurality of blades for pumping blood, the blades being arranged around the longitudinal axis so as to define an outer circumference. The impeller is configured to rotate around the longitudinal axis to pump the blood in a centrifugal manner toward the outer circumference. The support further comprises a diffuser integral with or joined to the casing, the diffuser configured to receive blood outflow from the impeller and direct the blood flow to the outlet. The diffuser is at least partially open to the internal volume of the main body of the casing along at least a portion of the outer circumference of the impeller.

The impeller may be a shrouded impeller. The shrouded impeller may comprise a blade passage chamber, an upper portion forming a ceiling to the blade passage chamber, and a lower portion forming a floor to the blade passage chamber. The upper portion may have an upper channel extending along the longitudinal axis from a top of the impeller to the blade passage chamber. The lower portion may have a lower channel extending along the longitudinal axis from the bottom of the impeller to the blade passage chamber. The blades may extend from an inner circumference around the longitudinal axis to the outer circumference, the blades extending axially between the floor and the ceiling of the blade passage chamber to join the upper portion and the lower portion together.

The casing may further comprise a projection extending from the bottom of the casing into the lower channel. The casing may be configured to allow blood to flow from the outer circumference of the blades along secondary flow paths between an internal surface of the casing and the lower portion of the impeller, and between the projection and an internal surface of the lower channel back to the blade passage chamber so as to prevent blood stagnation.

The impeller may be an unshrouded impeller.

The impeller may be magnetically suspended in an axial direction within the casing by a combination of axial-suspension permanent magnets coupled to a top half and a bottom half of the casing and permanent magnets coupled to a top half and a bottom half of the impeller. The axial-suspension permanent magnets coupled to the top half of the casing may be axially spaced apart from the permanent magnets coupled to the top half of the impeller. The axial-suspension permanent magnets coupled to the bottom half of the casing may be axially spaced apart from the permanent magnets coupled to the bottom half of the impeller. The impeller may be magnetically suspended in a radial direction within the casing by a radial-suspension permanent magnet coupled to the casing near the permanent magnet in the top half of the impeller and by a radial-suspension permanent magnet coupled to the casing near the permanent magnet in the bottom half of the impeller.

The impeller may be configured to be radially stabilized by an eccentric hydrodynamic journal bearing force between the impeller and the casing.

The impeller may be configured to be radially stabilized by at least two electromagnets positioned on opposite sides of each of the radial suspension permanent magnets, wherein the force of each of the electromagnets is driven according to impeller positioning information attained from eddy current sensors coupled to the casing.

At least one of the electromagnets coupled to the upper half of the casing may be axially displaced from the permanent magnet coupled to the upper half of the impeller and at least one of the electromagnets coupled to the lower half of the casing may be axially displaced from the permanent magnet coupled to the lower half of the impeller. The position of the impeller may be configured to be oscillated in the axial direction to create a pulsatile flow by pulsatile phases of current applied to the electromagnets.

The support may further comprise a motor for electromagnetically rotating the impeller around the axial direction. The motor may comprise a stator within the casing comprising a plurality of electromagnets and a rotor within the impeller comprising a plurality of permanent drive magnets, the rotor configured to be positioned concentrically within the stator.

The support may be configured to create a vortex in an outflow of blood exiting the outlet to emulate the naturally-occurring vortex in the native aorta of a healthy human heart.

The support may be configured to create a pressure rise in the introduced blood flow between about 40 mmHg and about 80 mmHg. The support may be configured to maintain a blood flow rate of about 5 L/min.

The support may be configured to be installed in-series with a portion of the descending aorta of a human aorta.

The inlet may be configured to redirect the blood flow 90 degrees before it enters the main body, such that the inlet and the outlet are parallel with each other.

The blood flow may be redirected toward an axial direction prior to reaching the outlet, such that the outlet is substantially collinear with the inlet.

The diffuser may wrap around the casing in a spiral configuration to facilitate the formation of a vortex in the outflow which emulates the naturally-occurring vortex in the native aorta of a healthy human heart.

The support may further comprise a splitter vane positioned within at least a portion of the diffuser which rotates with respect to a circumference of the diffuser to facilitate the formation of a vortex in the outflow which emulates the naturally-occurring vortex in the native aorta of a healthy human heart.

The support may further comprise a splitter vane positioned within at least a portion of a volute of the outlet which rotates with respect to a circumference of the volute to facilitate the formation of a vortex in the outflow which emulates the naturally-occurring vortex in the native aorta of a healthy human heart.

The support may further comprise a plurality of diffuser vanes positioned circumferentially around the outer circumference defined by the impeller.

The support may further comprise a plurality of stationary pre-swirl vanes positioned within in inlet.

A portion of a surface of the internal volume of the main body of the casing and/or a portion of an outer surface of the impeller may comprise spiraling grooves configured to facilitate secondary flow paths of blood between the impeller and the casing.

In some embodiments, a method of treating congestive heart failure in a patient comprises installing a mechanical circulation support within the descending aorta of the patient. The mechanical circulation support comprises a centrifugal blood pump configured to provide a pressure rise between about 40 mmHg and about 80 mmHg in the blood flow and to maintain a flow rate of about 5 L/min.

The support may be installed in series with the descending aorta. The method may further comprise severing the aorta into upper and lower portions, wherein the installing comprises grafting the upper portion to an inlet of the support and grafting the lower portion to an outlet of the support The support may be installed in parallel with the descending aorta. The method may further comprise installing a one-way valve in the native aorta in parallel with the support, such that blood cannot flow upstream through the native aorta to recirculate through the support.

The support may be installed such that both an inlet to the support and an outlet from the support are oriented at a non-linear angle to the native aorta.

The support may be installed such that both an inlet to the support and an outlet from the support are oriented to be substantially collinear with the native aorta.

The support may be installed such that both an inlet to the support and an outlet from the support are oriented to be parallel with the native aorta.

The patient may have stage III or stage IV congestive heart failure.

The patient may have late stage III or early stage IV congestive heart failure.

In various embodiments, the MCS device comprises one or more propellers which are configured to be installed within the lumen of a blood vessel, such as the descending aorta. The one or more propellers may be anchored within the lumen by an anchoring mechanism which surrounds the one or more propellers. In some embodiments, the one or more propellers may be driven by one or more motors which may be extra-corporeal or intravascular. In some embodiments, at least some of the propeller blades may be magnetic and the one or more propellers may be driven by a stator comprising electromagnets, the stator being positioned concentrically around the propeller blades. The stator may be configured to be placed intravascularly or may be placed around the outside of the blood vessel. The MCS device may include one or more pairs of contra-rotating impellers for modulating the tangential velocity component of the blood flow. The MCS device may include pre-swirler and/or de-swirler vanes coupled to the propeller or the anchoring mechanism. The blades of the one or more propellers may be foldable and the anchoring mechanism collapsible so that they may be delivered percutaneously via a catheter. A controller implanted within the body or positioned outside the body may provide power to the MCS device and control the electrical operations. In some embodiments, the MCS device may be powered by internal and/or external batteries. The internal batteries may be recharged and/or power may be delivered from external batteries through transcutaneous or percutaneous energy transfer systems. In various embodiments, the MCS device is specifically suited for late stage II and/or early stage III CHF and generates pressures rises between about 20 to about 50 mmHg and maintains a flow rate of approximately 5 L/min.

In some embodiments, a mechanical circulatory support for assisting the heart comprises at least one propeller. The at least one propeller comprises a plurality of blades arranged around an axis of rotation, the blades being configured to pump blood in a substantially axial direction parallel to the axis of rotation. In some embodiments, at least one of the plurality of blades is magnetic. The support further comprises a shaft aligned along the axis of rotation of the at least one propeller. The support further comprises an anchoring mechanism configured to anchor the at least one propeller within a lumen of a blood vessel. The anchoring mechanism comprises a proximal hub coupled to a proximal end of the shaft; a distal hub coupled to a distal end of the shaft; a collapsed configuration for installing the anchoring mechanism in the blood vessel; and an expanded configuration wherein at least a portion of the anchoring mechanism is configured to be pressed against a wall of the lumen of the blood vessel. The support further comprises at least one ring-shaped stator. The at least one stator comprises one or more electromagnets positioned around the circumference of the stator. The at least one stator is configured to be positioned concentrically around the blades of the at least one propeller to electromagnetically drive rotation of the at least one magnetic blade.

All of the blades of the at least one propeller may be configured to be foldable substantially along the shaft such that in the collapsed configuration of the anchoring mechanism the blades are in a folded position. The collapsed configuration may be configured for percutaneously installing the anchoring mechanism in the blood vessel through a catheter.

The at least one propeller may comprise a pair of contra-rotating propellers configured to rotate in opposite directions.

The support may further comprise a plurality of stationary de-swirler vanes coupled to either the shaft or the anchoring mechanism. The de-swirler vanes may be positioned downstream of the at least one propeller and may be configured to remove or reduce a tangential velocity component of blood flow as it leaves the support.

The support may further comprise a plurality of stationary pre-swirler vanes coupled to either the shaft or the anchoring mechanism. The pre-swirler vanes may be positioned upstream of the at least one propeller and may be configured to increase a tangential velocity component of blood flow entering the support.

The at least one stator may be configured to be positioned around an outer circumference of the blood vessel.

The at least one stator may comprise a hinge configured to allow the stator to open and close. The stator may have a circumference and may be configured to open along the circumference for positioning the stator around the blood vessel and to close for securing the stator around the outer circumference of the blood vessel.

The at least one stator may be configured to be positioned along an inner circumference of the lumen of the blood vessel.

The at least one stator may comprise a collapsed configuration for percutaneous delivery via a catheter and an expanded configuration.

The at least one stator may be coupled to or integral with the anchoring mechanism.

The at least one stator may comprise first and second discrete ring-shaped components. The first and second discrete ring-shaped components may each comprise circumferentially offset electromagnets, wherein the electromagnets of the second discrete ring-shaped component are configured to be positioned circumferentially between the electromagnets of the first discrete-ring shaped component.

The at least one propeller may comprise a plurality of propellers configured to rotate together.

At least one propeller may not comprise any magnetic blades.

All the blades of all the propellers may be magnetic.

A radial tip of at least one blade from each propeller may be connected via a magnetic connector extending substantially along an outer diameter of the plurality of propellers.

The at least one ring-shaped stator may comprise a plurality of ring shaped stators, each stator being axially aligned with one of the plurality of propellers.

The at least one magnetic blade may comprise a magnet positioned within or coupled to a radial tip of the blade.

The at least one magnetic blade may comprise a magnetic winglet coupled to the radial tip of the blade.

The at least one magnetic blade may comprise a magnetic ring coupled to the radial tip of the blade. The magnetic ring may join a plurality of blades of the at least one propeller.

The at least one magnetic blade may be formed from a magnetic material.

The support may further comprise a ferrous ring configured to be placed in the blood vessel between the propellers and the blood vessel wall.

The at least one propeller may be configured to rotate around the shaft. A bearing may be positioned between the shaft and the at least one propeller.

The shaft may be configured to rotate with the at least one propeller. A bearing may be positioned between the shaft and the proximal hub and a bearing may be positioned between the shaft and the distal hub.

The blades may be deformable so as to be foldable toward the shaft.

The support may comprise a partially disassembled configuration and a fully assembled configuration. The propeller may comprise a channel for receiving the shaft. The distal hub may comprise a first mechanical feature for coupling to a second mechanical feature on the shaft. The shaft may be fixedly coupled to the proximal hub. The shaft, proximal hub, and distal hub may not be rigidly secured together in the partially disassembled configuration. A tensioning line may connect the shaft and the distal hub in the partially disassembled configuration. The tensioning line may extend through the propeller channel. Applying tension to the tensioning line may place the support in the fully assembled configuration. In the fully assembled configuration, the shaft may extend through the propeller channel and the first mechanical feature and the second mechanical feature may be coupled together rigidly securing the shaft, proximal hub, and distal hub together. The plurality of blades may be configured to extend in a substantially perpendicular direction to the shaft in the assembled configuration.

The at least one propeller may comprise two blades. The blades may be foldable along the shaft in opposite directions.

The proximal hub may be adjustably displaceable along the shaft such that the proximal hub can be moved closer to the distal hub to place the anchoring mechanism in an expanded configuration and/or the proximal hub can be moved further from the distal hub to place the anchoring mechanism in a collapsed configuration.

The anchoring mechanism may comprise a proximal half and a distal half. The proximal half of the anchoring mechanism may be separate or separable from the distal half of the anchoring mechanism. The shaft may comprise a proximal half and a distal half. The proximal half of the shaft may be separable from and attachable to the distal half of the shaft.

The shaft may comprise a plurality of joints dividing the shaft into at least three foldable portions. The shaft may be in a straightened configuration when the foldable portions are aligned along the axis of rotation and the shaft may be in a folded configuration when the foldable portions are folded. The at least one propeller may be coupled to a foldable portion positioned between the most proximal fordable portion and the most distal foldable portion of the shaft such that the plurality of blades of the at least one propeller may be aligned substantially parallel to the most proximal foldable portion and the most distal foldable portion in the folded configuration.

The shaft may comprise two joints configured to allow the shaft to assume a z-shape configuration in the folded configuration.

The shaft may comprise four joints configured to allow the shaft to assume a c-shape configuration in the folded configuration.

The support may further comprise a securing shaft configured to be inserted through an internal lumen of the shaft to lock the shaft into a straightened configuration.

The anchoring mechanism may comprise a plurality of leaflet springs coupled to the propeller. The leaflet springs may be configured to extend in a radially outward direction from the propeller to contact the blood vessel wall and anchor the propeller within the blood vessel. The leaflet springs may comprise a deformed configuration configured to allow the anchoring mechanism to be compressed for percutaneous delivery via a catheter.

The anchoring mechanism may be configured to be installed in the descending aorta. The support may be configured to provide a pressure rise between about 20 mmHg and about 50 mmHg in the blood flow and to maintain a flow rate of about 5 L/min.

The support may be configured to produce a right handed helical blood flow comprising a vorticity about equal to that of the native descending aorta at an output of the support.

The anchoring mechanism may comprise a plurality of struts extending between the proximal hub and the distal hub. The struts may be bendable or flexible.

In some embodiments, a method of treating congestive heart failure in a patient comprises installing a mechanical circulation support within the lumen of the descending aorta of the patient. The support comprises at least one propeller; a shaft aligned along the axis of rotation of the at least one propeller; an anchoring mechanism; and at least one ring-shaped stator. The at least one propeller comprises a plurality of blades arranged around an axis of rotation. The blades are configured to pump blood in a substantially axial direction parallel to the axis of rotation. In some embodiments, at least one of the plurality of blades is magnetic. The anchoring mechanism is configured to anchor the at least one propeller within the lumen. The anchoring mechanism comprises a proximal hub coupled to a proximal end of the shaft and a distal hub coupled to a distal end of the shaft. The anchoring mechanism further comprises a collapsed configuration for installing the anchoring mechanism in the descending aorta and an expanded configuration wherein at least a portion of the anchoring mechanism is configured to be pressed against a wall of the lumen of the descending aorta. The at least one ring-shaped stator comprises one or more electromagnets positioned around the circumference of the stator. The at least one stator is configured to be positioned concentrically around the blades of the at least one propeller to electromagnetically drive rotation of the at least one magnetic blade.

The support may be configured to provide a pressure rise between about 20 mmHg and about 50 mmHg in the blood flow and to maintain a flow rate of about 5 L/min.

Installing the support may comprise percutaneously installing the rotor and the anchoring mechanism in the lumen through a catheter. The anchoring mechanism may assume the collapsed configuration during delivery. Installing the support may further comprise expanding the anchoring mechanism into an expanded configuration such that the anchoring mechanism anchors the rotor within the lumen.

Installing the support may further comprise percutaneously installing the at least one stator in the lumen through a catheter.

The at least one stator may be coupled to the anchoring mechanism.

The at least one stator may be installed prior to the anchoring mechanism.

The at least one stator may comprise first and second discrete ring-shaped components. The first and second discrete ring-shaped components may each comprise circumferentially offset electromagnets. The installing the at least one stator may comprise installing the first discrete ring-shaped component and subsequently installing the second discrete ring shaped component so that the electromagnets of the second discrete ring-shaped components are positioned circumferentially between the electromagnets of the first discrete-ring shaped component.

Installing the support may further comprise surgically installing the at least one stator around an outer circumference of the descending aorta such that the at least one stator is axially aligned with the at least one propeller.

The at least one stator may comprise a hinge allowing the stator to assume an open configuration and a closed configuration. Installing the stator may comprise positioning the stator around the descending aorta in an open configuration and closing the stator.

Installing the support may comprise making a surgical incision in the descending aorta and installing the anchoring mechanism into the lumen through the incision.

The patient may have stage II or stage III congestive heart failure.

The patient may have late stage II or early stage III congestive heart failure.

In some embodiments, a mechanical circulatory support for assisting the heart comprises at least one propeller; a shaft aligned along the axis of rotation of the at least one propeller; an anchoring mechanism; and at least one motor configured to drive rotation of the at least one propeller. The at least one propeller comprises a plurality of blades arranged around an axis of rotation. The blades are configured to pump blood in a substantially axial direction parallel to the axis of rotation. In some embodiments, at least one of the plurality of blades is magnetic. The anchoring mechanism is configured to anchor the at least one propeller within a lumen of a blood vessel. The anchoring mechanism comprises a proximal hub coupled to a proximal end of the shaft and a distal hub coupled to a distal end of the shaft. The anchoring mechanism further comprises a collapsed confguration for installing the anchoring mechanism in the blood vessel and an expanded configuration wherein at least a portion of the anchoring mechanism is configured to be pressed against a wall of the lumen of the blood vessel.

All of the blades of the at least one propeller may be configured to be foldable substantially along the shaft such that in the collapsed configuration of the anchoring mechanism the blades are in a folded position. The collapsed configuration may be configured for percutaneously installing the anchoring mechanism in the blood vessel through a catheter.

The at least one propeller may comprise a pair of contra-rotating propellers configured to rotate in opposite directions.

The support may further comprise a plurality of stationary de-swirler vanes coupled to either the shaft or the anchoring mechanism. The de-swirler vanes may be positioned downstream of the at least one propeller and may be configured to remove or reduce a tangential velocity component of blood flow as it leaves the support.

The support me further comprise a plurality of stationary pre-swirler vanes coupled to either the shaft or the anchoring mechanism. The pre-swirler vanes may be positioned upstream of the at least one propeller and may be configured to increase a tangential velocity component of blood flow entering the support.

The at least one motor may be configured to be extracorporeal. The motor may be configured to drive rotation of the propeller via a driveline percutaneously extending through the body of a patient and connecting the motor to the shaft.

The at least one motor may be configured to be positioned within the lumen of the blood vessel. The motor may be configured to rotate the shaft to drive rotation of the propeller.

The at least one motor may comprise a plurality of motors configured to be positioned within the lumen and the at least one propeller may comprise a plurality of propellers. Each motor may be configured to drive rotation of one of the plurality of propellers.

The at least one propeller may comprise a pair of contra-rotating propellers which are mechanically connected. The at least one motor may comprise a single motor configured to drive the pair of contra-rotating propellers in opposite directions.

In some embodiments, a temporary, removable mechanical circulatory support heart-assist device comprises at least two propellers or impellers, each propeller or impeller comprising a plurality of blades arranged around an axis of rotation, the blades being configured to pump blood, wherein two propellers or impellers of the at least two propellers or impellers rotate in opposite directions.

In some embodiments, the device may be configured to be implanted and removed with minimally invasive surgery. In some embodiments, the device may include an electric device configured to deliver power to motors, wherein the electric device is configured to be intra-corporeal and placed near the at least two propellers or impellers. In some embodiments, at least two propellers or impellers are configured to be placed in the vasculature to assist with perfusion. In some embodiments, the at least two propellers or impellers are configured to hold a heart valve in an open position to assist with perfusion. In some embodiments, the device may include a first gearbox placed between a motor and a downstream propeller or impeller of the at least two propellers or impellers, and a second gearbox between the upstream and downstream propeller or impeller of the at least two propellers or impellers. In some embodiments, diameters of the gears in the first and second gearboxes are configured to achieve equal rpm between the at least two propellers or impellers. In some embodiments, diameters of the gears in the first and second gearboxes are configured to achieve different rpm between the at least two propellers or impellers. In some embodiments, the blades are flexible. In some embodiments, the blades are foldable. In some embodiments, the blades are placed in a surrounding cage. In some embodiments, the cage and blades are configured to be folded and inserted in the blood vessel. In some embodiments, the device may include a balloon, wherein the balloon is configured to expand to fill the difference between minimum and maximum aorta sizes. In some embodiments, the device may include two motors, wherein the two motors are arranged back-to-back, wherein the two motors are connected to two propellers or impellers of the at least two propellers or impellers rotating in opposite directions. In some embodiments, the device may include a lubrication channel, where the lubricant is biocompatible and dispersed in the body. In some embodiments, the device may include one rotor and first and second stators, wherein a first stator is configured to be located upstream and a second stator is configured to be located downstream. In some embodiments, the device may include a gearbox comprising two concentric output shafts driving two propellers or impellers of the at least two propellers or impellers in opposite directions, and one input shaft connected via a flexible shaft to an electric motor or gearmotor. In some embodiments, the electric motor or gearmotor is intracorporeal. In some embodiments, the electric motor or gearmotor is extracorporeal. In some embodiments, an upstream propeller or impeller of the at least two propellers or impellers is driven by an epicyclic-type gearbox, a downstream propeller or impeller of the at least two propellers or impellers is driven in the opposite direction to the upstream impeller or propeller by a second epicyclic-type gearbox. In some embodiments, the suns of both epicyclic gearboxes are driven by sun gears connected via an input shaft to an electric motor. In some embodiments, the electric motor or gearmotor is intracorporeal. In some embodiments, the electric motor or gearmotor is extracorporeal. In some embodiments, the blades of the two propellers or impellers of the at least two propellers or impellers rotating in opposite directions comprise flexible connections to impeller hubs to accommodate insertion and removal with folded blades, and operation with unfolded blades. In some embodiments, the blades of the two propellers or impellers of the at least two propellers or impellers rotating in opposite directions comprise mechanical connections to the impeller hubs to accommodate insertion and removal with folded blades in a catheter, and operation with unfolded blades. In some embodiments, the mechanical folding mechanism for the blades variably folds open. In some embodiments, the inlet to the pump is configured to be anastomosed to a chamber of the heart, and the outlet of the pump is configured to be anastomosed to the vascular system. In some embodiments, the device may include an anchoring mechanism, the anchoring mechanism being configured to anchor the at least one propeller within a lumen of a blood vessel. In some embodiments, the anchoring mechanism comprises a collapsed configuration for installing the anchoring mechanism in the blood vessel and an expanded configuration wherein at least a portion of the anchoring mechanism is configured to be pressed against a wall of the lumen of the blood vessel. In some embodiments, the anchoring mechanism comprises 3D struts. In some embodiments, the anchoring mechanism comprises a balloon. In some embodiments, the device consists of two propellers. In some embodiments, the device may include a pre-swirler configured to increase a tangential velocity component of blood flow entering the support. In some embodiments, the device may include a de-swirler. In some embodiments, the device may include at least one stator. In some embodiments, the at least two propellers or impellers comprises a plurality of propellers configured to rotate together. In some embodiments, at least two propellers or impellers comprises a plurality of propellers configured to rotate independently. In some embodiments, the plurality of blades of a propeller or an impeller of the at least two propellers or impellers has a fixed open diameter. In some embodiments, the plurality of blades of a propeller or an impeller of the at least two propellers or impellers has a variable open diameter. In some embodiments, the propeller of the at least two propellers or impellers and a motor comprise a magnetic coupling. In some embodiments, the device may include one or more lubrication channels. In some embodiments, the device may include an articulated sleeve for insertion. In some embodiments, the device may include a motor configured to be placed within the body of the patient. In some embodiments, the device may include a motor configured to be placed outside the body of the patient. In some embodiments, the device may include at least one gearbox reducing shaft speed. In some embodiments, the device may include at least one gearbox providing contra-rotation. In some embodiments, the device may include at least one planetary gearbox.

In some embodiments, a method of treating congestive heart failure in a patient, the method comprises installing a mechanical circulation support within the lumen of the descending aorta of the patient, wherein the mechanical circulation heart-assist device comprises at least two propellers or impellers, each propeller or impeller comprising a plurality of blades arranged around an axis of rotation, the blades being configured to pump blood, wherein two propellers or impellers of the at least two propellers or impellers rotate in opposite directions.

In some embodiments, the device is configured to provide a pressure rise between about 20 mmHg and about 40 mmHg in the blood flow and to maintain a flow rate of about 5 L/min. In some embodiments, installing the device comprises inflating a balloon. In some embodiments, installing the device comprises expanding one or more struts. In some embodiments, the method can include expanding a pre-swirler or de-swirler. In some embodiments, the method can include expanding the plurality of blades to a fixed diameter. In some embodiments, the method can include expanding the plurality of blades to a variable diameter. In some embodiments, the device is implanted and removed with minimally invasive surgery. In some embodiments, the at least two propellers or impellers assist with perfusion. In some embodiments, the at least two propellers or impellers hold a heart valve in an open position to assist with perfusion. In some embodiments, the method can include a first gearbox placed between a motor and a downstream propeller or impeller of the at least two propellers or impellers to provide contra-rotation of the at least two propellers or impellers. In some embodiments, the at least two propellers or impellers rotate at equal rpm. In some embodiments, the at least two propellers or impellers rotate at different rpm. In some embodiments, the method can include folding the blades for insertion. In some embodiments, the method can include expanding a balloon to fill the difference between minimum and maximum aorta sizes. In some embodiments, the method can include at least one intracorporeal motor. In some embodiments, the method can include at least one extracorporeal motor. In some embodiments, the method can include pumping a biocompatible lubricant through at least a portion of the device.

BRIEF DESCRIPTION OF THE DRAWINGS

Embodiments of the invention will now be described, by way of example only, with reference to the accompanying drawings in which corresponding reference symbols indicate corresponding parts, and in which:

FIG. 5A illustrates a perspective view of an MCS. FIG. 5B depicts a photograph of an MCS prototype. FIG. 5C illustrates a side cross-sectional view of the MCS. FIG. 5D schematically illustrates a simplified side-cross-section of the MCS 100 along with example dimensions (in mm) of various components and spacing.

FIGS. 6A-6E illustrate an example of an impeller. FIG. 6A illustrates a perspective view of an example of an impeller configured to be used with an MCS. FIG. 6B illustrates a side cross section of the impeller. FIG. 6C illustrates a top cross section of the impeller. FIG. 6D illustrates a perspective view of an impeller assembly including a top cap and a bottom cap. FIG. 6E illustrates an exploded view of the impeller assembly in FIG. 6D.

FIGS. 7A-7D illustrate perspective views of further examples of impellers. FIG. 7A illustrates an example of a shrouded impeller. FIG. 7B illustrates another example of a shrouded impeller. FIG. 7C illustrates an example of an unshrouded impeller. FIG. 7D illustrates another example of an unshrouded impeller.

FIGS. 8A-8E illustrate examples of an MCS casing. FIG. 8A illustrates an exploded view of an example of an MCS casing. FIG. 8B illustrates a bottom view of the casing upper volute shown in FIG. 8A. FIG. 8C illustrates a perspective view of the casing lower volute shown in FIG. 8A. FIG. 8D illustrates a perspective view of another example of an MCS casing. FIG. 8E illustrates an exploded view of an example of an MCS impeller with inner and outer casings.

FIG. 10A illustrates an example of the relative positioning of axial-suspension magnets. FIG. 10B illustrates an example of an upper axial magnet holder. FIG. 10C illustrates an example of a lower axial magnet holder. FIG. 10D schematically illustrates the adjustability of the axial magnet holders relative to the ring magnets positioned on an MCS impeller.

FIGS. 11A-11E illustrate example components of an MCS magnetic radial suspension system. FIG. 11A illustrates an example of the relative positioning of radial suspension magnets and eddy current sensors. FIG. 11B illustrates an example of a top radial magnet holder. FIG. 11C illustrates an example of a bottom radial magnet holder. FIG. 11D illustrates an example of the upper radial suspension components seated on an MCS casing lid. FIG. 11E illustrates an example of the lower radial suspension components seated on an MCS casing lower volute.

FIG. 12A illustrates stabilization using a passive magnet and hydrodynamic journal bearing force. FIG. 12B illustrates stabilization using passive and active magnets.

FIG. 13A schematically illustrates a block diagram depicting the electrical operation of an electromagnetic stabilization system. FIG. 13B schematically illustrates an example of a circuit that may be used according to the flow chart depicted in FIG. 13A to operate the electromagnetic stabilization system.

FIG. 14A illustrates a top view of the rotor. FIG. 14B illustrates a perspective view of the rotor installed within the impeller of an MCS.

FIG. 15A illustrates a top view of the stator. FIG. 15B illustrates the positioning of the stator around an impeller as well as the relative positioning of the lower axial and radial suspension components.

FIG. 16A schematically illustrates an example of a transcutaneous energy transfer system. FIG. 16B schematically illustrates an example of a percutaneous energy transfer system. FIG. 16C schematically illustrates an example of motor driving circuit. FIG. 16D schematically illustrates an example of a battery charging circuit. FIG. 16E schematically illustrates an example of a power conditioning circuit. FIG. 16F depicts computational results of haemolysis simulations relative to other devices.

FIG. 18A shows an MCS installed using straight grafts. FIG. 18B shows an MCS installed using two curved grafts.

FIGS. 21A-21D schematically depicts simulated blood flow through various MCS configurations. FIG. 21A illustrates a MCS installed in an angled configuration with approximately 45 degree inlet and outlet angles relative to the aorta. FIG. 21B shows a MCS installed in an angled configuration with an approximately 65 degree inlet angle and an approximately 25 degree outlet angle relative to the aorta. FIGS. 21C and 21D show coaxial MCSs with 25 mm and 15 mm inlet radii, respectively, or MCSs installed in angled configurations with an approximately 90 degree inlet angle and an approximately collinear (0 degree) outlet relative to the aorta.

FIG. 22A illustrates a side cross-sectional view of the impeller, a portion of the diffuser, and the direction of fluid flow through the diffuser. FIGS. 22B and 22C illustrate different perspective views of the collinear MCS with wrap-around diffuser and the direction of fluid flow through the MCS.

FIG. 23A schematically illustrates a side cross-section of an example of an inlet of a device comprising stationary pre-swirl vanes. FIG. 23B schematically illustrates a side view of the opened circumference of another example of an inlet comprising stationary pre-swirl vanes. FIG. 23C schematically illustrates a top cross-sectional view of a casing comprising a splitter vane within the diffuser and volute. FIG. 23D schematically illustrates a top cross-sectional view of a casing comprising a splitter vane within the outlet volute. FIG. 23E schematically illustrates a top cross-sectional view of a casing comprising diffuser vanes circumferentially positioned around the diffuser.

FIGS. 31A-31B schematically illustrate examples of MCS devices comprising motors comprising extravascular stators.

FIGS. 32A-32C schematically illustrate various examples of extravascular stators positioned circumferentially around an intravascular rotor comprising multiple rows of blades.

FIGS. 33A-33C schematically illustrate an example of an MCS device comprising magnetic rings joining the blades.

FIGS. 38A-38C schematically illustrate an example of a method of installing a foldable MCS device.

FIG. 39 schematically illustrates a method of deploying an MCS device comprising two collapsible discrete rings of stator coils and a foldable rotor.

FIGS. 42A-42J schematically depict specifications and comparisons of various types of motors.

FIGS. 45A-45D schematically illustrate examples of an MCS device, which may be particularly suitable for in-vitro testing.

FIGS. 47A-47E schematically illustrate examples of an MCS device comprising foldable propeller blades.

FIGS. 48A-48D schematically illustrate examples of an MCS device comprising foldable propeller blades wherein only one blade in each row is magnetic.

FIGS. 50A-50C schematically illustrate effects of magnetic forces between magnetic blades of the MCS device.

FIGS. 51A-51E schematically illustrate an MCS device comprising a partially disassembled configuration for delivery and an operative fully assembled configuration.

FIGS. 55A-55E depict examples of an MCS device comprising a z-shape folding mechanism.

FIGS. 57A-57D depicts various parameters of blade design.

FIGS. 60A-60G schematically illustrate various examples of operating configurations of the MCS device.

FIGS. 62A-62E schematically illustrate various examples of internal features of the MCS device.

FIGS. 64A-64C schematically illustrate examples of an MCS device comprising various motor arrangements and features to facilitate insertion.

FIGS. 68A-68D schematically illustrate operating configurations of the MCS device comprising two gearboxes.

FIGS. 70A-70B schematically illustrate operating configurations of the MCS device comprising two gearboxes.

DETAILED DESCRIPTION

Figure 1:
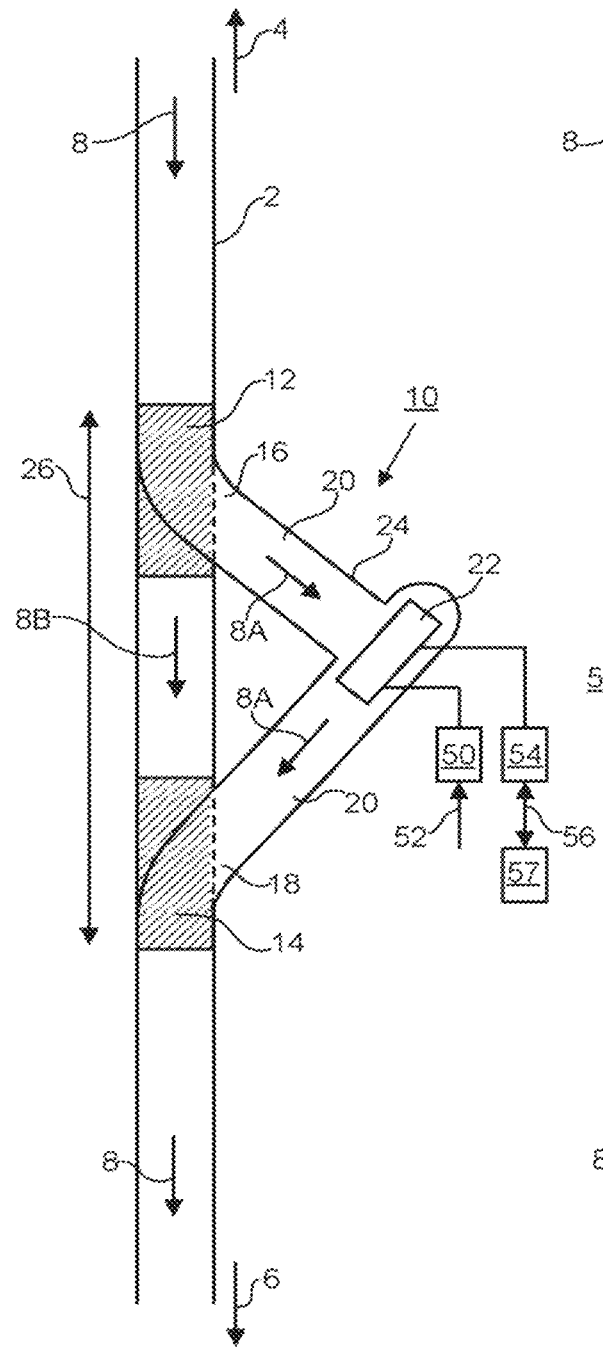
FIG. 1 depicts a mechanical circulatory support connected to a section of vasculature and configured to drive fluid flow in parallel with a small portion of the native blood vessel.

FIG. 1 depicts a section of vasculature 2. In an embodiment, the section of vasculature 2 comprises a section of the descending aorta. In an embodiment, the section of the descending aorta is below the diaphragm (arrow 4). In an embodiment, the section of the descending aorta is upstream and/or above the renal arteries and/or splanchnic arteries (arrow 6). Blood flow is shown schematically by arrows 8, 8A and 8B.

A mechanical circulatory support 10 comprises connections into (i.e. through the wall of) the vasculature via inlet port 12 and outlet port 14. The inlet port 12 is in fluid communication with a first end 16 of a lumen 20 defined by body portion 24 of the support 10. The outlet port 14 is in fluid communication with a second end 18 of the lumen 20. A pump 22 is provided within the lumen 20 and configured for driving fluid flow in a direction away from the inlet port 12 and towards the outlet port 14.

In an embodiment, the pump 22 is a centrifugal pump. The geometry of centrifugal pumps appears at first sight to be less convenient than that of axial pumps, which are used in some prior art MCS/VAD devices. However, the inventors have recognized that fluid-flow and turbomachine efficiencies gained from using centrifugal impellers, as opposed to axial impellers, at the selected pressure rise, flow rate, rotational speed, and device diameter, as well as from the less aggressive interaction between the pump and the blood for a given level of pumping more than outweigh any difficulties imposed by the geometry. Levels of pumping that are required in the context of pumping blood can be provided with less input power and less damage to the blood. Operation in-series in the described anatomic location results in lower power levels than devices designed as VADs configured to provide the full 120 mmHg pressure rise, and makes it possible to reduce the dimensions of the pump. Reducing damage to blood reduces the risk of adverse side-effects during use.

In an embodiment, the pump 22 is configured to provide a continuous flow, rather than a pulsatile flow (such as that provided by the native heart). The resulting pump 22 is simpler and can be optimized more easily. The inventors have recognized that it is not necessary to mimic the pulsatile flow of the heart. This is particularly the case when the support 10 is provided in series with the heart because the extent to which the operation of the support disrupts the normal functioning of the heart is reduced in comparison to prior art arrangements that are connected directly to the heart and arranged to operate in parallel with the heart.

In the embodiment shown in FIG. 1, the inlet port 12 is configured to divert a portion 8A of the blood flow within the blood vessel into the lumen 20 while allowing the remaining blood flow 8B to continue through the native blood vessel 2. The outlet port 14 is configured to allow the reintroduction of the diverted portion 8A of the blood flow back into the blood vessel 2 further downstream. In this embodiment, the support 10 therefore operates in parallel with a short portion 26 of the blood vessel 2. This approach minimizes disruption to the existing vascular system and can be installed using minimally invasive surgery. In addition, the provision of a region having parallel flow paths increases the overall flow capacity of the vascular system, thereby reducing the load on the heart to a degree. The resistance and impedance of segment 8B may need to be adjusted to prevent recirculating flow between the outlet and the inlet of the pump.

In an embodiment, a device is provided for driving the pump electrically. In an embodiment, the device is configured to be mounted to the body (e.g. having components that are mounted inside the body, outside the body, or both). The support can thus be installed for long periods of time (e.g. multiple weeks, months or years). The patient is thus not required to remain within a hospital ward after the support is installed. In the embodiment shown in FIG. 1, the device for driving the pump comprises a power receiving member 50, which receives power for driving the pump. The power receiving member 50 is configured to receive an input of power 52 from a power source located outside of the body (e.g. a battery mounted on the outside of the body) and/or a power source located inside the body (e.g. a battery mounted inside the body). In an embodiment, the connection between the power source and the power receiving member 50 is made wirelessly, for example using electromagnetic induction. In an embodiment, the power receiving member 50 comprises a coil. Where the wireless connection is made to a power source outside of the body, the connection may be referred to as a transcutaneous connection. In an embodiment, a wired connection is made between a power source located outside the body and the power receiving member 50. In an embodiment, the wired connection is established percutaneously.

In an embodiment, the support 10 further comprises a data transmitter/receiver 54 for transmitting/receiving data 56 to/from a controller 57 outside of the body. In an alternative embodiment, the controller 57, or a part of the controller 57, is configured to be installed within the body (i.e. under the skin). In an embodiment of this type, the controller 57 is sealed in a manner suitable for installation within the body and/or comprises a housing made from a material that is suitable for being in contact with tissue within the body for a prolonged period of time (e.g. a biocompatible material). In an embodiment, the controller 57 comprises a housing made from the same biocompatible material as a housing for an internal power source (e.g. internal batteries) for powering part or all of the support 10.

In an embodiment, the controller 57 is configured to interact with one or more sensors for monitoring one or more operating characteristics of the pump 22. For example, speed sensors can be used to measure the rotational speed of an impeller of the pump 22. In one embodiment three (3) Hall-effect sensors are used to measure impeller rotational speed. Alternatively or additionally, the pressure rise across the impeller is measured, for instance with two pressure transducers, one upstream and one downstream of the impeller. In an embodiment, the flow rate is measured, or calibrated as a function of other measured parameters. In an embodiment the set of measurements output from the sensors, or any subset of the measurements (e.g., impeller rotational speed and pressure rise) are used (for example by the controller 57) to adaptively control the rotational velocity of the impeller and therefore also the power input to the pump motor in order to achieve the required perfusion. In other embodiments, other operational characteristics are adaptively controlled in response to one or more sensor measurements.

In one embodiment, performance data, such as impeller rotational speed and/or pressure rise and/or flow rate is/are transmitted to an internal or external unit (e.g. the controller 57 or a part of the controller 57) that is configured to sound an alarm in case of acute conditions developing, or in case of a system malfunction. In an embodiment, the performance data is transmitted wirelessly to an external unit that collects the data in an application installed in a smartphone or similar device by the patient's bedside, and for example sends them electronically to a monitoring station. In an embodiment, the monitoring station is set up to send an alarm to the patient's guardian or physician, or to emergency services. Alternatively or additionally, the system may be set up to intelligently tune operation of the pump to improve performance. Further details of the electrical operation of the mechanical circulatory support are described elsewhere herein.

Figure 2:
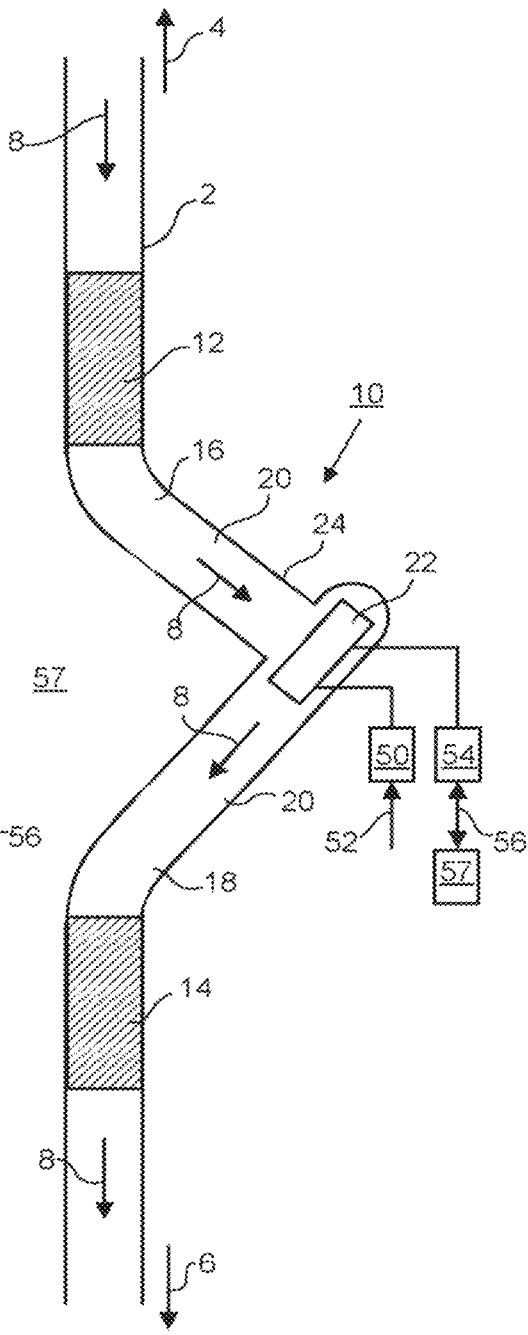
FIG. 2 depicts an alternative configuration for the mechanical circulatory support of FIG. 1 in which the support drives blood flow that is entirely in series with the native blood vessel, bypassing a short portion of the native blood vessel.

FIG. 2 illustrates an alternative embodiment in which the mechanical circulatory support 10 is configured to bypass a portion of the blood vessel 2, rather than operate in parallel with this portion of the blood vessel 2, as in the embodiment of FIG. 1. The inlet port 12 in this embodiment diverts all of the flow 8 within the blood vessel 2 into the lumen 20 of the support 10. Similarly, the outlet port 14 is configured to reintroduce all of the flow 8 back into the native blood vessel 2. Specific examples of mechanical circulatory supports installed either in-series and in-parallel with the aorta will be described herein.

Figure 3:
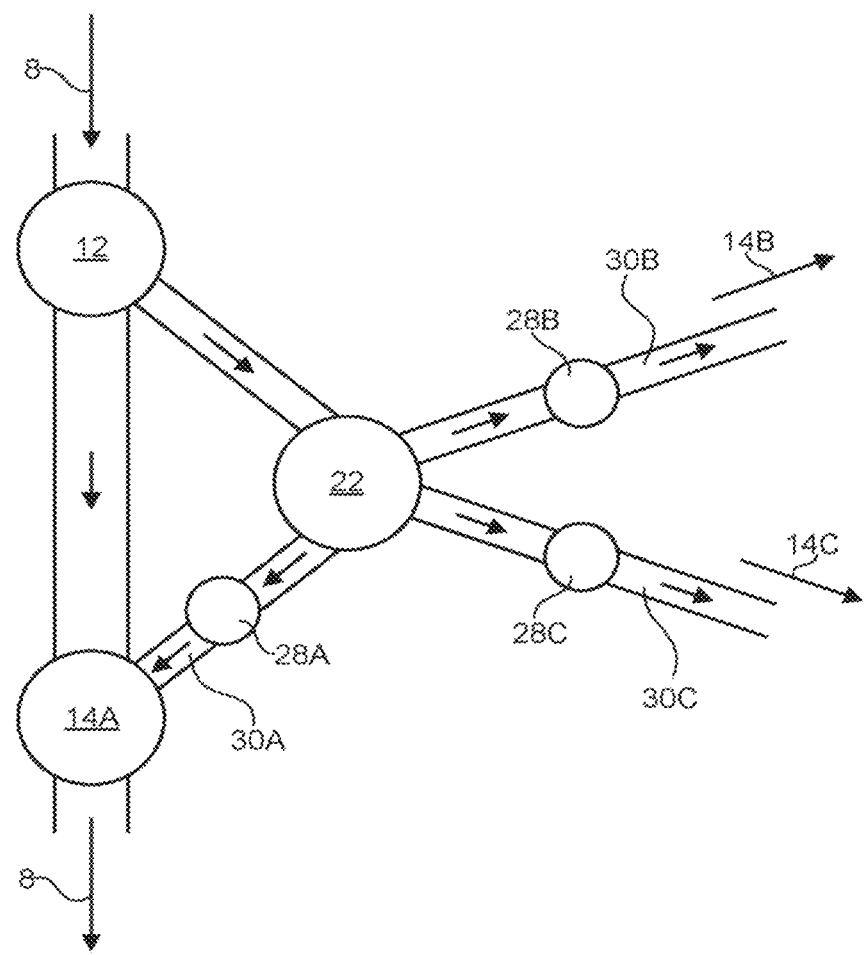
FIG. 3 depicts a mechanical circulatory support comprising multiple outlet ports and impedance setting members.

In the embodiments described with reference to FIGS. 1 and 2, the support 10 has a single inlet port 12 and a single outlet port 14. However, this is not essential. In alternative embodiments, the support 10 may comprise two or more inlet ports 12 and/or two or more outlet ports 14. In an embodiment, the support 10 comprises a single inlet port 12 within the descending aorta and two outlet ports 14. In an embodiment, the first outlet port 14 is configured to be connected into the descending aorta and the second outlet port 14 is configured to be connected into the ascending aorta. In an embodiment, the support 10 has a single inlet port 12 connected into the descending aorta and a single outlet port 14 connected into the ascending aorta. Providing an outlet to the ascending aorta may be useful for example to provide additional support to the brain, or to 'prime' the pump. Other configurations are possible according to clinical need.

Where a multiplicity of outlet ports 14 are provided, flow characteristics associated with each of the different outlet ports 14 and/or flow paths leading to the outlet ports 14, may be chosen so as to control the distribution of blood flow provided by the pump 22 according to clinical need. The flow characteristics may include the flow resistance, flow compliance and/or flow inductance. For example, where only a small contribution to the flow is required at a particular outlet port 14, the flow resistance associated with that outlet port 14 may be arranged to be relatively high. Conversely, where a relatively high flow output from the outlet port 14 is required, the flow resistance associated with that outlet port 14 may be arranged to be relatively low. FIG. 3 illustrates, highly schematically, such a configuration.

Here, support 10 comprises a single inlet port 12 and three different outlet ports 14A, 14B, 14C. Outlet port 14A is positioned downstream of the inlet port 12 in the same section of vasculature 2. The other outlet ports 14B and 14C are located elsewhere in the vascular system and are not shown in FIG. 3. Flow characteristic setting members 28A, 28B, 28C, which may be valves for example or sections of tubing of controlled diameter, are positioned on respective flow paths between the pump 22 and each of the three outlet ports 14A, 14B, 14C. By varying the flow characteristics using the flow characteristic setting members 28A, 28B, 28C, it is possible to define the proportion of the total flow output by the pump 22 that will be present in the respective flow paths 30A, 30B and 30C.

In an embodiment, the pump is configured to provide a pumping output that is equivalent to or greater than the total pumping requirement of the body within which the support is installed, so that no additional pumping from the native heart is required. In an embodiment, the pump 22, 34 is configured to provide a pressure of at least 125 mmHg and/or flow rates equivalent to the normal cardiac output of 5 liters per minute. The centrifugal pump approach of the present invention allows such pressure and flow rates to be achieved in a compact device with minimum damage to the blood. In another embodiment, the pumping output is lower than the total pumping requirement of the body. In such an embodiment the pump assists the native heart, which must provide a portion of the total pumping power.

Figure 4:
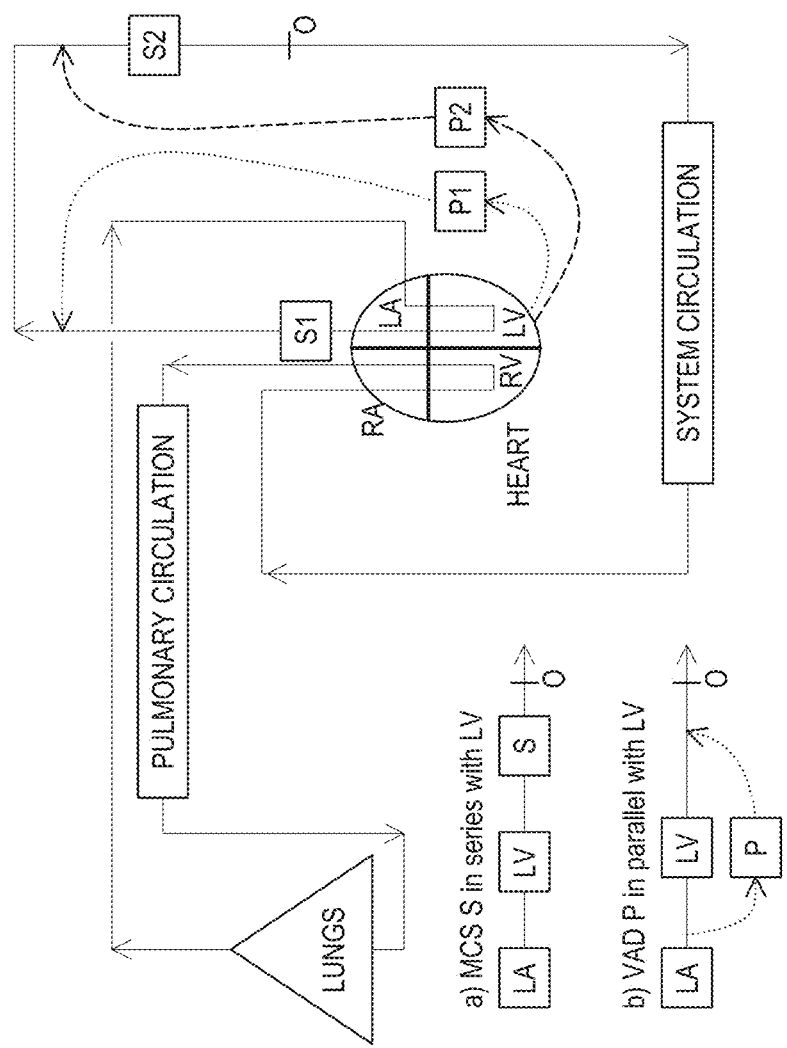
FIG. 4 schematically illustrates various installation configurations of VADs in the vasculature.

FIG. 4 schematically depicts the differences in installation of various devices within the vasculature, including a VAD installed in-parallel with the left ventricle and outflow connected to the ascending aorta (P1), a VAD installed in-parallel with the left ventricle and outflow connected to the descending aorta (P2), an MCS installed in-series with the ascending aorta (S1), and an MCS installed in-series with the descending aorta (S2), where "MCS" and "VAD" are here used to differentiate devices installed in-parallel with the left ventricle and devices installed in-series with the left ventricle, respectively. As discussed elsewhere, each installation configuration may affect the operating requirements and the installation procedure of the VAD. Installation of a VAD in-parallel with the left ventricle competes for blood flow with the native heart and may essentially take-over the pumping function. In-parallel installation may disrupt the natural functioning of the heart and may not allow for full regenerative potential of native heart tissue. VADs installed in-parallel may be required to generate the full physiological pressure rise (about 120 mmHg). VADs installed in-parallel generally need to be installed through highly invasive surgery (e.g., sternotomy) which generally require performing a cardiopulmonary bypass, though there have been recent attempts to modify installation of some VADs to less invasive surgeries, such as described in Makdisi, G, Wang, I-W., "Minimally invasive is the future of left ventricular assist device Implantation" (2015) Journal of Thoracic Disease 7(9), E283-E288 (incorporated herein by reference). MCSs installed in-series add to the pressure rise of the native heart, thus unloading the pressure rise required by the diseased native heart and supporting its natural function, allowing for regenerative potential of the heart. Therefore, because of the lower pressure rise requirement by the in-series devices, MCSs designed for in-series installation may have lower power requirements. In-series installation of a MCS, particularly within the descending aorta, may be performed via minimally invasive procedures, without a cardiopulmonary bypass, as the device's flow inlet need not be adjoined directly to the heart. Installation of MCSs with outlets in the ascending aorta may be used to support cerebral blood flow. Installation of MCSs with outlets in the descending aorta may advantageously avoid risks of blood damage from the MCS causing a cerebral thromboembolism or stroke, and they may also increase renal perfusion thus assisting in overcoming cardio-renal syndrome.

Figure 5A:
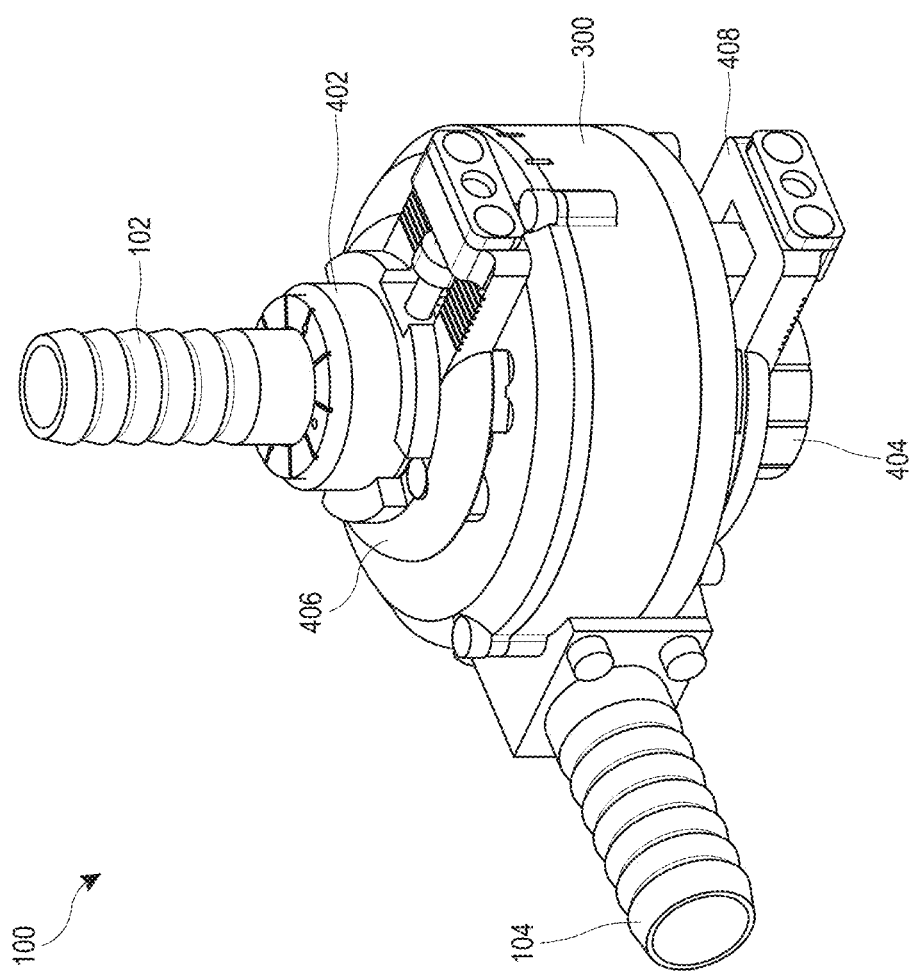
FIGS. 5A-5D illustrate an example of an MCS.
Figure 5B:
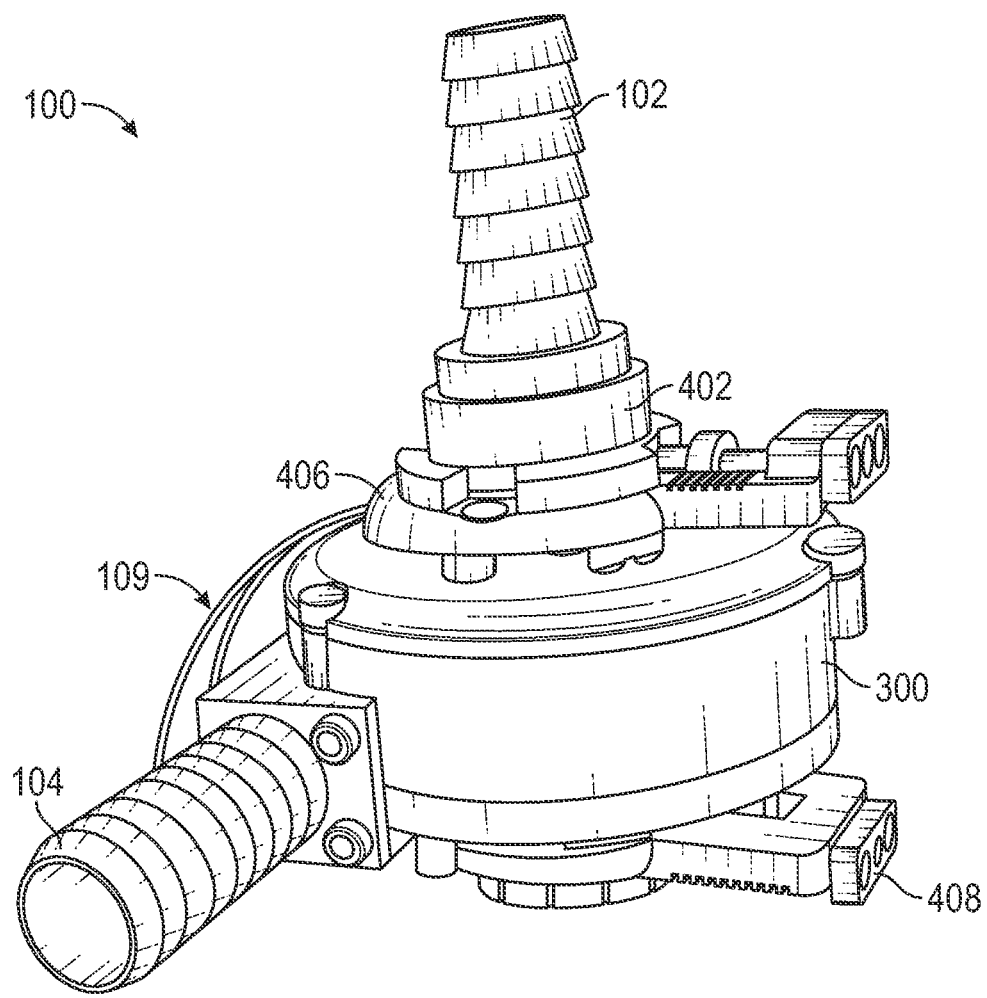
Figure 5C:
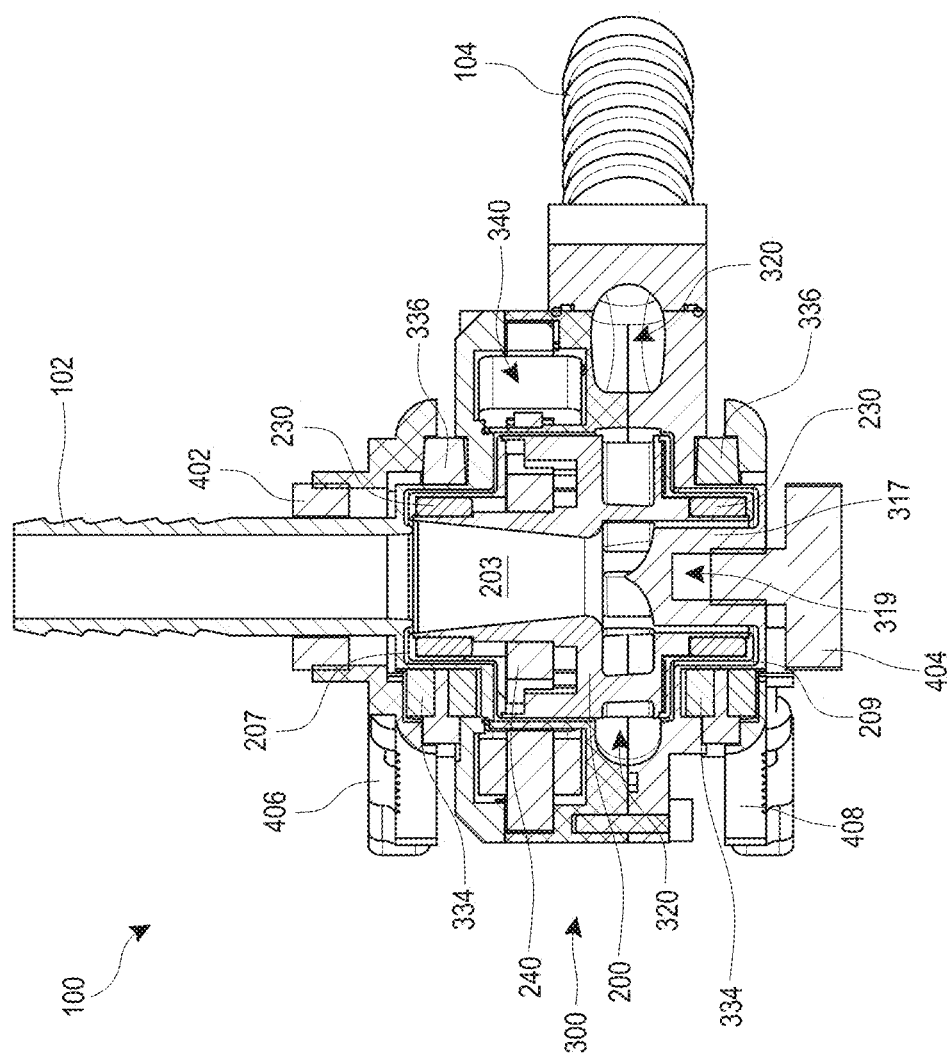
Figure 5D:
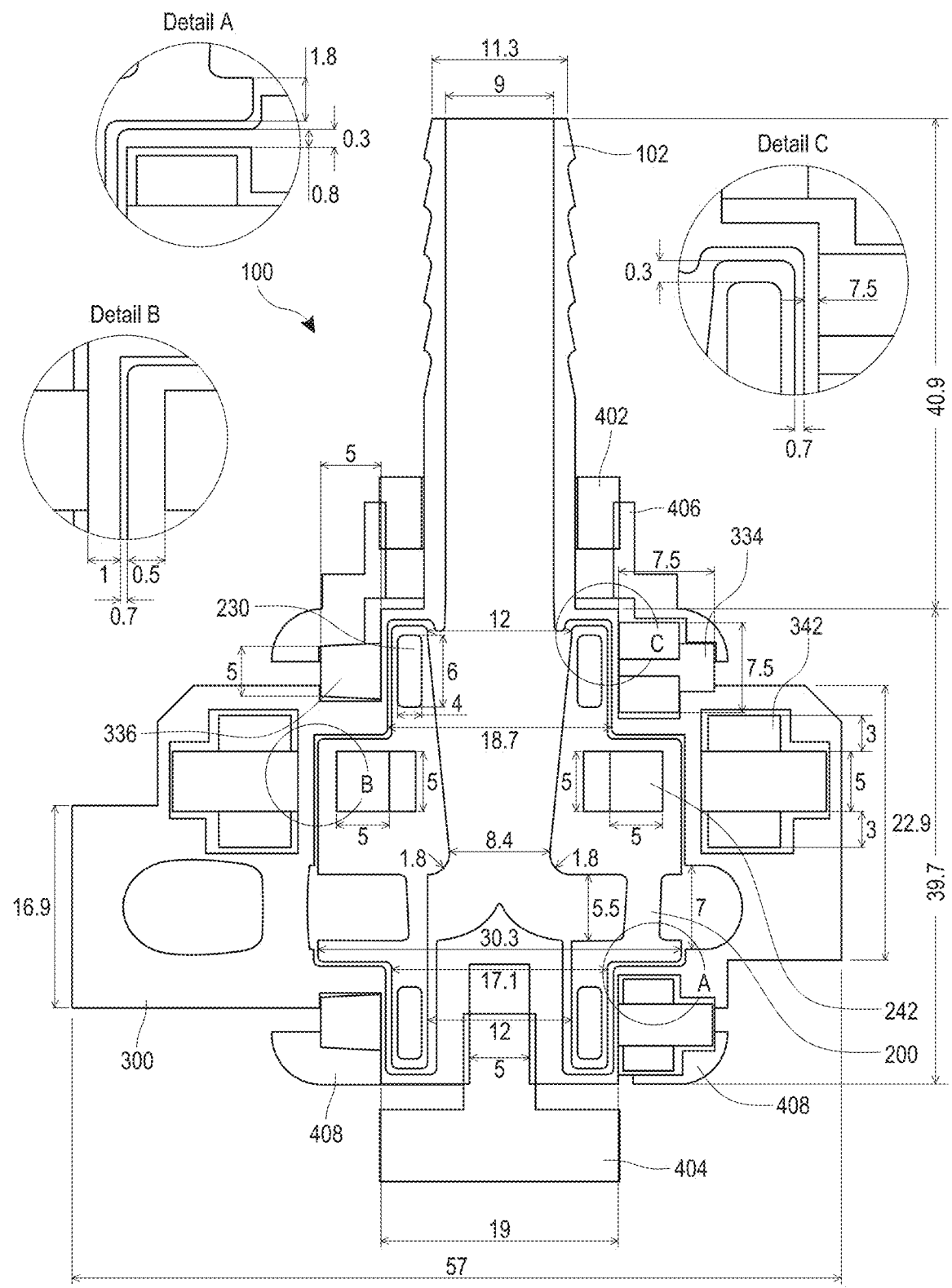

FIGS. 5A-5D illustrate an example of an MCS 100. FIG. 5A illustrates a perspective view of the MCS 100. FIG. 5B shows a photograph of a prototype of the MCS 100, demonstrating the approximate size of the MCS 100 in a person's hand. FIG. 5C illustrates a side cross-section of the MCS 100. FIG. 5D schematically illustrates a simplified side cross-section of the MCS 100 along with example dimensions (in mm) of various components and the overall dimensions of the MCS 100. The MCS 100 may generally comprise an impeller 200, a casing 300, and magnet holders 402, 404, 406, 408. The casing 300 may include an inlet 102 for receiving blood flow into the MCS 100, and an outlet 104 for directing exiting blood flow from the MCS 100, both extending from a main body for housing the impeller 200. The inlet 102 and outlet 104 shown in FIGS. 5A-5D are configured particularly for in-vitro testing, and may be modified accordingly for in-vivo applications (e.g., shortened and/or configured for attachment to vascular grafts). The impeller 200 may be contained entirely within the casing 300 and configured to be magnetically suspended, hydrodynamically suspended, or suspending by a combination of hybrid bearings within the casing 300 such that it does not contact the inner surface of the casing 300. The impeller 200 may be configured to be electromagnetically rotated within the casing 300 in a contactless manner. The impeller 200 may act as a centrifugal pump moving blood received through the inlet 102 from an axial direction and expelling it centrifugally along the circumference of the impeller 200 into the outlet 104. The magnet holders 402, 404, 406, 408 may be coupled to the casing 300 and position magnets and/or electromagnets around the casing 300 and impeller 200, which can be used to electromagnetically suspend and stabilize the impeller 200 within the casing 300. Other magnets, such as those that drive the rotation of the impeller 200, may be positioned within the casing 300. As shown in FIG. 5B, one or more electrical wires 109 may extend from the MCS 100 (e.g., they may extend between a controller described elsewhere herein and the casing 300). The electrical wires may provide power to the device and/or transmit sensor input to the controller. Each of the operative components of the MCS 100 will be described in further detail elsewhere herein.

Figure 6B:
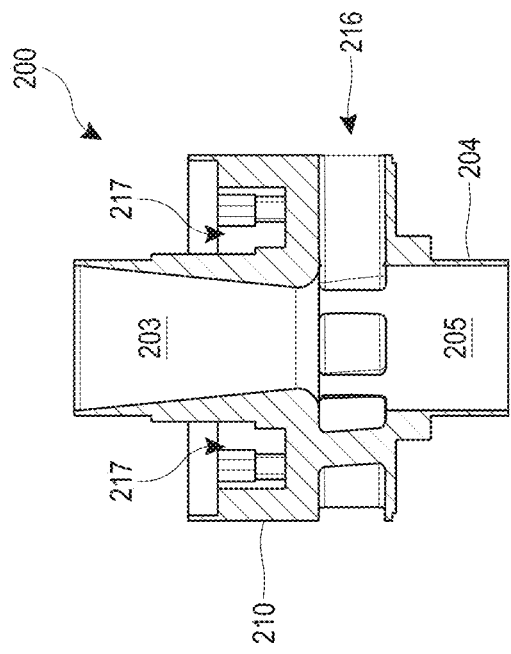
Figure 6C:
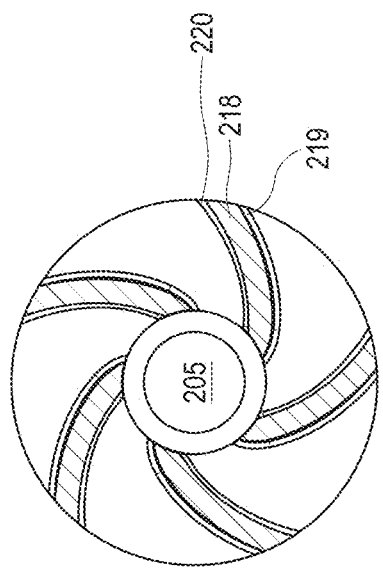
Figure 6A:
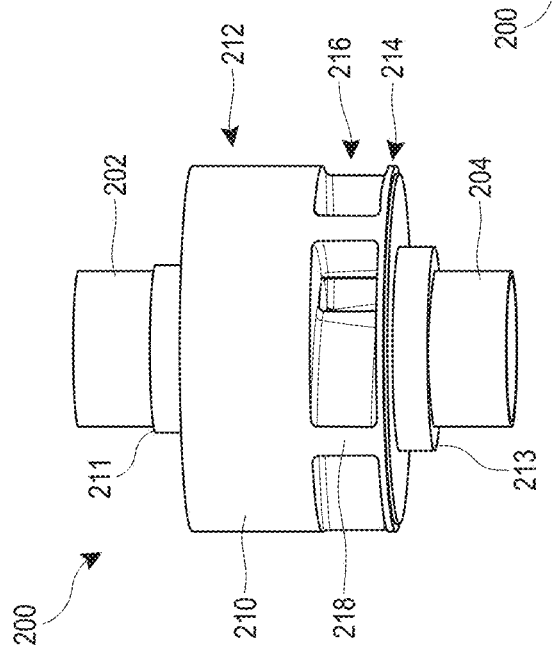

FIGS. 6A-6E illustrate examples of the impeller 200 and impeller assembly 201. FIG. 6A illustrates a perspective view of the impeller 200. FIG. 6B illustrates a side cross section of the impeller 200. FIG. 6C illustrates a top cross section of the impeller 200. FIG. 6D illustrates a perspective view of the impeller assembly 201, comprising the impeller 200, a top cap 207, a bottom cap 209, and other components not visible. FIG. 6E illustrates an exploded view of the impeller assembly 201 depicted in FIG. 6D. The impeller 200 can be configured to be magnetically suspended within the casing 300 such that the impeller 200 is sealed off from the external physiological environment except for blood entering the MCS 100 through the inlet 102. As shown in FIG. 6A, the impeller 200 may comprise a top port 202, a bottom port 204, and a main body 210, each of which may be generally shaped as bodies of revolution (e.g., cylindrical). The main body 210 may have a larger diameter than the top port 202 and/or the bottom port 204. The main body 210 may comprise an upper portion 212 (forming an impeller shroud), a lower portion 214 (forming an impeller hub), a blade passage chamber 216 between the upper portion 212 and lower portion 214, and a plurality of impeller blades 218 positioned within the blade passage chamber 216.

Figure 14B:
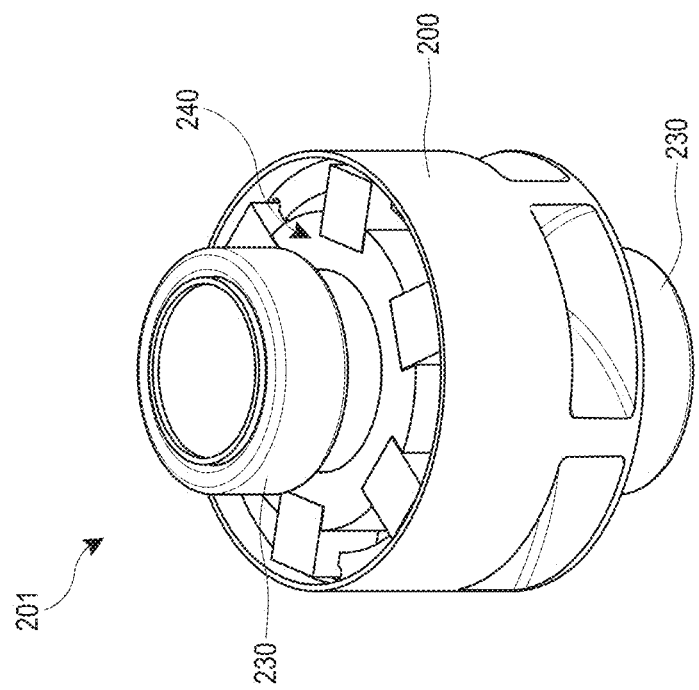
FIGS. 14A-14B illustrate an example of a MCS rotor.

As shown in FIG. 6B, the top surface of the upper portion 212 may be generally open and may extend into an upper chamber 217 configured to receive a rotor 240, described elsewhere herein, as indicated in FIG. 6E. In other embodiments, the lower portion 214 may additionally or alternatively include an open chamber. The outer diameter of the upper chamber 217 may comprise indentations configured to seat and secure magnets of the rotor 240 (FIG. 14B). The upper portion 212 can include an upper channel 203 which may extend from the top surface of the top port 202 to the bottom surface of the upper portion 212 for receiving blood flow into the blade passage chamber 216. The upper channel 203 may comprise generally circular top and bottom openings. The upper channel 203 may be generally cylindrical or frusto-conical in shape, or shaped as a body of revolution to optimize flow patterns at the inlet 102. The edge between the upper channel 203 and the blade passage chamber 216 may be generally rounded or curved for directing blood flow in a radially outward direction. A lower channel 205 may extend from the top surface of the lower portion 214 to the bottom surface of the bottom port 204. The lower channel 205 may comprise generally circular top and bottom openings. The lower channel 205 may be generally cylindrical or frusto-conical in shape. The edge between the lower channel 205 and the blade passage chamber 216 may be slightly rounded to reduce damage to the blood. The upper channel 203 and/or the lower channel 205 may be aligned generally in the center of the upper and lower portions 212, 214. The upper and lower channels 203, 205 may have the same or similar diameters and may be generally aligned with each other in an "axial" direction of the MCS 100, perpendicular to the plane containing the impeller blades 218 and aligned with the direction blood flow is received by the impeller 200.

The bottom surface of the upper portion 212 may form a ceiling to the blade passage chamber 216 and the top surface of the lower portion 214 may form a floor to the blade passage chamber 216. The impeller blades 218 may extend from the ceiling of the blade passage chamber 216 to the floor of the blade passage chamber 216 (i.e. between the impeller shroud and the impeller hub). The blades 218 may be integral with the upper portion 212 and the lower portion 214 and may be formed by machining a monolithic piece of material. The impeller 200 shown in FIGS. 6A-6E is an example of a shrouded impeller, as the blades 218 are covered on the top and bottom by the upper portion 212 and the lower portion 214 such that fluid may not flow over or under the blades 218. In other embodiments, unshrouded impellers may be used as described elsewhere herein. The impeller blades 218 may be generally perpendicular to the ceiling and the floor of the blade passage chamber 216 and may form a plane perpendicular to the axial direction of incoming blood flow (the axial direction of the MCS) in order to facilitate manufacturing considerations. In other configurations the impeller blades 218 may be three-dimensional bodies with lean from the axial direction between the hub and tip (where the blade meets the shroud), in order to optimize flow parameters. Three-dimensionally shaped blades 218 may be made with advanced manufacturing techniques such as investment casting or three-dimensional printing of the biocompatible impeller material. As shown in FIG. 6C, the blades 218 may each comprise a pressure-side 219 and a suction-side 220. The blades 218 may extend in a generally radial or meridional direction from an inner diameter (the leading edge of the blade) to an outer diameter (the trailing edge of the blade). In some embodiments, the blades 218 may be somewhat curved. The pressure-side 219 may be convex and the suction-side 220 may be concave, particularly near the tip of the blade. The inner diameter (leading edge) of the blades 218 may be aligned with the upper channel 203 and/or the lower channel 205. The outer diameter (trailing edge) of the blades 218 may be aligned with the outer diameter of the main body 210. In some embodiments, the upper portion 212 and the lower portion 214 may have different diameters and the blades 218 may extend to the larger diameter of the two diameters. The blades 218 may be of a generally uniform thickness as they extend from their leading edge to their trailing edge. In other embodiments, and particularly with advanced manufacturing methods employed, the blades 218 may be shaped as in modern centrifugal compressors and radial-inflow turbines of modern turbochargers. The edge of the blades along the inner diameter (the leading edge) and/or outer diameter (the trailing edge) may be shaped (e.g., rounded) to match the radius of curvature of the inner circumference or outer circumference, respectively, of the impeller main body 210 (the shroud and/or the hub) to which the blades 218 may be aligned. The shapes of the blades 218 along the meridional direction may be shaped with advanced turbomachinery blade-design methods, such as described by T. Korakianitis, I. Hamakhan, M. A. Rezaienia, A. P. S. Wheeler, E. Avital and J. J. R. Williams, "Design of high-efficiency turbomachinery blades for energy conversion devices with the three dimensional prescribed surface curvature distribution blade design (CIRCLE) method" Applied Energy, Vol 89, No. 1, pp.-215-227, January 2012. (hereby incorporated by reference). Each of the plurality of blades 218 may be of identical shape and configuration to the other. The blades 218 may be spaced uniformly around the circumference of the main body 210. The impeller 200 may include any number of blades 218 (e.g., three, four, five, six, seven, eight, nine, etc.). Blood flow may be directed from the inlet 102 to the blade passage chamber 216 and pumped in a centrifugal direction between the blades 218 and out the open circumference portions of the blade passage chamber 216.

FIGS. 6D and 6E illustrate the shrouded impeller assembly 201 in assembled and exploded views, respectively. The top port 202 and bottom port 204 may have the same or similar diameters. The top port 202 and/or the bottom port 204 may comprise shapes in bodies of revolution. The top port 202 and/or the bottom port 204 may comprise shoulders 211, 213 (shown in FIG. 6A) upon which a ring magnet 230 may be seated or partially seated, as indicated in FIG. 6E. The ring magnets 230, described elsewhere herein, may be configured to slide over the top port 202 and/or bottom port 204. In some embodiments, the ring magnets 230 may form a tight interference fit with the impeller 200, may be attached with advanced joining techniques, or may be fully-inserted into the impeller material. A rotor 240, described elsewhere herein, may be configured to be received within the impeller 200. The impeller assembly 201 may further comprise a top cap 207 and/or a bottom cap 209. The top cap 207 and bottom cap 209 may be generally shaped as bodies of revolution (e.g., tubular). The caps 207, 209 may comprise flat annular rims extending radially outward at one end configured to be seated against and coupled with the top and bottom surfaces of the main body 210, respectively. The caps 207, 209 may have thin annular rims extending radially inward at the other ends configured to be seated over the edges of the top port 202 and bottom port 204, respectively.

The top cap 207 may be configured to receive the upper port 202 and/or the bottom cap 209 may be configured to receive the bottom port 204 within inner diameters of their bodies. The top cap 207 and/or bottom cap 209 may be configured to sit over top of the ring magnets 230 and to seal them off from the external environment, such as the casing 300. The radially outward rim of the top cap 207 may be configured to seal the upper chamber 217 and close off the rotor 240 from the external environment, such as the casing 300. In other embodiments, the rotor 240 may be positioned in a lower chamber, as described elsewhere herein, or an additional rotor may be positioned in a lower chamber. The top cap 202 and/or bottom cap 204 may be coupled to the main body 210 by any suitable means, including laser welding or a biocompatible adhesive. In some embodiments, the top cap 207 is contour laser welded to the impeller 200 and the bottom cap 209 is contour laser welded to the impeller 200. The impeller assembly may comprise an axial target 221, which may comprise a flat annular right. The axial target 221 may be seated on the bottom surface of the lower portion 214 of the impeller 200. The axial target 221 may be fabricated from stainless steel or other suitable materials. The axial target may be magnetic. The impeller 200, top cap 207, and bottom cap 209 may comprise a biocompatible material, such as polyether ether keytone (PEEK), for example PEEK OPTIMA, biocompatible titanium, and/or biocompatible titanium coated with biocompatible alloys, because they comprise blood-contacting surfaces.

FIGS. 7A and 7B depict alternative embodiments of impellers 250, 252 which exclude top ports and bottom ports. In some implementations, these impellers 250, 252 may be subsequently joined to upper and lower ports after fabrication. As shown in FIGS. 7A and 7B the impellers 250, 252 may comprise upper and lower portions 212, 214 of approximately the same axial length. In some embodiments, as seen in FIG. 7B, the leading edges of the blades 218 of impeller 252 may be rounded off. In some embodiments, as seen in FIG. 7B, the leading edges of the blades 218 may extend inward of the bottom opening of the upper channel 203. This configuration may allow for easier machining of the leading edges of the blades 218 from the top. Embodiments in which the leading edges of the blades 218 are aligned with the bottom opening of the upper channel 203, as seen in FIG. 6C, may cause less disruption to the incoming blood flow.

In some embodiments, the impeller may be an unshrouded impeller, as opposed to the shrouded impeller 200 described above. FIG. 7C illustrates an example of an unshrouded impeller 254 with blades 255 that are uncovered on the top and FIG. 7D illustrates an example of another unshrouded impeller 256 with blades 257 that are uncovered on the top. Shrouded impellers have a top (a shroud) and a bottom (a hub) surrounding the impeller blades 218. Unshrouded impellers are uncovered on one or both sides (top and bottom) of the blades. Fluid may flow over the tip of the blades 255, 257 in the unshrouded impellers 254, 256 illustrated in FIGS. 7C and 7D. Shrouded impellers may have higher efficiencies than unshrouded impellers, due to tip leakage in unshrouded impellers (i.e. the flow leaks over the rotating blades). Shrouded impellers introduce more shear to the blood in the region between the shroud and the casing. The MCS may be modified to support an unshrouded impeller (e.g., with an overhung impeller design). For instance, the motor, comprising the rotor and stator, may be axially positioned around the hub of the unshrouded impeller, rather than around a shroud, and the radial and/or axial stabilization systems (bearings) may also be adjusted appropriately to account for the absence of a shroud. For instance, the impeller may be stabilized using the bottom radial and axial stabilization system components of the impeller along with the stabilization components of the casing, described elsewhere herein.

Figure 8B:
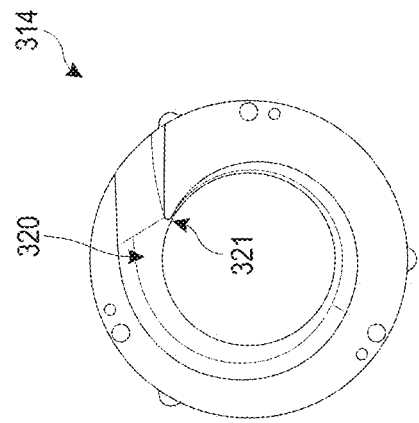
Figure 8D:
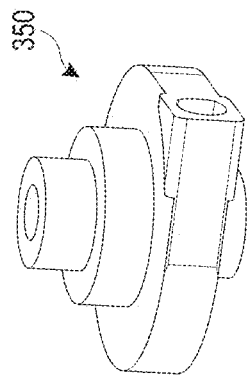
Figure 8A:
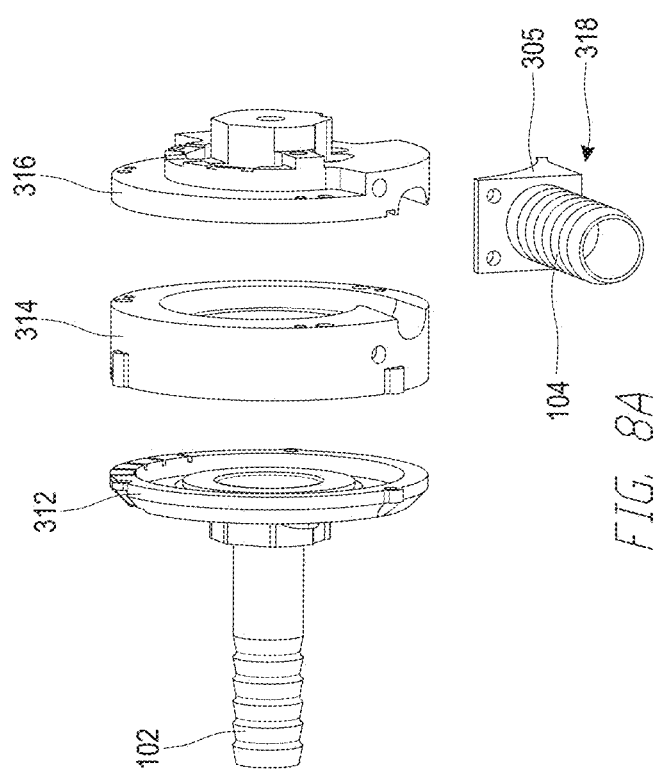

FIGS. 8A-8E illustrate examples of a casing or components thereof. The casing 300 may be configured in shape and dimension to surround the impeller 200 in such a manner that the impeller 200 may be suspended within the casing 300 and rotated around the axial direction of the MCS 100 without any portion of the impeller 200 coming into contact with the casing 300. The blood contacting surfaces, including casing 300 and the impeller 200, may comprise one or more biocompatible materials, including but not limited to polyether ether keytone (PEEK), for example PEEK OPTIMA, biocompatible titanium, and/or biocompatible titanium coated with biocompatible alloys. The casing 300 may comprise multiple components which can be assembled around the impeller 200. For example, FIG. 8A illustrates an exploded view of an example of the casing 300. The casing may comprise a lid 312, an upper volute 314, a lower volute 316, and an outlet attachment 318. The outlet attachment 318 may be particularly suitable for in-vitro testing and may be removed or modified for in-vivo applications, as described elsewhere herein. The lid 312 may include the inlet 102 or may be joinable to the inlet 102. The outlet attachment 318 can include the outlet 104 and may include a curved section 305 for coupling to the outer circumference of the upper volute 314 and/or lower volute 316. The components of the casing 300 may be assembled using screws and/or pins, biocompatible adhesives, or any other suitable means.

Figure 8C:
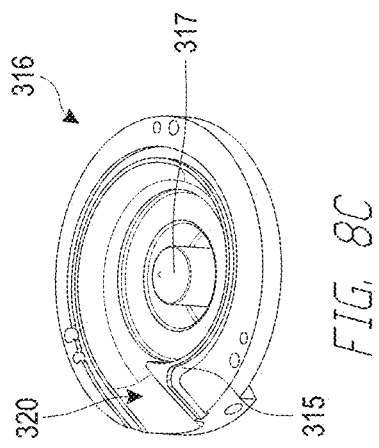

FIG. 8B illustrates a bottom view of the upper volute 314 shown in FIG. 8A, and FIG. 8C illustrates a perspective view of the lower volute 316 shown in FIG. 8A. The casing 300 can include a diffuser 320. The diffuser 320 may comprise a passage for receiving blood pumped by the impeller 200 and may extend into a volute passage in the outlet 104. The diffuser 320 can be formed directly in the internal surface of the casing 300, as shown in FIGS. 8A-8C. The diffuser 320 may be formed across the interface of the upper volute 314 and the lower volute 316. For instance, approximately half the cross-sectional circumference of the diffuser 320 may be formed in the upper volute 314 and approximately half of the circumference may be formed in the lower volute 316. The upper volute 314 and/or the lower volute 316 may include an indentation 315 for receiving a fluid sealing member, similar to an O-ring, shaped to match the circumference of the diffuser 320. A portion of the diffuser 320 circumference may be open to the internal diameter such that blood pumped through the impeller 200 may enter the channel. In other embodiments, the diffuser 320 may be formed by the addition of a component, such as a scroll, along the outer surface of the casing 300, as described elsewhere herein. The diffuser 320 may comprise a partially circular cross-section. The diffuser 320 may extend along the circumferential direction of the MCS 100 to the outlet 104. In some embodiments, the diffuser 320 may simultaneously extend in an axial direction downward, such that the diffuser 320 begins to spiral. The diffuser 320 may extend around the entire circumference of the casing 300 or only a portion of the circumference. In embodiments in which the diffuser 320 extends around more than a full circumference, the diffuser 320 may wrap behind itself closer to the outlet forming an entirely closed cross-section, as seen in FIGS. 8A-8C. In some embodiments, the size of the cross-section of the diffuser 320 may increase as the channel extends toward the outlet 104. For example, as best seen in FIG. 8B, the radial width of the diffuser 320 may continuously increase from an origin point 321 to the outlet 104. The origin point 321 may have a very small thickness such that it forms the beginning of the channel which expands in the direction of impeller 200 rotation. In some embodiments, the width of the diffuser 320 may expand along a clockwise or counter-clockwise direction when viewed from the top. The direction of fluid flow within the diffuser is set by the direction of impeller rotation and blade lean from the radial direction. In some embodiments, the flow-area distribution along diffuser 320 may be chosen to optimize vortex formation in the outlet 104 blood flow. The optimized vortex formation may emulate the weak passage vortex in the healthy native descending aorta, as described elsewhere herein.

In various embodiments, the outlet 104 is configured to extend perpendicular to the axial direction of the MCS 100, as shown in FIGS. 5A-5D and 8A. The outlet attachment 318 may comprise a volute that forms a continuation of the diffuser 320. The outlet attachment 318 may form a substantially straight channel. The outlet attachment 318 may provide a convenient means for attaching an outlet graft which can be anastomosed to the aorta. In some embodiments, the outlet attachment 318 may be excluded. FIG. 8D illustrates a perspective view of another example of a casing 350 in which the outlet is integral with or contiguous with the main body such that it does not form a cylindrical shaft. In some embodiments, the MCS may comprise multiple layers of casing. FIG. 8E illustrates an exploded view of another example of a casing 352 comprising an inner upper volute 354 and inner lower volute 356, similar to upper volute 314 and lower volute 316, respectively, as well as an outer upper casing 358 and an outer lower casing 360 which are configured to surround the inner casing 354, 356 and to interface with each other along a circumferential seam. In some embodiments, the diffuser 320 may extend into a volute of a scroll ending at the outlet 104, as described elsewhere herein. The scroll may further reorient fluid flow, such as by reorienting the fluid flow into a downward axial direction, such that the MCS may be configured for collinear installation within the aorta.

Figure 9:
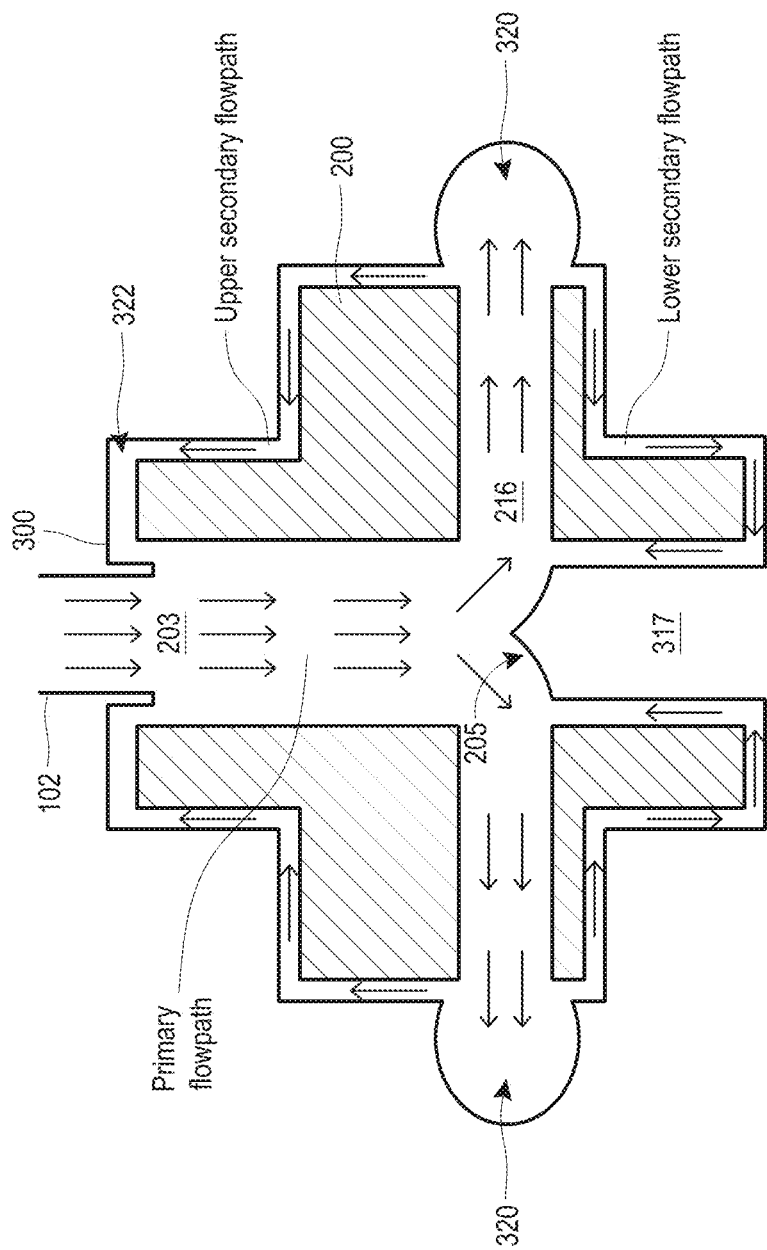
FIG. 9 schematically illustrates an example of blood flow through the impeller and internal casing surface of an MCS.

FIG. 9 schematically illustrates in simplified cross-section the suspended positioning of the impeller 200 within the inner surface of the casing 300 and the flow of blood through those components. The casing 300 forms a small peripheral space 322 around most portions of the impeller 200, excluding the inlet 102 and diffuser 320, each of which forms larger spaces continuous with the primary flow path through the impeller 200. The peripheral space 322 allows for contactless rotation of the impeller 200 by electromagnetic and/or hydrodynamic forces and forms secondary flow paths for blood that fills the peripheral space 322 during operation. The impeller 200 and casing 300 form a primary blood flow path, schematically depicted by arrows, from the inlet 102 to the diffuser 320 leading to the outlet 104 (not shown). Blood can enter the impeller 200 in an axial direction through the upper channel 203 and progress through the rotating passages between the impeller blades 218 which accelerate the blood flow in a tangential and radially outward direction. The blood is forced through the blade passage chamber 216 (between the blades 218 which are not shown), past the outer circumference of the impeller 200, and into the diffuser 320 formed in the inner surface of the casing 300. The impeller 200 increases the velocity and stagnation pressure of the blood as it passes through. The diffuser 320 decelerates the blood flow and increases the static pressure. In some implementations, less than half of a generally circular cross-section defining the diffuser 320 passage may be open to the internal casing volume containing the impeller 200, as seen in FIG. 9. In other embodiments, half or more than half the generally circular cross-section may be open. Although the cross-sections of the diffuser 320 on the right and left side of FIG. 9 are shown as equal in size, the cross-sections may be of dissimilar size as the diffuser passage 320 can increase in cross-sectional area as it extends downstream to the outlet 104.

Blood may also flow through secondary blood flow paths, also schematically depicted by arrows, formed via the peripheral space 322 between the impeller 200 and the casing 300, as shown in FIG. 9. The secondary blood flow paths may include an upper secondary blood flow path and a lower secondary blood flow path. The secondary blood flow paths may originate in the peripheral space 322 between the blade passage chamber 216 of the impeller 200 and the casing 300, by flowing upward or downward between the impeller 200 and the casing 300 rather than into the diffuser 320. Blood caught in between the impeller 200 and the casing 300 within the peripheral space 322 provides a hydrodynamic journal bearing force which helps prevent contact between the impeller 200 and casing 300. In an alternative embodiment, the top and bottom flat surfaces of the impeller assembly 201 have spiral grooves, which become part of the secondary flow area in the device gaps, and assist the hydrodynamic flow through the narrow gaps in order to minimize blood trauma within secondary flow paths. Blood may be forced along these paths either back to the junction of the inlet 102 and the impeller 200 or to the blade passage chamber 216 through the lower channel 205. The lower volute 316 may include a main stationary shaft 317 (also shown in FIG. 8C) configured to extend from the bottom of the casing 300 into the lower channel 205 of the impeller 200. The main stationary shaft 317 can be cylindrical or slightly conical in shape, with a corresponding variation in the shape of the lower channel 205 with which shaft 317 forms a hydrodynamic journal bearing. The main stationary shaft 317 may be configured to reside within the lower channel 205 such that the impeller 200 can rotate around the shaft 317 in a contactless manner. The upper end of the main stationary shaft 317 may comprise an apex. The upper end of the main stationary shaft 317 may be shaped to direct flow toward the circumference of the blade passage chamber 216. The upper end of the main stationary shaft 317 may be flat, conical, conical with concave surfaces (as shown in FIG. 9), domed, bullet-shaped, rounded, or other suitable shapes. The dimensions of the main stationary shaft 317 may be configured to prevent substantial flow in these clearance (gap) areas of the peripheral space 322 rather than along the primary flow path. The presence of the lower channel 205 allows blood along the secondary flow path to return to the impeller 200 so that it does not sit stagnant in the residual space around the lower portion 214 of the impeller 200, thereby enhancing washout of the MCS 100. The axial position of the impeller may affect the geometry of the flow paths and therefore the flow rates.

The impeller 200 can be magnetically suspended in the axial direction via passive (i.e. permanent) magnets positioned within the impeller 200 and casing 300. FIGS. 10A-10D illustrate examples of the MCS 100 components used to axially suspend the impeller 200. The impeller assembly 201 can include two magnets or two sets of magnets positioned at upper and lower ends of the impeller 200. The casing 300 can include two magnets or two sets of magnets positioned at upper and lower ends of the casing 300. The impeller 200 can be suspended using the magnets to create either approximately equal attractive forces between the impeller 200 and the casing 300 at the upper and lower ends of the MCS 100 or approximately equal repulsive forces between the impeller 200 and the casing 300 at the upper and lower ends of the MCS 100, accounting for other possible forces such as gravity or accelerations from the patient's motions. FIG. 10A illustrates an example configuration of passive magnets for axial suspension of the MCS 100. The impeller assembly 201 may comprise two ring magnets 230 which can be configured to be seated around the top port 202 and bottom port 204 (not shown) of the impeller 200. The MCS 100 may comprise sets of axial-suspension magnets 330 positioned outside the impeller 200. The axial-suspension magnets 330 may be positioned within the casing 300, coupled to the casing 300, and/or positioned between the casing 300 and other components external to the impeller 200, such that the axial-suspension magnets 330 remain stationary relative to the housing 300 and physically uncoupled from the impeller 200. There may be one or more axial-suspension magnets 330 positioned uniformly around the upper and lower circumference of the casing 300. For instance, there may be four axial-suspension magnets 330 positioned axially above the upper ring magnet 230 and four axial-suspension magnets 330 positioned axially below the lower ring magnet 230, as shown in FIG. 10A. In other embodiments, the axial-suspension magnets 330 may be ring magnets similar to ring magnets 230. In an alternative embodiment, the axial suspension magnets may be positioned slightly further apart in the axial direction, and by activation via electromagnets coupled to the casing, as described elsewhere herein, be used to axially oscillate the impeller assembly 201 in the casing 300, thus providing pulsatile flow at impeller outlet.

Figure 10C:
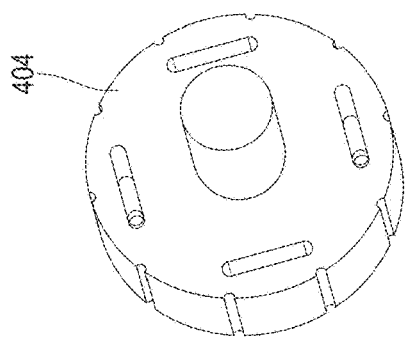
FIGS. 10A-10D illustrate example components of an MCS magnetic axial suspension system.
Figure 10B:
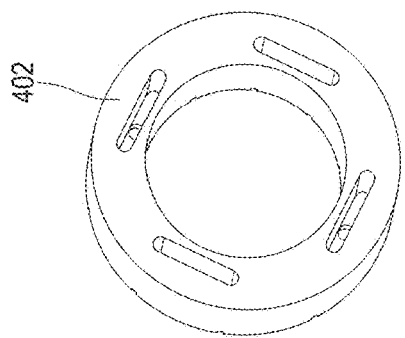
Figure 10A:
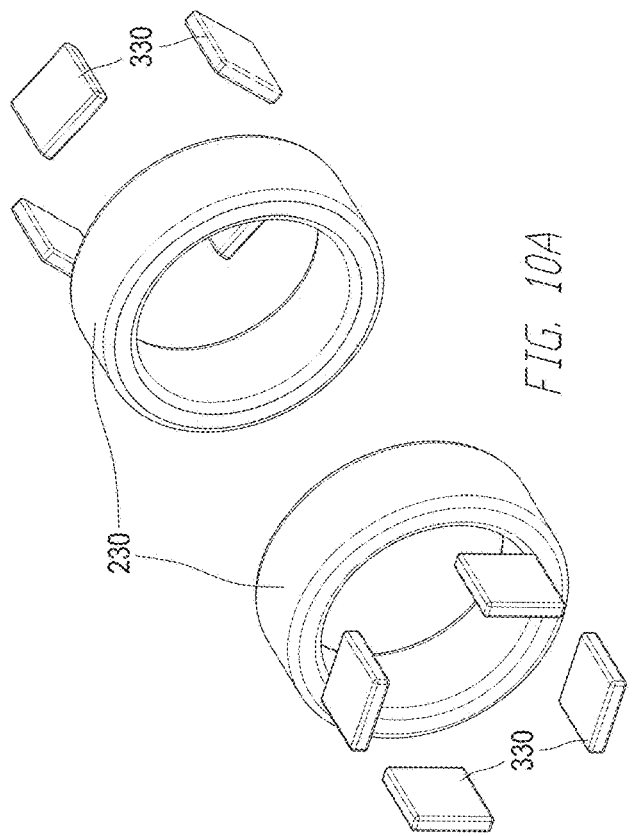

The upper axial-suspension magnets 330 may be positioned within an upper axial magnet holder 402, such as that shown in FIG. 10B, and/or the lower axial-suspension magnets 330 may be positioned within a lower axial magnet holder 404, such as that shown in FIG. 10C. The axial magnet holders 402, 404 may comprise slots for receiving each of the axial-suspension magnets 330. The axial-suspension magnets 330 may be coupled to the axial magnet holder 402, 404 via interference fit or other suitable means, such as adhesives, screws, pins, etc. In some embodiments, the upper axial magnet holder 402 may comprise a ring shape configured to fit over the inlet 102, as shown in FIGS. 5A-5D. The upper axial magnet holder 402 may be secured to the inlet 102 by a friction fit. The upper axial magnet holder 402 may be slidable along the length of the inlet 102 under sufficient force. The lower axial magnet holder 404 may be configured as a plate with a central post. The plate may be generally circular. The post may be generally cylindrical. The post may be configured to be received within a channel 319 formed generally in the center of the bottom outer surface of the casing 300 (e.g., the lower volute 316), as depicted in FIGS. 5C and 5D. The length of the channel 319 may extend into the main stationary shaft 317. The lower axial magnet holder 404 may be secured to the casing 300 by a friction fit. The lower axial magnet holder 404 may be translatable within the channel 319 under sufficient force.

Figure 10D:
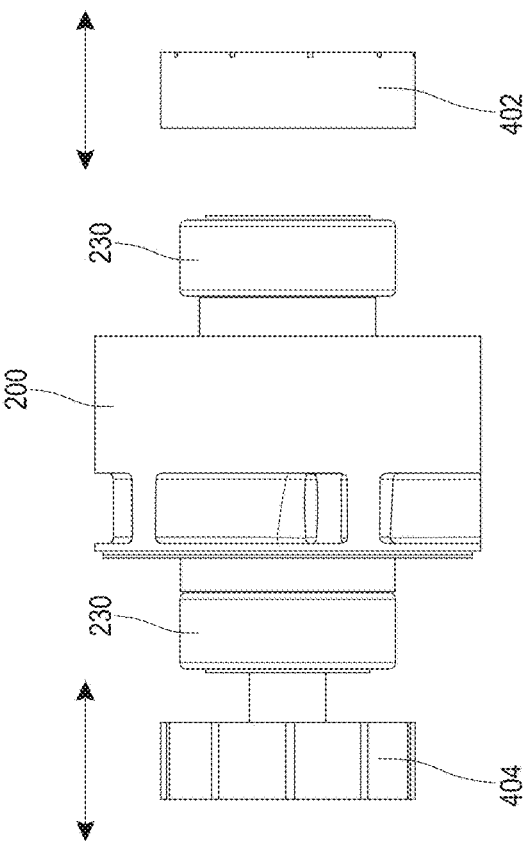

FIG. 10D illustrates the ring magnets 300 coupled to the impeller 200 and schematically illustrates the positioning of the upper axial magnet holder 402 and the lower axial magnet holder 404 relative to the impeller 200. In some embodiments, the ring magnets 230 may be of a first polarity (e.g., positive or negative). The axial-suspension magnets 330 may be of a second polarity, opposite the first polarity, such that the upper ring magnet 230 is pulled axially upward toward the upper set of axial-suspension magnets 330 and the lower ring magnet 230 is pulled axially downward toward the lower set of axial-suspension magnets 330. In other embodiments, the bottom ring magnet 230 and bottom set of axial-suspension magnets 330 are of a first polarity and the upper ring magnet 230 and the upper set of axial-suspension magnets 330 are of a second polarity, such that the upper ring magnet 230 is pushed axially downward and the lower ring magnet 230 is pushed axially upward. The axial-suspension magnets 330 may be adjustable. For example, as schematically illustrated by the arrows in FIG. 10D, the magnets 330 may be translatable in an axial direction to modulate the magnetic force and optimize the axial suspension, as described elsewhere. Positioning the axial-suspension magnets 330 within the upper axial magnet holder 402 and lower axial magnet holder 404 provides for easy axial adjustability relative to the casing 300.

Figure 11E:
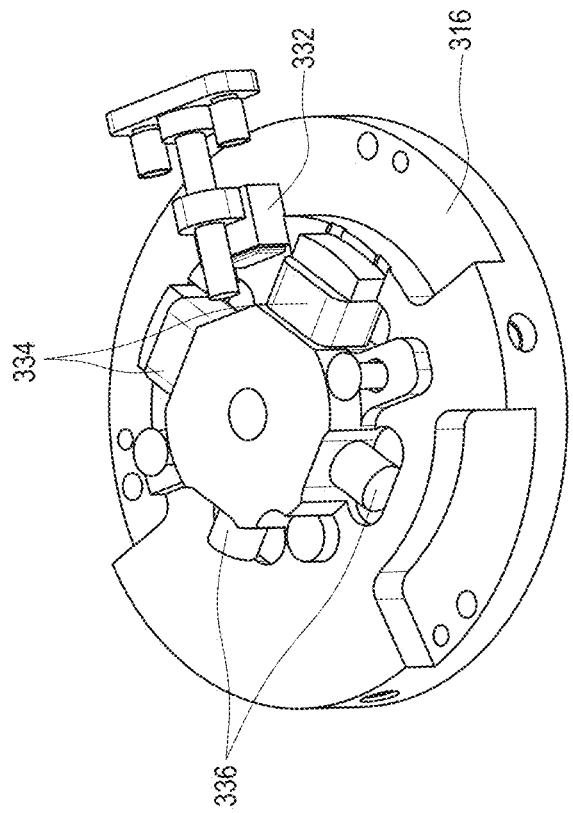
Figure 11D:
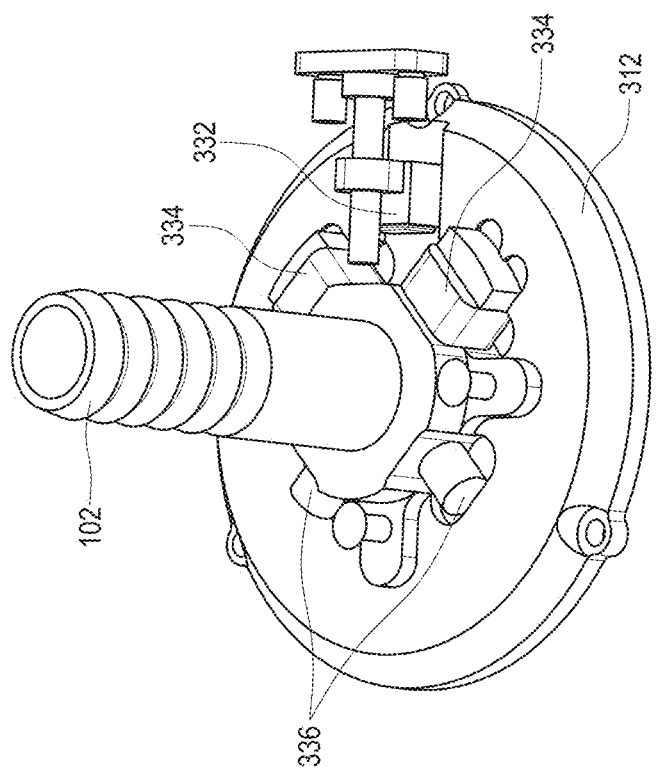

The impeller 200 can be magnetically suspended in the radial direction via various combinations of passive (i.e. permanent) magnets, active (i.e. electrically activated) magnets or electromagnets (e.g., conductive coils wrapped around a metal core), and a hydrodynamic journal bearing effect between the impeller 200 and the internal surface of the casing 300. FIGS. 11A-11E illustrate the components that can be used for radial suspension and stabilization. FIG. 11A shows an example of the orientation of magnets and sensors used for radial suspension. A passive radial-suspension magnet 332 may be positioned adjacent to each impeller ring magnet 230 (e.g., behind the internal surface of the casing 300) along the axial direction. The passive radial-suspension magnets 332 may be adjustable. For instance, the passive magnets 332 may be manually translatable in a radial direction such that the passive magnets 332 may be moved closer to or further from the impeller 200. In some implementations, the passive magnets 332 may be positioned in magnet irons comprising an aperture that can be slid or translated along a rod, pin, or screw in the radial direction. One or more active radial-suspension magnets 334, described elsewhere herein, may similarly be positioned adjacent to each impeller ring magnet 230 (e.g., behind the internal surface of the casing 300). One or more eddy current sensors 336, described elsewhere herein, may be positioned adjacent to each impeller ring magnet 230 (e.g., behind the internal surface of the casing 300). FIG. 11B illustrates an example of a top radial magnet holder 406 and FIG. 11C illustrates an example of a bottom radial magnet holder 408. The radial magnet holders 406, 408 can be used to position (e.g., clamp) the radial-suspension magnets 332, 334 and/or eddy current sensors 336 adjacent to the casing 300. The radial magnet holders 406, 408 may comprise indentations and/or spaces sized to receive or partially receive the radial suspension components, as shown in FIGS. 11B and 11C. FIGS. 11D and 11E illustrate the radial-suspension magnets 332, 334 and eddy current sensors 336 seated on the surface of the casing 300. In some embodiments, the upper and lower outer surfaces of the casing 300 are configured to seat all or some of the radial suspension components. FIG. 11D illustrates the upper radial suspension components seated on the top of the lid 312. FIG. 11E illustrates the lower radial suspension components seated on the bottom of the lower volute 316. The casing 300 may comprise identical or similar indentations as the radial magnet holders 406, 408 for partially receiving the radial suspension components, as shown in FIGS. 11D and 11E. The components may be sandwiched between the casing 300 and the radial magnet holders 406, 408. The top and bottom radial magnet holders 406, 408 may each comprise a ring-like shape configured to be coupled around generally cylindrical projections extending from the top and bottom of the casing 300, respectively (e.g., the lid 312 and the lower volute 316). The radial magnet holders 406, 408 may be configured to be secured to the casing 300 by a friction fit or other suitable means.

Figure 12B:
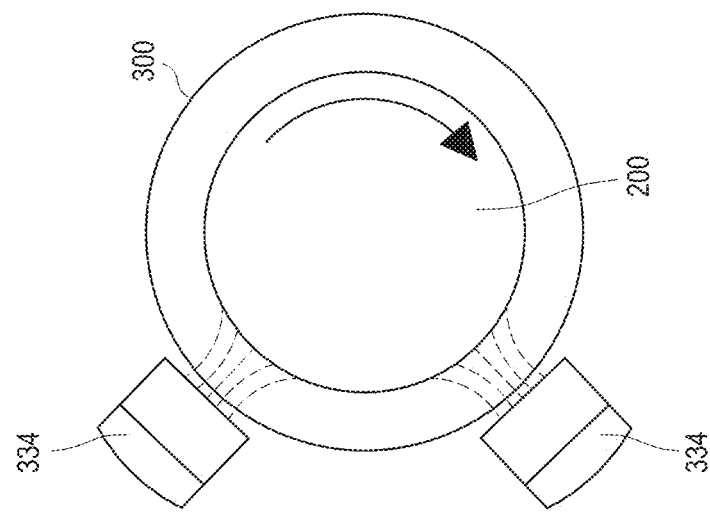
FIGS. 12A-12B schematically illustrate two modes of stabilizing an impeller within the casing of an MCS.
Figure 12A:
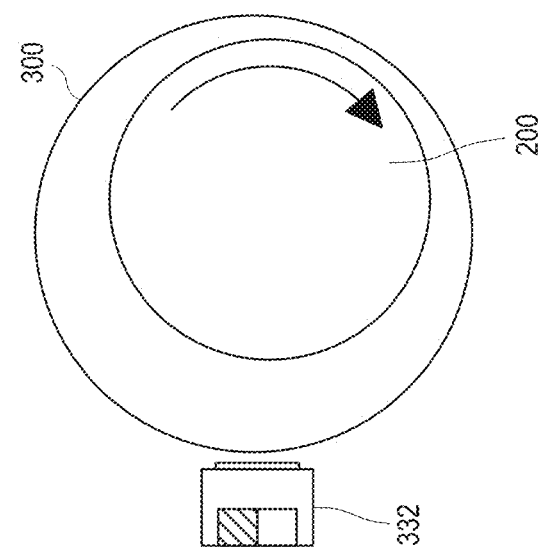

FIGS. 12A and 12B schematically illustrate two different modes of radial suspension and stabilization. The impeller 200 may be radially suspended by the passive radial suspension magnets 332. This can result in radial instability, according to Earnshaw's theorem, resulting from the axial stiffness. Instability may further result from the magnetic attraction between the motor's rotor 240 and stator 340, described elsewhere herein, and from turbulent flow, including vortices, within the MCS 100. The impeller 200 can be further stabilized by journal bearing forces and/or the active radial suspension magnets 334, as described below.

In some embodiments, as shown in FIG. 12A, a single passive radial-suspension magnet 332 is used to push the impeller 200 toward the opposite side of the casing 300, creating a large hydrodynamic bearing effect between the impeller 200 and casing 300. The combined magnetic force between the passive radial-suspension magnet 332 and the impeller ring magnet 230 and the journal bearing force may create a radial equilibrium which is highly eccentric, such that the impeller 200 rotates around an axis offset from the central longitudinal axis of the casing 300. This mode of radial suspension advantageously does not consume additional power because only passive magnets are used and stabilization can be accomplished without additional circuity and/or sensors. In some embodiments, more than one passive radial-suspension magnet 332 may be positioned around each impeller ring magnet 230.

In other embodiments, as shown in FIG. 12B, the passive radial-suspension magnet 332 may be positioned further from the casing 300 than the mode depicted in FIG. 12A, such that the impeller equilibrium axis is positioned approximately along the central longitudinal axis of the casing 300. Because a less strong journal bearing force is created in this arrangement, the equilibrium point may be less stable. The active radial-suspension magnets 334 may be used to prevent or inhibit oscillations from the equilibrium point. Eddy current sensors 336 may be used to monitor the position of the impeller 200, as depicted in FIG. 12B. The active radial-suspension magnets 334 may be actuated by a control circuit according to input from the eddy current sensors 336 to stabilize oscillations. The active radial-suspension magnets 334 may not act to independently suspend the impeller 200 in order to limit power consumption. This mode of radial stabilization may be advantageous because it may result in lower shear stress on the impeller 200. Lower shear stress may also reduce the amount of haemolysis in the pumped blood. Additionally, the active stabilization allows the MCS 100 to react to dynamic shocks, such as a patient falling over. In some embodiments, two active radial-suspension magnets 334 may be positioned around the passive radial suspension magnet 332. The active magnets 334 may be positioned on the same side of the impeller 200 as the passive magnet 332 and may be symmetrically spaced relative to the passive magnet 332. Two eddy current sensors 336 may be positioned on the opposite side of the impeller 200 as the magnets 332, 334. Each eddy current sensor 336 may be positioned opposite one of the active magnets 334. In alternative embodiments, the MCS 100 may rely on one or more other types of bearings to suspend and stabilize the impeller, including ball bearings, roller bearings, and/or needle bearings.

In some embodiments, the active magnets 334 may be positioned near the ring magnets 230 in a position at least slightly axially displaced from the ring magnets 230 such that activation of the active magnets 334 creates magnetic axial displacement forces between the impeller 200 and the casing 300. The axial displacement forces may be used to modulate the axially suspended position of the impeller 200 with respect to the casing 300. Application of pulsatile phases of current to the active magnets 334 may be used to oscillate the impeller 200 along an axial direction and to produce a pulsatile flow. In other embodiments, additional electromagnets distinct from the active magnets 334 may be used to produce the pulsatile flow. In some implementations, the additional magnets may only be positioned near the upper or lower ring magnets 230 rather than both.

In some embodiments, the inner axial surface of the casing 300 and/or the outer axial surface of the impeller 200, or portions thereof, may comprise circumferential grooves. In some implementations, the grooves may be spiraled axially. The grooves may have axial gaps between about 100 µm and about 1 mm (e.g., 200 µm, 500 µm, 710 µm, etc.). The grooves may decrease skin friction drag, thereby increasing the efficiency of the MCS 100, and may enhance washout flow from the MCS 100. The grooves also may improve impeller 200 stability by making it easier to axially suspend the impeller 200 by adjusting the axial-suspension magnets 330.

Figure 13A:
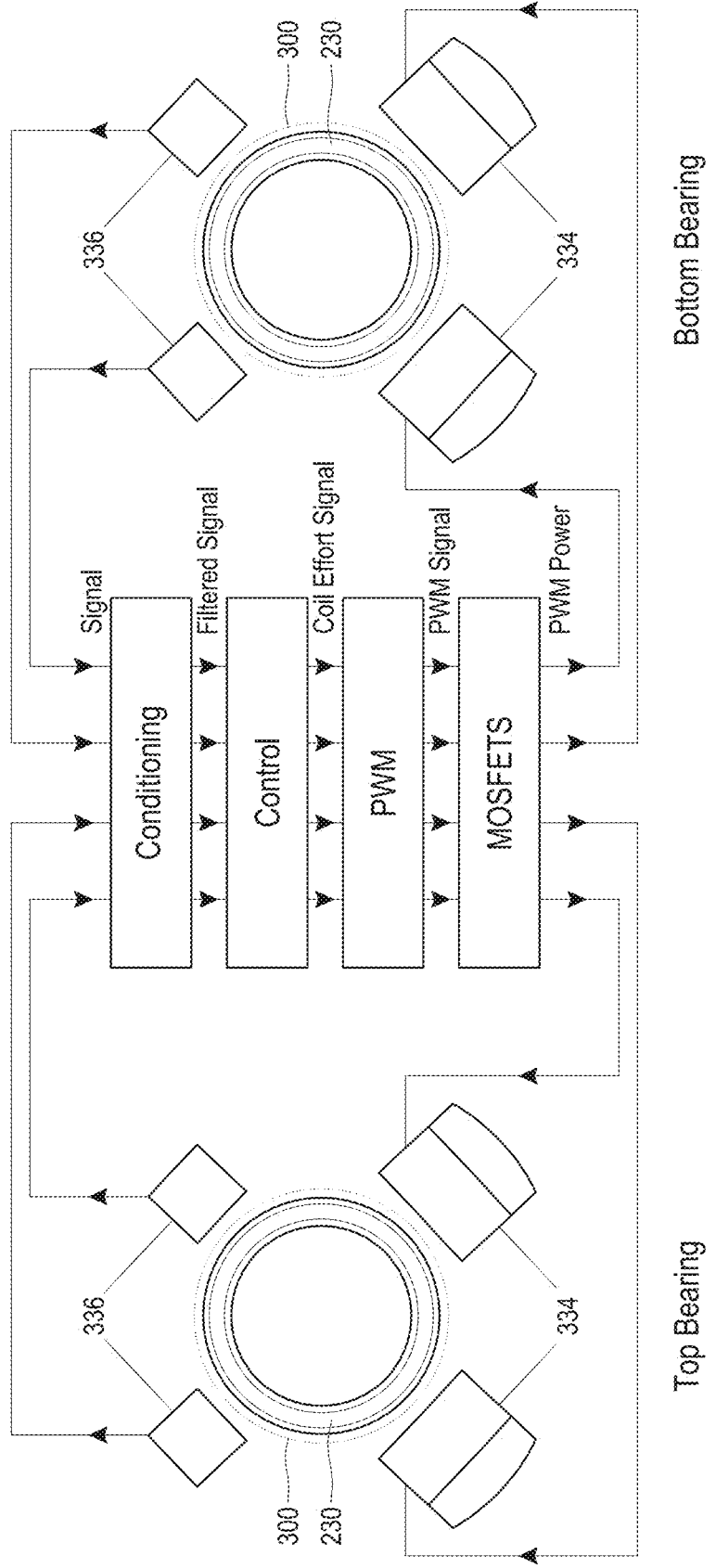
FIGS. 13A-13B schematically illustrate the electrical operation of the electromagnetic stabilization system.
Figure 13B:
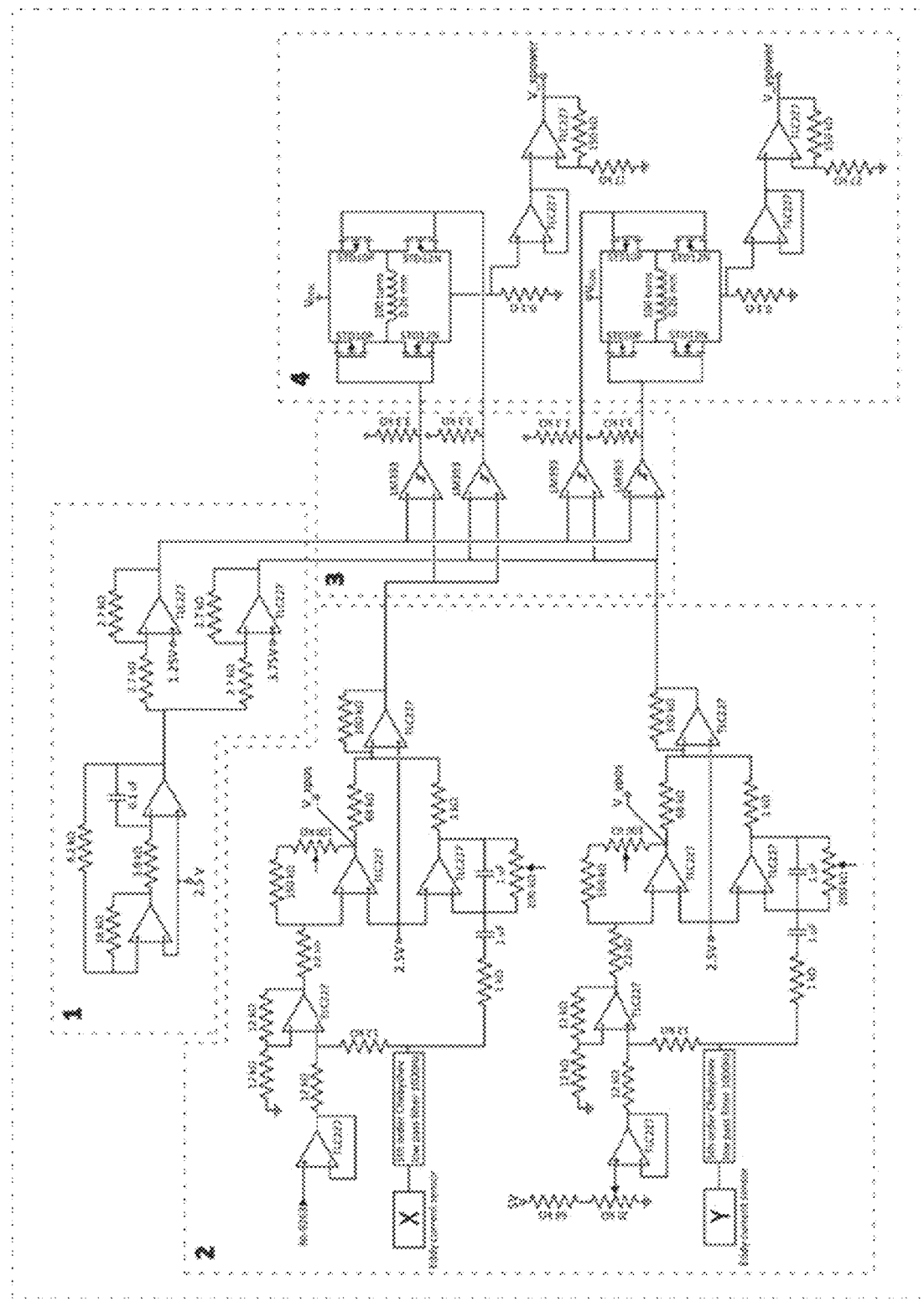

FIG. 13A schematically illustrates a block diagram showing an example of the circuitry components for operating the magnetic suspension (i.e. maglev) system. FIG. 13B schematically illustrates the circuit as divided between the four components (blocks 1-4) of the block diagram in FIG. 13A. A conditioning component (block 1) converts and filters the eddy current sensor 336 output into a voltage that can be read by the control circuit. The conditioning component may be a sawtooth generator. The control circuit (block 2) uses the sensor input along with external input (the maglev offset) to determine the effort in the corresponding coils of the active radial-suspension magnets 334. The pulse width modulation (PMW) component (block 3) converts the control circuit output into a pulse width modulated signal that can be used to drive coil switching in the active radial suspension magnets 334. The PMW component may use comparators. Finally, power MOSFETS (block 4) are driven by the pulse width modulated signal to supply power to the active radial-suspension magnets 334 configured to stabilize the impeller 200.

Figure 14A:
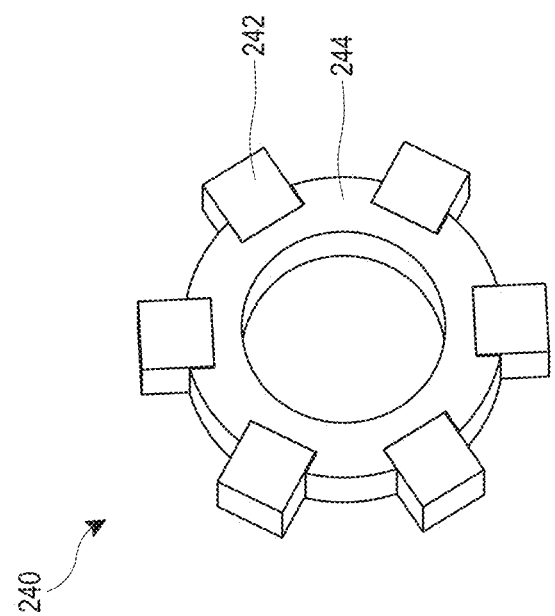

The magnetically suspended impeller 200 may be electromagnetically actuated to rotate around its longitudinal axis within the casing 300 via an electromagnetic motor. In some embodiments, the motor may be a radial brushless motor, such as a radial brushless DC motor. The motor may be a radial three-phase brushless DC motor. The motor generally comprises a stator 340 positioned within the casing 300 and a rotor 240 positioned within the impeller assembly 201 and aligned concentrically inward of the stator 340. FIGS. 14A and 14B depict examples of a rotor 240. FIG. 14A shows a perspective view of the rotor 240. FIG. 14B shows a perspective view of the rotor 240 assembled with the impeller 200 in the impeller assembly 201. The rotor 240 may include passive drive magnets 242 positioned around a ring 244. The drive magnets 242 may be positioned on the outer circumference of the ring 244 such that they extend radially outward from the ring 244. The drive magnets 242 may be partially embedded within the ring 244. The drive magnets 242 may be uniformly spaced around the circumference of the ring 244. There may be any number of drive magnets 242. In some embodiments, there is a 3:2 ratio of stator magnets to drive magnets 242. In some embodiments, there may be six drive magnets 242. The drive magnets 242 may comprise neodymium (NdFeB). The drive magnets 242 may be generally cubic in shape and may have dimensions of about 5×5×5 mm. The ring 244 may comprise steel. The rotor 240 may be configured to be inserted into the impeller 200. For example, as shown in FIG. 14B, the rotor 240 may be dimensioned to be inserted into the upper chamber 212 of the upper portion 212 of the impeller 200 as described elsewhere herein. The rotor 240 may be coupled to the impeller 200 by any suitable means, including but not limited to, welding, biocompatible adhesive, or a tight interference fit with the outer circumference of the top port 202.

Figure 15B:
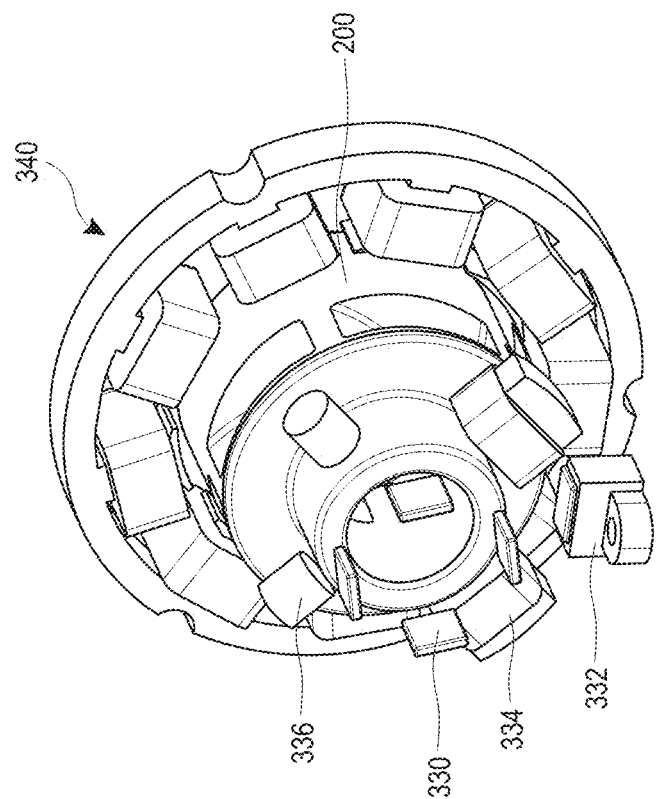
FIGS. 15A-15B illustrate an example of a MCS stator.
Figure 15A:
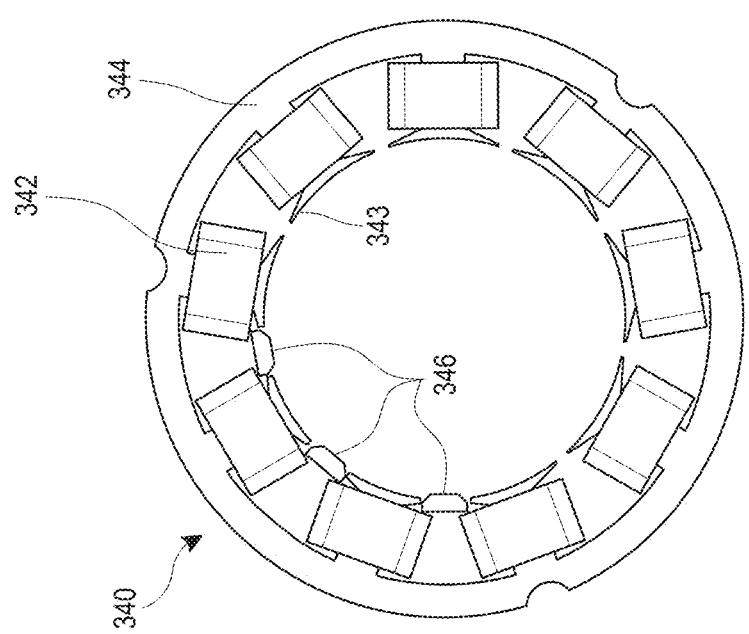

FIGS. 15A and 15B depict examples of a stator 340. FIG. 15A shows a top view along the longitudinal axis of a stator 340. FIG. 15B shows a perspective view of the stator 340 positioned around the outer circumference of the impeller 200. The stator 340 may include active magnets 342 positioned around a ring 344. The ring 344 may comprise silicon steel. The stator magnets 342 may be positioned on the inner circumference of the ring 344 such that they extend radially inward from the ring 344. The stator magnets 342 may be uniformly spaced around the circumference of the ring 344. There may be any number of stator magnets 342. In some embodiments, there is a 3:2 ratio of stator magnets 342 to drive magnets 242. In some embodiments, there may be nine stator magnets 342. The stator magnets 342 may comprise metal conductive coils wrapped circumferentially around projections extending inward from the ring 344. The coils may comprise copper. Electric current provided to the conductive coils may be used to create the electromagnetic forces of the active magnets. The radially inward end of the projections around which the coils are wrapped may comprise circumferentially extending flanges 343 which extend towards each other and align with each other to form a partially closed inner diameter configured to sit around an outward facing surface of the casing 300 (not shown). Larger gaps may be formed between several of the flanges on adjacent projections. The gaps may be configured for allowing the positioning of hall effect sensors 346, described elsewhere herein, adjacent to the outer surface of the casing 300, as shown in FIG. 15A. In some embodiments, multiple axially-aligned stators 340 (e.g., three stators 340) may be used. The stator 340 may be positioned within the casing 300. For example, the stator 340 may be positioned within the upper volute 314.

The motor may be driven by sequentially applying three phases of voltage (positive voltage, zero voltage, and negative voltage) to each stator magnet 342 to induce three phases of current (positive, zero, and negative) and polarity (positive, non-polar, negative). Pulses of positive and negative polarities may travel circumferentially around the stator ring 344 to continuously drive the rotor 240 through magnetic interaction with the drive magnets 242. A controller, which may be external to the MCS 100, may be used to time the charging of each stator magnet 342 so as to induce continual rotation of the rotor 240. One or more bipolar hall effect sensors 346 (e.g., three sensors) positioned within the casing 300 may be used to detect the positioning of the rotor 240 with respect to the stator 340 by detecting the proximity of a drive magnet 242. The controller may monitor the output of the one or more hall effect sensors 346 and use the positioning location to modulate the activation of the stator magnets 342. In some embodiments, the hall effect sensors may be Honeywell part number SS411A sensors.

Figure 16A:
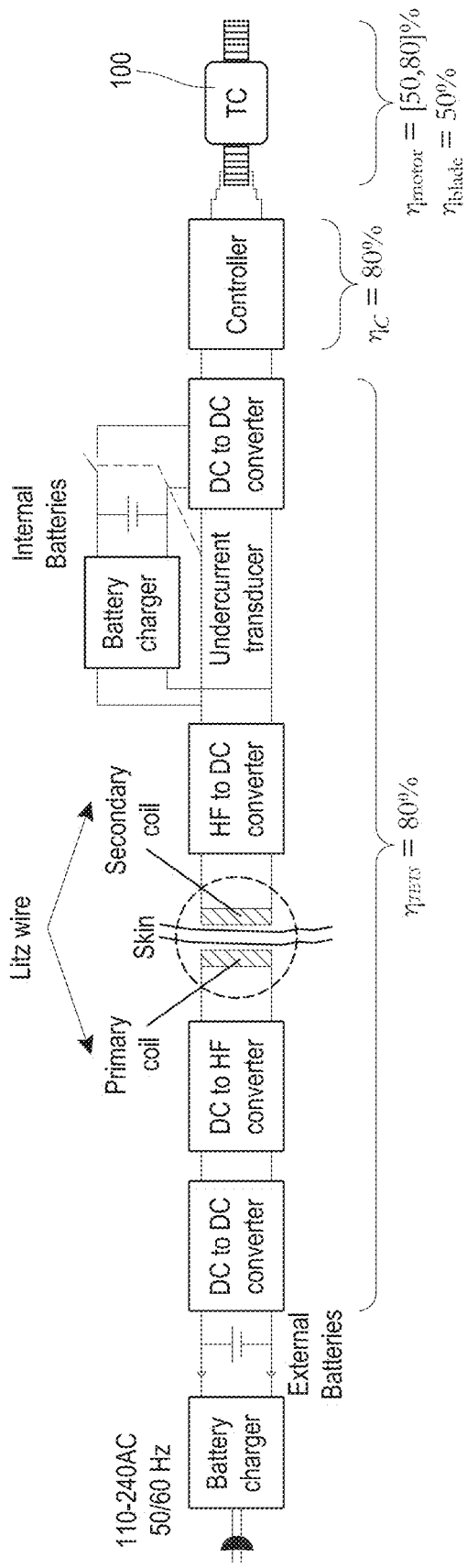
FIGS. 16A-16F illustrate examples of MCS power systems and operating parameters.

The electrical systems of the MCS 100 may control the motor and magnetic suspension systems, as well as power conditioning and battery charging. The electrical systems, or a portion of the electrical systems, may be external to the MCS 100. The electrical systems may be powered by an internal rechargeable battery, such as a chemical battery (e.g., lithium ion) or the battery may be used as a backup power source. The internal battery (or batteries) may be implanted within the body at a position separated from the MCS 100 device. For example, the internal batteries may be contained in a separate controller device implanted in the body, similar to the manner in which a pacemaker is implanted within a body. The controller may also contain the other electrical systems. In some embodiments, the battery may be charged transcutaneously, via inductive power transfer through the skin. In some embodiments, the MCS 100 is primarily powered by an external battery (e.g., a 16.8 V battery), but may have an internal battery for backup. Power from the external battery may also be transferred transcutaneously through the skin. FIG. 16A, schematically depicts the components of an example of a transcutaneous energy transmission system (TETS), including various component efficiencies (TO. An external battery charger may receive line AC voltage (e.g., 110-240 VAC) and convert it to DC voltage to charge external batteries (e.g., lithium ion batteries). A DC-DC converter may be used to stabilize the DC voltage provided by the external batteries (e.g., while they discharge). A DC to high frequency (HF) converter may convert the DC voltage into a high frequency (e.g., 250 kHz) AC voltage for transcutaneously charging a secondary coil beneath the skin from an external primary coil (e.g., spaced 20 mm apart). Higher frequencies may be required to transfer energy between coils spaced further apart. The coils may be made of Litz wire. An HF to DC converter may be used to convert the energy back to DC within the body. An internal DC-DC converter may be used to stabilize the DC voltage supplied to the controller. The controller may be electrically connected to the MCS 100 (denoted as "TC") via suitable wiring, including input and output capabilities. The controller may include intelligent functioning mechanisms, including constant monitoring of power consumption, impeller rpm, blood pressure, and other performance parameters. Information may be wireless transmitted to and/or from the controller, such as to a patient, physician, or hospital.

Figure 16B:
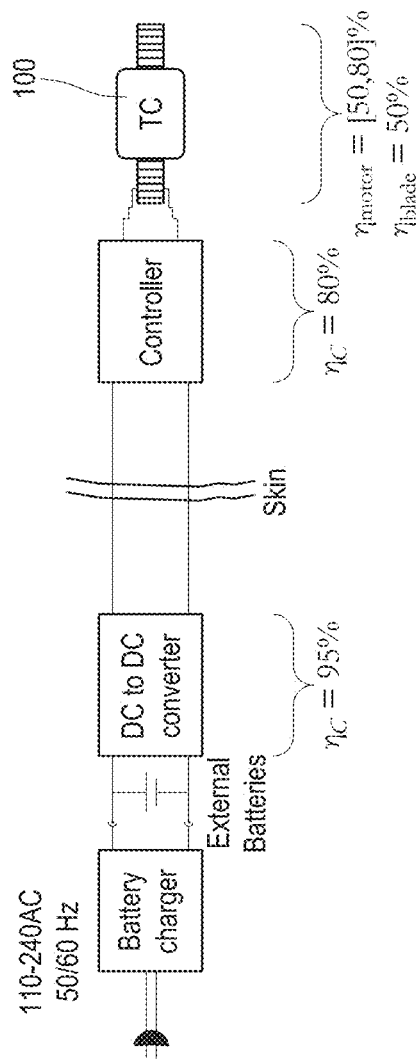

The controller may also include internal rechargeable batteries. The internal batteries may serve as temporary backup for when the TETS is disconnected. The internal batteries may be charged from the output of the HF to DC converter. An undercurrent transducer may be used to sense current from the external batteries and switch between power supplied directly from the HF to DC converter to power supplied from the internal batteries, if the current is below a predetermined threshold. Larger batteries may provide longer independent operation times. Charging the batteries at lower currents (e.g., 0.2 A) may advantageously limit the temperature rise of the devices, although longer charging times may be needed. In some embodiments, the battery may be charged percutaneously. FIG. 16B, schematically depicts the components of an example of a percutaneous energy transmission system (PETS), including various component efficiencies (TO. The MCS 100 may include any suitable means for minimizing the electromagnetic interference from other sources, including but not limited to, optimizing the voltage and current for a constant power, modifying the frequency of the signals, and using filters, shields, and/or snubber circuits.

Figure 16C:
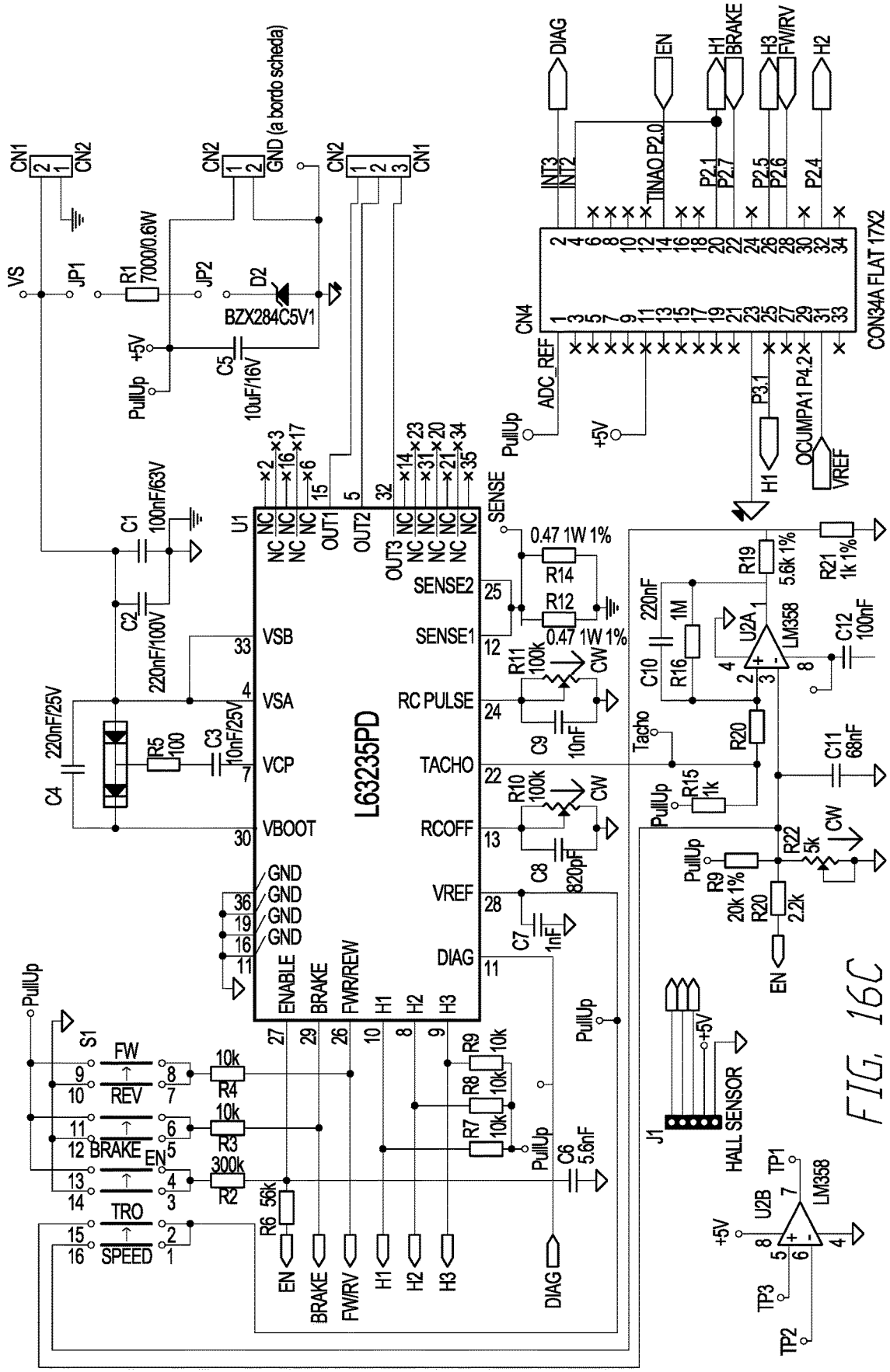
Figure 16D:
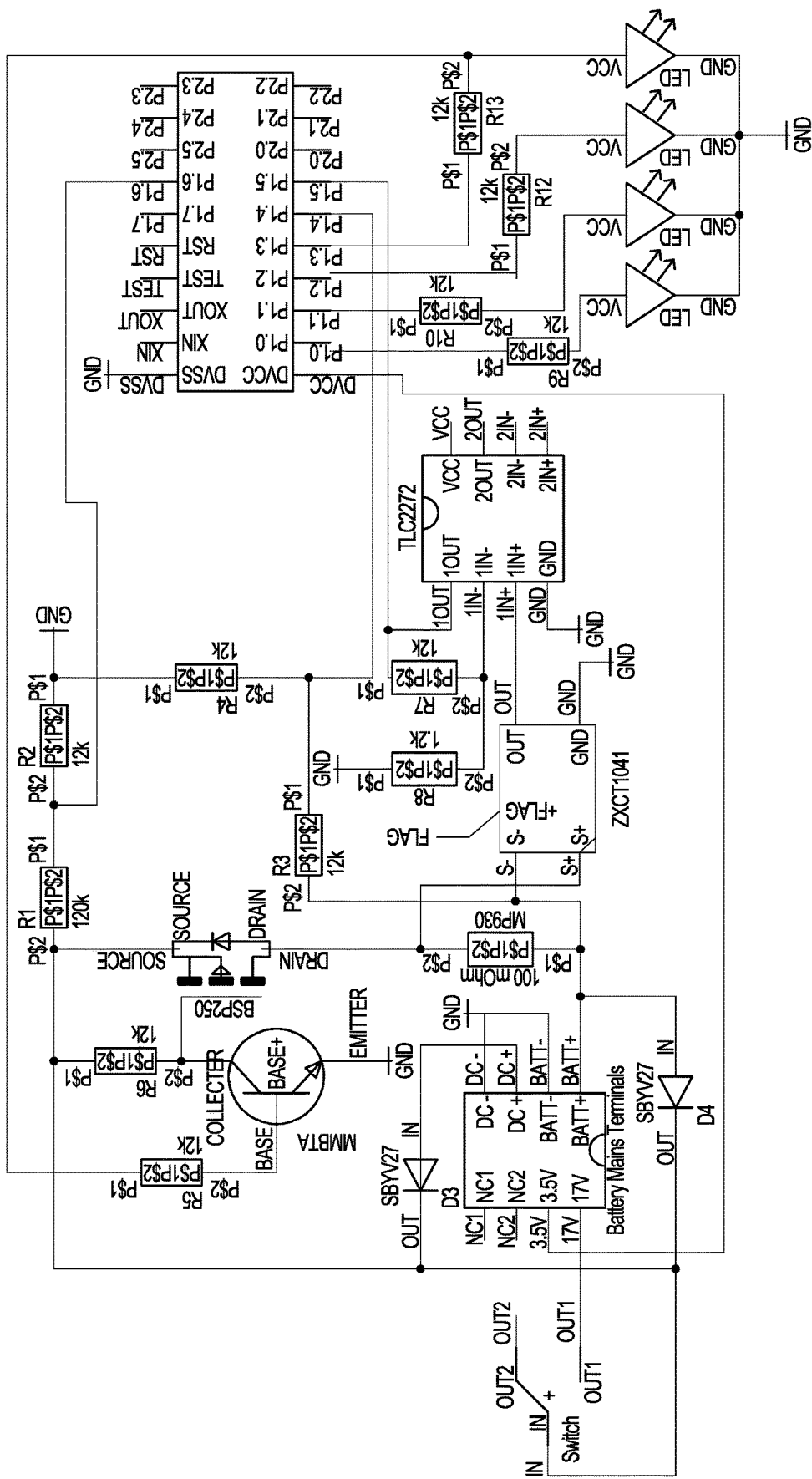
Figure 16E:
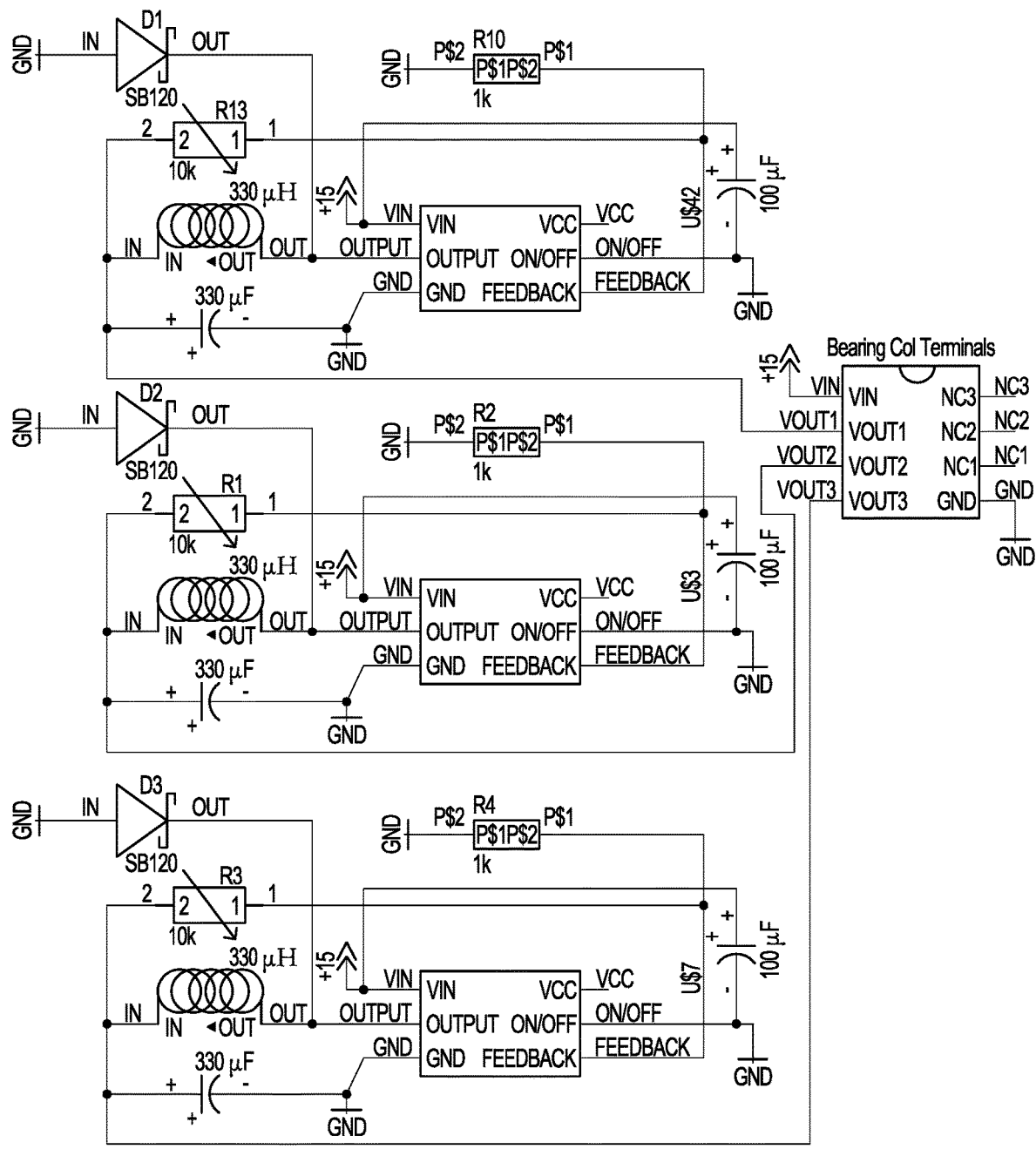

The controller may contain electronic circuitry for operating the MCS 100. In some embodiments, the motor can be driven using an L6235 driver chip (ST Microelectronics). FIG. 16C schematically illustrates the L6235 driver chip circuit. This circuit can be used to power the hall effect sensors, monitor their output, and drive the three phases accordingly. FIG. 16D schematically illustrates a battery charging circuit. The battery charging circuit may use an MSP430 microcontroller to monitor battery voltage and/or current into the battery via a ZXCT1041 current monitor. The microcontroller may stop charging to prevent overcharging if the battery is fully charged and the current into the battery is below 0.02 C. Charging may resume when the battery voltage drops below a predetermined threshold. Power into the battery may be controlled by an MMBTA bipolar junction transistor and a BSP250 MOSFET. A variety of charging algorithms may be programmed into the microcontroller. FIG. 16E schematically illustrates a power conditioning circuit. The power conditioning circuit can be used to create lower voltage levels from the battery (e.g., a 16.8 V battery) as described elsewhere herein. Running some circuits at lower voltages may reduce the power consumption of the MCS 100. Adjustable DC-DC current regulators may be used to ensure efficient conversion. In some implementations, the control electronics, digital filtering, and maglev actuators may be powered at 3.5 V, 5 V, and 6.5 V respectively. In some implementations, the control electronics, digital filtering, and maglev actuators may be powered at 3.5 V, 3.5 V, and battery power (e.g., 16.8 V) respectively, which may provide lower cost, complexity, and power consumption. Electrical power may be provided from the controller to the MCS 100 via electrical wires 109, illustrated in FIG. 5B. There may be multiple wires extending between the controller and the MCS 100. For instance, there may be a wire providing power to the radial suspension electromagnets, a wire providing power to the electromagnets of the motor, a wire receiving input from the eddy current sensors, a wire receiving input from the hall effect sensor, etc. Power and data may be transferred between the controller and the MCS according to any suitable means known in the art.

The MCS 100 may be optimized for performing in-series in a patient with late stage III and/or early stage IV CHF. The MCS 100 may be optimized to provide maximum power efficiency, minimize occupying space, and/or reduce device weight. Optimizing power efficiency may reduce battery weight and/or maximize untethered time during which the device may be operated via battery power. The device may be configured to optimize stability of the rotating impeller 200 to prevent damage to the device and/or blood trauma. Losses in motor efficiency may be electrical, magnetic, and/or mechanical. Electrical efficiency losses may, for example, include winding resistance (i.e. copper loss), especially in low speed applications. Magnetic efficiency losses may include hysteresis, eddy current losses, and/or excess eddy current. Mechanical losses may include windage, ventilation, and/or bearing friction. In some embodiments, the efficiency is at least 15%. In some embodiments, the efficiency is at least 20%. In some embodiments, the power consumption may be about 10 W or less. Efficiency may generally be increased by using a smaller impeller with reduced skin friction to improve hydraulic efficiency. Efficiency may generally be increased allowing more space for coils and/or reducing the stator-rotor gap to improve electromechanical efficiency at the operating condition. Stability may generally be improved by increasing the stator-rotor gap.

Figure 16F:
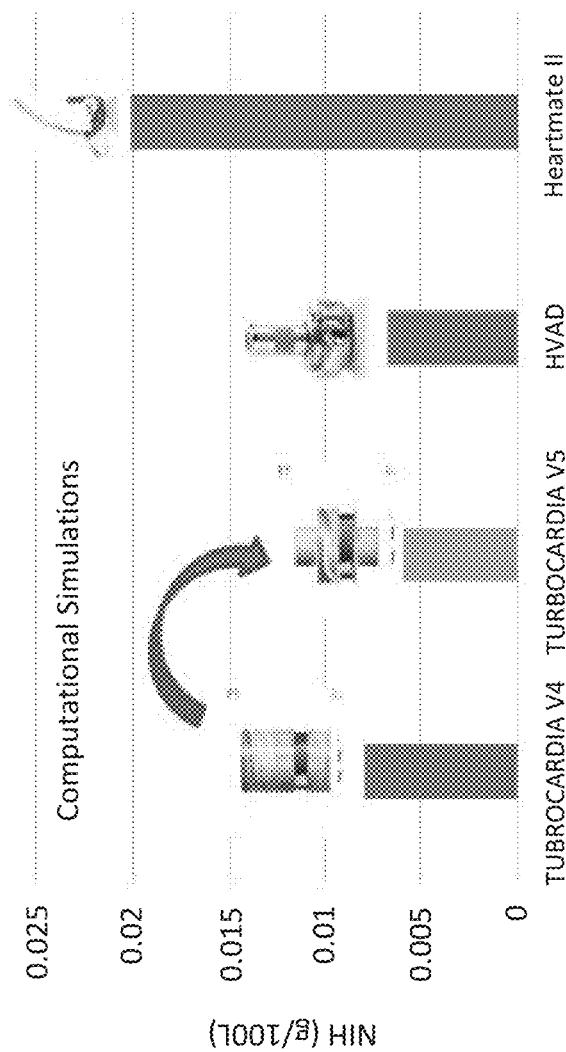

The operating design may be configured to minimize damage to the blood so that haemolysis is low. Haemolysis is the result of blood trauma imparted by high shear and by time of exposure (or length of flow passage) in high-shear flow conditions. For a set flow rate (e.g., 5 L/min) and to a first approximation, increasing the pressure requires larger power inputs to the flow and therefore results in larger losses by friction. Accordingly, the blood trauma imparted by a VAD or MCS increases as the pressure rises. Therefore, as the MCS 100 is designed to provide 40-80 mmHg, it will result in lower haemolysis than another MCS or VAD delivering 5 L/min at much higher pressure rises (e.g., 120-140 mmHg). FIG. 16F depicts the Normalised Index of Haemolysis (NIH, g/100 L) of computation simulations on the MCS 100 (depicted as TURBOCARDIA V5) as well as a prior version having an impeller comprising larger upper and lower portions 214, 216 amongst other design differences (depicted as TURBOCARDIA V4) and other VADs known in the art (the HVAD and Heartmate II). In some embodiments, as demonstrated in FIG. 16F the computed haemolysis of MCS 100 may be around 0.6 g/100 L. In other embodiments, the computed haemolysis may be less than 0.6 g/100 L.

The MCS 100 may be configured for installation within a portion of the descending aorta. The MCS 100 may be configured to provide approximately a 40-80 mmHg pressure rise (e.g., about 70 mmHg) at a continuous flow rate of about 5 L/min. The MCS 100 may be configured to operate the rotor 240 at approximately 2600 rpm. In some embodiments, the device may weigh about 150 g. The displacement volume may be about 70 cm$^3$. Referring back to FIG. 5D, example dimensions (in mm) of various MCS 100 components and the overall dimensions of the MCS 100 are depicted (the illustrated dimensions may not be drawn to scale). The outer diameter of the MCS 100 (around the casing 300) may be between about 30 mm and about 100 mm, between about 40 mm and about 70, between about 50 mm and about 60 mm, and ranges there between (e.g., about 57 mm). The axial length of the casing 300 may be between about 20 mm and about 60 mm, between about 30 mm and about 50 mm, between about 35 mm and about 45 mm, and ranges there between (e.g., about 40 mm), excluding the length of the inlet 102. The impeller 200 may have a maximal radial diameter between about 10 mm and about 60 mm, between about 20 mm and about 50 mm, between about 25 mm and about 40 mm (e.g., 30 mm). The diameter of the upper channel 203 may be between about 3 mm and about 25 mm, between about 5 mm and about 20 mm, between about 8 mm and about 12 mm, and ranges there between (e.g., about 10 mm). In some embodiments, as shown in FIGS. 5C, 5D, and 6B the diameter of the upper channel 203 may decrease from the inlet 102 to the blade passage chamber 216. For example, the diameter of the upper channel 203 may linearly decrease from about 12 mm to about 8 mm. In other embodiments, the upper channel may have a constant diameter or a diameter than decreases in a non-linear manner. The diameter of the lower channel 205 may be between about 3 mm and about 30 mm, between about 5 mm and about 20 mm, between about 8 mm and about 12 mm, and ranges there between (e.g., 10 mm). The diameter of the lower channel 205 may be constant as shown in FIGS. 5C, 5D, and 6B. In other embodiments, the diameter may increase in a linear or non-linear manner from the blade passage chamber 216 to the bottom of the impeller

200. The height of the blade passage chamber 216 may be between about 2 mm and about 30 mm, between about 3 mm and about 10 mm, and ranges there between (e.g., 5.5 mm). The height of the diffuser 320 may be between about 2 mm and about 30 mm, between about 3 mm and about 10 mm, and ranges there between (e.g., 7 mm). In some embodiments, as described elsewhere herein, the height and/or depth of the diffuser 320 may vary depending on the circumferential position. The gaps between the impeller 200 and the casing 300 in the peripheral space 322 may be between about 100 µm and 1 mm (e.g., 710 µm). The width of the peripheral space 322 may be the same or may vary around different portions of the impeller 200 and casing 300. The precise width of the peripheral space 322 may depend on the operation of the MCS 100, including the axial and radial suspension, as described elsewhere herein. The inlet 102 may have an inner diameter of about 9 mm. The inner diameter of the inlet 102 may be the same or less than the diameter of the upper channel 203 where the inlet 102 and upper channel 203 meet. The outlet 104 (not shown) may have an inner diameter of about 11 mm. In alternative embodiments, the MCS may be configured for installation in the ascending aorta. The MCS configured for installation in the ascending aorta may comprise a second outlet which could be configured to send about 5% of the blood flow to the coronary arteries and the remainder of the blood flow downstream.

The MCS 100 can be installed within the vasculature 2 in various configurations. In various embodiments, the MCS 100 comprises an inlet 102 and an outlet 104, which may be arranged generally perpendicular to each other as described elsewhere herein. The outlet 104 may be positioned at the end of a diffuser for altering and/or reorienting the fluid outflow. The MCS 100 can be installed into the vasculature using vascular grafts comprising standard biocompatible graft material (e.g., polytetrafluorethylene, polyethylene terephthalate, etc.). In some implementations, patient allografts may be used. The grafts may be connected to the inlet 102 and outlet 104 of the MCS 100 in any suitable manner which creates a fluid tight seal. The grafts may be sutured into the native vasculature.

Figure 17:
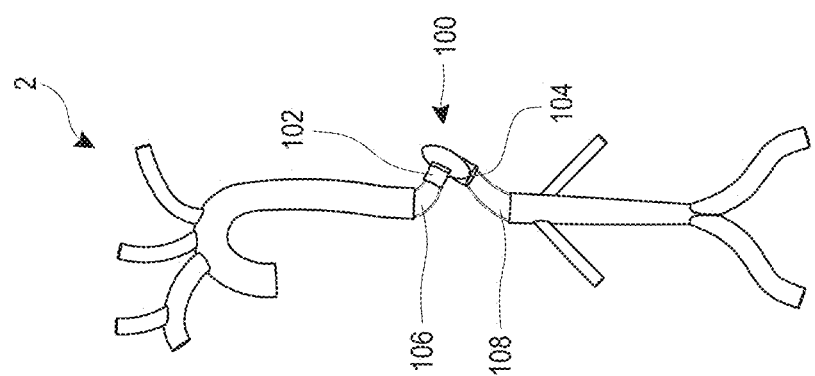
FIG. 17 schematically illustrates an example of an MCS installed in-series with a portion of the descending aorta in an angled configuration.

In some embodiments, the MCS 100 is installed at an angle relative to the axis of the aorta. For example, FIG. 17 schematically depicts an example of an MCS 100 installed in-series with the descending aorta, in which the inlet 102 and the outlet 104 of the MCS 100 are anastomosed to the aorta by an inlet graft 106 and an outlet graft 108. The grafts 106, 108 may extend from the axis of the aorta at an angle selected from a wide array of angles generally between 0 degrees and 90 degrees. For embodiments of the MCS 100 in which the inlet 102 is substantially perpendicular to the outlet 104 (i.e. 90 degrees), the sum of the angle of the inlet 102 relative to the aorta and the angle of the outlet 104 relative to the aorta is approximately 90 degrees, when the MCS 100 is installed within a generally straight portion of the aorta. For example, as shown in FIG. 17, the inlet 102 and outlet 104 of the MCS 100 are each arranged approximately 45 degrees relative to the descending aorta. The installation of the MCS 100 within the aorta, particularly at an angle, may somewhat displace or alter the orientation of the upstream and/or downstream portion of the aorta to which the MCS 100 is anastomosed.

In some embodiments in which neither the inlet 102 nor the outlet 104 of the MCS 100 is configured to be collinear with the aorta (the MCS 100 is laterally displaced from the aorta), the MCS 100 may be connected in-parallel with the aorta. In embodiments where the MCS 100 is connected in-parallel, the inlet and outlet grafts 106, 108 may be anastomosed with the native vasculature in a branched fashion. In some in-parallel embodiments, the native aorta may be occluded between the inlet graft 106 and the outlet graft 108, effectively making the MCS 100 in-series with the aorta. In some in-parallel embodiments, a one-way valve (e.g., a one-way artificial heart valve) may be installed in the native aorta between the inlet graft 106 and the outlet graft 108, permitting blood flow only in the downstream direction. Mechanically preventing upstream blood flow within the native aorta may advantageously prevent recirculation of blood along a path of least-resistance up the native aorta and back through the MCS 100 when installed in-parallel, which may excessively damage the blood and/or disrupt downstream blood flow.

Figure 18B:
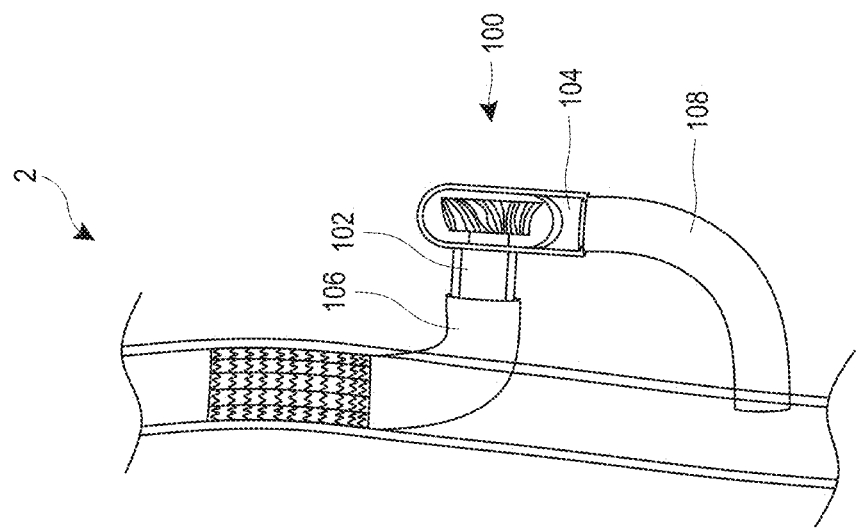
FIGS. 18A-18B schematically illustrate examples of an MCS installed in-parallel with a portion of the descending aorta in angled configurations.
Figure 18A:
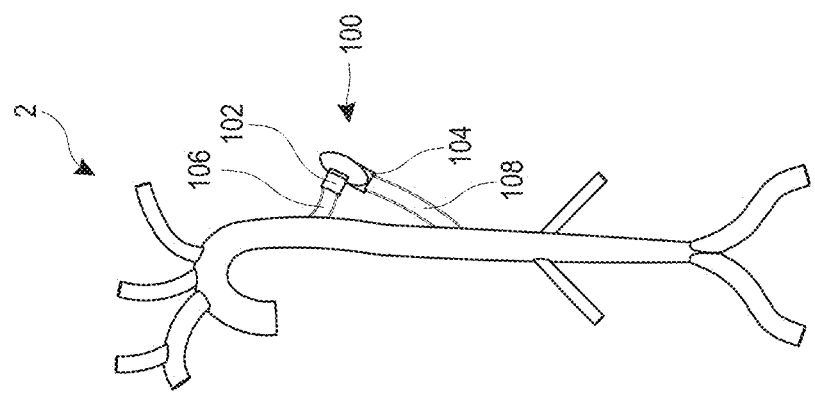

FIGS. 18A and 18B schematically depict an example of an MCS 100 installed in-parallel with the descending aorta. FIG. 18A shows the MCS 100 installed at approximately a 60 degree angle between the inlet 102 and aorta and approximately a 30 degree angle between the outlet 104 and aorta. FIG. 18B shows the MCS 100 installed at approximately a 90 degree angle between the inlet 102 and the aorta. The outlet 104 is parallel to the bottom portion of the aorta (i.e. 0 degrees) and connected via a curved outlet graft 108. In the example illustrated in FIG. 18B, the inlet and outlet grafts 106, 108 are substantially curved. Using curved grafts may allow the installation of the MCS 100 in the vasculature at sharper angles and/or may minimize the amount of space occupied by the grafts 106, 108 and the MCS 100. The curvature of the grafts may also effect vortex formation as described elsewhere herein. The grafts 106, 108 may be substantially rigid to support the MCS 100 within the vasculature. Grafts of various shapes or flexibility may be employed depending on the amount of curvature desired. Embodiments which use more moderate angles (e.g., 45 degrees) can be advantageous in that their installation can be accomplished using relatively short and/or relatively straight grafts 106, 108, which may minimize the total installation space of the MCS 100. Use of straight grafts 106, 108 may impart less turbulence on the blood flow than use of more curved grafts 106, 108.

Figure 19:
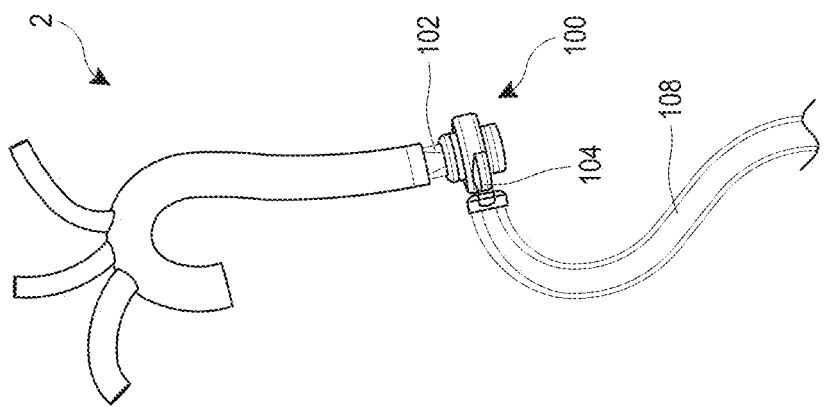
FIG. 19 schematically illustrates an example of an MCS installed collinear with a portion of the descending aorta using a question-mark shaped outlet graft.

In some embodiments, the outlet 104 of the MCS 100 is connected to a substantially curved graft 108 to return blood to the downstream portion of the aorta. The curved outlet graft 108 may extend from the outlet 104 of the MCS 100 in a direction substantially perpendicular to the inlet 102 and curve toward the downstream portion of the aorta until the graft 108 is substantially collinear with the aorta at which point the graft and downstream portion can be anastomosed. FIG. 19, schematically depicts an example of a MCS 100 installed in-series with the descending aorta, in which the inlet 102 is anastomosed to the upper portion of the descending aorta in a collinear manner or at a relatively small angle (e.g., 0-10 degrees) and the outlet 104 is anastomosed to the lower portion of the descending aorta via a generally "question mark" shaped outlet graft 108. This configuration may be advantageous in that it allows installation of the MCS 100 with both the inlet and outlet grafts 106, 108 anastomosed to the native vasculature in a generally collinear fashion. Collinear installation of the MCS 100 may minimize the amount of manipulation required in the native aorta to accommodate the MCS 100. Use of an outlet graft 108 with a large radius of curvature may minimize the amount of turbulence imparted to the blood flow through the MCS 100.

Figure 20:
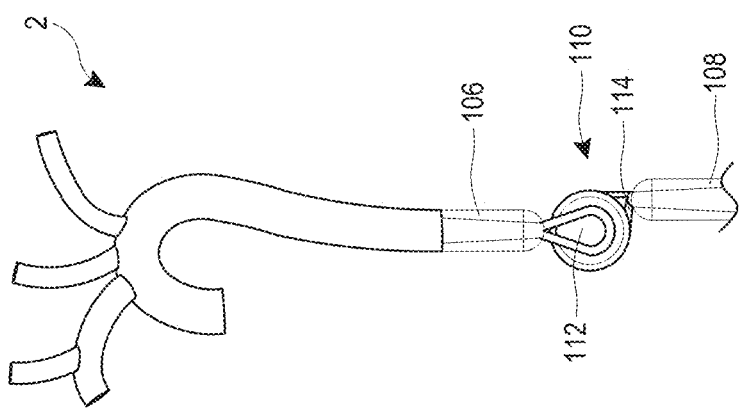
FIG. 20 schematically illustrates an example of a coaxial MCS comprising a 90 degree flow turn at the inlet installed in-series with a portion of the descending aorta.

In some embodiments, an MCS 110 may be installed within the aorta in a co-axial configuration, in which the inlet 112 and outlet 114 are not perpendicular but are coaxial, such that they inlet 112 and outlet 114 are parallel to a common axis, generally aligned with a longitudinal axis of the native aorta. FIG. 20 schematically depicts an example of a coaxial MCS 110 installed within the descending aorta. The inlet 112 includes a 90 degree bend, allowing the inlet graft 106 to remain collinear with the upper portion of the descending aorta. Blood flow enters the coaxial MCS 110 impeller from the 90 degree bend "sideways" with respect to a standing patient. The diffuser sends the blood flow vertically downward with respect to a standing patient. This configuration can result in minimal losses in pump efficiency at the inflow graft 106 as the pressure at that point is relatively low relative to other configurations. The remaining features of the MCS 110 may be the same as that of MCSs 100 installed in angled configurations. The coaxial configuration may result in the formation of a vortex at the MCS outlet 114. In embodiments comprising a sharp 90 degree bend in the inlet 112, the MCS 110 can be installed with relatively short grafts 106, 108 and with minimal installation space. The coaxial MCS 110 may be especially conducive to installation by minimally invasive surgery. In some embodiments, the downstream portion of the severed aorta may be slightly displaced upon installation, such as by 3-10 cm, for example. In other embodiments, the outlet 114 may bend to wrap partially around the body of the MCS 110 such that the inlet 114 and outlet 116 are collinear.

FIGS. 21A-21D schematically depict simulated fluid flow through MCS devices installed in-series with the aorta in various configurations. FIG. 21A shows a MCS 100 installed in an angled configuration with approximately 45 degree angles between the inlet 102 and aorta and the outlet 104 and aorta. FIG. 21B shows a MCS 100 installed in an angled configuration with an approximately 65 degree inlet 102 angle and an approximately 25 degree outlet 104 angle relative to the aorta. FIGS. 21C and 21D show MCSs 100 installed in angled configurations with an approximately 90 degree inlet 102 angles and approximately collinear (0 degree) outlets 104 relative to the aorta. The simulations depicted in FIGS. 21C and 21D may be used to approximate the fluid flow through a coaxial MCS 110 comprising a 90 degree bend in the MCS inlet 112. The example shown in FIG. 21C has a 25 mm radius at the inlet 112 and the example shown in FIG. 21D has a 15 mm radius at the inlet 112. The coaxial MCSs 110 shown in FIGS. 21C and 21D show no discernible vortices in the outflow. The angled MCSs 100 shown in FIGS. 21A and 21B show discernible vortex formation in the outflow of each. The simulation results suggest that bending in the outlet may create more fluid vortices than does bending in the inlet. The relatively low pressure at the inlet 102 and the relatively high pressure at the outlet 104, of the angled MCS devices 100, may stimulate vortex formation. The size of the diffuser at the outlet may also effect vortex formation.

Vortex formation in the outflow of the MCS 100, 110 may be beneficial. For instance, vortex flow may enhance the perfusion of side arteries branching from the aorta and/or may enhance washout in the descending aorta. Using the MCS to recreate physiological flow conditions may reduce the risk of thrombosis or other pathological conditions. Studies have shown the identification of right-handed helix formation through the ascending aorta and aortic arch into the descending aorta during systolic outflow in healthy individuals. See Markl, M. et al. (July 2004). Time-Resolved 3-Dimensional Velocity Mapping in the Thoracic Aorta: Visualization of 3-Directional Blood Flow Patterns in Healthy Volunteers and Patients, *Journal of Computer Assisted Tomography,* 28(4), 459-468 (in corporated herein by reference). In some embodiments, the MCS and/or the installation of the device may be configured to optimize vortex formation (e.g., to form a right-handed helix) in the outflow of the device. For example, the direction of impeller rotation, orientation of the diffuser, inflow angle, outflow angle, inlet diameter, and/or outlet diameter may be selected to emulate optimal physiological conditions, including a weak vortex. Depending on the geometry of the MCS, these parameters may be used to either increase or decrease the amount of vortex formation to mimic that of the native aorta. Prior MCS devices have aimed to eliminate any vortex formation altogether.

Figure 22A:
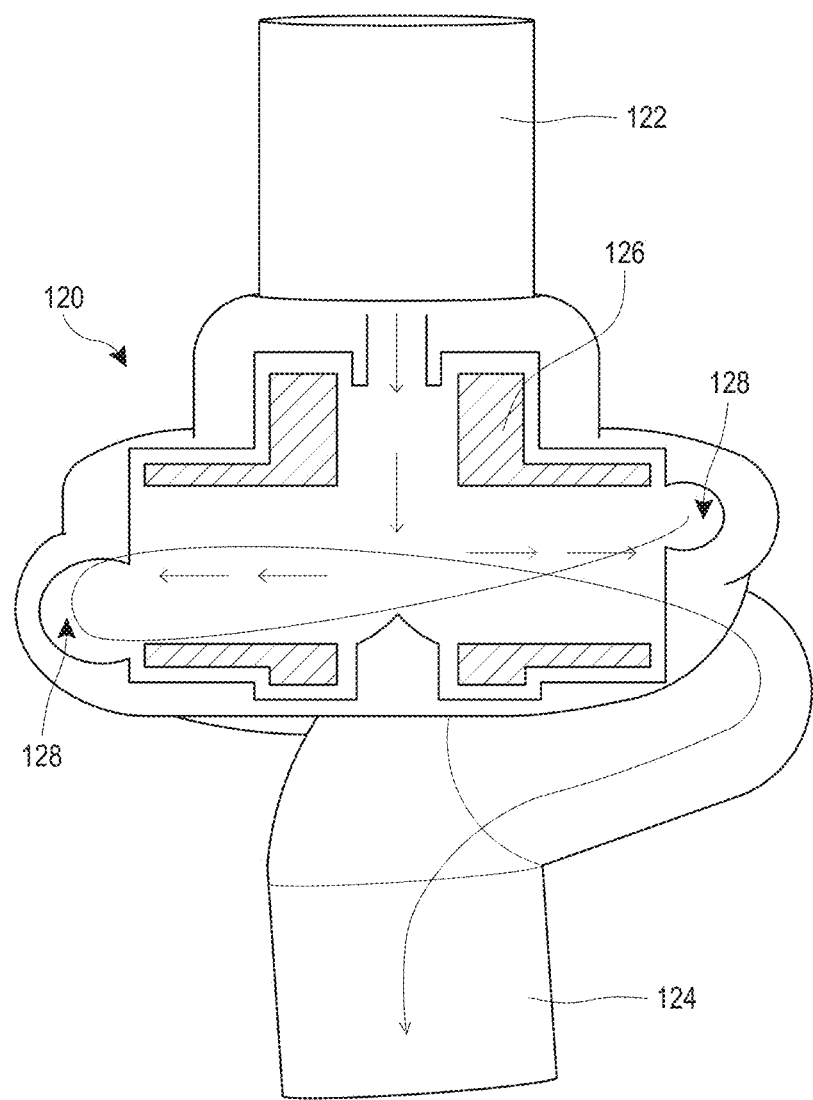
FIGS. 22A-22C schematically illustrate an example of a collinear MCS with a wrap-around diffuser and volute passage.
Figure 22C:
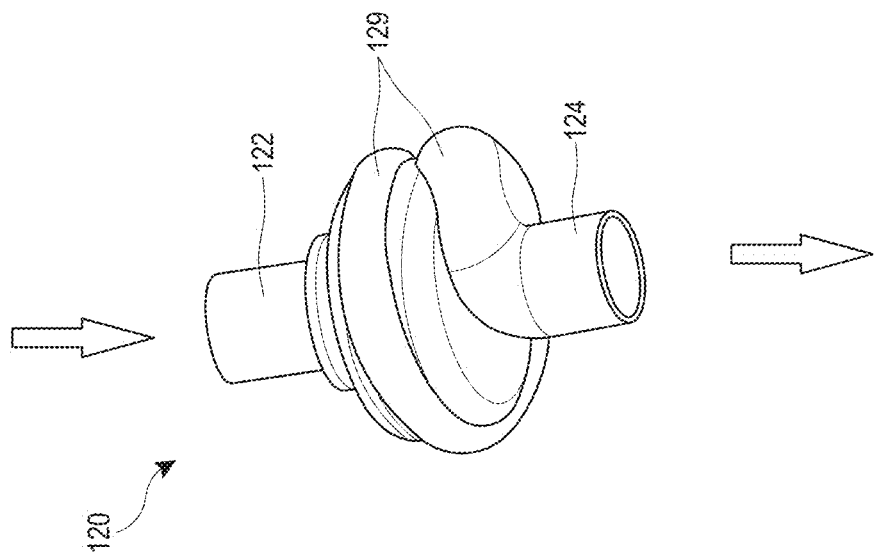
Figure 22B:
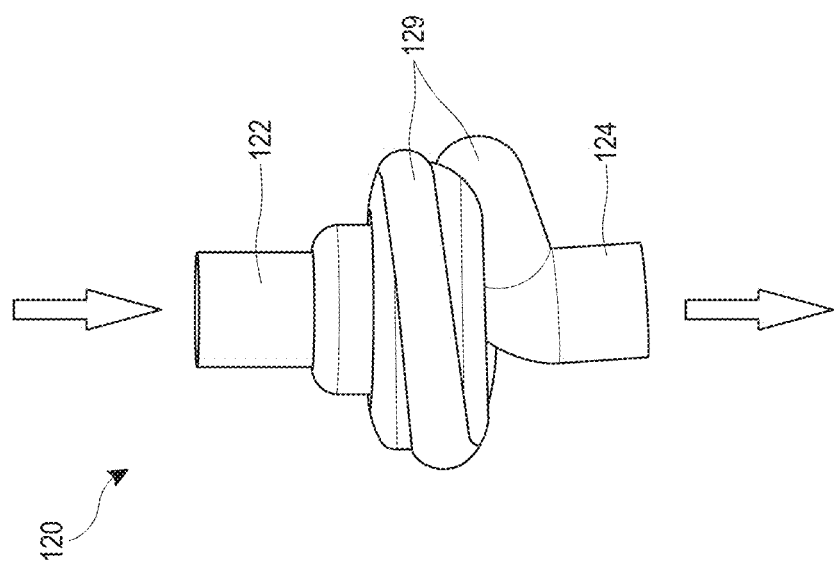

In some embodiments, the MCS is collinear with both the upper portion and the lower portion of the aorta, so that there is no axial or angular displacement in the inflow or outflow. FIGS. 22A-22C illustrate an example of a collinear MCS 120. FIG. 22A schematically illustrate a cross section of an example of a collinear MCS 120, including an impeller 126 and diffuser 128. FIGS. 22B and 22C illustrate perspective views of an example of a collinear MCS 120. The inlet 122 of the MCS 120 may be grafted directly in-line with the upper portion of the descending aorta. In some variations, the inlet 122 may include pre-swirl stationary vanes (not shown) above the impeller 126, described elsewhere herein. Blood may be pushed by the impeller 126 in a radially outward direction into the diffuser 128. The diffuser 128 may reorient the outflow from a radial direction, aligned 90 degrees relative to the inflow, to an axial direction, aligned collinear with the inflow and with the lower portion of the descending aorta. The diffuser scroll 129 may wrap-around the casing of the MCS 120. The diffuser scroll 129 may extend inward toward the longitudinal axis of the MCS 120 once it extends below the bottom of the MCS 120 casing. The diffuser scroll 129 may extend in a spiral/helical fashion. In some implementations, the diffuser scroll 129 may progressively turn toward the axial direction as it wraps around the casing. The diffuser scroll 129 may gradually shift flow from a circumferential to an axial direction or may turn to the axial direction primarily near the outlet 124. The wrap-around diffuser 128 sends flow vertically downward and may terminate in a funnel-like shape at the outlet 124 with an expanding diameter. The diameter of the diffuser scroll 129 may increase as it extends from the impeller 126 toward the outlet 124. As seen in the cross-section of FIG. 22A, the cross-section of the diffuser scroll 129 may be smaller on one side of the MCS 120 (e.g., the right side of the figure) than the other side (e.g., the left side of the figure). Blood may travel through the diffuser scroll 129 along the direction of the diffuser's increasing size. The helical direction of blood flow through the diffuser 128 is schematically illustrated by the continuous arrow in FIG. 22A. The increasing diameter of the diffuser 128 may promote vortex formation in the outflow.

The diffuser 128 may perform only a partial revolution around the axis of the MCS 120, a single revolution, multiple revolutions, or any degree of revolutions there between. For example, the diffuser 128 may make a half turn, a three-quarter turn, a whole turn, one and a half turns, two turns, two and a half turns, three turns, etc., before terminating at the outlet 124. The azimuthal turning in the scroll 129 from point 321 of the diffuser 320 to the end of the turning in the scroll 129 could be any angle or could be at a varying angle. The diffuser 128 may make a sharp bend in the axial direction just before reaching the outlet 124. The wrap-around design may be useful for inducing vortex formation in the outflow of the MCS 120. The design parameters of the diffuser 128 may be altered to optimize helix formation. These may include the diameter of the diffuser 128, the change in the diameter of the diffuser 128, the number of revolutions made by the diffuser 128, the pitch of the turns, and the sharpness in the bend toward the axial direction, particularly toward the outlet. The configuration of the collinear MCS 120 may be relatively compact. The wrap-around diffuser 128 may minimize the overall diameter of the MCS 120. The collinear configuration may reduce the length of inlet and/or outlet grafts 106, 108, thus reducing the overall axial length of the MCS 120. The generally small size of the collinear MCS 120 may make it particularly conducive for installation via minimally invasive surgery.

Figure 23A:
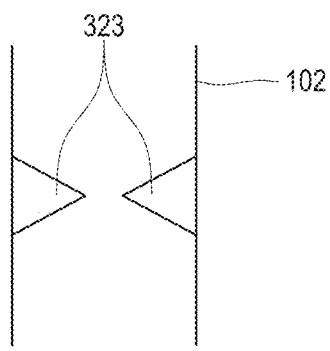
FIGS. 23A-23E schematically illustrate examples of vanes positioned within the inflow or outflow paths of an MCS for altering fluid flow.
Figure 23B:
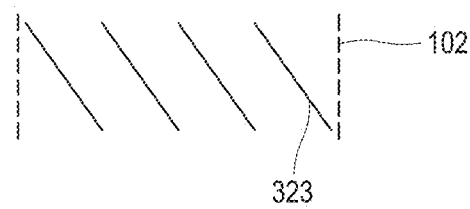

The MCS 100 (and other MCSs disclosed herein) may employ stationary vanes to further alter the inflow and/or outflow of blood through the device. In some embodiments, the MCS 100 may include stationary pre-swirl vanes 323 (also known as inlet guide vanes). FIG. 23A schematically depicts a side view of an inlet 102 comprising stationary pre-swirl vanes 323. FIG. 23B schematically depicts an opened/flattened circumferential portion of inlet 102 comprising stationary pre-swirl vanes 323. One or more of these vanes 323 may extend from the inner circumference of the inlet 102 into the axial flow path of the introduced blood. The vanes 323 may be substantially flat. In other embodiments, the vanes 323 may have a curved surface. The vanes 323 may curve the blood flow in the direction of impeller rotation. In some implementations, the curves may curve the flow in the direction of the native aortic passage vortex. As shown in FIG. 23A, the vanes 323 may decrease in width as they extend from the inner diameter of the inlet 102 toward the longitudinal axis of the inlet 102. In some embodiments, the vanes may extend to the longitudinal axis. The decreasing width may allow the accommodation of adjacent vanes 323 around the circumference of the inlet 102. As shown in FIG. 23B, the vanes 323 may be angled with respect to the circumference of the inlet such that they extend partially in a circumferential direction and partially in an axial direction. The vanes 323 may all be identical in shape or they may vary in shape. The vanes 323 may all extend at the same angle relative the circumference and longitudinal axis or they may extend at different angles. In some implementations, as shown in FIG. 23A, the vanes 323 may be configured such they cumulatively occupy the entire cross section of the inlet 102, but because they are angled blood may flow between the vanes 323. In some embodiments, the vanes 323 may partially overlap each other in the axial direction. In some embodiments, the vanes 323 do not occupy the entire cross section of the inlet 102, such that blood could potentially flow in a purely axial direction between the vanes 323. The vanes 323 may pre-swirl the blood entering the MCS 100 prior to reaching the impeller 200. The vanes 323 may improve fluid dynamics of blood flow through the MCS 100 (add a rotational velocity to the blood flow) at the cost of increased friction with the blood. The improved fluid dynamics may be used to adjust the flow rate and/or improve the efficiency of the turbomachine. For example, the vanes 323 may allow increased rotational speed with reduced motor power. In some embodiments, there may be multiple rows of pre-swirl vanes 323 along the axial direction. In some embodiments, the vanes 323 may not all be positioned at the same axial position but may be axially spaced from each other (e.g., in a helical formation). In some embodiments including pre-swirl vanes 323, pre-swirl vanes 323 may be directly incorporated into the upper channel 203 of the impeller in addition to or alternatively to the inlet 102.

In some embodiments, the vanes 323 may be incorporated into the outlet 104 in addition to or alternatively to the inlet 102.

Figure 23C:
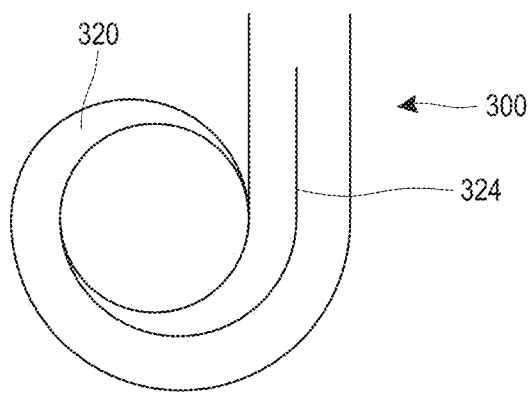
Figure 23D:
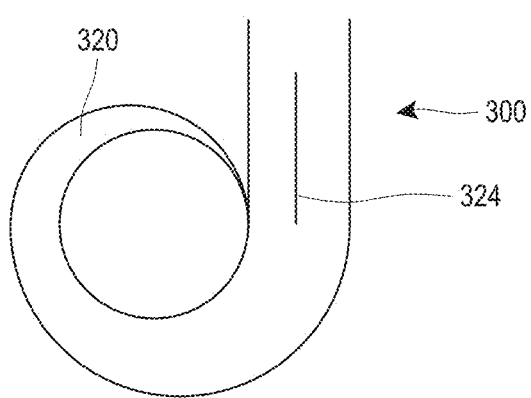
Figure 23E:
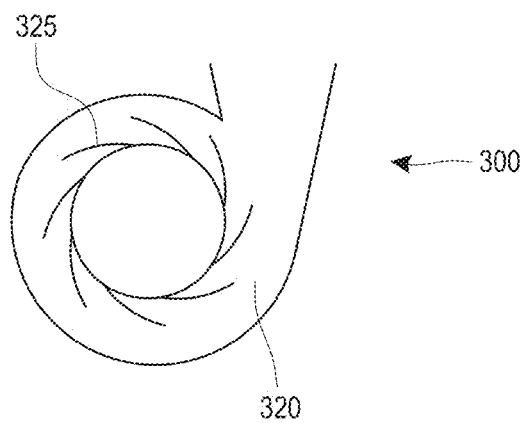

In some embodiments, the MCS 100 may include a vaned diffuser 320 (and/or a vaned volute extending at the terminal end of the diffuser 320). The vaned diffuser 320 may be used to optimize fluid dynamics, such as vortex formation, in the outflow of the device. FIG. 23C schematically illustrates an example of a top cross-section of a casing 300 comprising a diffuser 320 with a single splitter vane 324 which creates a split double volute at the outlet 104, comprising two parallel fluid passages. One or more splitter vanes 324 may be used to even out flow distribution, particularly between the inner side of the volute (left side of FIG. 23C) and the outer side of the volute (right side of FIG. 23C). FIG. 23D, schematically illustrates a variation of the split diffuser shown in FIG. 23C, in which the diffuser vane 324 only extends partially or not at all into the circumferential diffuser 320 passage (the portion of the passage prior to the straight volute passage). In some embodiments, the splitter vane(s) 324 is not a wall aligned purely with the axial direction of the device. The splitter vane(s) 324 may rotate relative to the cross-sectional circumference of the passage as it extends along the diffuser and/or volute. The use of a rotating splitter vane(s) 324 may add rotational velocity to the blood outflow and may be used to help emulate the naturally occurring vortex formation in the healthy aorta. FIG. 23E schematically illustrates an example of a casing 300 with a vaned diffuser comprising a plurality of diffuser vanes 325 surrounding the inner circumference of the diffuser 320. The diffuser vanes 325 may be slightly curved in a direction configured to orient the blood toward the outlet 104. The diffuser vanes may be uniformly spaced around the circumference of the diffuser 320. In some embodiments, not all portions of the circumference of the diffuser 320 may incorporate diffuser vanes. The diffuser vanes 325 may be used to improve distribution of fluid flow within the diffuser 320. Similar to the stationary pre-swirl vanes 323, the vanes within the diffuser and/or volute may impart additional friction to the blood.

The embodiments disclosed herein may be designed with considerations from the following references in mind, each of which is hereby incorporated by reference in its entirety. Considerations for geometric optimization of centrifugal impellers related to MCSD specifications of pressure rise, flow rate, diameter and rotational speed are described by: Korakianitis, T., Rezaienia, M. A., Paul, G. M., Rahideh, A., Rothman, M. T., Mozafari, S., "Optimization of Centrifugal Pump Characteristic Dimensions for Mechanical Circulatory Support Devices" (2016) ASAIO Journal, 62 (5), pp. 545-551; and Mozafari, S., Rezaienia, M. A., Paul, G. M., Rothman, M. T., Wen, P., Korakianitis, T., "The Effect of Geometry on the Efficiency and Hemolysis of Centrifugal Implantable Blood Pumps" (2017) ASAIO Journal, 63 (1), pp. 53-59.

The machinability of centrifugal impellers is described by: Paul, G., Rezaienia, A., Avital, E., Korakianitis, T., "Machinability and optimization of shrouded centrifugal impellers for implantable blood pumps" (2017) Journal of Medical Devices, Transactions of the ASME, 11 (2), art. no. 021005. The effects of a patient's motion on device operation are described by: Paul, G., Rezaienia, A., Shen, X., Avital, E., Korakianitis, T., "Slip and turbulence phenomena in journal bearings with application to implantable rotary blood pumps" (2016) Tribology International, 104, pp. 157-165; and Paul, G., Rezaienia, M. A., Rahideh, A., Munjiza, A., Korakianitis, T., "The Effects of Ambulatory Accelerations on the Stability of a Magnetically Suspended Impeller for an Implantable Blood Pump" (2016) Artificial Organs, 40 (9), pp. 867-876.

The effects of device implantation in the descending aorta are described by Rezaienia, M. A., Paul, G., Avital, E. J., Mozafari, S., Rothman, M., Korakianitis, T. "In-vitro investigation of the hemodynamic responses of the cerebral, coronary and renal circulations with a rotary blood pump installed in the descending aorta" (2017) Medical Engineering and Physics, 40, pp. 2-10; Rezaienia, M. A., Paul, G., Avital, E., Rahideh, A., Rothman, M. T., Korakianitis, T., "In-vitro investigation of cerebral-perfusion effects of a rotary blood pump installed in the descending aorta" (2016) Journal of Biomechanics, 49 (9), pp. 1865-1872; Rezaienia, M. A., Rahideh, A., Alhosseini Hamedani, B., Bosak, D. E. M., Zustiak, S., Korakianitis, T., "Numerical and In Vitro Investigation of a Novel Mechanical Circulatory Support Device Installed in the Descending Aorta" (2015) Artificial Organs, 39 (6), pp. 502-513; and Rezaienia, M. A., Rahideh, A., Rothman, M. T., Sell, S. A., Mitchell, K., Korakianitis, T., "In vitro comparison of two different mechanical circulatory support devices installed in series and in parallel" (2014) Artificial Organs, 38 (9), pp. 800-809.

Considerations for MCSD electric motor design are described by: Rahideh, A., Mardaneh, M., Korakianitis, T., "Analytical 2-D calculations of torque, inductance, and back-EMF for brushless slotless machines with surface inset magnets" (2013) IEEE Transactions on Magnetics, 49 (8), art. no. 6418033, pp. 4873-4884; Rahideh, A., Korakianitis, T., "Analytical calculation of open-circuit magnetic field distribution of slotless brushless PM machines" (2013) International Journal of Electrical Power and Energy Systems, 44 (1), pp. 99-114; Rahideh, A., Korakianitis, T., "Analytical magnetic field distribution of slotless brushless PM motors. Part 2: Open-circuit field and torque calculations" (2012) IET Electric Power Applications, 6 (9), pp. 639-651; Rahideh, A., Korakianitis, T., "Analytical magnetic field distribution of slotless brushless permanent magnet motors—Part I. Armature reaction field, inductance and rotor eddy current loss calculations" (2012) IET Electric Power Applications, 6 (9), pp. 628-638; Rahideh, A., Korakianitis, T., "Analytical magnetic field calculation of slotted brushless permanent-magnet machines with surface inset magnets" (2012) IEEE Transactions on Magnetics, 48 (10), art. no. 6203591, pp. 2633-2649; Rahideh, A., Korakianitis, T., "Subdomain Analytical Magnetic Field Prediction of Slotted Brushless Machines with Surface Mounted Magnets" (2012) International Review of Electrical Engineering, 7 (2), pp. 3891-3909; Rahideh, A., Korakianitis, T., "Analytical armature reaction field distribution of slotless brushless machines with inset permanent magnets" (2012) IEEE Transactions on Magnetics, 48 (7), art. no. 6126045, pp. 2178-2191; Rahideh, A., Korakianitis, T., "Brushless DC motor design using harmony search optimization" (2012) Proceedings-2011 2nd International Conference on Control, Instrumentation and Automation, ICCIA 2011, art. no. 6356628, pp. 44-50; Rahideh, A., Korakianitis, T., "Analytical open-circuit magnetic field distribution of slotless brushless permanent-magnet machines with rotor eccentricity" (2011) IEEE Transactions on Magnetics, 47 (12), art. no. 5893946, pp. 4791-4808; Rahideh, A., Korakianitis, T., "Analytical magnetic field distribution of slotless brushless machines with inset permanent magnets" (2011) IEEE Transactions on Magnetics, 47 (6 PART 2), art. no. 5706366, pp. 1763-1774; and Rahideh, A., Korakianitis, T., Ruiz, P., Keeble, T., Rothman, M. T., "Optimal brushless DC motor design using genetic algorithms" (2010) Journal of Magnetism and Magnetic Materials, 322 (22), pp. 3680-3687.

Numerical simulations of the cardiovascular system with implanted MCSDs are described by: Shi, Y., Korakianitis, T., Bowles, C., "Numerical simulation of cardiovascular dynamics with different types of VAD assistance" (2007) Journal of Biomechanics, 40 (13), pp. 2919-2933; Korakianitis, T., Shi, Y., "Numerical comparison of hemodynamics with atrium to aorta and ventricular apex to aorta VAD support" (2007) ASAIO Journal, 53 (5), pp. 537-548; Shi, Y., Korakianitis, T., "Numerical simulation of cardiovascular dynamics with left heart failure and in-series pulsatile ventricular assist device" (2006) Artificial Organs, 30 (12), pp. 929-948; Korakianitis, T., Shi, Y., "Effects of atrial contraction, atrioventricular interaction and heart valve dynamics on human cardiovascular system response" (2006) Medical Engineering and Physics, 28 (8), pp. 762-779; Korakianitis, T., Shi, Y., "A concentrated parameter model for the human cardiovascular system including heart valve dynamics and atrioventricular interaction" (2006) Medical Engineering and Physics, 28 (7), pp. 613-628; and Korakianitis, T., Shi, Y., "Numerical simulation of cardiovascular dynamics with healthy and diseased heart valves" (2006) Journal of Biomechanics, 39 (11), pp. 1964-1982.

Devices for emulating the human cardiovascular system for in-vitro testing of VADs and MCSD are described by: Ruiz, P., Rezaienia, M. A., Rahideh, A., Keeble, T. R., Rothman, M. T., Korakianitis, T., "In vitro cardiovascular system emulator (Bioreactor) for the simulation of normal and diseased conditions with and without mechanical circulatory support" (2013) Artificial Organs, 37 (6), pp. 549-560.

In some embodiments, an MCS installed in-series with the vasculature may comprise turbomachinery configured to be installed within the vasculature such that the vasculature need not be severed as described elsewhere herein. For instance, the MCS may comprise turbomachinery, including a rotor, which is installed into the lumen of the aorta for assisting blood flow through the aorta. The MCS may be installed in the descending aorta as described elsewhere herein or may be installed in other portions of the aorta. The MCS device may be installed in other blood vessels as well. In some implementations, the MCS may be installed percutaneously through a catheter such as through the femoral artery or via any other suitable site. The MCS device may comprise a folded configuration configured for intravascular delivery and a deployed or expanded configuration configured for operation within the blood vessel as described elsewhere herein. In some implementations, the MCS device may be surgically inserted into the blood vessel through an incision in the blood vessel. The device may be surgically implanted through an incision in the chest such as through a thoracotomy. The descending aorta may be particularly conducive to installation via minimally invasive surgery because of its location, especially compared to the ascending aorta. Devices comprising intravascular rotors may be particularly suitable for treatment of late stage II or early stage III CHF. The devices may be configured to provide a pressure rise in the range of about 20 to about 50 mm Hg. In some embodiments, the devices may be configured to maintain a blood flow rate of about 5 L/min. In some embodiments, the devices may be configured maintain a blood flow rate of about 8 L/min. In some embodiments, the device may be configured to maintain a blood flow rate between about 5 L/min and about 8 L/min. In some embodiments, the device may be configured to operate at about 12,000 rpm. As described elsewhere herein, turbomachines are configured for specific angles of attack with respect to fluid flow and must be operated substantially close to their design points, such as with respect to pressure rise, flow rate, rpm, etc., or efficiency losses, shear stress, and/or turbulence may result from the consequent separation between the fluid flow and the blades. Operating a turbomachine outside of its designed operating parameters could eventually lead to device stalls. MCS devices which are configured to generate pressure rises less than the full physiological pressure of approximately 120 mmHg, may be smaller, require less power, and easier to surgically implant. Accordingly, such devices are also more suitable for transcutaneous energy transmission via TET.

Figure 24B:
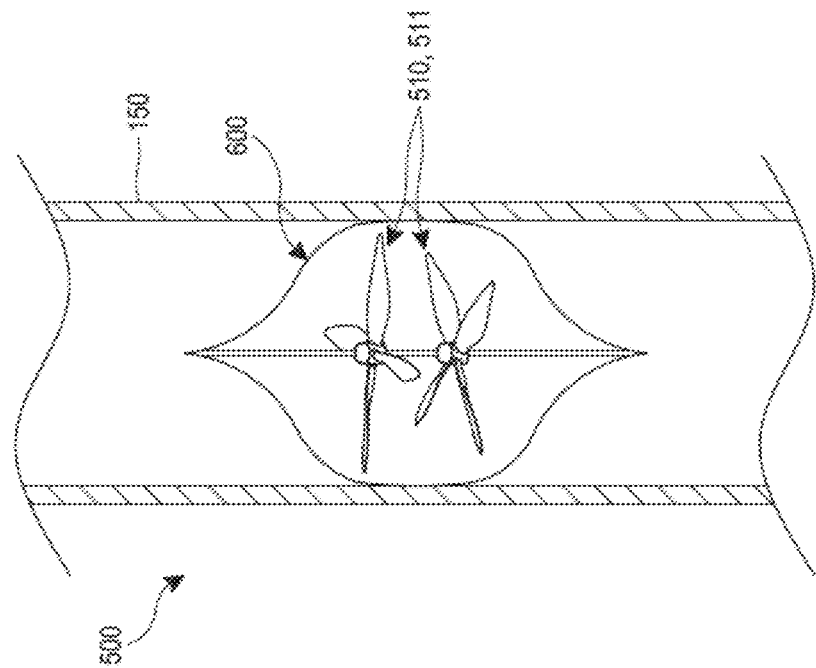
FIGS. 24A-24F schematically illustrate examples of MCS devices configured for installation in the lumen of a blood vessel.
Figure 24A:
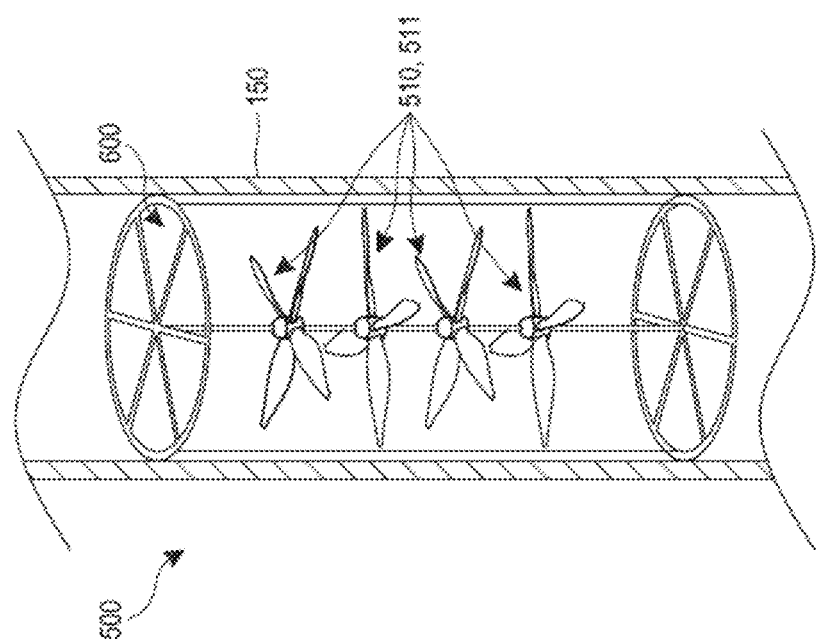
Figure 24D:
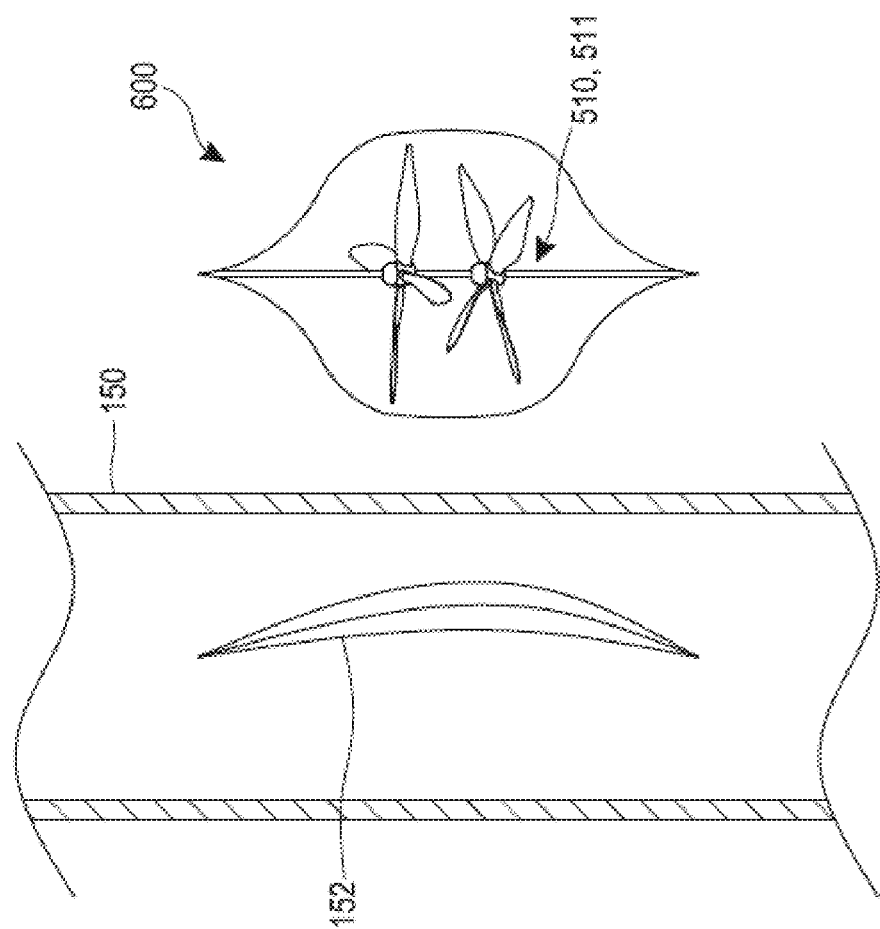
Figure 24C:
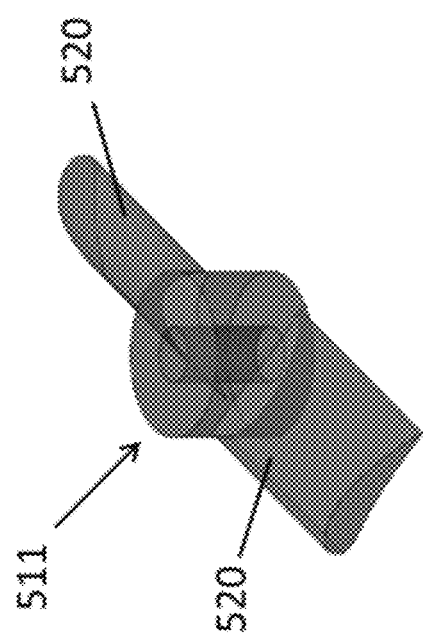

FIGS. 24A and 24B schematically illustrate examples of MCS devices 500 configured for installation in the lumen of a blood vessel. In some embodiments, the MCS 500 may comprise one or more rotors 510. The rotors 510 may comprise propellers 511. The propellers 511 may comprise one or more radially extending blades 520 configured to transfer force to the blood flowing through the vasculature. FIG. 24C illustrates an example of a propeller 511 having two diametrically opposed blades 520. The MCS device 500 may comprise an anchoring mechanism 600 for anchoring the turbomachinery within the blood vessel. The anchoring mechanism 600 may be a cage or other support structure configured to surround the turbomachinery and to allow blood flow to pass through. In some embodiments, the anchoring mechanism 600 may have a barrel-shape configuration as shown in FIG. 24A. In some embodiments, the anchoring mechanism may have a football-shape configuration as shown in FIG. 24B, in which the cage structure may comprise upstream and downstream points substantially aligned with the axis of rotation of the one or more rotors 510. The anchoring mechanisms 600 may be configured to hold the MCS device 500 in place within the blood vessel through pressure exerted on the blood vessel wall at points where the anchoring mechanism 600 contacts the blood vessel. The anchoring mechanism 600 may be expandable as described elsewhere herein.

Figure 24F:
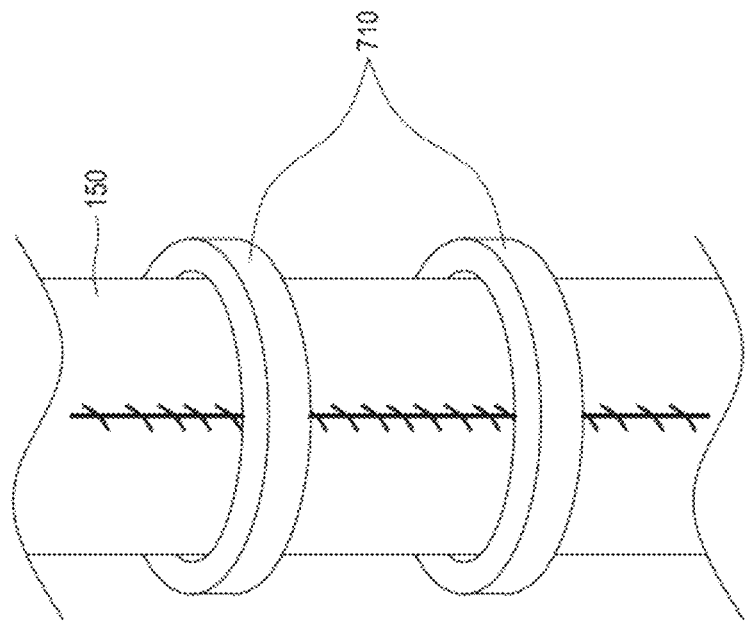
Figure 24E:
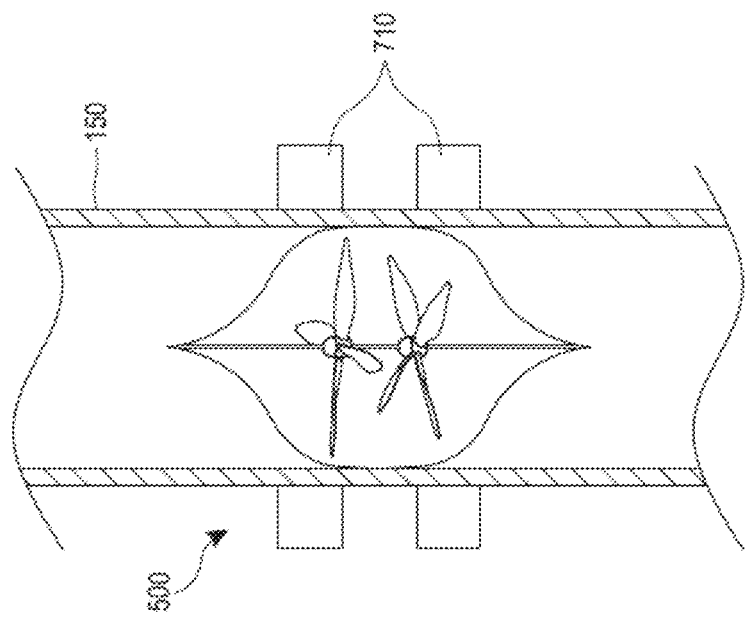

In some implementations, the MCS device 500 may be installed surgically in a blood vessel 150. FIGS. 24D-24F, schematically illustrates the surgical installation of an MCS device 500. An incision 152 may be made in the blood vessel, as shown in FIG. 24D. In some embodiments, after installation of the MCS device 500 in the blood vessel 150, one or more stators 710 may be positioned around the outside of the blood vessel 150, as described elsewhere herein. The stators 710 may be positioned after the incision 152 is sutured. FIG. 24E schematically illustrates a cross section of the MCS device 500 installed in the blood vessel 150. FIG. 24F schematically illustrates a side view of the MCS device 500 installed in the blood vessel 150 with the incision 150 sutured and the stators 710 (comprising electromagnetic coils) enclosed around the blood vessel 150. In some implementations, the MCS device 500, or at least the rotor 510 and anchoring mechanism 600, may be percutaneously installed as described elsewhere herein.

Figure 25C:
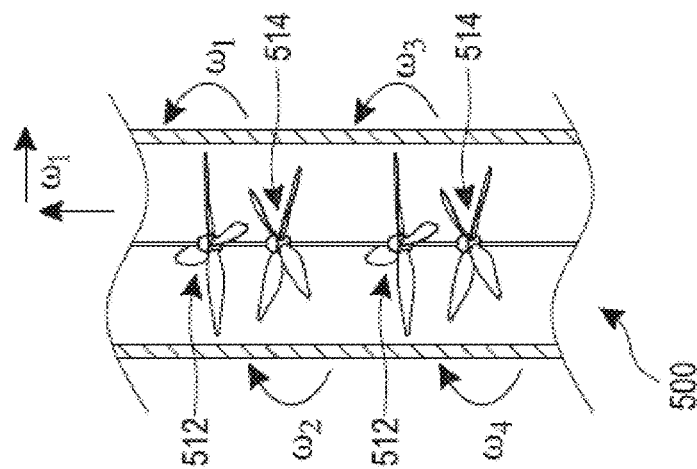
FIGS. 25A-25C schematically illustrate examples of MCS devices comprising one propeller, two propellers, and four propellers, respectively.
Figure 25B:
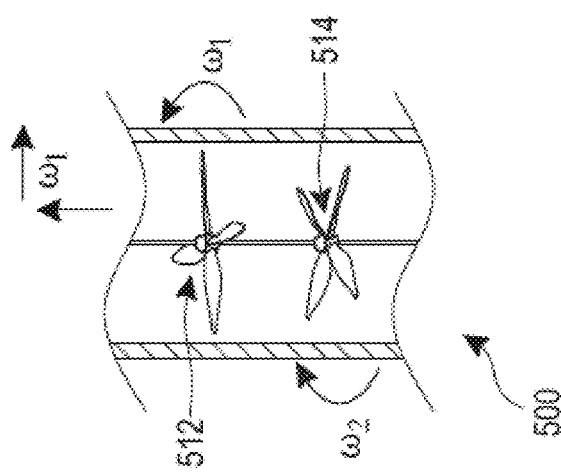
Figure 25A:
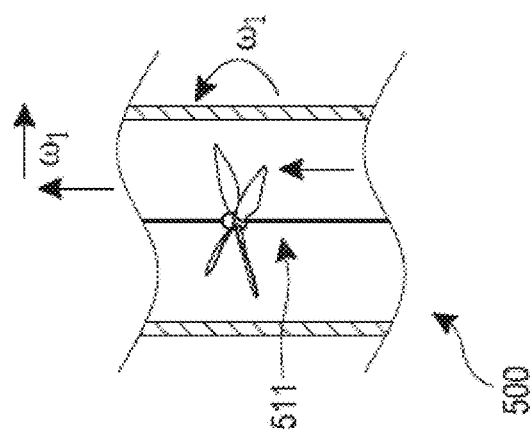

In some embodiments, the MCS device 500 may comprise more than one rotor 510. Each rotor 510 may comprise a propeller 511 configured to rotate independently of the propellers of other rotors. A propeller 511 may be considered one or more radially extending blades 520 which are aligned at a given axial position of the MCS device 500. In some embodiments, one or more rotors 500 may comprise more than one propeller 511 or rows of blades 520. The propellers 511 of the same rotor 510 may be configured to rotate together. FIGS. 25A-25C schematically illustrate embodiments comprising one propeller, two propellers, and four propellers, respectively. Each propeller 511 may be its own rotor 510 and configured to rotate at an angular velocity, w, independent of the other rotors/propellers 510/511. The propellers 511 may impart a velocity on blood flowing through the vasculature in which the MCS device 500 is installed. The one or more propellers 511 may be aligned along an axial dimension of the blood vessel. The axial dimension may extend parallel to the overall direction of blood flow within the vessel (upstream to downstream) and define a central axis of the MCS device 500. The axis of rotation of the one or more propellers 511 may be aligned substantially along the central axis of the MCS device 500. The axis of rotation of each of the propellers 511 may be aligned such that they are collinear. In some embodiments, the axis of rotation of each of the propellers 511 may be parallel but not collinear.

The blades 520 of the propeller 511 may impart a velocity on the blood having an axial component and a tangential component, the tangential component being orthogonal to the axial component. Blood flow through the native vasculature, such as the descending aorta, may comprise an axial component and a tangential component, such that a helical blood flow pattern is formed in healthy vessels, such as the right-handed helix described elsewhere herein. The axial component may be substantially larger than the tangential component in healthy blood flow. Efficiency tests including flow visualization experiments and mathematical modeling have shown that MCS devices having only a single propeller impart a large tangential velocity on blood flow passing through the MCS. The imparted tangential velocity component is much larger than the tangential component of healthy helical flow described elsewhere herein, thus inputting a large amount of peripheral kinetic energy into the blood. The large tangential velocity component imparted by a single propeller can be reduced or eliminated by pairing the propeller with a contra-rotating propeller. The contra-rotating propeller may be positioned axially adjacent (e.g., downstream) the first propeller and may be configured to rotate in an opposite direction than the first propeller (e.g., clockwise vs. counter-clockwise or vice-versa). The contra-rotating propeller can be used to modulate the tangential velocity component at the output of the second propeller of the pair such that the tangential velocity component is between 0 and the tangential velocity component of the first propeller of the pair. The contra-rotating propeller may change the direction of the tangential velocity component but the magnitude of the tangential velocity component may be less than the magnitude of the tangential velocity component resulting from the first propeller. In some embodiments, an MCS device 500 may comprise one or more pairs of contra-rotating propellers 512, 514 such that the MCS device 500 comprises an even number of propellers (e.g., 2, 4, 6, 8, 10, etc.). In some embodiments, the final (most downstream) propeller 511 may be configured result in a blood flow at the outlet of the MCS device having a small tangential velocity component. For example, the blood flow at the outlet may comprise axial and tangential velocity components replicating the velocity components of natural helical blood flow in healthy individuals, as described elsewhere herein.

Figure 26:
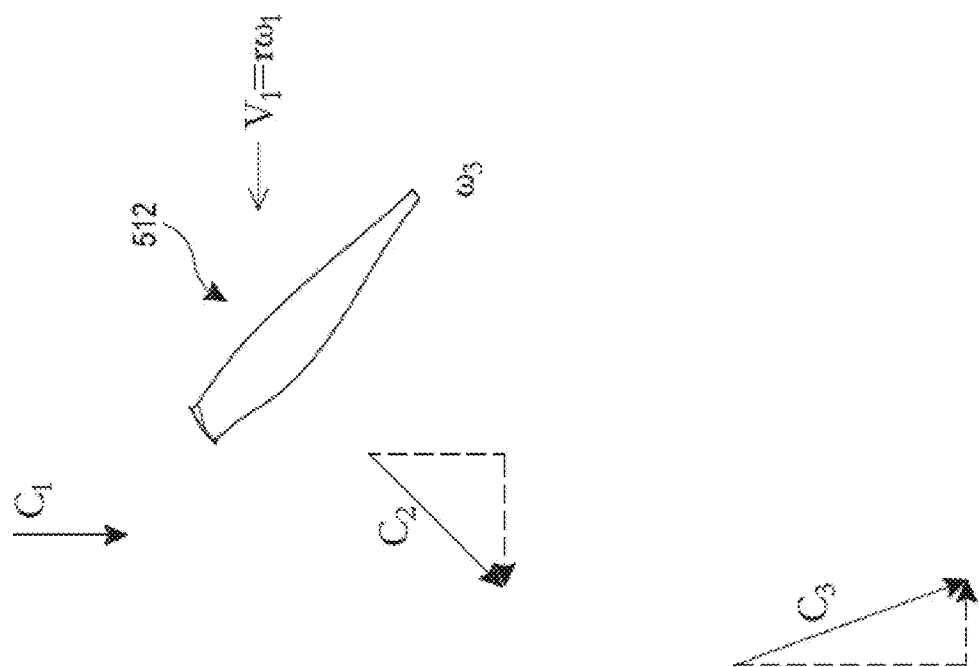
FIG. 26 schematically illustrates the velocity vectors of blood flow passing through a pair of contra-rotating propellers.

FIG. 26 schematically illustrates the velocity vectors of blood flow passing through a pair of contra-rotating propellers 512, 514. The tangential velocity of the propeller blades 520 is defined at each point by $v=wr$, wherein v is the tangential velocity, w is the angular velocity and r is the radius of the blade 520 at that point relative to the axis of rotation. The absolute velocity of the blood flow (e.g., the average velocity) is represented by the vectors $c_1$, $c_2$, and $c_3$. Vector $c_1$ represents blood flow entering the first propeller 512 of the pair, which may be the first encountered propeller 511 of the MCS device 500. Vector $c_1$ may be substantially axial in direction, having little or no tangential velocity. In some implementations, vector $c_1$ may have a small tangential velocity component from the natural helical blood flow of the blood vessel, particularly if the blood vessel is the aorta. Vector $c_2$ represents blood flow between the first propeller 512 and the second propeller 514. The first propeller 512 may impart a substantial tangential velocity component to the blood flow such that the blood flow comprises both a substantial tangential velocity component and a substantial axial velocity component. Vector $c_3$ represents blood flow output from the second propeller 514, which is configured to rotate in an opposite direction of the first propeller 512. The second propeller 514 may dampen the tangential velocity component. In some implementations, the second propeller 514 may reverse the direction of the tangential velocity component. The magnitude (absolute value) of the tangential velocity component of vector $c_3$ may be less than that of vector $c_2$. The magnitude of the tangential velocity component of vector $c_3$ may be the same, greater than, or less than the tangential velocity component of vector $c_1$. Each propeller 511 of the pair of contra-rotating propellers 512, 514 may add to the axial velocity component of the blood flow. For example, the axial component of vector $c_2$ may be greater than that of vector $c_1$. The axial component of vector $c_3$ may be greater than that of vector $c_2$. For MCS devices comprising more than two propellers 511, each propeller 511 may be configured to add to the axial velocity component of the blood flow such that the axial velocity of the blood is continually increased as it passes through the MCS device.

The final velocity vector at the output of the MCS device 500 may be modulated by the blade geometry (e.g., the size of the blades, the tilt of the blades, the number of blades), the distance between the various propellers 511, and the angular velocities of the propellers 511. In some embodiments, the magnitude of angular velocities of two propellers 511 within a pair of contra-rotating propellers 512, 514 may be equal. Contra-rotating propellers 512, 514 with equal angular velocity magnitudes may result in output velocity vectors comprising small tangential velocity components, such as that necessary to replicate natural helical blood flow in the aorta. In some embodiments, the angular velocity magnitudes of two propellers 511 within a pair of contra-rotating propellers 512, 514 may be approximately equal (e.g., variability less than 0.1%, 0.5%, 1%, 2%, 3%, 4%, 5%, 10%, etc.). Contra-rotating propellers 512, 514 with approximately equal angular velocity magnitudes may result in output velocity vectors comprising small tangential velocity components, such as that necessary to replicate natural helical blood flow in the aorta. In some embodiments comprising multiple pairs of contra-rotating propellers 512, 514, the angular velocity magnitude of the propellers 511 within each pair may be approximately equal but the angular velocity magnitude may differ between different pairs of contra-rotating propellers 512, 514. In some embodiments comprising multiple pairs of contra-rotating propellers 512, 514, the angular velocity magnitude of the propellers 511 within each pair may be approximately equal and the angular velocity magnitude between two or more pairs may be approximately equal. For example, in some embodiments, all propellers 511 (e.g., 4 propellers, 6 propellers, 8 propellers) may have approximately equal angular velocities. In some implementations, embodiments comprising multiple pairs of contra-rotating propellers 512, 514 in which each propeller 511 of a pair has equal or approximately equal angular velocity magnitudes may result in a final output blood flow at the downstream end of the propellers 511 or the device having a small tangential velocity component that replicates natural helix formation in blood flow (e.g., right-handed helix in the descending aorta). The direction of rotation and the ordering of the propellers 511 within the contra-rotating pairs of propellers 512, 514 may be used to control the direction of the final tangential velocity component in the output blood flow. For instance, the tangential velocity component in the output blood flow may be in the same direction as the final propeller 511 (e.g., right-handed or left handed). In some embodiments, all of the propellers 511 may be axially spaced uniform distances from each other. In some embodiments, propellers 511 within a pair of contra-rotating propellers 512, 514 may be spaced a first distance from each other and pairs of contra-rotating propellers 512, 514 may be spaced a second distance from each. The first distance may be less than, the same, or greater than the second distance. In some embodiments, all of the propellers 511 may be spaced variable distances from each other or the spacing may comprise a configuration of the various patterns disclosed herein.

Figure 27:
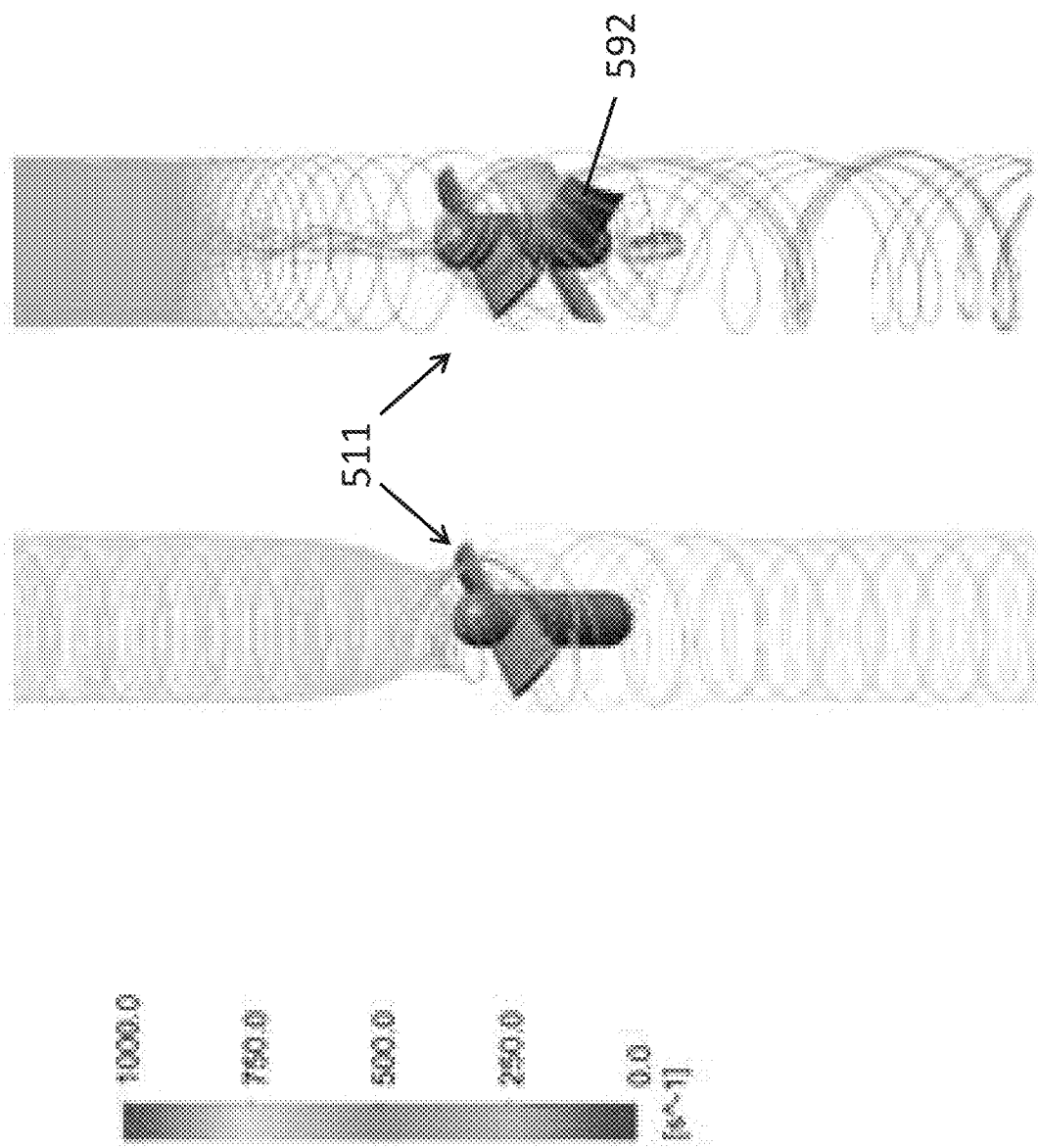
FIG. 27 illustrates velocity contours for an MCS device comprising a single impeller.

In some embodiments, the MCS device 500 may comprise stator elements which can be used to modulate the velocity vector (e.g., the tangential velocity component) of the blood flow, such as either at the inlet or outlet of the device. For instance, the MCS device 500 may include pre-swirler vanes 590 (inlet guide vanes or blades) prior to the first (most upstream) propeller 511, such as at the inlet of the device, and/or de-swirler vanes 592 (flow-straightener vanes or blades) after the last (most downstream) propeller 511, such as at the outlet of the device. Pre-swirler vanes 590 and/or de-swirler vanes 592 may be the same or identical to vanes described elsewhere herein. In some embodiments, the pre-swirler vanes 590 and/or de-swirler vanes 592 may be part of the anchoring mechanism 600. In some embodiments, the pre-swirler vanes 590 and/or de-swirler vanes 592 may be coupled to one or more rotors 510, in a fashion such that the vanes do not rotate with the rotor 510. The vanes may be foldable against the rotor as described elsewhere herein, which may be advantageous for delivery of the MCS. In some embodiments, an MCS device may comprise a single propeller 511 and may use de-swirler vanes 592 to dampen the large tangential velocity component of the single propeller 511. The use of pre-swirler vanes 590 and/or de-swirler vanes 592 may improve the efficiency of the MCS device 500. FIG. 27 illustrates velocity contours for an MCS device 500 having a single propeller 511, wherein the vorticity magnitude is indicated by the scale bar in $s^{-1}$. The MCS device 500 on the left does not include de-swirler vanes 592. The MCS device 500 on the right does include de-swirler vanes 592, coupled to the rotor 510. As seen in FIG. 27, the de-swirler vanes 592 reduce the vorticity of the fluid flow, reducing the tangential component of the velocity contours. The MCS device 500 without de-swirler vanes demonstrates a vorticity of approximately 750 $s^{-1}$ both upstream and downstream of the propeller 511, with a slightly lower vorticity immediately upstream the propeller 511 (approximately 500 $s^{-1}$) and a slightly higher vorticity immediately downstream the propeller 511 (slightly higher than 750 $s^{-1}$). The MCS device 500 with de-swirler vanes 592 demonstrates a vorticity that is generally less than 500 $s^{-1}$, with a lower vorticity (generally less than 250 $s^{-1}$) downstream the propeller 511 than upstream the propeller 511.

Figure 28A:
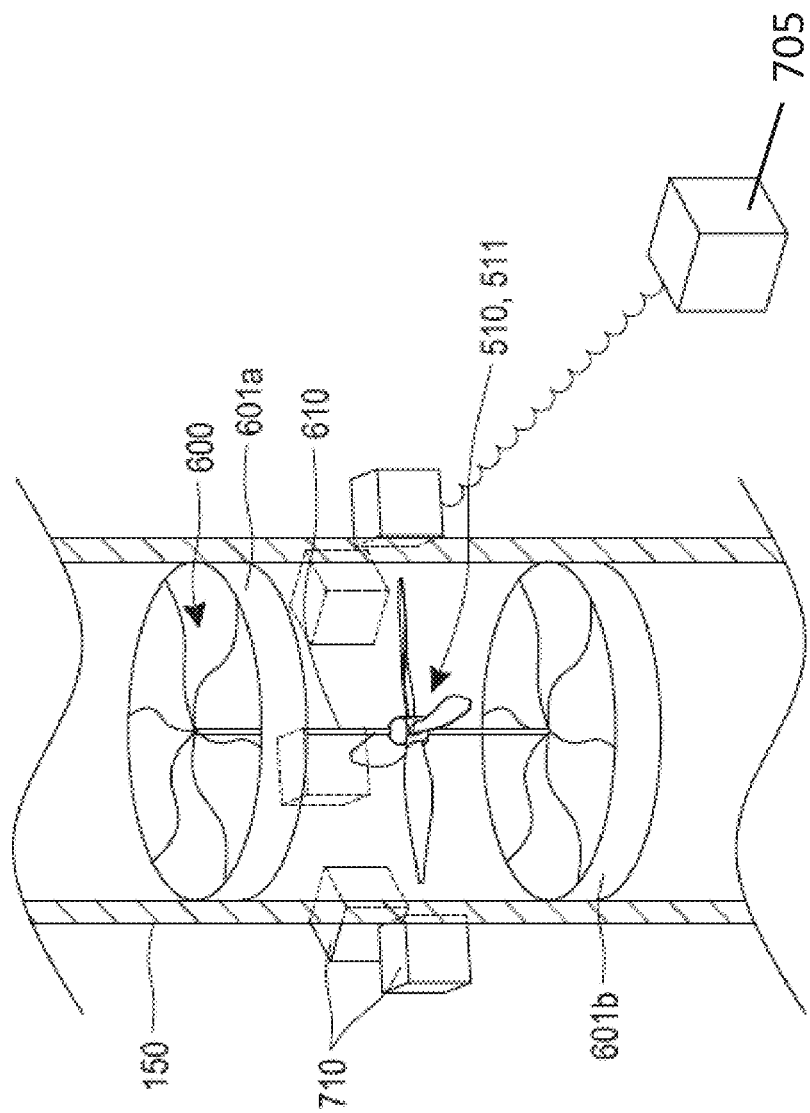
FIGS. 28A-28C schematically illustrate examples of MCS devices of various configurations.
Figure 28C:
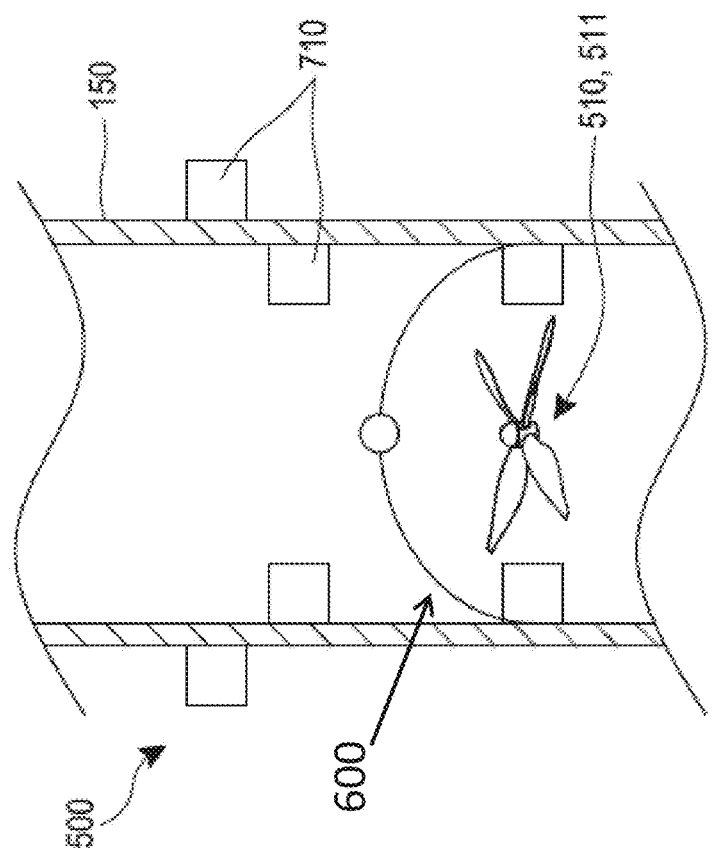
Figure 28B:
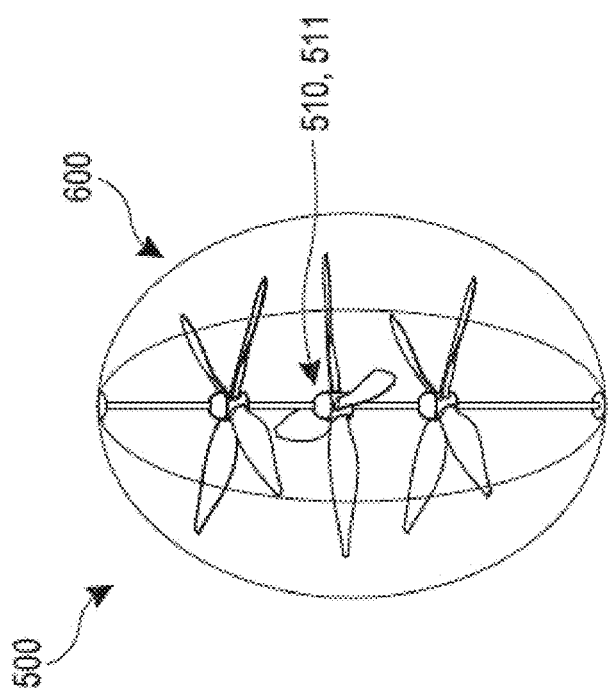

FIG. 28A schematically illustrates an example of an MCS device 500 comprising pre-swirler vanes 590 and de-swirler vanes 592 incorporated into the anchoring mechanism 600. The anchoring mechanism 600 may be a self-expanding cage structure comprising a self-expanding upper support 601a and/or a self-expanding lower support 601. The anchoring mechanism may comprise a shaft 610 which one or more propellers 511 may be mounted on. The shaft 610 may be a tube and may be configured for receiving a guidewire during percutaneous insertion of the MCS device 500. The MCS device 500 may include an electro-coupling drive belt in the form of extravascular stators 710 as described elsewhere herein. The stators 710 may be coupled via a line or cable to an interface box 705 or other connection. The power may be provided percutaneously or transcutaneously as described elsewhere herein. FIG. 28B schematically illustrates an MCS device comprising a football-shape anchoring mechanism 600 and three propellers 511. FIG. 28C schematically illustrates a portion of an MCS device comprising a propeller 511 and an anchoring mechanism 600 being inserted into a blood vessel 150. As schematically depicted, in some embodiments the MCS device 500 may comprise an intravascular and/or an extravascular stator 710 for electromagnetically driving the impeller 512.

The MCS may comprise one or more motors 700 coupled to the one or more rotors 510 and configured to provide rotational force to the one or more rotors 510. In embodiments comprising more than one rotor 510, some or all of the rotors 510 may be driven by the same motor 700 or all the rotors 510 may be separately driven by different motors. The one or more motors 700 may be provided power by a power source 750. The power source 750 may be an external power source (e.g., an AC outlet) or an internal power source (e.g., a rechargeable battery) as described elsewhere herein. In some embodiments, the motor 700 may be extra-corporeal (positioned outside of the body). In some embodiments, the motor may be intra-corporeal (positioned inside the body). In embodiments comprising an intra-corporeal motor, the motor or motors may be positioned within the lumen of the blood vessel (intravascular) and/or around the exterior of the blood vessel in which the rotor 510 is installed or in a remote location from the blood vessel. In some embodiments, the rotor/propeller 510/511 may be coupled to the motor by a shaft, a driveline, and/or by other mechanical means. In some embodiments, the rotor/propeller 510/511 may be directly rotated by the motor stator 710 and may be referred to as part of the motor 700. For instance, magnets driven by the electromagnetic stator 710 of the motor may be coupled to or installed within the rotor or rotors 510, such as within the blades 720 of the one or more propellers 511. In embodiments comprising an intra-corporeal motor, the motor 700 may be provided power transcutaneously or percutaneously (via TET or PET) as described elsewhere herein. A controller 760 may be configured to control the power provided and the rotor 510 and to control the operation of the rotor 510, including operating speeds. In embodiments comprising an intra-corporeal motor, the controller 760 may be extra-corporeal or intra-corporeal as described elsewhere herein.

In some embodiments, the MCS device 500 may be line connected. Mechanical and/or electrical power and/or control-system signals may be transferred from outside the body to the turbomachinery via a percutaneous line, such as through Percutaneous Energy Transfer (PET) as described elsewhere herein. The line may extend through a catheter. In some embodiments, the line may be a catheter. The catheter may extend into the vasculature in which the MSC device 500 is installed. In some implementations, the MCS device 500 may be delivered using the same catheter through which the line extends. In embodiments comprising an extra-corporeal motor, the motor 700 may be coupled to the rotor 510 through a driveline that transfers the rotary motion from the motor 700 to the rotor 510. The driveline may extend through a catheter into the vasculature. An advantage of using an extra-corporeal motor is that the motor 700 is not limited in size by the physical constraints within the body. Larger and/or heavier motors configured to provide more power to the rotor 510 may be more readily used in MCS devices 500 comprising an extra-corporeal motor. Extra-corporeal motors may be more easily lubricated and heat dissipation from the motor 700 is not a concern. In some embodiments, a lubricating fluid may be provided through the catheter to lubricate the driveline and/or promote the removal of debris from the device. For example, a lubricating fluid may be transported through small channels in the catheter to a proximal bearing of the rotor 510 and returned through a line comprising the driveline. The distal bearing of the rotor 510 may be lubricated by blood flow. Cardio-Bridge's Reitan Catheter Pump is an example of percutaneous intra-aortic devices with extra-corporeal motor. Intravascular motors may require less complex coupling mechanisms and no need for driveline lubrication. Some intravascular motors may require sealing, motor lubrication, and temperature control. Intravascular motors may comprise purge systems designed to keep blood from entering the motor compartment by creating a pressure barrier against the blood. CardioBridge's Impella™ and Procyrion's Aortix™ are examples of pumps comprising intravascular motors.

In some embodiments, the MCS device 500 may be configured particularly for short-term use. Short-term use may be defined as less than one day, one day, two days, three days, four days, five days, six days, seven days, etc. Devices with extra-corporeal components may be especially suitable for short-term use as the patient may be restricted to bed by the percutaneous line. Short-term devices may be particularly useful for recovering a patient after cardiogenic shock or cardiopulmonary failure or during high risk percutaneous coronary interventions (HR-PCI) to eliminate the risk of acute myocardial infarction (AMI), to restore the systemic hemodynamic function, and to reserve the end organ perfusion. In some embodiments, the MCS device 500 may be particularly configured for long-term use. Long-term use may be defined as more than 1 week, 2 weeks, 3 weeks, 1 month, etc. Long-term devices may be used as a bridge to heart transplant or destination therapy. LVADs, such as Heartmate and LVAD, may be considered long-term devices. Long-term devices generally include intra-corporeal motors. Haemolytic performance (e.g., with respect to haemolysis, thrombosis, etc.) and durability become increasingly important design considerations for long-term devices. Previously, many long-term devices were powered directly by a PET line which was connected to an external ambulatory power source, such as a battery pack. Recently, TET power transfer has become more popular for long-term devices. In some embodiments, the MCS device 500 may be particularly configured particularly for intermediate-term use. Intermediate-term use may be defined as a term of use between short-term use and long-term use. Often the intermediate term is a critical period during which patient eligibility for heart transplant or other long-term devices is decided. Intermediate-term devices generally incorporate extra-corporeal power sources and may be driven via PET or TET. Intermediate-term devices may be surgically implanted or percutaneously installed. The design considerations for intermediate-term devices are similar to that for long-term devices.

Figure 29B:
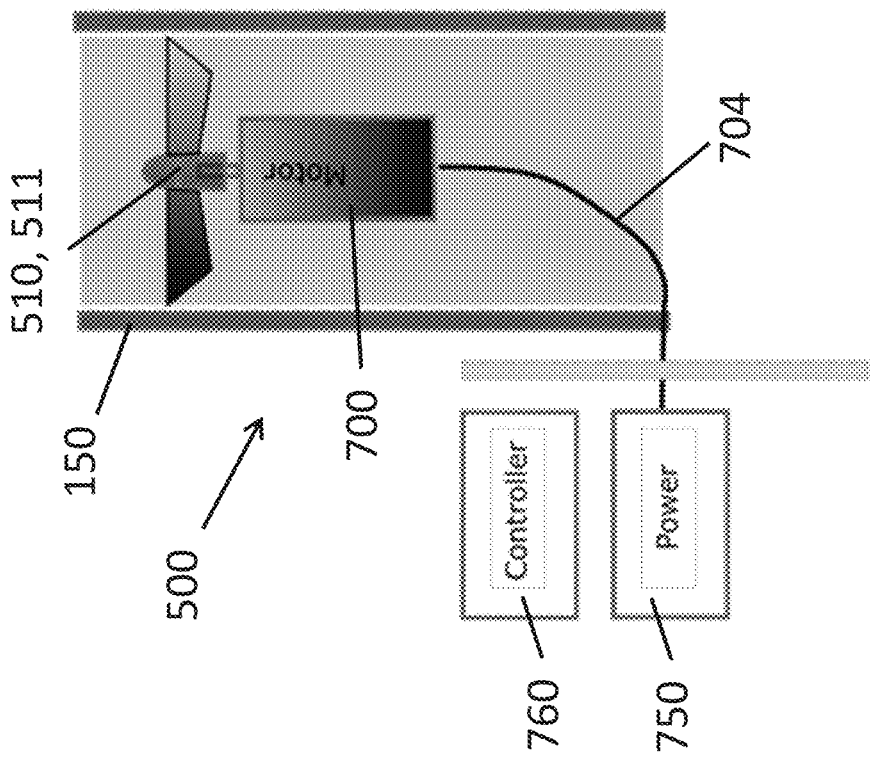
FIGS. 29A-29E schematically illustrate various examples of operating configurations of the MCS device.
Figure 29A:
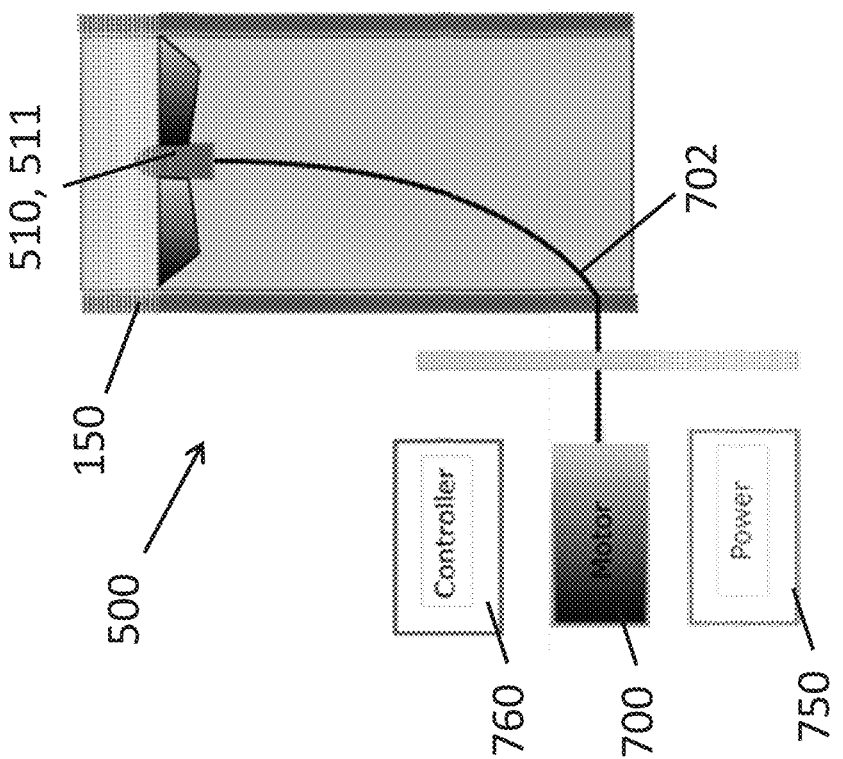
Figure 29D:
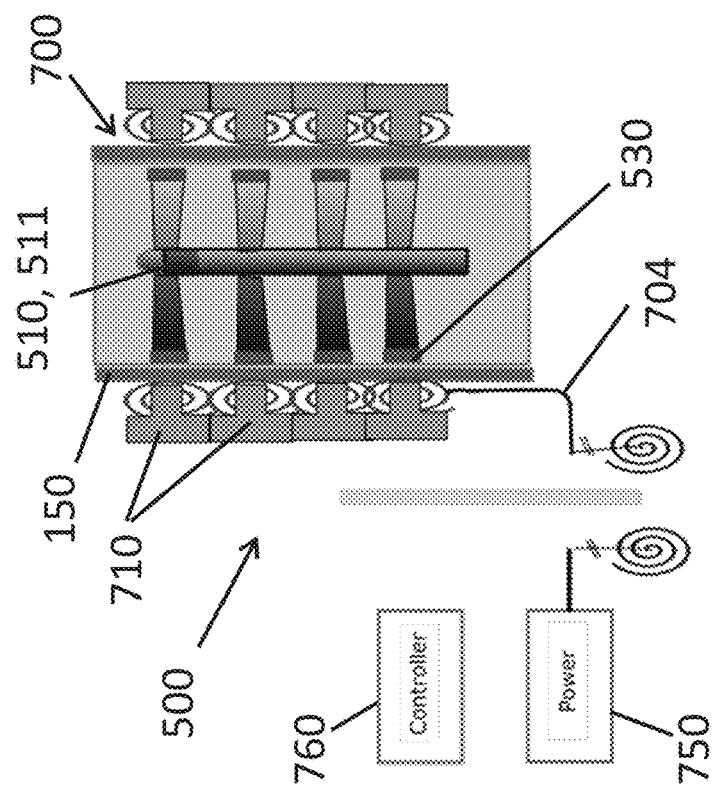
Figure 29C:
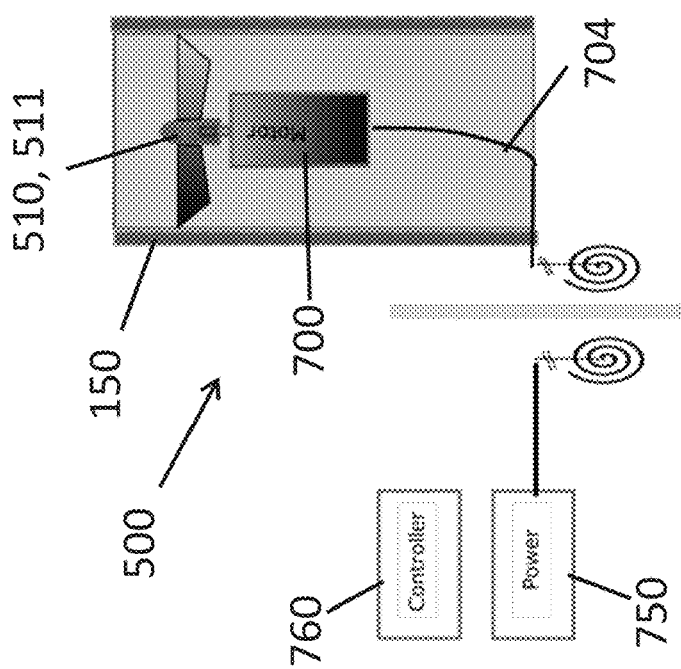
Figure 29E:
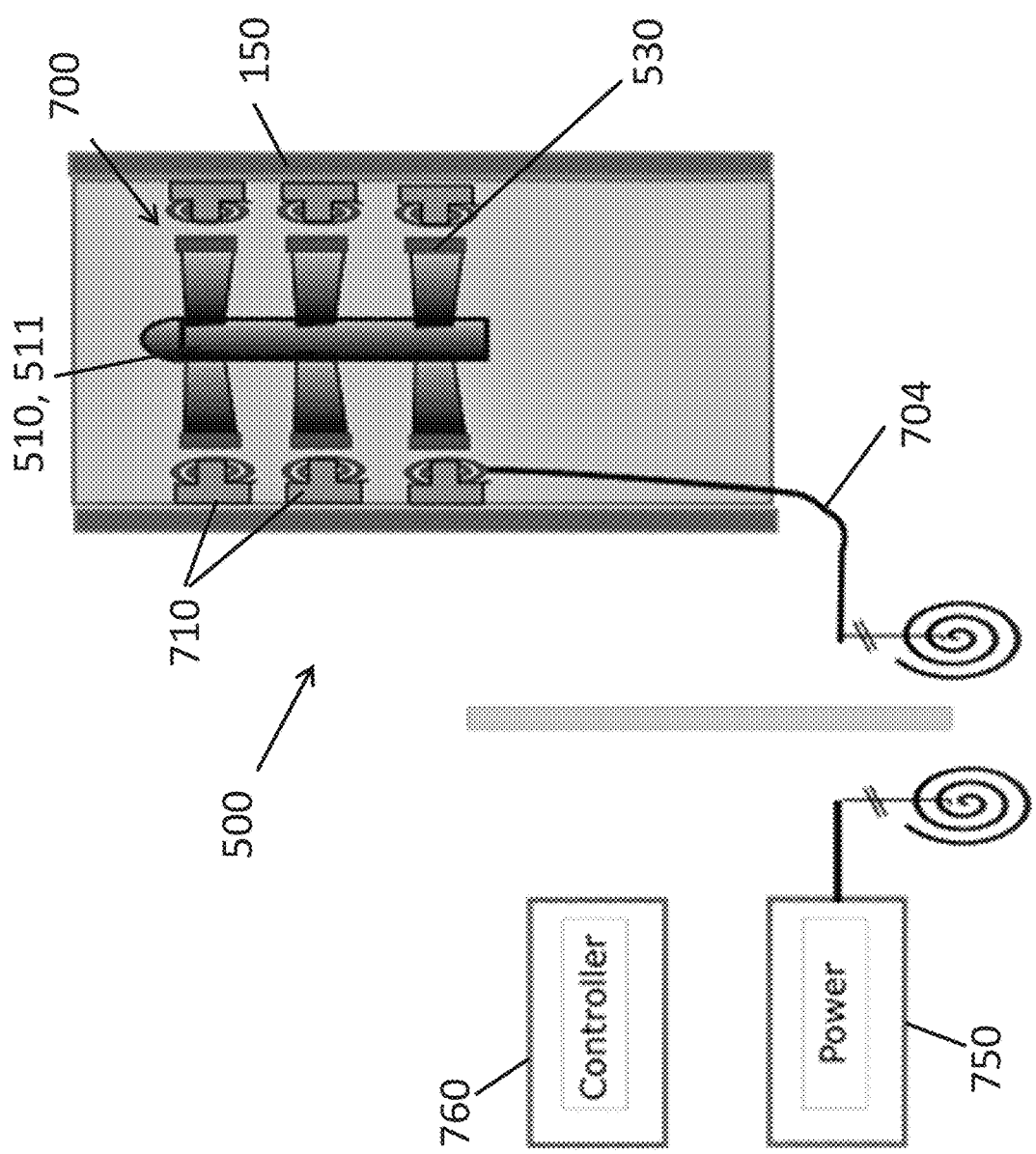

FIGS. 29A-29E schematically illustrate an overview of various examples of operating configurations in which the MCS device 500 may be designed. FIG. 29A depicts a rotor 510 coupled via a driveline to an extra-corporeal motor 700, controller 760, and power source 750, which is especially suitable for short-term use. FIG. 29B depicts a rotor 500 coupled to an intravascular motor 700, which is coupled via a line to an extra-corporeal power source 750 and controller 760 and is also especially suitable for short-term use. FIG. 29C depicts a rotor 510 coupled to an intravascular motor 700 which is coupled by a line to an internal TET coil. The TET coil receives power and/or signals from an extra-corporeal power source and controller via an extra-corporeal TET coil and may be especially suitable for intermediate-term use. FIG. 29D depicts a rotor 510 comprising multiple propellers 511, each of which is driven by an extravascular stator 700. The stators 710 may be connected by a line to a TET system, as described elsewhere. FIG. 29E depicts a rotor 510 comprising multiple propellers 511, each of which is driven by an intravascular stator 700. The stators 710 may be connected by a line to a TET system, as described elsewhere. The configurations depicted in FIGS. 29D and 29E may be especially suitable for long-term use.

Figure 30B:
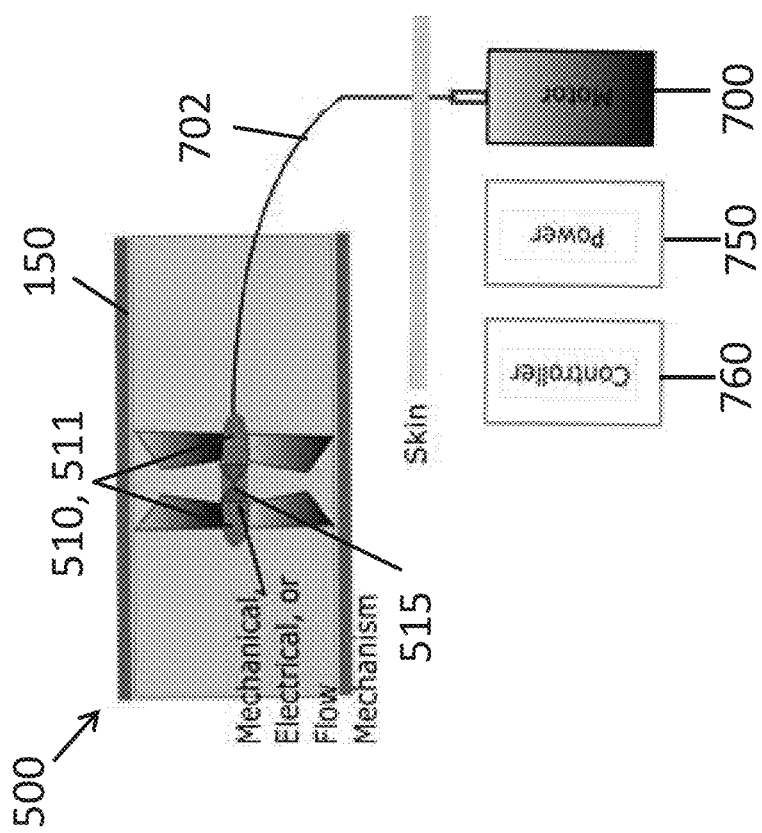
FIGS. 30A-30F schematically illustrate example of MCS devices having various configurations of motors and rotors.
Figure 30A:
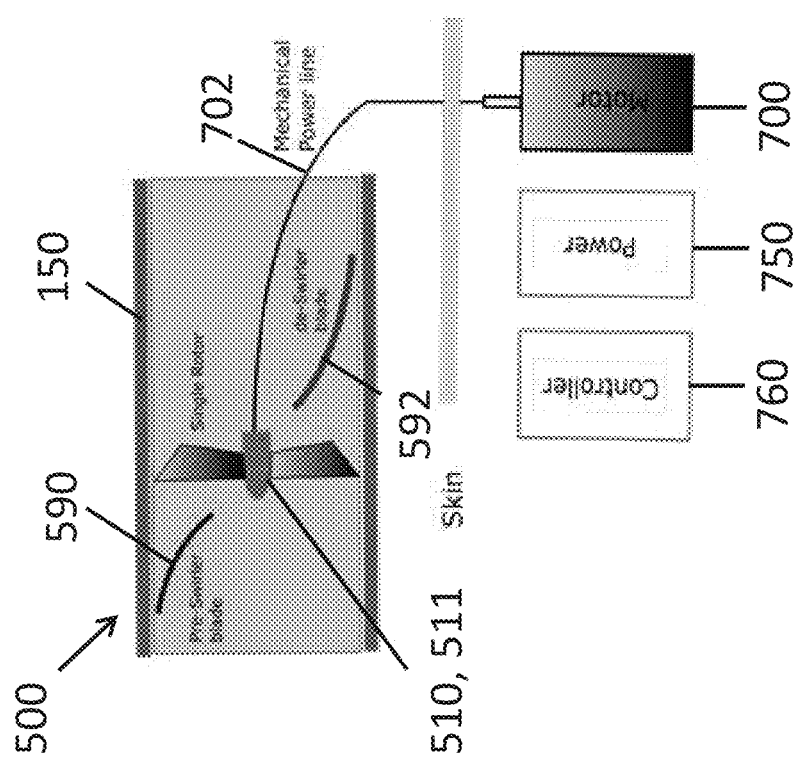

FIG. 30A schematically illustrates an example of an MCS device 500 comprising a single rotor 510 coupled via a driveline 702 to an extra-corporeal motor 700. The motor 700 is further coupled to an extra-corporeal power source 750 and an extra-corporeal controller 760. The MCS device 500 may also include pre-swirler vanes 590 and de-swirler vanes 592, similar to those illustrated in FIG. 27 or 28A. The pre-swirler vanes 590 and/or de-swirler vanes 592 may be coupled to either the rotor 510 or the anchoring mechanism 600. The pre-swirler vanes 590 and/or de-swirler vanes 592 may be foldable against either the rotor 510 (e.g., along the central axis of the rotor) or the anchoring mechanism 600 to assist deploying the MCS device 500 intravascularly.

FIG. 30B schematically illustrates an example of an MCS device 500 comprising two rotors 500 (e.g., a pair of contra-rotating propellers 512, 514) and an extra-corporeal motor 700. The pair of propellers 511 may be coupled through a mechanical, electrical, and/or fluid flow mechanism 515 such that the two propellers 511 may be driven by a single motor. The propellers 511 may be coupled such that they rotate in opposite directions. The propellers 511 may be configured to rotate at the same speed or at different speeds. The MCS device 500 may or may not include pre-swirler vanes 590 and/or de-swirler vanes 592 as described elsewhere herein.

Figure 30D:
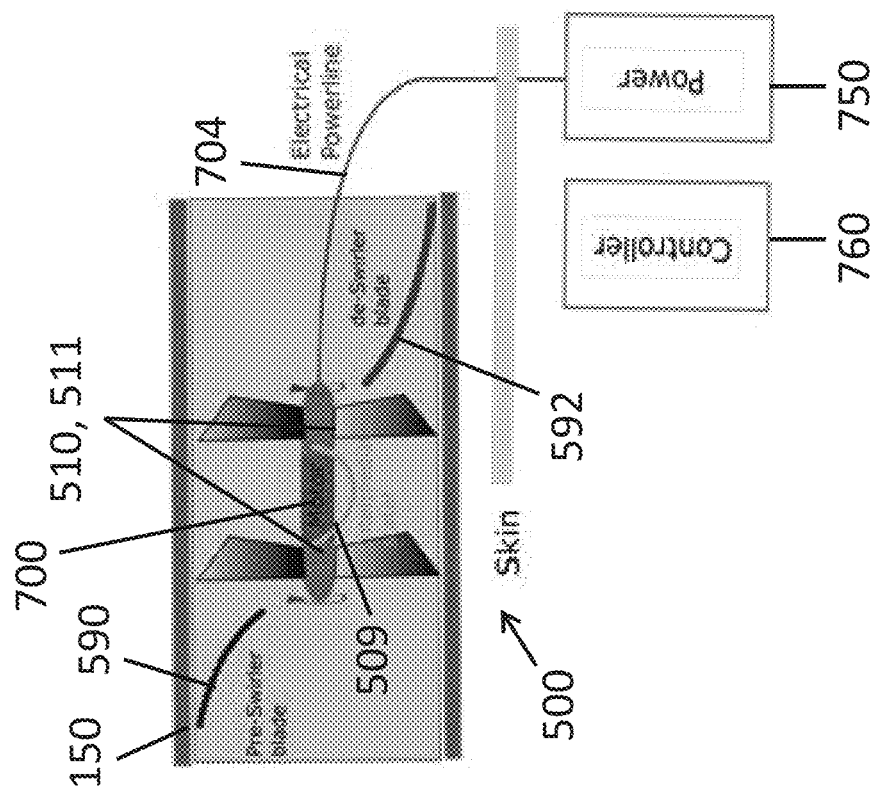
Figure 30C:
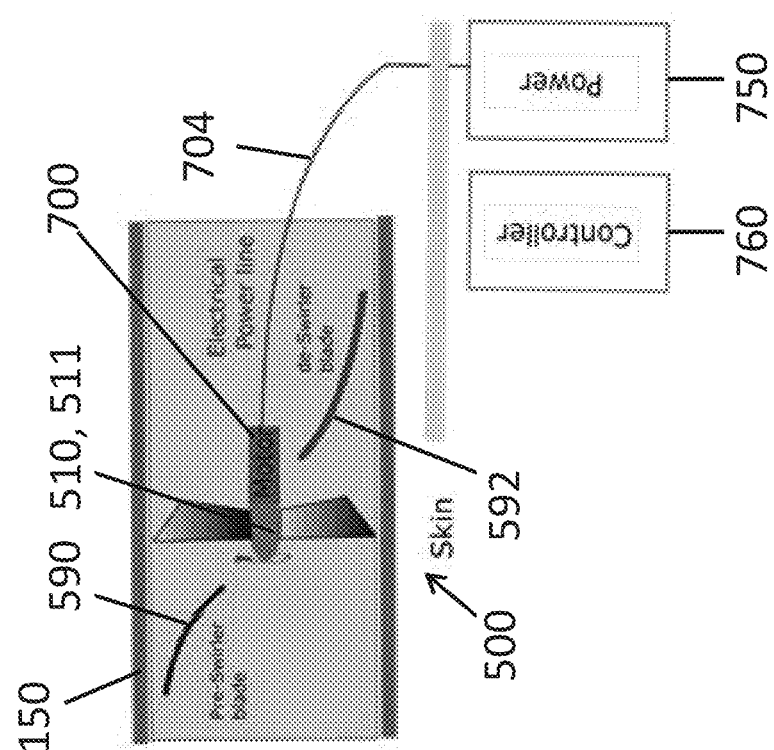

FIG. 30C schematically illustrates an example of an MCS device 500 comprising a single rotor 510 coupled to an intravascular motor 700. The motor 700 may be connected via a power line or cable 704 to an extra-corporeal power 750 source and controller 760. The MCS device 500 may include pre-swirler vanes 590 and/or de-swirler vanes 592 as described elsewhere herein. An advantage of using an intra-corporeal motor 700 is that it does not require a mechanical driveline 702 between the motor 700 and the rotor 510 or lubrication of a driveline 702. In some embodiments, intravascular motors 700 may have diameters between about 4 mm and 6 mm. Intravascular motors may be provided by Maxon Motor.

FIG. 30D schematically illustrates an example of an MCS device 500 comprising two rotors 510 coupled to a single intravascular motor 700 and configured to rotate in the same direction. The motor 700 may be axially positioned between the two rotors 510. The motor 700 may sever as a spindle around which the two rotors 510 may rotate. In some embodiments, an intermediate stator 509 may be deployed between the two rotors 510 as part of the anchoring mechanism 600 or as part of a hub of the rotor 510, as schematically indicated in FIG. 30D. The use of an intermediate stator 509 may reduce the mechanical complexity required to rotate both of the rotors 510. The MCS device 500 may include pre-swirler vanes 590 and/or de-swirler vanes 592 as described elsewhere herein. An advantage of using a single motor 700 to drive multiple rotors 510 is that there is no need to insulate the magnetic fields of separate motors 700 from each other. The use of a single motor 700 may reduce the size and weight of the MCS device 500.

Figure 30F:
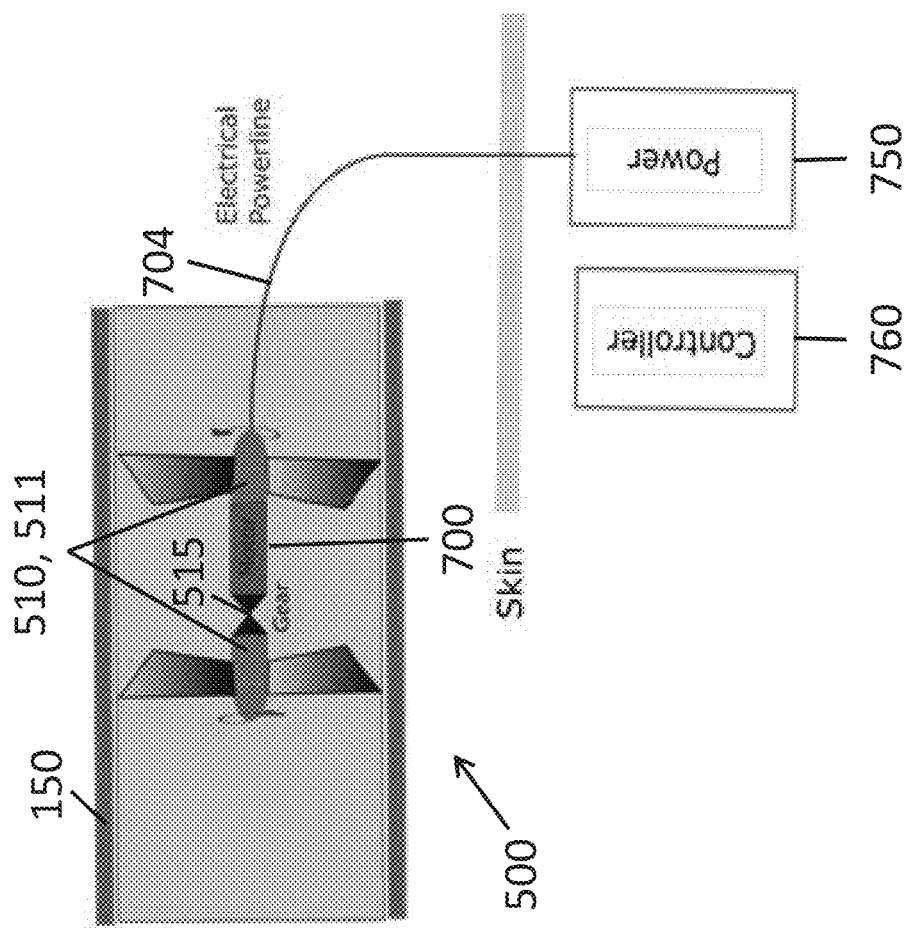
Figure 30E:
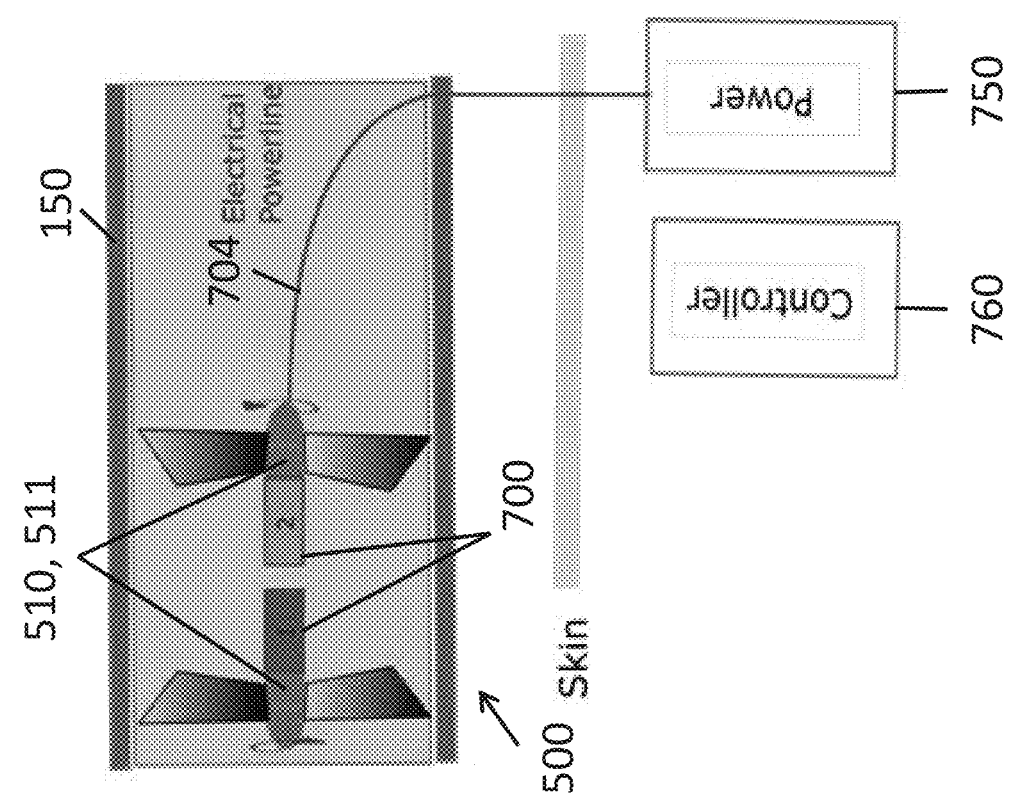

FIG. 30E schematically illustrates an example of an MCS device 500 comprising two rotors 510 (e.g., contra-rotating propellers 512, 514), each coupled to an individual intravascular motor 700. The MCS device 500 may or may not include pre-swirler vanes 539 and/or de-swirler vanes 592 as described elsewhere herein. The use of separate motors 700 to drive each rotor 510 may be advantageous in that no mechanical gearing is required to couple the two rotors 510 (e.g., contra-rotating propellers 512, 514) to a single motor 700. The absence of such mechanical gearing can make the MCS device 500 more durable and/or more efficient.

FIG. 30F schematically illustrates an example of an MCS device 500 comprising two rotors 510 (e.g., contra-rotating propellers 512, 514) driven by a single intravascular motor 700 and coupled by a mechanical, electrical, and/or fluid flow mechanism 702. The mechanical, electrical, and/or fluid flow mechanism 702 may be the same as or similar to that described with respect to FIG. 30B. The rotors 510 may be configured to run in the same or different directions. The rotors 510 may be configured to run at the same or different speeds. The MCS device 500 may or may not include pre-swirler vanes 590 and/or de-swirler vanes 592 as described elsewhere herein.

In some embodiments, the MCS device 500 may comprise an intra-corporeal motor 700 comprising an extravascular stator 710 positioned concentrically outside of the rotor 510. FIG. 31A schematically illustrates an example of an MCS device 500 comprising a single rotor 510 and an extravascular stator 710 positioned circumferentially around the blood vessel 150. The stator 710 may be delivered power by a line 704 which extends to a power source 750 and controller 760. The controller 760 and power source 750 may be implanted in the body, as described elsewhere herein, or may be extra-corporeal. In some embodiments, the MCS device 500 may be configured to use an implanted rechargeable battery as a primary power source 750 and/or a backup source. Power and/or control signals may be transmitted across the skin percutaneously or transcutaneously, as described elsewhere herein. The rotor 510 may comprise one or more magnets 530 (permanent magnets) that drive rotation of the rotor 510. In some embodiments, the blades 520 are fabricated from magnetic material such that magnetic blades are the magnets 530. In some embodiments, the stator 710 may be positioned outside the blood vessel 150 such that it circumferentially surrounds an external surface of the blood vessel 150. In some embodiments, the blades 520 or a portion thereof may be fabricated from magnetic material such that the blade 520 forms the magnet 530. FIG. 31B illustrates a perspective view of an example of an MCS device 500 comprising an intravascular rotor 510 and an extravascular stator 710 configured to drive rotation of the rotor 510. The stator 710 may have a ring-like body 711. The stator 710 may comprise one or more teeth 712 positioned around the circumference of the stator. An electric conductor may be wrapped around the circumference of the one or more teeth 712 to form electromagnets (electromagnetic coils 714), as described elsewhere herein and as is well-known in the art. In some implementations, the stator 710 may be implanted in the body through a small incision via a thoracotomy in the left side of the chest.

The efficiency of motors 700 comprising extravascular stators 710 and concentrically positioned intravascular rotors 510 may be increased by compensating for the gap size between the rotor 510 and the stator 710. Positioning the stator 710 and rotor 510 on opposite sides of the blood vessel wall may increase the gap size between the rotor 510 and the stator 710, reducing the efficiency of transferring power from the stator 710 to the rotor 510 via electromotive force. A number of means, discussed herein, may be used individually or together to improve the efficiency of the electromotive force transfer across the gap.

In some embodiments, the efficiency is increased by increasing the number of propeller blades 520 that are coupled to the rotor 510. Increasing or maximizing the number of blades 520 in an MCS device 500 maximizes the amount of magnetic material located at the radial tip 521 of the blades 520 which is the closest point to the circumferential stator 710. The total blade number can be increased by increasing the number of blades 520 in a row of blades 520 and/or by increasing the number of rows of blades 520. Each row of blades 520 extending from the axis of rotation at a given axial length along the rotor 510 may be considered a propeller 511, where a rotor 510 may comprise one or more propellers 511 configured to rotate together. For example, in some embodiments a rotor 510 may comprise two blades, four blades, six blades, eight blades, ten blades, etc. The blades 520 may be distributed in 1 row, 2 rows, 3 rows, 4 rows, etc. In some embodiments, the blades 520 are evenly distributed amongst the rows of blades. In some embodiments the blades 520 may be unevenly distributed. In some embodiments, the blades 520 of one or more rows/propellers 511 are circumferentially aligned. In some embodiments, the blades 520 of one row may be circumferentially offset from the blades 520 of another row. For instance, the blades 520 of one row may be spaced uniformly within the gaps between the blades 520 of another row. In some embodiments, the blades of the various rows may be incrementally spaced across the circumference of the rotor 510 relative to each other to maximize the circumferential distribution of blades 520.

FIGS. 32A-32C schematically illustrate various examples of extravascular stators 710 positioned circumferentially around an intravascular rotor 510 comprising multiple rows of blades 520. FIG. 32A illustrates the use of multiple stators 710 axially aligned with multiple rows of blades 520. Magnets may be positioned within or coupled to the radial tips 521 of the blades 520. The blade radial tips 521 may be configured to self-align with the stators 710. In some embodiments, each blade 520 comprises a magnet 530, which may maximize the efficiency of the motor 700. In some embodiments, not all blades 520 may comprise a magnet 530. FIG. 32B illustrates the use of a single stator 710 surrounding multiple rows of blades 510. The axial length of the stator 710 may encompass all rows of the rotor 510. FIG. 32C illustrates the use of a single stator 710 surrounding multiple rows of blades 520, in which a least some of the radial tips 521 from each row of blades 520 are connected. The blades 520 may be circumferentially aligned and connected by a substantially axially aligned connector 532. The connector 532 may be a magnet 530. The use of a magnetic connector 532 can increase the magnetic density near the stator 710. In some embodiments, the blades 520 may not be circumferentially aligned. The blades 520 may be connected by a non-linear connector 532, such as a helical shaped connector. The helical shaped connector 532 may be magnetic. In some embodiments, each blade radial tip 521 may be connected to one other blade radial tip 521 from each row of blades 520. In some embodiments, only some blades 520 (e.g., one blade, two blades, etc.) are connected to blades 520 from other rows.

Figures 34A, 34B, 34C:
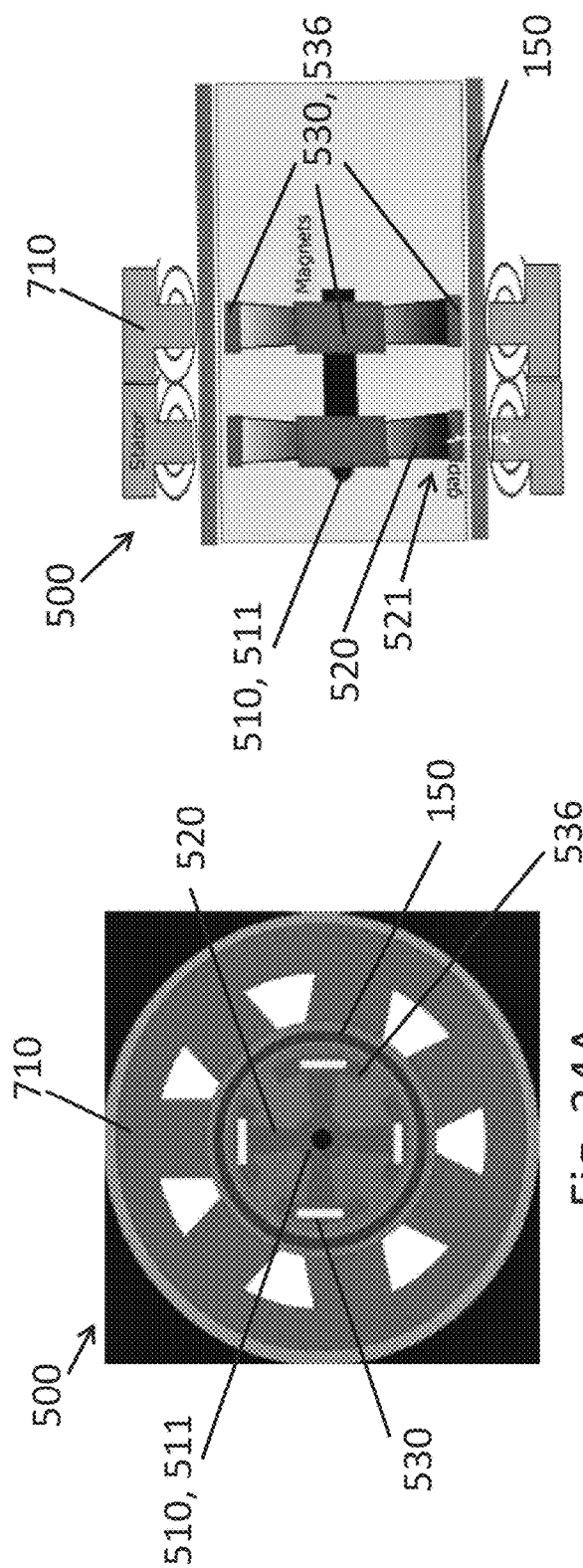
FIGS. 34A-34C schematically illustrates an example of an MCS device comprising magnetic winglets.

In some embodiments, the magnetic density along the outer periphery of the blades 520 may be increased via magnetic rings 534 or winglets 536. FIGS. 33A-33C schematically illustrate an example of an MCS device 500 comprising magnetic rings 534 joining the blade radial tips 521 in each row of blades 520. The magnetic rings 534 may be aligned along a circumferential direction substantially perpendicular to the axial direction of the blood vessel 150 or central axis of the MCS device 500. The magnetic rings 534 may increase the magnetic density along an outer circumference positioned inside of the stator 710. FIG. 32A schematically illustrates a cross-section intersecting the central axis. FIG. 32B schematically illustrates a side view along the central axis. FIG. 32C illustrates a perspective view of the rotor 510. FIGS. 34A-34C schematically illustrates an example of an MCS device 500 in which the blade radial tips 521 comprise magnetic winglets 536. The winglets 536 may extend along a circumferential direction in a right-handed and/or left-handed direction from the radial tips 521 of the blades 520. The winglets 536 may be configured as partial sections of a magnetic ring, similar to that illustrated in FIGS. 33A-33C. FIG. 34A schematically illustrates a cross-section intersecting the central axis. FIG. 34B schematically illustrates a side view taken along the central axis. FIG. 34C illustrates a perspective view of the rotor 510. The magnetic rings 534 and/or winglets 536 may be fabricated of magnetic material, comprise magnetic inserts 530, or otherwise couple with magnets 530, according to any of the means described elsewhere herein. The magnetic rings 534 and/or winglets 536 may be configured with profiles along the axial direction that optimize fluid flow over the ring 534 or winglet 536 and/or prevents or minimizes haemolysis.

Figures 35A, 35B:
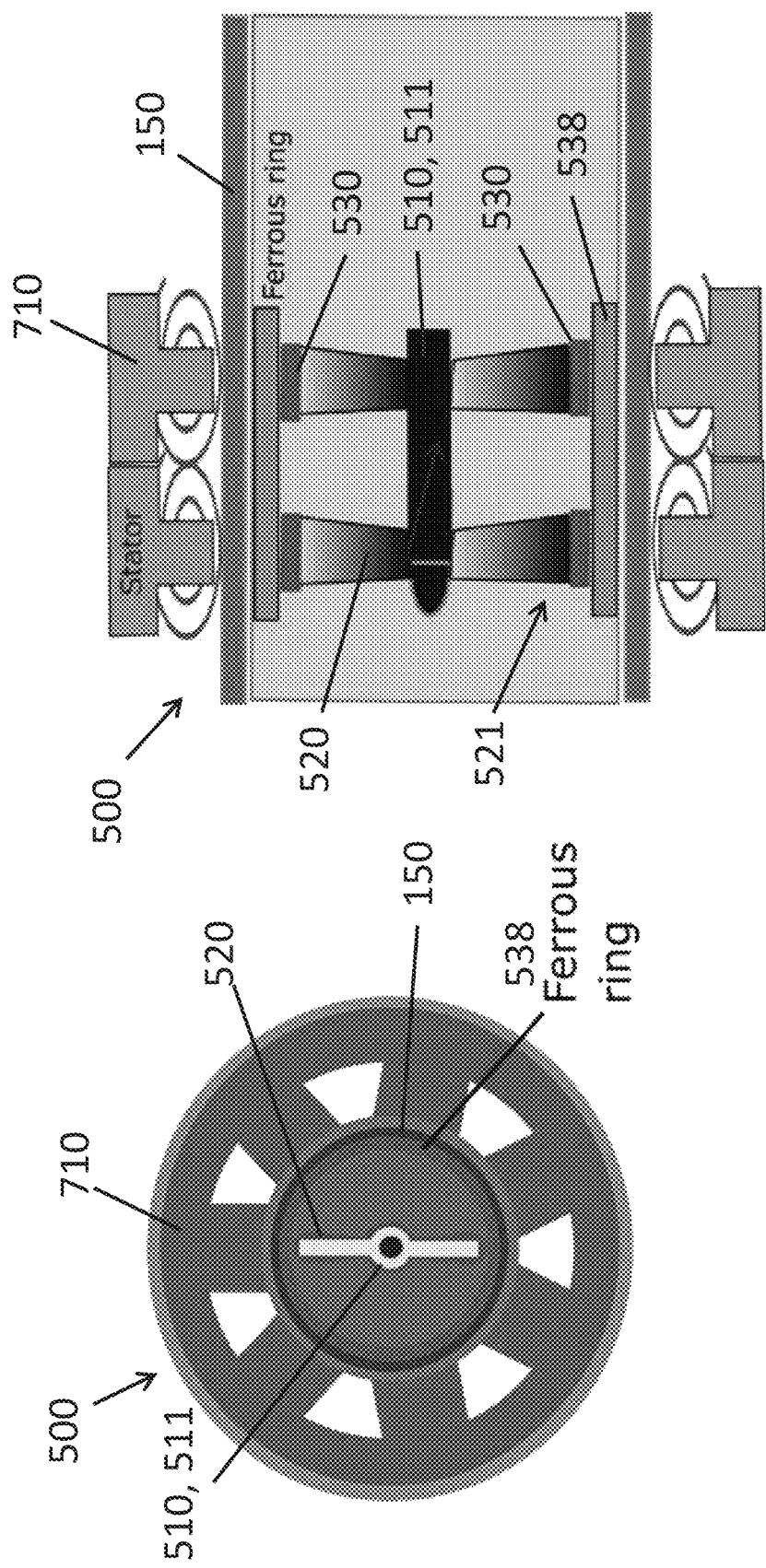
FIGS. 35A-35B schematically illustrate examples of an MCS device comprising a ferrous ring.

In some embodiments, the MCS device 500 can include a ferrous ring 538 positioned inside the blood vessel 150 between blade radial tips 521 and the stator 710. The ferrous ring 538 may improve motor efficiency by facilitating or enhancing the transmission of the electric field from the stator or stators 710 to the rotor magnets 530. FIGS. 35A-35B schematically illustrate examples of an MCS device 500 comprising a ferrous ring 538. FIG. 34A schematically illustrates a cross-section intersecting the central axis. FIG. 34B schematically illustrates a side view along the central axis. In some embodiments, the ferrous ring 538 may be a discrete component of the MCS device 500. In some embodiments, the ferrous ring 538 may be integrated with or coupled to the anchoring mechanism 600. In some implementations, the ferrous ring 538 is coupled to the anchoring mechanism 600 after the anchoring mechanism 600 is installed in the blood vessel 150. In some implementations, the ferrous ring 538 is implanted in the blood vessel 150 in a similar fashion to the outer ring in artificial valves. In some embodiments, the ferrous ring 538 may be configured to be positioned between rotor 510 and the anchoring mechanism 600. In some embodiments, the ferrous ring 538 may be configured to be positioned between the anchoring mechanism 600 and the blood vessel wall. In some embodiments, the ferrous ring may be a continuous ring, such that it is effectively tubular, and configured to extend along the length of the rotor 510 to encompass multiple rows of blades 520. In some embodiments, multiple discrete ferrous rings 538 may be incorporated. The multiple ferrous rings 538 may be axially aligned between stators 710 and rows of blades 520. In some embodiments, the ferrous ring or rings 538 may not form a closed circumference but may extend along only a portion or portions of the circumference.

Figure 36:
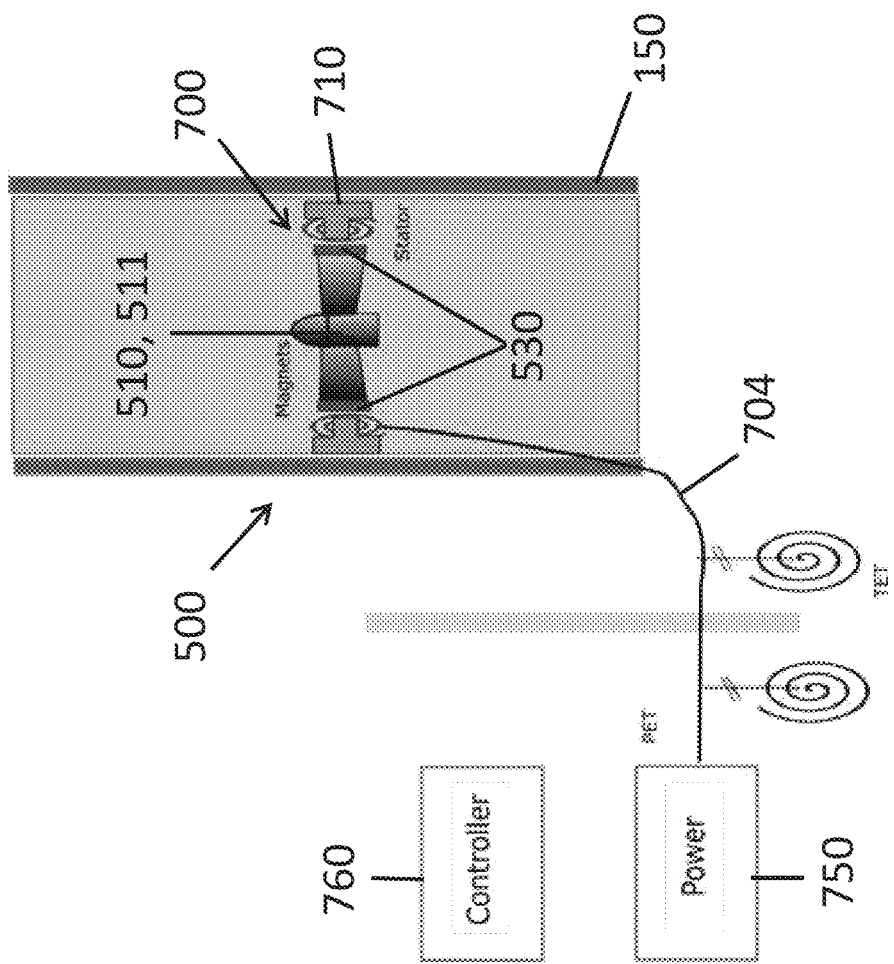
FIG. 36 schematically illustrates an MCS device comprising a rotor and an intravascular stator.

In some embodiments, an MCS device 500 may comprise an intravascular motor 700 comprising an intravascular stator 710. The use of an intravascular stator 710 may be advantageous in that it reduces the gap between the stator 710 and the rotor 510, since the blood vessel wall is not positioned between the rotor 510 and the stator 710. FIG. 36 schematically illustrates an MCS device 500 comprising a rotor 510 and an intravascular stator 710. The stator 710 may be delivered power by a line 704 which extends to a power source 750 and controller 760, as described elsewhere herein. In some implementations, the line 704 may be percutaneously connected to an extra-corporeal power source 750 and/or controller 760. The line 704 may extend through the same catheter through which the MCS device 500 was deployed. In some implementations, the line 704 may exit the blood vessel or a connected blood vessel at an internal location in the body. In some embodiments, the line is connected to an intra-corporeal power source 750 and/or controller 760 as described elsewhere herein.

Figure 37A:
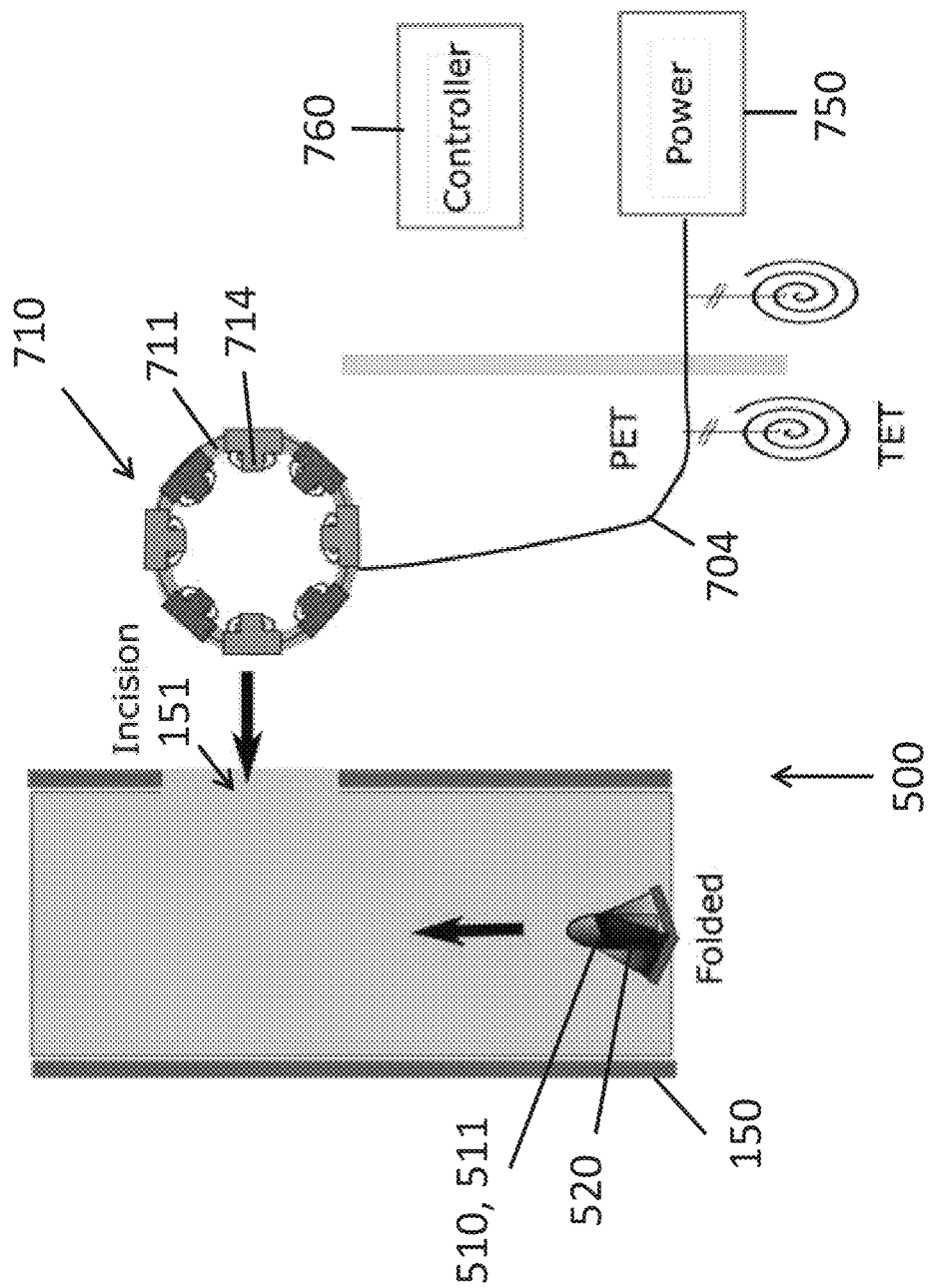
FIGS. 37A-37B schematically illustrate an example of a method of installing an MCS device comprising a foldable rotor 510 and an intravascular stator.
Figure 37B:
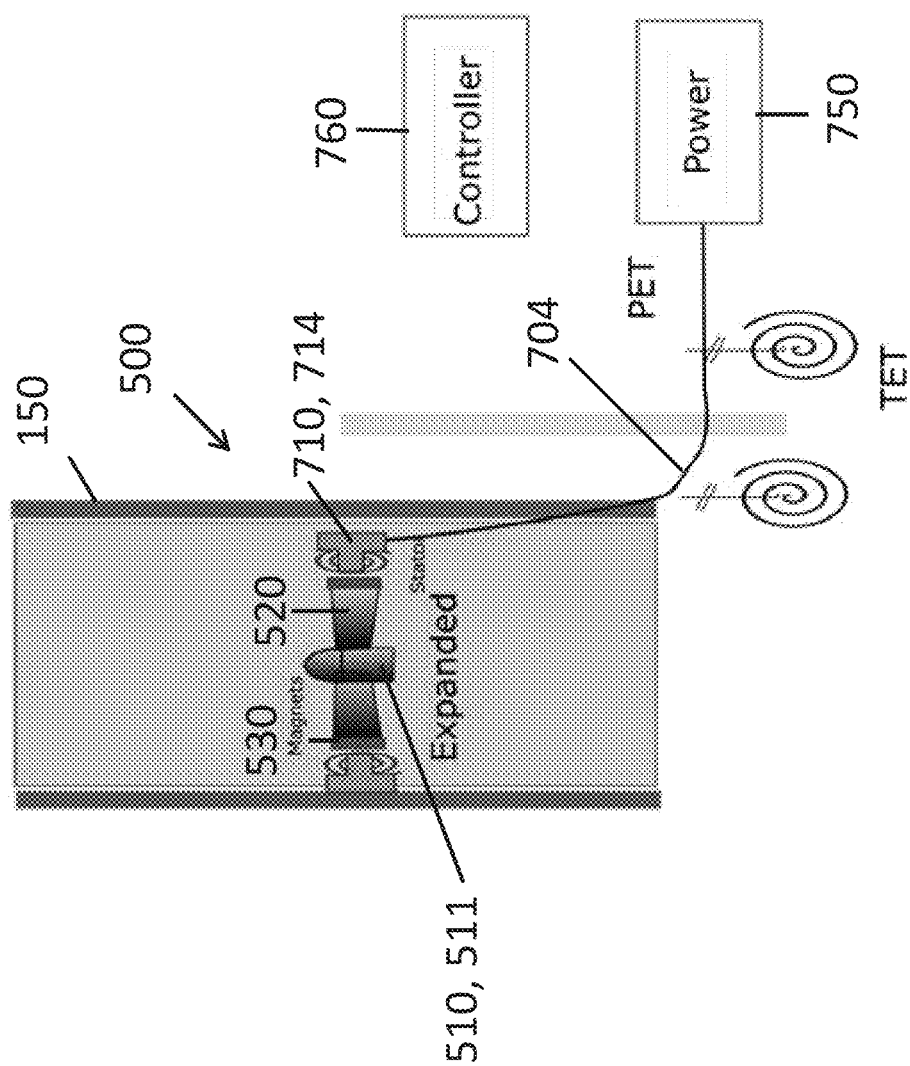

FIGS. 37A-37B schematically illustrate an example of a method of installing an MCS device 500 comprising a foldable rotor 510 and an intravascular stator 710. In some implementations, the motor stator 710 can be installed in the blood vessel via an incision in the blood vessel as schematically illustrated in FIG. 37A. Once the stator 710 is in position, the rotor 510, which may be delivered percutaneously via a catheter, may be positioned concentrically within the stator 710. In some embodiments, the rotor 510 may be foldable (or otherwise collapsible) as described elsewhere herein. In some implementations, the rotor is expanded into its operative configuration upon insertion within the stator 710, as illustrated in FIG. 37B. The rotor 510 may be coupled to an anchoring mechanism 600, as described elsewhere herein. The anchoring mechanism 600 may be foldable/collapsible. The anchoring mechanism 600 may be configured to anchor the rotor 510 within the stator 710 and/or anchor the rotor 510 within the internal diameter of the blood vessel 150. In some embodiments, the stator 710 may be coupled to an anchoring mechanism for anchoring the stator 710 within the blood vessel wall. The stator anchoring mechanism may be the same or similar to the rotor anchoring mechanisms described elsewhere herein.

Figure 38C:
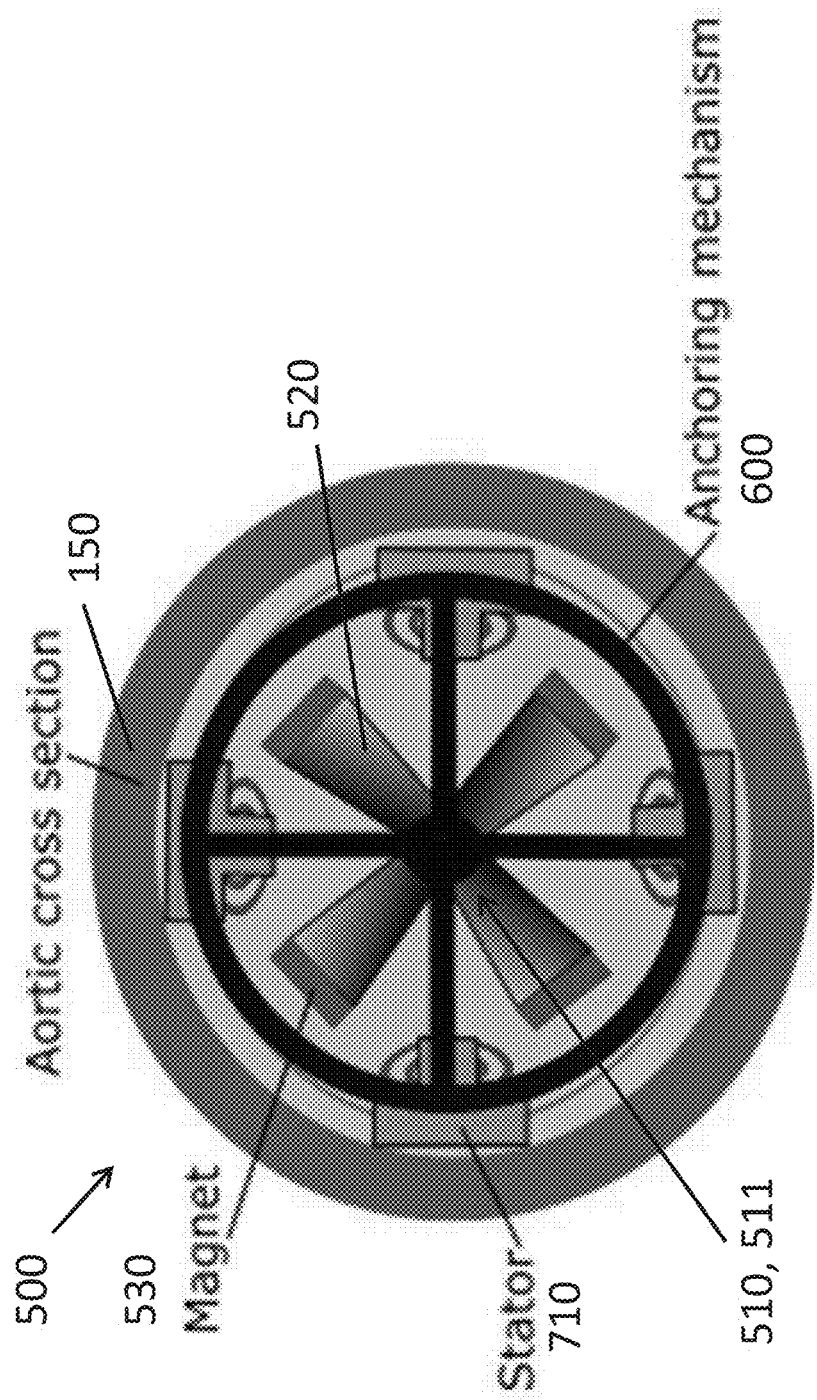

In some implementations, the stator 710 may be foldable, such that it may be deployed percutaneously, similar to or along with the rotor 510. For example, the stator 710 may be incorporated into a foldable anchoring mechanism 600. FIGS. 38A-38C schematically illustrate an example of a method of installing a foldable MCS device 500 comprising a foldable configuration which includes a rotor 510, stator 710, and anchoring mechanism 600. FIG. 38A schematically illustrates the foldable MCS device 500 in a collapsed configuration. The propeller blades 520 may be folded along the axis of rotation of the one or more rotors 510 as illustrated and as described in more detail elsewhere herein. The anchoring mechanism 600 may comprise collapsible struts 602 which are connected via flexible or articulable joints at a proximal hub 604 and distal hub 606 of the MCS device 500. The one or more stators may be coupled to the struts of the anchoring mechanism. As shown in FIG. 38B, the struts may be expanded and the blades unfolded to place the MCS device 500 into an operative configuration. The axial length of the MCS device 500 may be shorter in its expanded configuration relative to its collapsed configuration. FIG. 38C schematically illustrates a cross section interesting the central axis of the MCS device 500 in an expanded configuration.

In some implementations the stator 710 and the rotor 510 may each be deployed percutaneously in consecutive stages. The stator 710 may comprise a folded or collapsed configuration which allows the stator 710 to be deployed percutaneously such as through a delivery sheath. The stator 710 may automatically expand upon removal of the delivery sheath from the stator. For instance, the delivery sheath may be retracted in a proximal direction and/or the stator may be advanced in a distal direction to force a separation of the stator 710 from the delivery sheath. In some embodiments, the stator 710 may comprise a plurality of circumferentially spaced electromagnetic coils 714 (active magnets). The coils may be coupled to an expandable ring 711 forming the teeth 712 of the ring. In some embodiments, in order to more efficiently pack the stator, the coils 714 of a single stator 710 may be partitioned into two or more discrete rings 711a, 711b which axially overlap each other such that the coils 714 of each ring are circumferentially offset from the coils of the one or more other rings of the stator 710. In this manner, each ring 711 can be packed separately and consecutively deployed.

FIG. 39 schematically illustrates a method of deploying an MCS device 500 comprising a discrete stator 710 comprising two collapsible discrete rings 711a, 711b of stator coils 714a, 714b and a foldable rotor 510. As illustrated, a first set of stator coils 714a (on a first set of teeth 712a) are packed in a delivery sheath 160 and then deployed next to the blood vessel wall. Subsequently, a second set of stator coils 714b (on a second set of teeth 712b) are packed in a sheath 160 and then deployed next to the blood vessel wall such that the second set of coils 714b are configured to be positioned within the circumferential gaps between the of the first set of coils 714a. Finally, the folded rotor 510 is positioned, such as through a removable sheath 160, concentrically within the stator 710 comprising first and second sets of coils 714a, 714b and expanded. The first and second expandable rings 711a, 711b comprising first and second sets of coils 714a, 714b may be configured to interact with each other upon deployment. For example, the first and/or second sets of stator coils 714a, 714b may include a mechanism for coupling, locking, and/or aligning the stator components with respect to one another. In some embodiments, the first and second sets of stator coils 714a, 714b remain uncoupled. In some embodiments, the rings 711a, 711b may have smaller widths along the axial direction than the coils 714a, 714b. The ring 711a of a first set of stator coils 714a may be coupled to the proximal sides of the first set of coils 714a and the ring 711b of the second set of stator coils 714b may be coupled to the distal sides of the second set of coils 714b to allow the coils of different rings 711a, 711b to overlap along an axial width. In some embodiments, the rings 711a, 711b may use a radial spring mechanism to expand the stator coils 714a, 714. In some embodiments, the rings 711a, 711b may be at least somewhat flexible and/or may comprise jointed segments to allow packing of the rings 711a, 711b in the sheath 160. The rings 711a, 711b may use any suitable means as is well-known in the art for packing into the sheath 160. In some embodiments the stator coils 714a, 714b of each deployable set may be coupled by structures other than rings.

Figure 40:
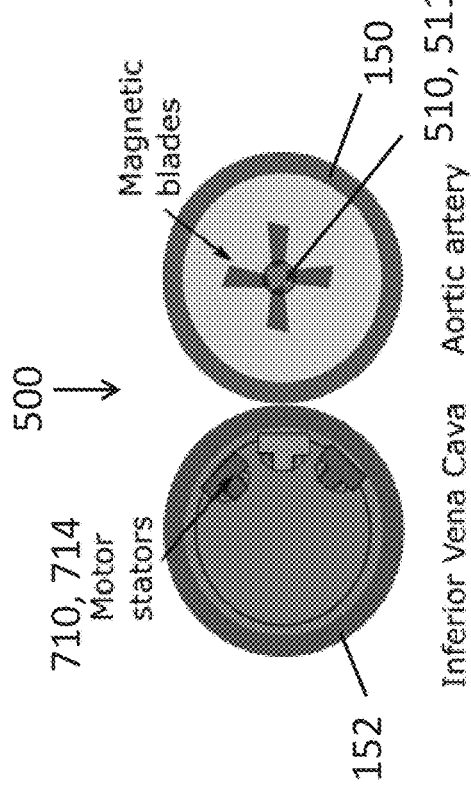
FIG. 40 schematically illustrates an example of the placement of a motor stator in the inferior vena cava in a manner configured to drive a rotor positioned in the aorta.

In some embodiments, the motor stator 710 may be installed intravascularly in a different blood vessel 152 from the blood vessel 150 in which the rotor 510 is installed. For example, FIG. 40 schematically illustrates an example of the placement of a motor stator 710 in the inferior vena cava in a manner configured to drive a rotor 510 positioned in the aorta. The stator may be installed in a blood vessel 152 significantly adjacent to the blood vessel 150 in which the rotor 510 is installed. Many other blood vessels may be used as suitable locations for installing a stator configured to drive a rotor in the descending aorta, including adjuvant veins and channels. The stator 710 and/or the rotor 510 may be installed via percutaneous deployment or via a surgical incision in the blood vessel wall as described elsewhere herein. In some embodiments, the stator 710 may be configured for driving an adjacent rotor 510. For example, as illustrated in FIG. 40, the stator 710 may not comprise a full circumference of electromagnetic coils 714, but may position coils 714 only along one side or portion of the blood vessel 152 in which it is implanted, such that the coils 714 are as proximate as possible to the rotor 510. In some embodiments, the coils 714 may be more densely concentrated along this portion of the circumference. In some embodiments, a stator 710 with coils uniformly distributed around the circumference may be used. In some implementations, only select coils 714 may be activated.

Figure 41:
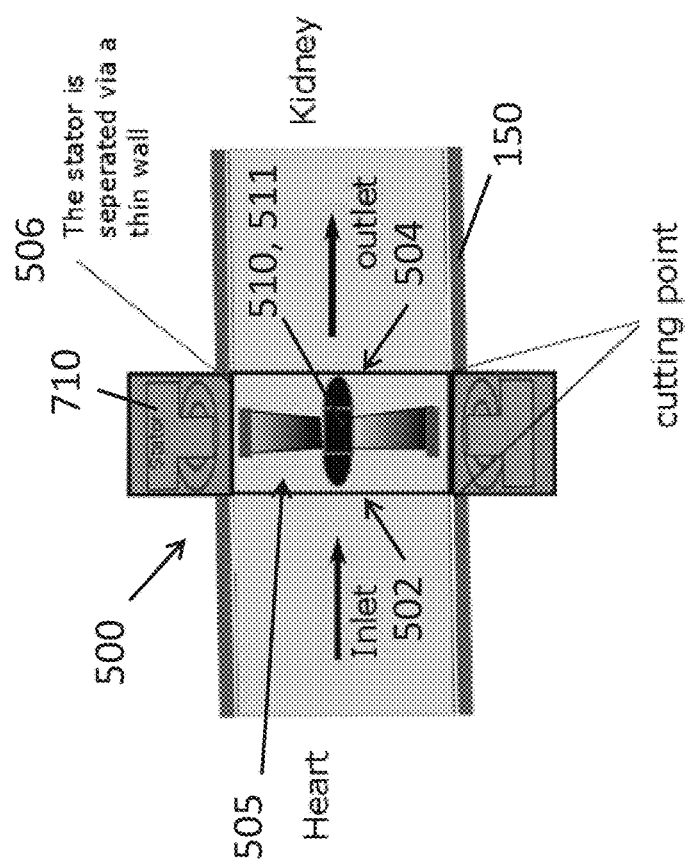
FIG. 41 schematically illustrates an example of an MCS device surgically installed in-series with the descending aorta which is severed.

In some embodiments, the MCS device 500 may comprise a rotor 510 and a stator 710 that are integrated as a single unit having an inlet 502 and an outlet 504 for surgical insertion in-series with the blood vessel 150. FIG. 41 schematically illustrates an example of an MCS device 500 surgically installed in-series with the descending aorta. The MCS device 500 may be installed through a minimally invasive surgery (e.g., a thoracotomy in the left side of the chest). The MCS device 500 may comprise a fluid-tight channel 505 formed by a separator wall 506 between the inlet 502 and the outlet 504 to allow blood to flow through. The rotor 510 may be positioned within the channel 506. The inner diameter of the channel 505 may be about the same as the diameter of the blood vessel 150 into which the MCS device 500 is inserted, which may provide minimal disruption to the blood flow. The stator 710 may be positioned concentrically around the channel 505 and may be configured such that it does not come into contact with the blood flow. The separator wall 506 may be relatively thin to minimize the gap between the stator 710 and the radial tips 521 of the rotor blades 520. In some embodiments, the MCS device 500 may comprise an inlet 502 and/or outlet 504 that extends axially beyond the stator 710 to facilitate connecting the device to the severed blood vessel 150. The MCS device 500 may be connected to the blood vessel 150 via any suitable means, including any means disclosed elsewhere herein for connecting pumps to severed blood vessels.

Figure 42A:
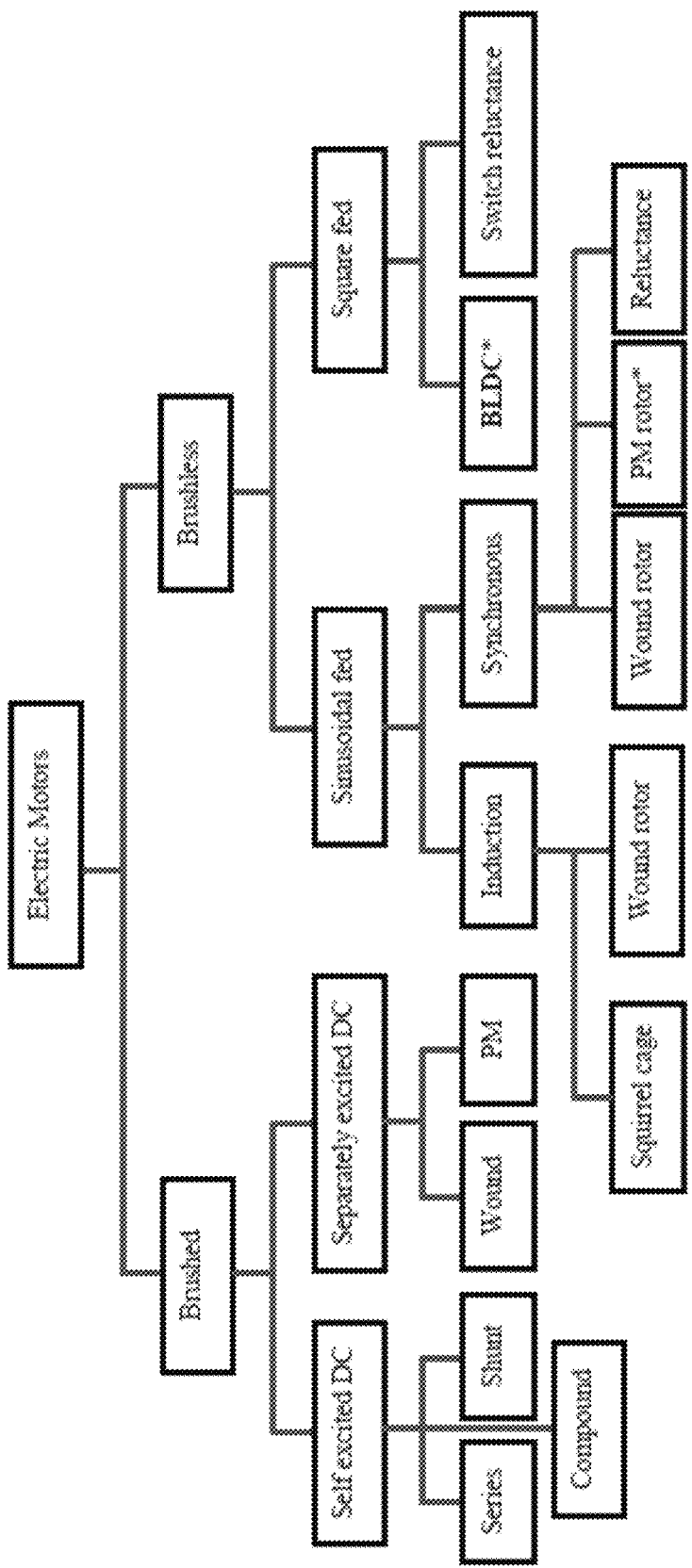

Electric motors convert electrical energy to mechanical energy. FIG. 42A depicts types of electric motors, where "DC" stands for direct current, "PM" stands for permanent magnet, and BLDC stands for brushless DC. Based on the principle theory of electromechanical systems, if a current-carrying conductor is located in a magnetic field, a force is exerted on the conductor as depicted in FIG. 42B. The force, f, is directly proportional to the current I, magnetic field density B and the length of the conductor 1 and according to the Lorentz law, the force can be expressed as $f=Il\times B$, where $\times$ implies a vector cross product. FIG. 42B schematically illustrates the electromagnetic force to a current-carrying conductor located in a magnetic field, B, I and f being mutually perpendicular.

An electric motor needs two sets of windings to be able to work properly; one is the so-called field winding, producing a magnetic field, and the other is the armature winding, which carries the armature current. In the case of a permanent magnet motor, a set of permanent magnets substitutes the field winding for generating a constant magnetic flux. The armature winding of a brushless DC motor is located on the stationary part, the stator, and a set of permanent magnets are located on the non-stationary part, the rotor. If a conductor moves with speed v inside a magnetic field with density B, a voltage E will be induced in the conductor which is expressed as, $E=vl\times B$. The MCS device 500 may comprise a rotor which is inaccessible for winding. The rotor 510 may be permanent magnet excited, such as by a brushless DC motor (BLDC) or a permanent magnet synchronous motor (also known as a brushless AC motor). Permanent magnet DC motors have permanent magnets on the stator. To control permanent magnet synchronous motors (PMSMs), an accurate position or rotational velocity sensor (such as shaft encoder or resolver) is required to be coupled to the rotor shaft. In contrast, BLDC motors just need a set of discrete position sensors (such as hall sensors) which can measure the position of the rotor proximately without requiring to be coupled to the rotor shaft, which may make BLDC motors particularly suitable for the MCS devices 500 disclosed herein.

Figure 42D:
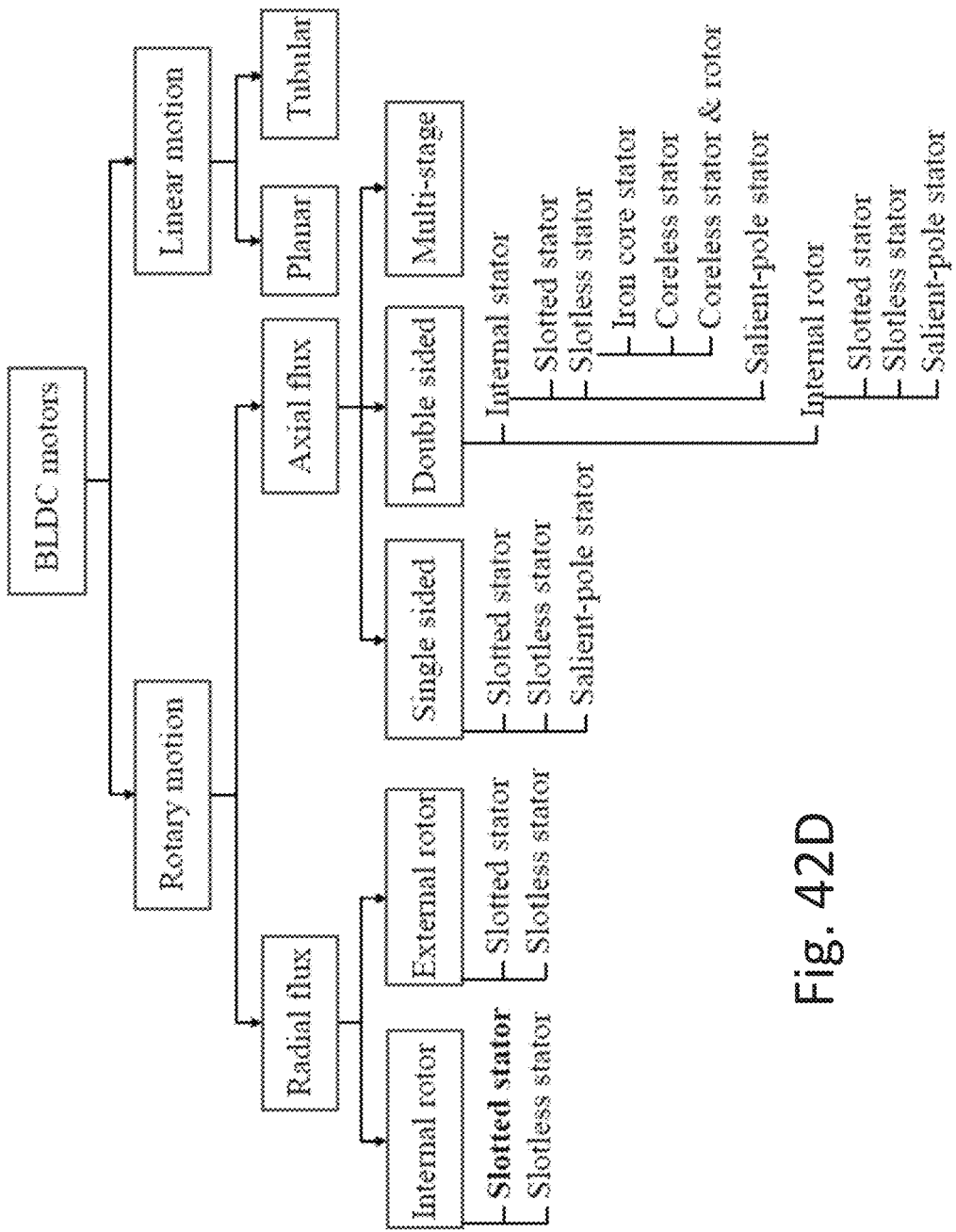

The structure of a permanent magnet BLDC motor may similar to a PMSM; however, there are some differences as listed in the table of FIG. 42C. FIG. 42D depicts the classification of different types of BLDC motors. In general, depending on the motion, a BLDC motor is either rotary or linear. Although a rotational movement can be mechanically transferred to a linear movement, due to efficiency, performance and other restrictions, sometimes direct linear motion BLDC motor is advantageous. Depending on the flux path, BLDC motors are categorized as radial and axial flux. The application of either a radial flux or axial flux BLDC motor can strongly depend on physical space limitations. FIG. 42E presents a comparison between radial and axial flux configurations of BLDC motors. The rotor of a radial BLDC motor is generally located inside the stator, and is called an internal rotor. Sometimes the stator is inside the rotor in what it referred as external rotor or inside-out motor. FIG. 42F compares these two configurations. The stator of a BLDC motor can be either slotted or slotless and each type has its own advantages and disadvantages as presented in FIG. 42G.

The type of permanent magnet material may be selected according to some criteria such as the energy product, cost, resistance to corrosion and temperature performance of available magnets. In some cases, the complexity of the required magnet shape may limit the choice. The most common materials for permanent magnets are NdFeB (neodymium-iron-boron), SmCo (samarium-cobalt), Alnico (aluminium-nickel-cobalt), and ferrite. The production technique, e.g. sintering, injection molding, compression bonding and casting, has significant effects on magnet properties as shown in FIG. 42H, where $B_r$, $H_c$ and $H_{ci}$ are the magnet remanence, coercivity and intrinsic coercivity, respectively. Various structures can be used to allocate the permanent magnets of a BLDC motor as schematically illustrated in FIG. 42I. FIG. 42I depicts various configurations of permanent magnets (in dark) in radial flux slotless BLDC motors having a cylindrical rotor, including: (a) surface mounted magnets, (b) surface mounted with parallel edges, (c) ring magnets (d) bread-loaf magnets, (e) surface inset magnets, (f) surface inset magnets with airspace between, (g) buried or interior magnets, (h) spoke magnets, (i) multi-segment interior magnets, and (j) multilayer interior magnets. FIG. 42J compares these configurations in terms of cost, robustness, maximum speed, direct-per quadrature-axis reluctance, eddy current losses in permanent magnets and the harmonics of the stator winding magneto-motive force (MMF) in permanent magnets. For instance, the surface inset magnet structure may have superior over surface mounted magnet structure in terms of field weakening capability and therefore can extend the power capability since it has higher q-axis per d-axis reactance ratio compared to the latter one.

The motor type selection may strongly depend on application and application-specific limitations. Use of axial flux BLDC motors in the MCS devices 500 disclosed herein may be limited due to physical structures. The external rotor radial flux BLDC motors are generally inapplicable since the rotating part should be accommodated in the blood vessel and the stationary part outside the blood vessel. Since the magnetic air-gap of the slotless BLDC motors is higher than that of the slotted BLDC motors and the thickness of the blood vessel wall is also added to the magnetic air-gap, slotted configuration BLDC motors may be more efficient than slotless BLDC motors in use with the MCS devices 500 disclosed herein. A slotted radial flux internal rotor BLDC motor may be particularly well-suited for use in the MCS devices disclosed herein.

NdFeB magnets with sintering manufacturing techniques may result in the highest energy density, but may be difficult to fabricate into a complex shape like a propeller. Sm2Co17 magnets with compression bonding technique may be particularly well-suited for the MCS devices disclosed herein, as they possess better resistance to corrosion and temperature performance compared to that of the NdFeB. Some permanent magnet structures (i.e. surface mounted magnet, surface mounted with parallel edges, ring magnet, bread-loaf magnet, surface inset magnet, surface inset magnet with airspace between, buried or interior magnet, spoke magnet, multi-segment interior magnet and multilayer interior magnet) may be particularly suited for a cylindrical rotor and/or inapplicable for use with a propeller. The propeller may be made out of permanent magnet and coated with a biocompatible material.

The optimal geometry of a motor may be determined via a model of the motor (a set of equations which relate the performance of the motor to its geometry). An optimization problem may be formed and solved to find the optimal geometry of the motor subject to desired requirements. A model can be dynamic or static. Normally, to study and simulate the transient as well as steady state behaviors of a motor or to design a controller for the motor, the model is dynamic and the equations are represented in a combination of ordinary differential equations (ODEs) and algebraic equations. The dynamic equations of a motor can be, in more general form, represented by partial differential equations (PDEs) with both time and space derivatives. However, modeling may also be static. The static equations of a BLDC motor may be written in the form of PDEs using Maxwell's equations. In some cases, the derived PDEs may be analytically solved while in others only numeral solution can be obtained. For instance, the two-dimensional PDE-based magnetic analysis problem of surface mounted magnet BLDC motors and those with ring magnets can be solved analytically for different magnetization topologies. However, in the case of surface inset magnet BLDC motors, a semi-analytical solution can be represented. Magnetic equivalent circuits, or more generally lumped magnetic circuit models, have been employed to analytically but approximately solve the magnetic field analysis in the case of other magnet structures. However, some of the motor specifications cannot be obtained using magnetic equivalent network or lumped magnetic circuit techniques. In all cases, numerical solutions of the PDE-based magnetic analysis problem can be obtained. From the motor design point of view, analytical techniques, such as separation of variables, conformal mapping and series expansion, are often preferred since they implicitly show the influence of each motor parameter on each motor specification. Numerical solutions, such as finite element and finite difference methods, are mostly used to analyze the performance of a designed motor for verification purposes; however, they may be employed in an iterative design procedure which is a time-consuming approach and may result in suboptimal design specifications. The PDE-based problem of the motors disclosed herein may not be analytically solvable due to the complex shape of the rotor (i.e. the propeller) and therefore a magnetic equivalent network technique may be well-suited. The numerical solution of the PDE-based problem can be obtained for verification of the optimization results.

In order to design a brushless DC motor, the specifications of the motor may be expressed in terms of motor geometric parameters. The nominal output power, which for rotary motors represented in terms of the developed electromagnetic torque and rotational velocity, may be a fundamental motor specification. The instantaneous torque consists of the cogging, reluctance and electromagnetic torques in which the first term is a pulsating torque and the last component is divided into average and ripple torques. In the case of BLDC motors, it is generally desired to minimize the pulsating torque components such as cogging and ripple torques. The cogging torque is generated due to the interaction between the permanent magnet and the stator slots; this torque is independent of armature current. In slotless BLDC motor configurations, the cogging torque may be almost zero. The reluctance torque is due to the armature reaction field and the rotor saliency; in non-salient rotor motor, reluctance torque may be zero. The torque ripple originates from the unwanted harmonics in the current and back-emf waveforms as well as the presence of the stator slots. Hence, to find different components of torque, the magnetic field distribution due to PMs and the armature current waveform are required. In magnetic equivalent network techniques, only the peak of flux density can be obtained and not the distribution. The electromagnetic torque can be approximately calculated.

The back-emf, which is the induced voltage in the armature winding due to a rotating permanent magnet field, may comprise another important specification. The induced emf waveform of BLDC motors depends on the flux density distribution in the air gap which in turn is a function of the magnetization of the permanent magnets and stator teeth and slot structure. The conductor distribution may have a significant effect on the back-emf waveform.

To express the efficiency of the motor, various sources of power loss can be identified and represented as functions of motor geometric parameters. The power losses of an electric motor are, generally, divided into three categories: electrical, magnetic and mechanical losses. The power loss due to the winding resistance, known as copper loss, may be the most significant electrical loss, especially in low-speed applications. Hysteresis, eddy current and excess eddy current losses are the dominant magnetic losses. Mechanical losses may include windage, ventilation, and bearing friction. Knowing the armature current and the specification of armature winding, copper loss can be easily expressed. The stator iron losses depend primarily on the magnetic field components of the permanent magnets and their frequencies as well as the type, volume and thickness of the lamination materials. The armature reaction field may have little influence on the stator iron losses. The eddy current loss in the permanent magnets and rotor back-iron is a function of the armature reaction filed components and their frequencies relative to the rotor motion, in addition to the permanent magnet electrical conductivity and volume.

Nominal and maximum rotational velocities may be important specifications. Motor rotational velocity may be limited by electrical and/or mechanical constraints. The bearings may not impose any restriction on the rotational velocity since they can generally withstand relatively high rotational speed; however, the robustness of other rotating parts, such as permanent magnets, may require analysis. Specifically, in surface mounted permanent magnet structures, a restriction on maximum rotational velocity may result from adhesive between the permanent magnets and the rotor. A non-magnetic (carbon or glass fiber) retaining sleeve can be used to increase the mechanical robustness of the rotor. The electrical time constant of the motor may restrict the maximum rotational velocity. Self- and mutual-inductances may accordingly be expressed in terms of motor geometric parameters.

By way of a non-limiting overview, the following quantities and/or specifications may be determinable for optimizing motor design: (1) magnetic flux density distribution due to permanent magnets; (2) armature current waveform (depends on the adopted control technique); (3) winding configuration and winding factors; (4) magnetic flux density distribution due to the armature current (from 2 and 3); (5) back-emf calculation (from 1 and 3); (6) electromagnetic torque (from 2 and 5); (7) ripple and average electromagnetic torques (from 6); (8) cogging torque (from 1, needs both radial and tangential PM flux distribution); (9) reluctance torque, just for salient rotor motors (from 2 and rotor structure); (10) stator iron losses: hysteresis, eddy current and excess eddy current (from 1, for more accuracy 4 can be included); (11) eddy current loss in permanent magnets (from 4); (12) rotor iron losses: hysteresis, eddy current and excess eddy current (from 4); (13) copper loss (from 2); (14) self and mutual inductances (from 2, 3 and 4); and (15) mechanical losses: windage, ventilation and bearing friction. Some of these parameters may be unobtainable and/or can be approximately calculated. However, using finite element analyses all quantities can be obtained after the design process.

Figure 43A:
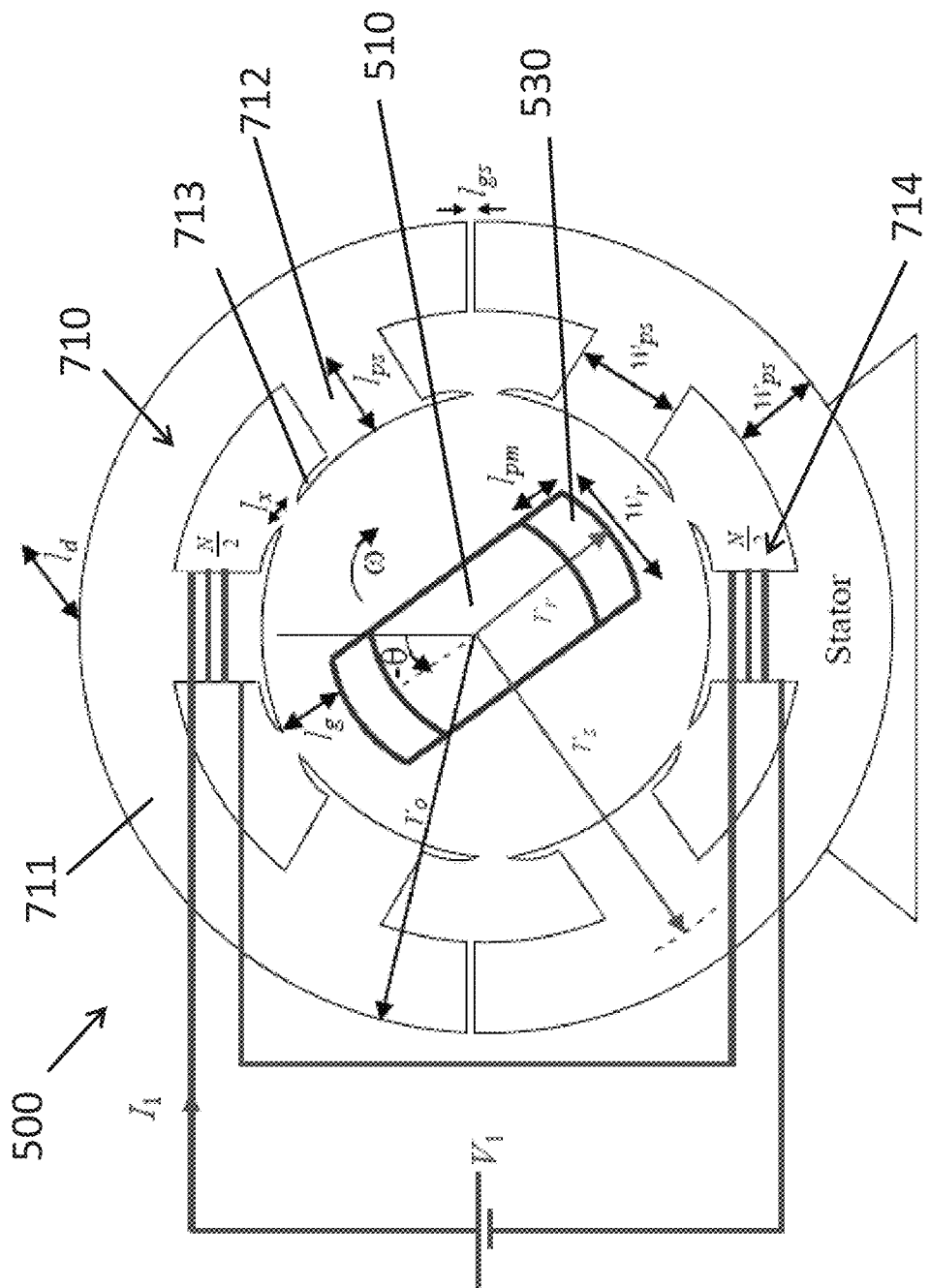
FIGS. 43A-43N schematically illustrate an example of a hinged stator and examples specifications of related components.
Figure 43F:
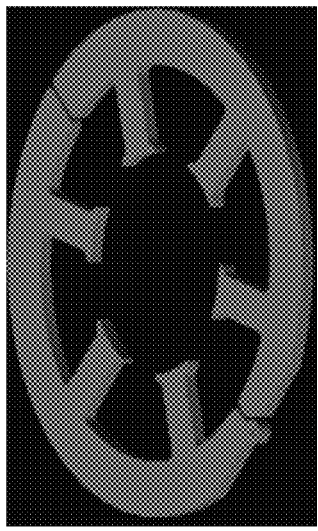
Figure 43G:
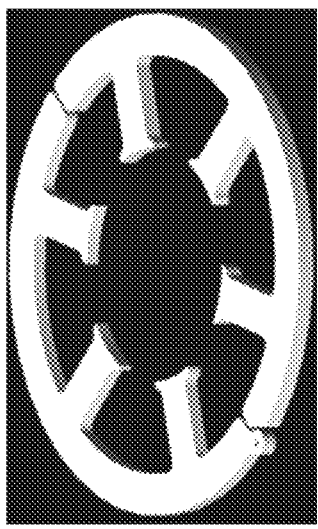
Figure 43H:
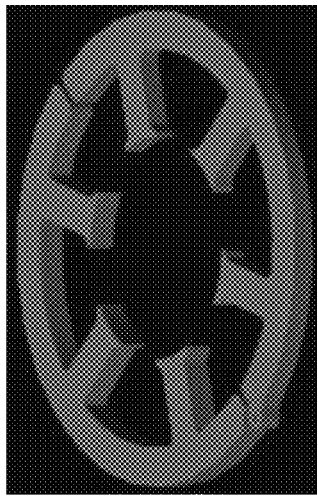
Figure 43J:
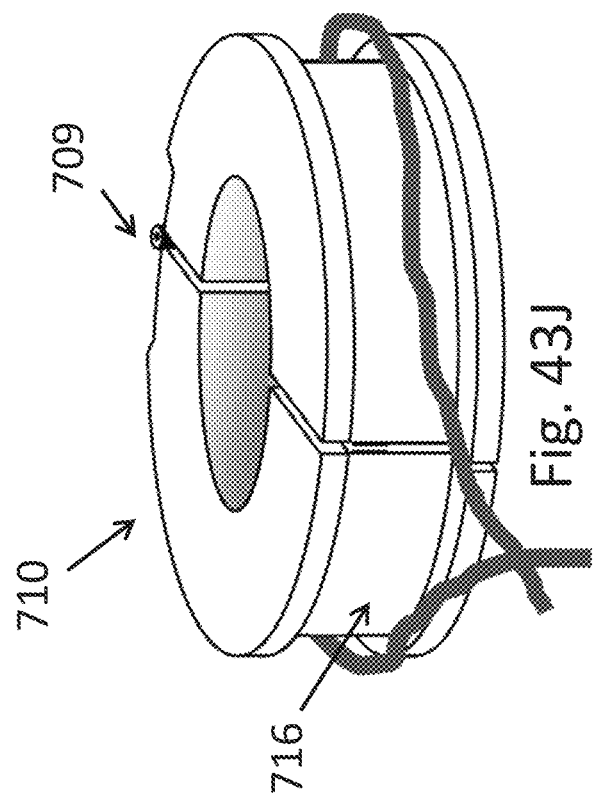
Figure 43I:
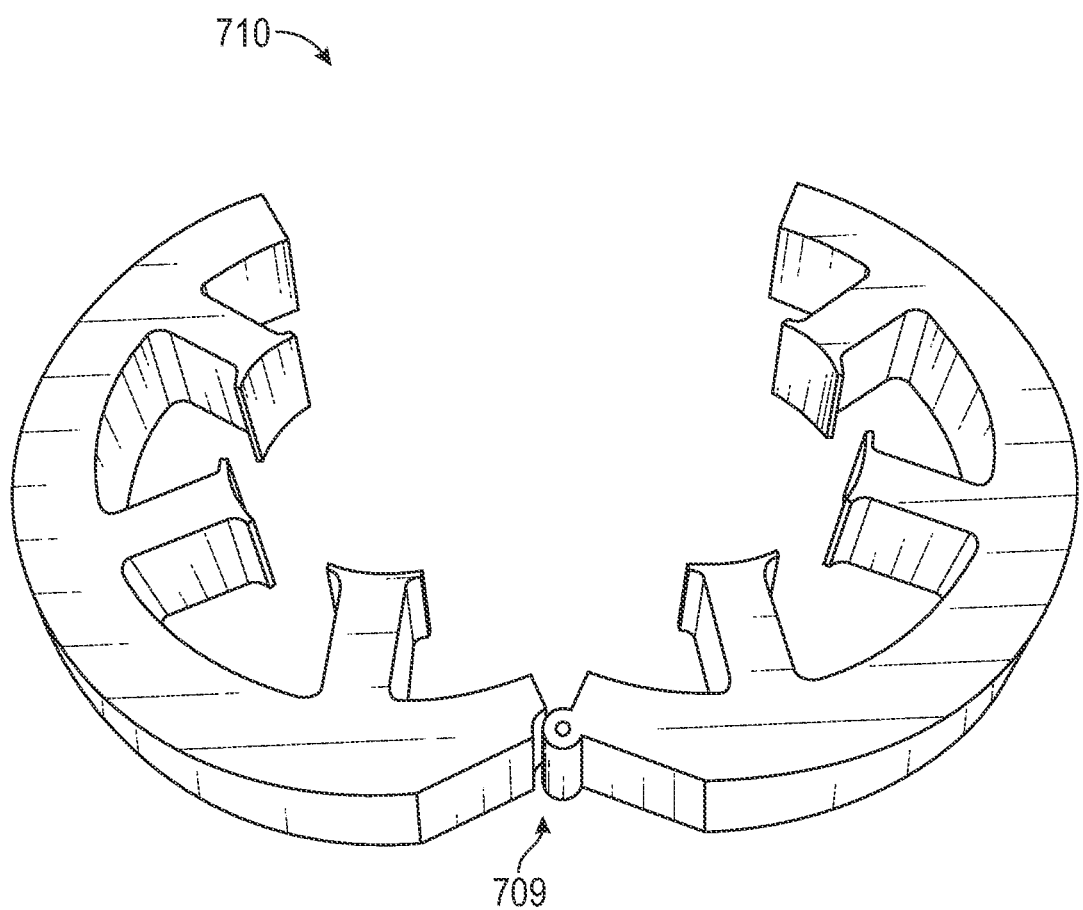
Figure 43K:
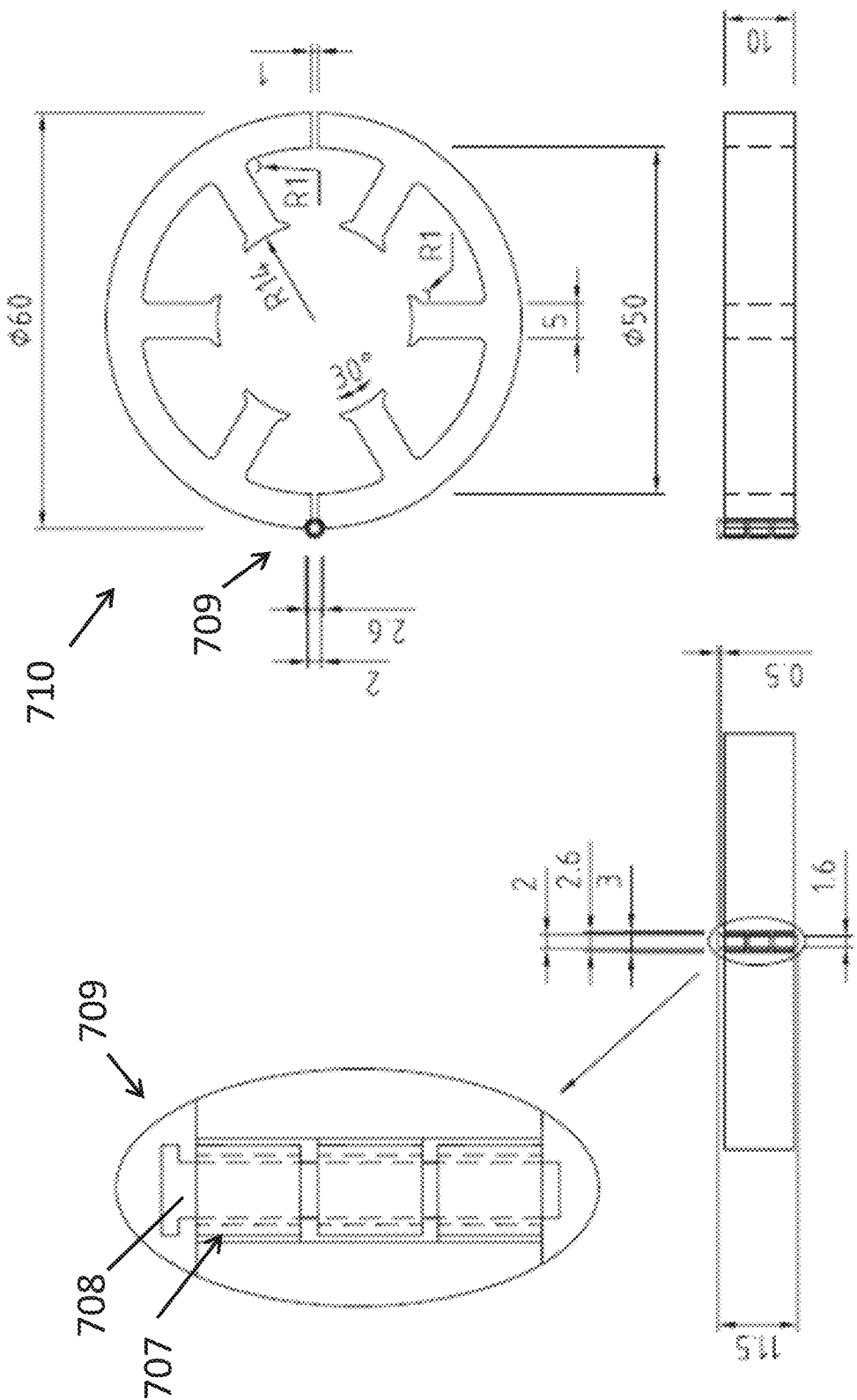

In some embodiments, the MCS device 500 may comprise an extravascular stator 710 configured to surround the blood vessel along a portion in which the rotor 510 is installed, as described elsewhere herein. In some implementations, the stator 710 may comprise a hinge 709 such that it can be in an open configuration for installing the stator 710 around the blood vessel and a closed operative configuration, in which the stator 710 forms a complete or substantially complete circumference enclosing the blood vessel. FIGS. 43A-43K illustrate an example of a hinged stator and examples specifications of related components. FIG. 43A schematically illustrates a cross-section intersecting the central axis of the MCS device 500 and labeling various geometric parameters. In some embodiments, the stator teeth 712 may be about 5 mm wide. The teeth 712 may comprise an inner circumferential flange 713. Each flange 713 may comprise an arc that is about 30 degrees. The hinge 709 may have an outer diameter of about 3 mm. The hinge 709 may comprise an aperture 707 for receiving a pin 708. The aperture 707 may comprise a diameter of about 1 mm. The overall shape and configuration of the stator 710 may be the same or similar to other stators 710 described herein. The stator 710 may be designed to minimize power loss and/or to minimize stator mass and/or volume. The stator 710 may be designed to optimize maximum temperature and/or maximum flux density to prevent magnetic saturation. In some embodiments, the stator 710 may comprise six poles (electromagnetic coils 714 formed on the stator teeth 712). FIG. 43B schematically illustrates a perspective view of the hinged stator 710. FIG. 43C schematically illustrates a top view of the hinged stator 710. FIG. 43D schematically illustrates a left view of the hinged stator 710. FIG. 43E schematically illustrates a right view of the hinged stator 710. FIG. 43F is a perspective view of an example of a top and/or bottom layer of the hinged stator 10. FIG. 43G is a perspective view of an example of an upper intermediate and/or lower intermediate layer of the hinged stator 10 (positioned between a center layer and a top or bottom layer). FIG. 43H is a perspective view of an example of a center layer of the hinged stator 10. FIG. 43I is a perspective image of an example of a hinged stator 710. The stator 710 may be fabricated by laminating shaped sheets. The stator sheets may comprise steel (e.g., 30 cast steel sheets approximately 0.35 mm thick). The stator 710 may comprise any number of suitable sheets. In some embodiments, the stator 710 may comprise multiple layers, wherein each layer comprises one or more sheets. The sheets of each layer may comprise the same design. For example, the stator 710 may comprise 2, 3, 4, 5, 10, 15, 25 layers, etc. Each layer may have the same or different number of sheets. The number of sheets may determine the ultimate thickness of each layer. The stator 710 illustrated in FIG. 43B comprises five layers in which the center layer comprises 8 sheets, the top and bottom layer are identical and each comprise 5 sheets, and the two intermediate layers are identical and comprises 5 sheets on the side with the hinge 709 and 6 sheets on the side without the hinge 709. The sheets may be insulated, such as by an epoxy resin. Insulation may reduce the eddy loss of the stator core. In some embodiments, the surface forming outer circumference of the stator may comprise a groove 716 along the circumferential direction, as seen in FIG. 43B. The groove 716 may be formed by differences in the dimension of the stator layers. The groove 716 may facilitate tightening or securing the stator 710 to the blood vessel. For example, a line 717 such as a suture, wire, or cable may be positioned in the groove 716 and tightened around the stator 710 to secure the stator in a closed configuration, as is schematically illustrated in FIG. 43J. FIG. 43K schematically illustrates multi-perspective views of a hinged stator 710 including example dimensions, with distances represented in mm.

Embodiments of intravascular stators may be substantially the same or similar to the extravascular stator. Intravascular stators may not comprise a hinge 709. Intravascular stators may comprise a complete closed circumference and may be installed for example by a surgical incision in the blood vessel, as described elsewhere herein. Intravascular stators may be similar to the extravascular stators but may be collapsible/expandable as described elsewhere herein.

Figures 43L, 43N:
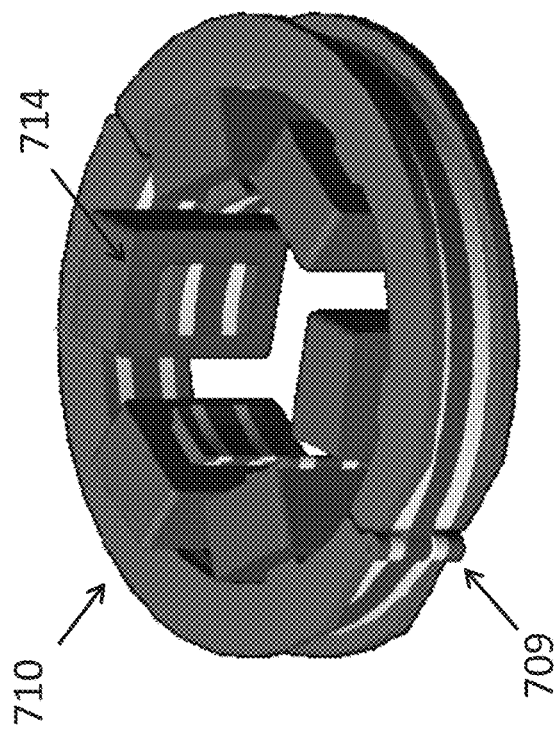
Figure 43M:
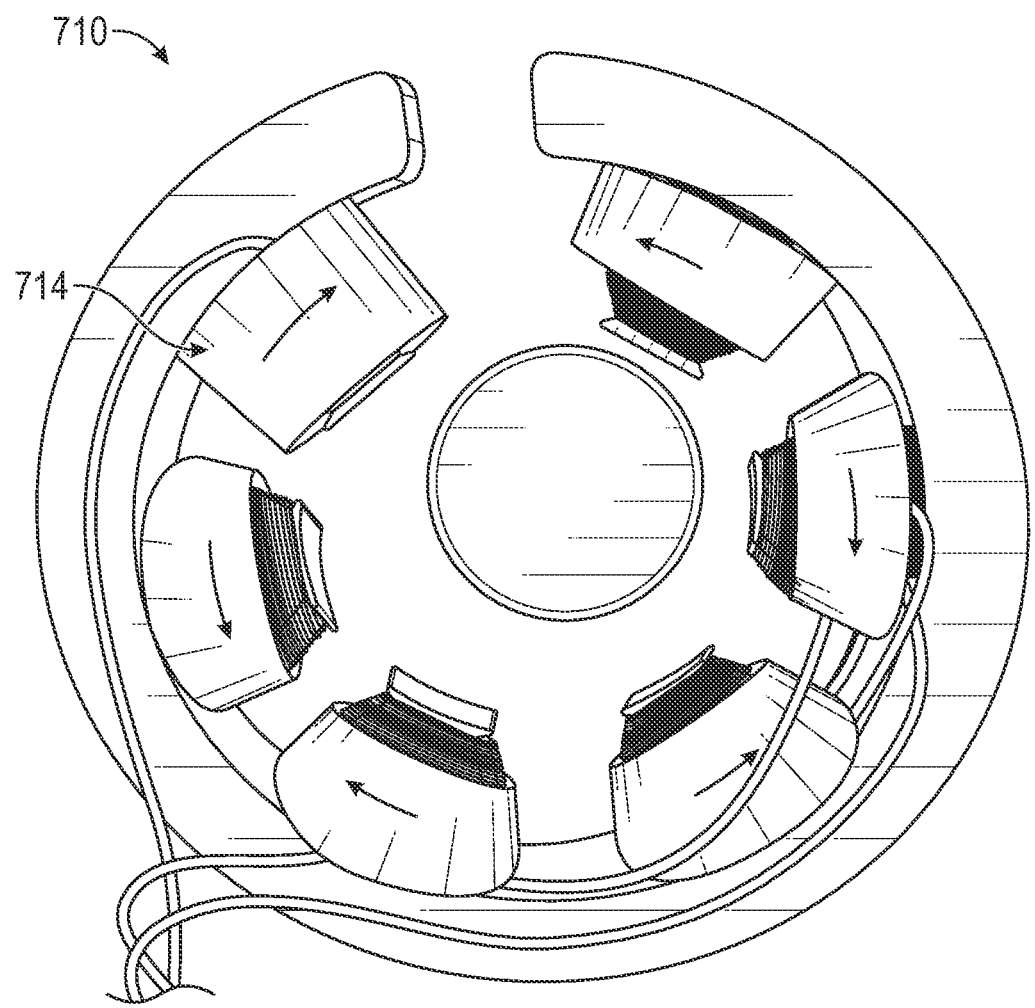

In some embodiments, electromagnets may be formed on the stator by winding conductive wire around stator teeth 712 to form electromagnetic coils 714 as described elsewhere herein. In some embodiments, the conductive wire may be copper wire. The wire may be enameled. The wire may have a gauge of about AWG 18. The wire may have a diameter of about 1 mm and a cross-sectional area less than 1 mm². The wire may be configured to carry at least up to about 2.3 Amp current. Each stator pole may comprise about 150 mm² of available area for the winding of the coil. Each stator pole may have sufficient area to allow at least 60 turns of the wire around the stator tooth 712, which may accommodate at least 120 turns for each phase of a six pole three-phase motor. FIG. 43L schematically illustrates the hinged stator 710 comprising electromagnetic coils 714 around the stator teeth 712. FIG. 43M illustrates an image of a hinged six pole stator 710 as well as a coin as a reference for size. The arrows indicate the direction in which the coils are wound around each stator tooth 712. In some embodiments, adjacent poles may comprise coils 714 wrapped in opposite directions. FIG. 43N depicts a table of example specifications for a wire to be used to fabricate the coils 714.

The controller 760 may comprise a closed loop system. Feedback can be used to modulate the driving of the motor 700. For example, current and position feedback signals may be used to control the speed of the rotor 510 in a reliable and accurate manner. The MCS device 500 may include sensors to measure outputs such as angular position of the rotor and/or angular velocity of the rotor 710. In some embodiments, sensors may comprise one or more shaft encoders, tacho-generators, and/or hall sensors. The controller 760 may comprise a processor. The processor may comprise a micro-processor, a digital signal processor (DSP), and/or a transputer.

Figure 44A:
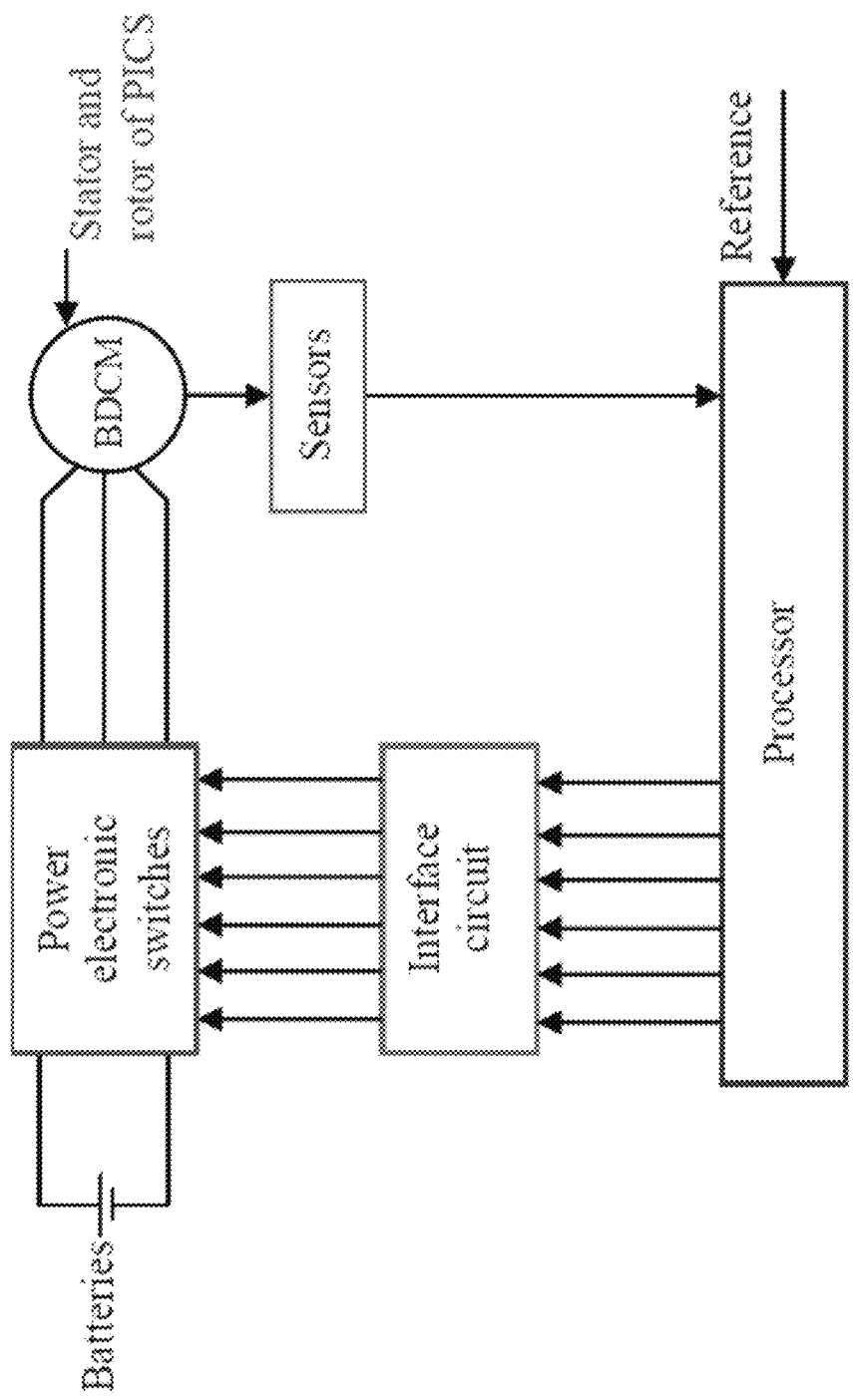
FIGS. 44A-44E schematically illustrate examples of controllers and waveforms for driving the MCS device.
Figure 44B:
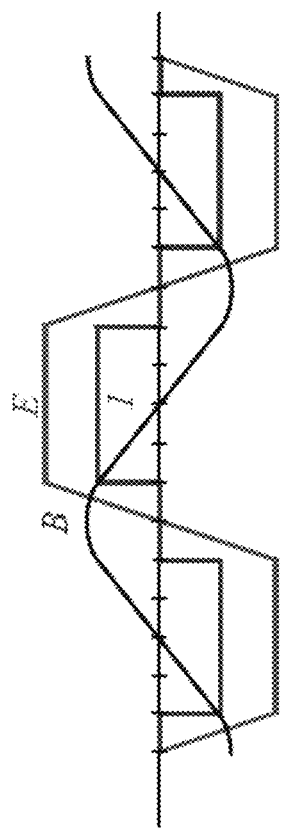
Figure 44C:
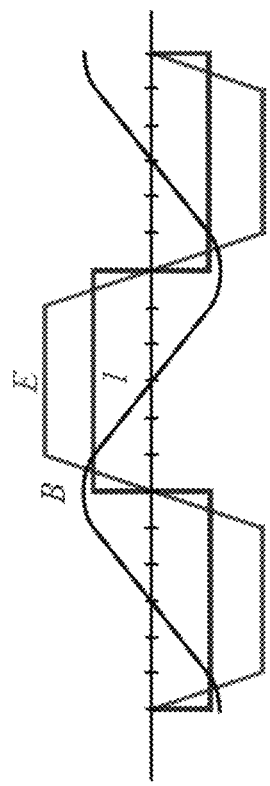
Figure 44D:
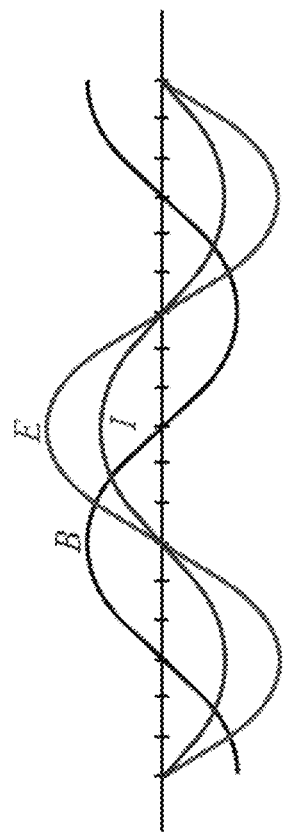

The controller 760 may comprise power electronic switches for converting a fixed AC or DC power source to an appropriate power level and wave shape, depending on the motor type. An interface circuit may convert the output signals of the processor to suitable signals for the power electronic switches. FIG. 44A schematically illustrates a block diagram of a BLDC motor control system (the MCS device 500 may be referred to herein as "PICS"). In some embodiments comprising a BLDC motor, the power electronic switches may comprise metal oxide semiconductor field effect transistors (MOSFETs) and/or insulated gate bipolar transistors (IGBTs), depending on the power requirement and switching frequency. IGBTs may generally be used for higher power requirements, while MOSFETS may generally be used for lower power requirements but higher switching frequencies. In a BLDC motor, the current may comprise a 2-phase, 120 degree conduction (BLDC-120) or 3-phase, 180 degree conduction (BLDC-180) rectangular waveform. The magnetic flux density waveform may be configured to induce a trapezoidal back electromotive force (EMF) in the windings. The winding and magnet configurations may play important roles in obtaining a trapezoidal back-EMF. FIGS. 44B and 44C depict examples of magnetic flux density which may induce trapezoidal back-EMF in a concentrated winding. FIG. 44B illustrates ideal waveforms of current, flux density, and back-EMF for BLDC motors with 2-phase, 120 degree conduction with no phase advancing. FIG. 44C illustrates ideal waveforms of current, flux density, and back-EMF for BLDC motors with 3-phase, 180 degree conduction with no phase advancing. Any deviation from the ideal current and back-EMF waveforms may reduce the developed torque and increase torque ripples. For instance, due to the inductive nature of electric motors, current cannot jump suddenly; also because of the dynamic nature of motors, the current at the constant 120 degree region contains switching harmonics. In brushless AC (BLAC) motors, all of the waveforms may be sinusoidal. FIG. 44D depicts ideal waveforms of current, flux density, and back-EMF for BLAC motors with no phase advancing. In the region below the base speed where the torque is constant, phase advancing can be utilized to include the contribution of saliency torque. Above the base speed which is the constant power region, phase advancing may be used to improve the torque-speed characteristics.

Figure 44E:
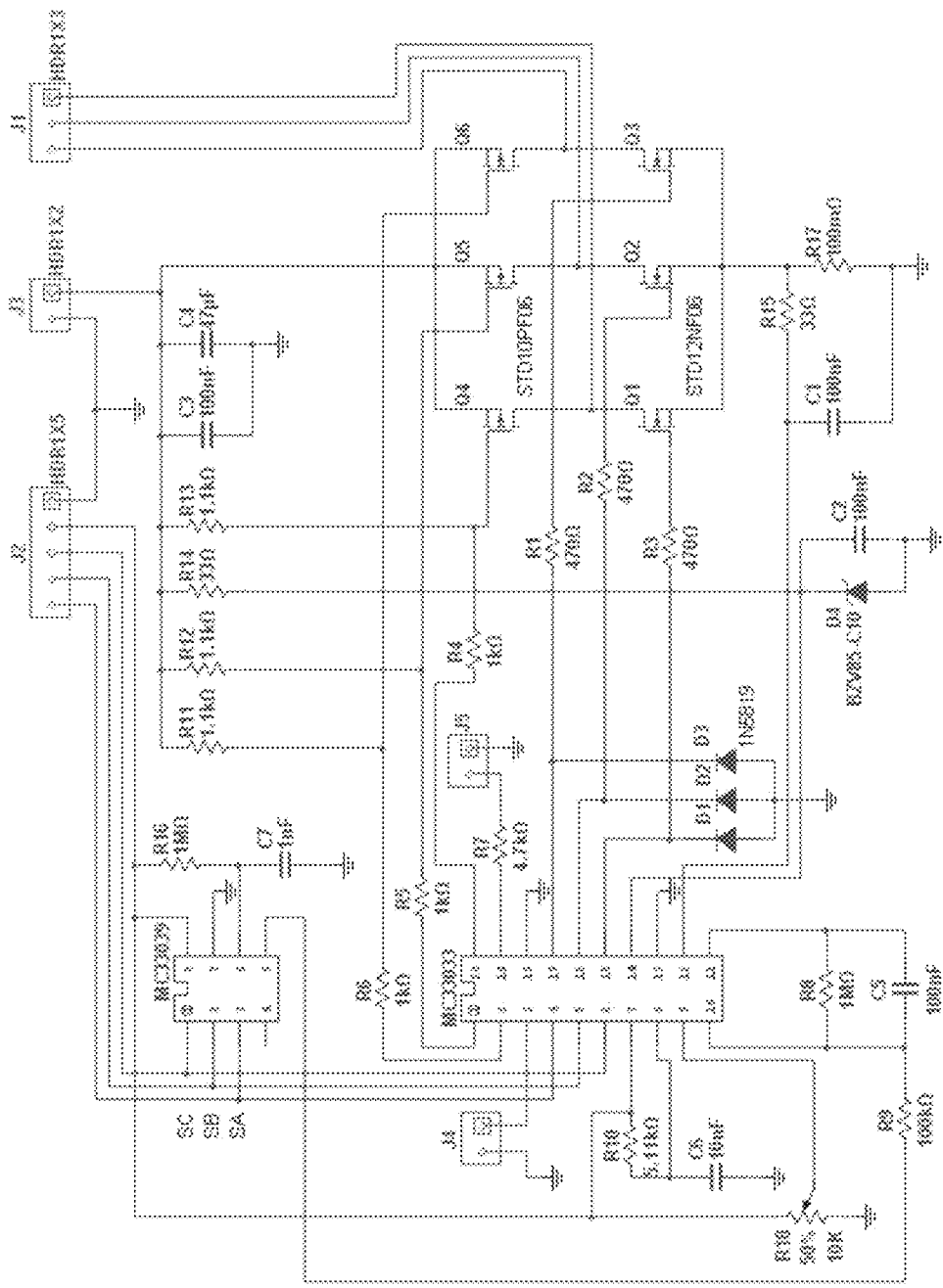
Figure 45D:
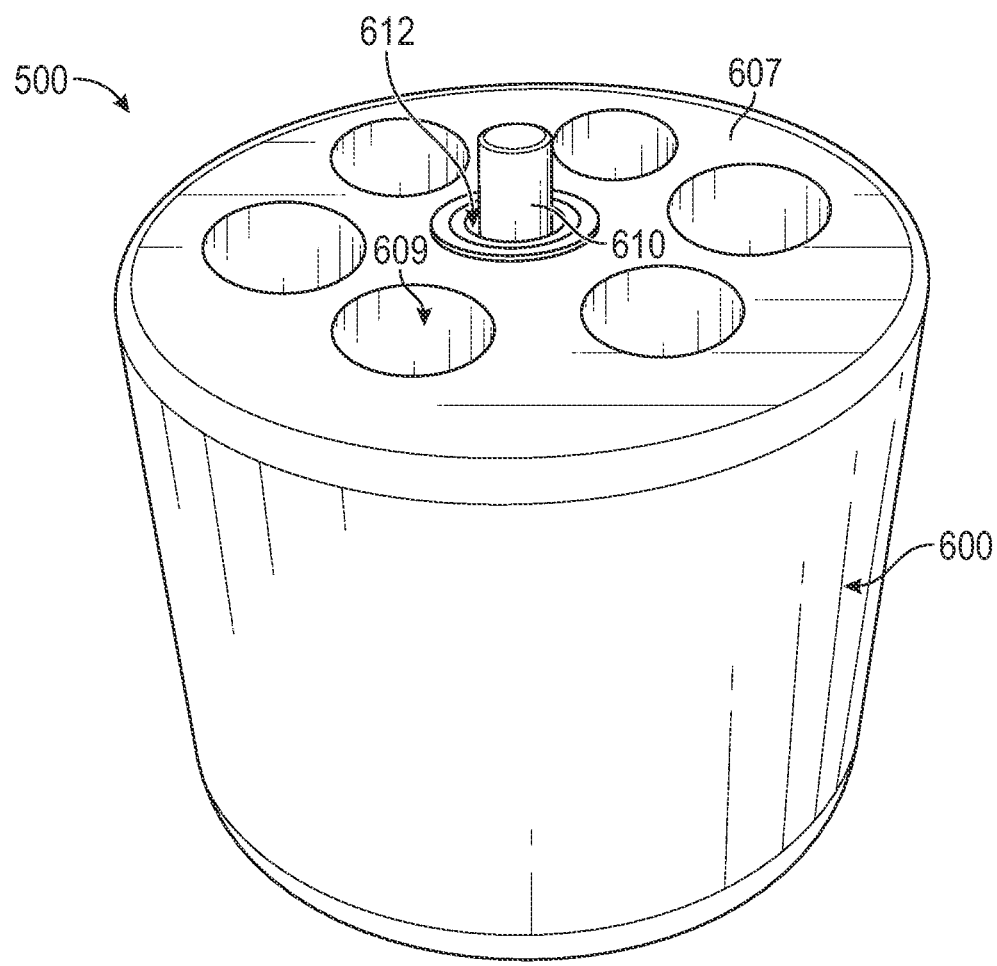

In some embodiments, a controller 760 circuit may be formed on a printed circuit board (PCB). In some embodiments, the controller may be positioned within a biocompatible casing, such as for intra-corporeal plantation, and may be about 40×40×7 mm or smaller. FIG. 44E schematically illustrate an example of a controller circuit. The design of the controller circuit may be optimized to reduce the power loss of the electrical components. In some implementations, the power loss may be less than, for example, 1 W from 1.9 W of power.

FIGS. 45A-45D illustrate examples of an MCS device 500, which may be particularly suitable for in-vitro testing. FIG. 42A schematically illustrates a perspective view of the MCS device 500 including example dimensions. FIG. 42B schematically illustrates a perspective view of a cross section of the device along the central axis. FIG. 42C schematically illustrates a cross section of the device intersecting the central axis. FIG. 42D illustrates a perspective image of an example of a rotor 510 enclosed in an anchoring mechanism 600. The MCS device 500 may comprise a barrel-shape anchoring mechanism 600. The anchoring mechanism 600 may comprise acrylic. The anchoring mechanism 600 may be a tube comprising a proximal end and a distal end. The proximal end may comprise a proximal end cap 605. The distal end may comprise a distal end cap 607. The end caps 605, 607 may comprise radial spokes 608 joined at a central axis. The radial spokes 608 may be joined to a proximal hub 604 and/or a distal hub 606. For in-vitro testing, the end caps 605, 607 may comprise apertures 609 that allow fluid flow through the tube. The rotor 519 may comprise polymethyl methacrylate (e.g., Perspex®). For in-vitro testing, the rotor 510 may be a non-airfoil rotor. The rotor 510 may comprise a number of permanent magnets 530 (e.g., four magnets). The rotor 510 may be fixedly secured to a shaft 610 (e.g., a brass shaft). The shaft 610 may be aligned with the central axis and be coupled to the spokes 608 of the proximal and distal end caps 605, 607 via bearings 612 that allow rotation of the shaft. The bearings 612 may be steel ball bearings or any other suitable bearings known in the art or disclosed elsewhere herein, including roller bearings, needle bearings, and/or hydrodynamic journal bearings. Hall-effect sensors 630, as described elsewhere herein, may be used for monitoring the rotation of the rotor 510. hall-effect sensors 630 may be positioned outside the blood vessel. For example, hall-effect sensors 630 may be coupled to the stator 710. For example, hall-effect sensors 630 may be positioned in gaps between stator coils 714. In some embodiments, three hall-effect sensors 630 uniformly spaced from each other by 120 degrees are used to monitor the rotation of the rotor 510.

Figures 46A, 46B:
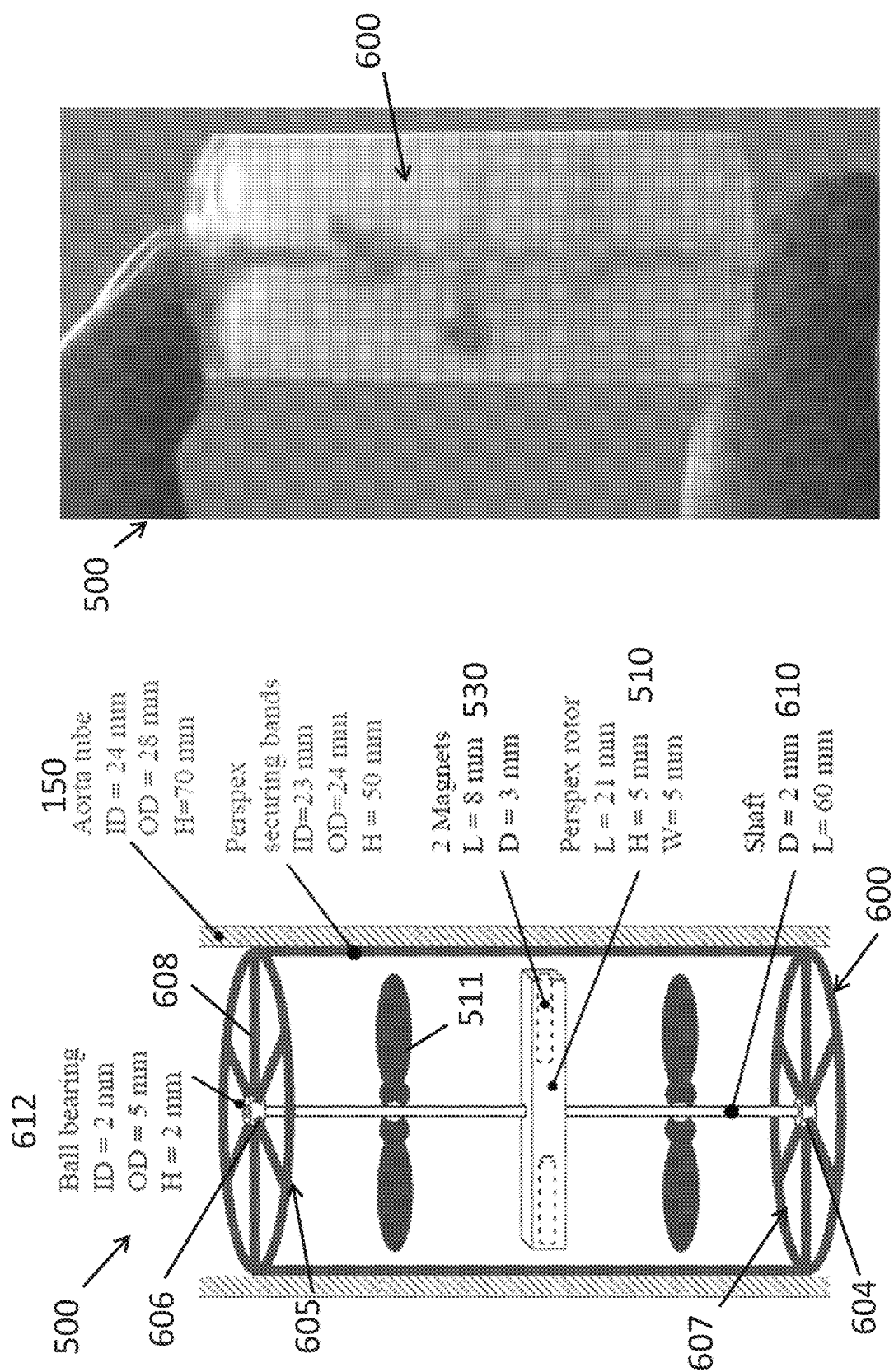
FIGS. 46A-46E schematically illustrate examples of an MCS device, which may be particularly suitable for in-vitro testing.
Figure 46C:
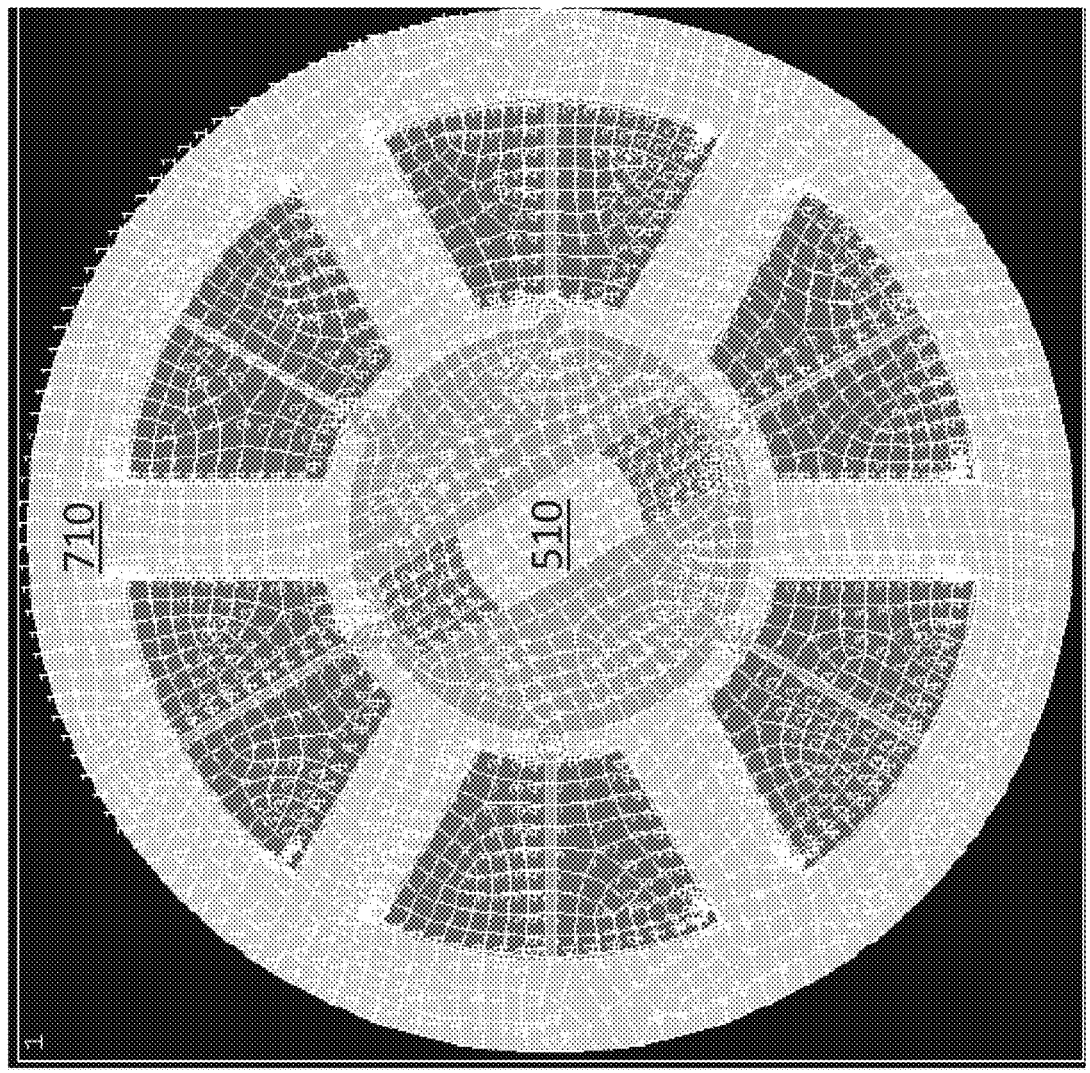
Figure 46D:
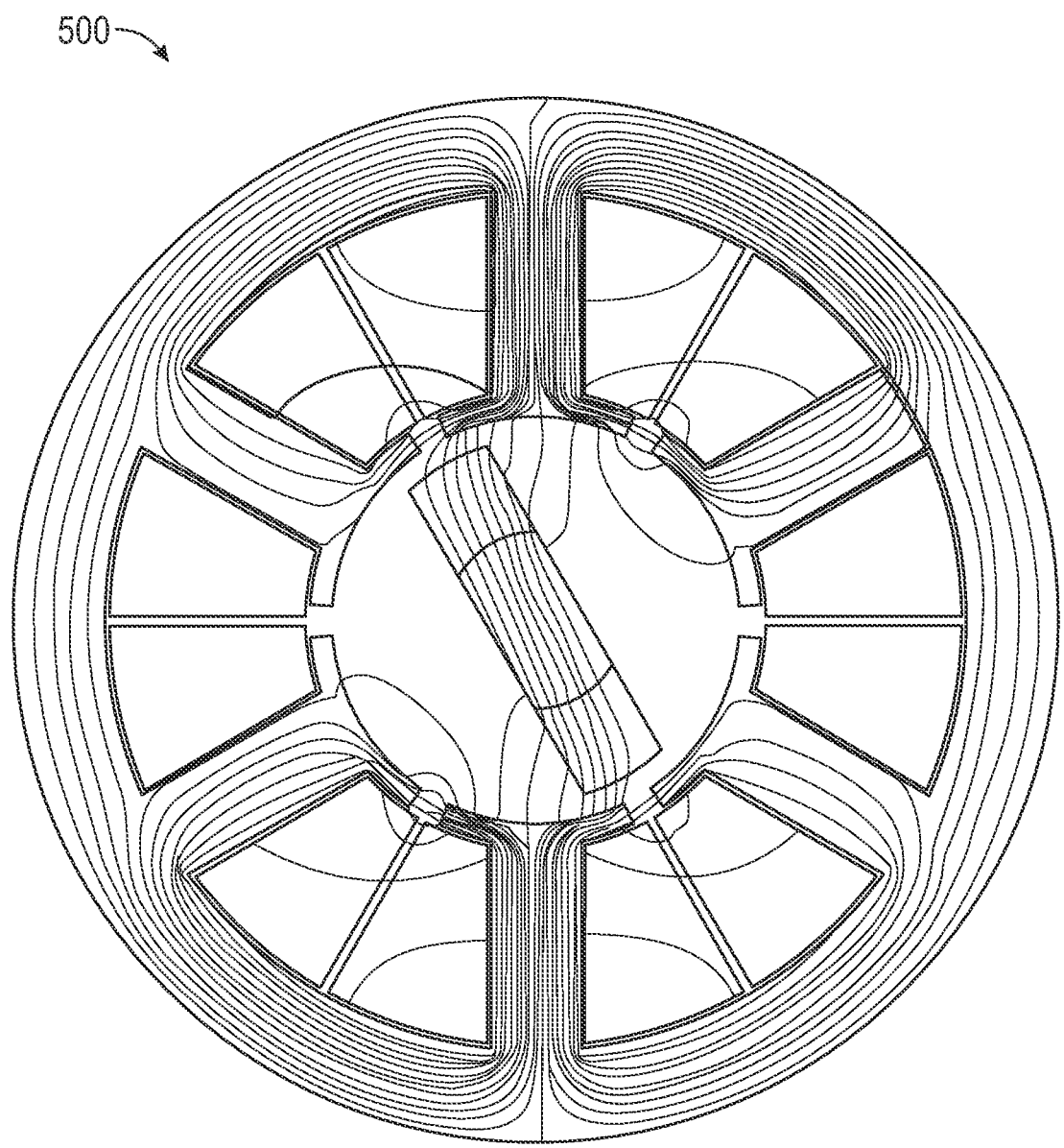
Figure 46E:

FIGS. 46A-46E illustrate another example of an MCS device 500, which may be particularly suitable for in-vitro testing. FIG. 46A schematically illustrates a perspective view of the MCS device 500 including example dimensions. FIG. 46B illustrates a perspective image of an example of a rotor 510 enclosed in an anchoring mechanism 600. FIGS. 46C-46E illustrate results obtained from finite element analysis performed on the MCS device 500. The MCS device 500 of FIGS. 46A-46B may be substantially similar to the device of FIGS. 45A-45D. The MCS device 500 of FIGS. 46A-46B comprises two propellers 511 fixedly coupled to the shaft 610. The rotor 510 comprises two magnets 530 and is used to drive rotation of the propellers 511. One propeller 511 is positioned upstream of the rotor magnets 530 and one propeller is positioned downstream of the rotor magnets 530. Each propeller 511 comprises two blades 520. The propeller 511 may be the same or similar to that illustrated in FIG. 24C. The two propellers 511 and the rotor magnets 530 may be circumferentially offset by 120 degrees from each other. FIG. 46C illustrates the mesh structure of the motor 700. FIG. 46D illustrates the magnetic flux distribution induced by the permanent magnets 530 in the rotor 510 and the armature winding current of the first phase of the three-phase motor 700. FIG. 46E illustrates the magnetic flux density due to the permanent magnets 530 of the rotor 510. In some embodiments, the motor 700 may be able to operate up to at least 30,000 rpm. In some embodiments, the motor 700 may consume about 1.4 W of power at its operating point. Embodiments of the MCS device 500 that are optimized for in-vivo use may comprise the same or similar features as those optimized for in-vitro testing.

FIG. 47A illustrates a perspective view of an example of an MCS device 500. In some embodiments, the MCS device 500 may comprise one or more rotors coupled to a shaft 610. In some embodiments the shaft 610 may be a tube having a lumen. The tube may incorporate mechanical mechanisms within its lumen. In some embodiments, lines (e.g., drivelines 702 or power lines 704) joining the rotor 510 to extracorporeal components may extend through the tubular shaft 610. The shaft 610 may be joined to proximal and distal hubs 604, 606 of the anchoring mechanism 600 via bearings 612 that allow rotation of the shaft 610. The anchoring mechanism 600 may comprise a plurality of circumferentially spaced struts 602 (e.g., 2, 3, 4, 5, 6, 7, 8, 9, 10, 15, 20 struts, etc.) joined to proximal and distal hubs 604, 606. The struts 602 may extend from the proximal hub 604 to the distal hub 606 along a direction substantially parallel to the central axis. The struts 602 may form a substantially football-shape anchoring mechanism 600. In some embodiments, the struts 602 may be somewhat flexible. The struts 602 may be generally convex. The struts 602 may be configured to bend radially outward towards the center of the strut 602. In some embodiments, the struts 602 may comprise joints spaced along the length of the strut which allow the strut to bend. The proximal hub 605 and/or distal hub 606 may comprise an atraumatic shape (e.g., a dome shape 614 or a bullet shape). In some embodiments, the proximal hub 604 and/or distal hub 606 may be configured to allow blood flow there through. In some embodiments, the proximal hub 605 and/or the distal hub 606 may be configured to prevent blood flow there through. The proximal hub 605 and/or the distal hub 606 may be displaceable along the shaft 610, such that when they are brought closer together along the central axis, the struts 602 expand in a radially outward direction. For example, the proximal strut 604, which may be coupled to a delivery catheter or other delivery device, may be translatable along the shaft 610 while the distal hub 606 is fixed at the distal end of the shaft 610. Pushing the proximal hub 604 toward the distal hub 606 may expand the struts 602 for anchoring in the blood vessel, while pulling the proximal hub 604 away from the distal hub 606 may collapse the anchoring mechanism 600, such as for repositioning the MCS device 500 or removing the MCS device 500 from the body (e.g., through a catheter). Expansion of the struts 602 may be used to exert pressure on the blood vessel wall and secure the MCS device 500 within the blood vessel.

In some embodiments, the propeller blades 520 of the MCS device 500 comprise a folded configuration and a deployed configuration. FIG. 47A illustrates a perspective view of the MCS device 500 in a deployed configuration. FIG. 47B illustrates a perspective view of the MCS device 500 of FIG. 47A in a folded configuration. The propeller blades 520 may comprise a joint or hinge 522 joining the blade 520 to the shaft, the joint or hinge 522 being positioned at the opposite end of the blade 520 from the blade radial tip 521. The propeller blades 520 may be folded against the shaft 610 such that the radial length of the blade 520 from the joint to the radial tip 521 is substantially parallel with the shaft, reducing the overall outer diameter of the rotor. The rotors 510 may be deployed in the blood vessel and/or removed from the blood vessel with the blades 520 in a folded position to minimize the size of the MCS device 500. The use of a foldable or otherwise collapsible MCS device 500 may facilitate deployment via percutaneous delivery through a catheter and/or removal of the MCS device 500 through a catheter.

FIG. 47C schematically illustrates a cross section of a portion of the MCS device 500 taken along the central axis of the device. FIG. 47D illustrates a perspective view of a portion of another example of an MCS device 500. The propeller blades 520 may each comprise an extension or handle 523 passing through an aperture in the shaft 610 to form a hinge 522 with the shaft 610. The handle 523 may begin to curve as it extends into the shaft 610 such that it forms a rounded (e.g., semi-circular) profile that is configured to rotate around a hinge 522 axis as it slides in and out of the aperture. In some embodiments, the propeller 511 (row of blades 520) may comprise two blades 520. The blades 520 may be positioned circumferentially opposite each other and may be joined together inside the shaft 610 via a connector 524. In some embodiments the connector 524 may comprise a pivot point 525 or be hinged as depicted in FIG. 47C. In some embodiments, as illustrated in FIG. 47C, the blades 520 may be configured to fold in opposite directions (e.g., one folded in a proximal direction and one folded in a distal direction). Folding the blades 520 in opposite directions may advantageously position magnetic blades 520 further away from each other. Folding blades 520 in opposite directions may avoid overcoming repulsive forces in placing blades 520 of opposite polarity in close proximity to each other and/or overcoming attractive forces in extending blades 520 of the same polarity away from each other In some embodiments the connector 524 may comprise a pivot point 525 or be hinged as depicted in FIG. 47C. FIG. 47E depicts a top view of a cross section intersecting the central axis of the MCS device 500, including ball bearings 612 between the shaft 610 and the distal hub 606. The ball bearings 612 may comprise a number of uniform spherical steel balls 613 positioned in a circumference between the outer diameter of the shaft 610 and an inner diameter of the hub 604, 606 which allows the shaft 610 to rotate with respect to the hub 604, 606. The foldable blades 520 may be configured to extend outwards into an operative deployed position by any suitable means. In some embodiments, the blades 520 may be expanded by a mechanical mechanism. The shaft 610 may be tubular and may allow incorporation of an internal mechanical mechanism for deploying the blades 520. The mechanical mechanism may extend through a percutaneous catheter and may be actuated outside the body. In some embodiments, the blades 520 may naturally and substantially instantaneously expand by the application of centrifugal force applied to the rotor 510. Embodiments comprising hinged blades 520 may be particularly suitable for MCS devices 500 configured for short term use, as described elsewhere herein.

Figure 48D:
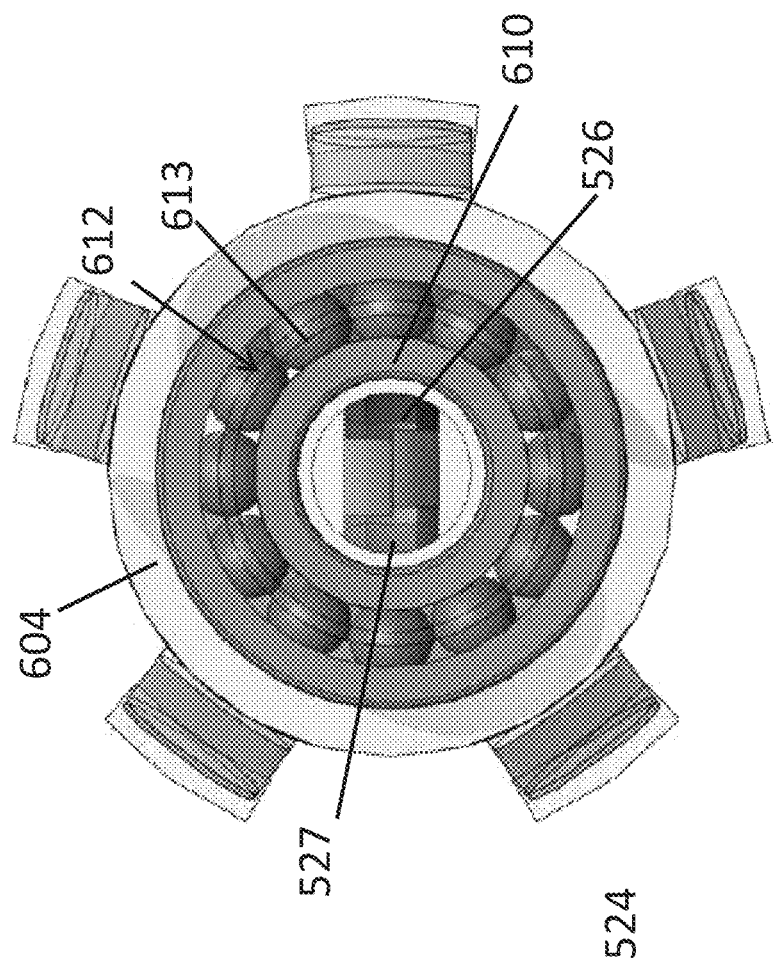
Figure 48C:
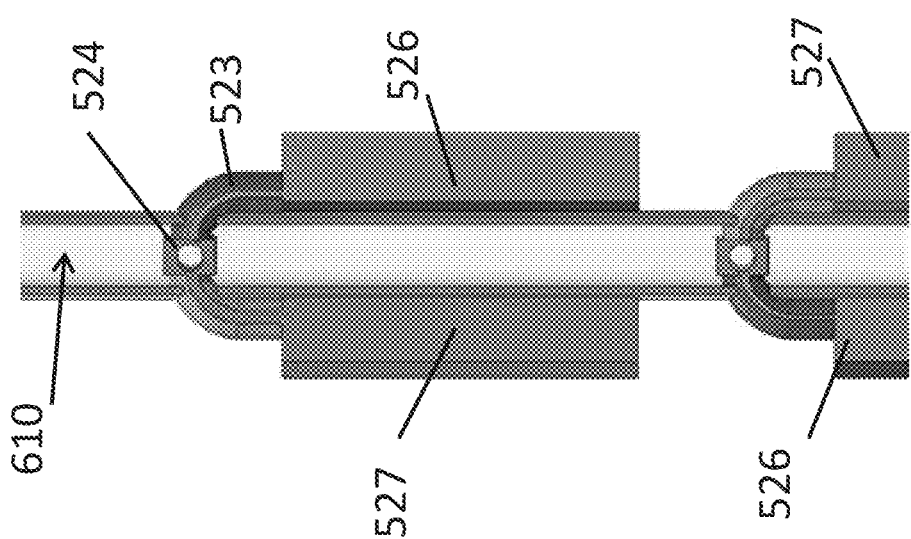

FIGS. 48A-48D schematically illustrate another example of an MCS device 500. FIG. 48A depicts the device in an expanded operative configuration. FIG. 48B depicts the device in a folded or collapsed configuration. FIG. 48C depicts a cross section taken along the central axis of a portion of the device comprising folded blades 520. FIG. 48D depicts a top view of a cross section intersecting the central axis of the MCS device 500, including ball bearings 612 between the shaft 610 and the distal hub 606. The MCS device 500 may comprise two rows of blades 520 (propellers 511). Each row of blades 520 may comprise two diametrically opposed blades 520. In some embodiments, only one blade 526 from each row is magnetic or comprises a magnet 530, while the other blade 527 is non-magnetic. The blades 520 of each row may be configured to fold in the same direction, as shown in FIG. 48A. Propellers 511 comprising only one magnetic blade 526 may be advantageous in folding the blades 520 in the same direction. In some embodiments, as shown in FIG. 48A, all the blades 520 of all propellers 511 of the MCS device 500 may be configured to fold in the same direction. Magnetic blades 526 from different propellers 511 may be circumferentially oriented apart from each other (e.g., about 180 degrees from each other), which can be advantageous in maximizing the distance between the magnetic fields of the blades 526. The blades 520 in each row may be coupled by their handles 523. The blades may be coupled inside a lumen of the shaft 610. The blades 520 may be coupled by a pivot or hinge 522 which allows the blades 520 to fold.

Figure 49:
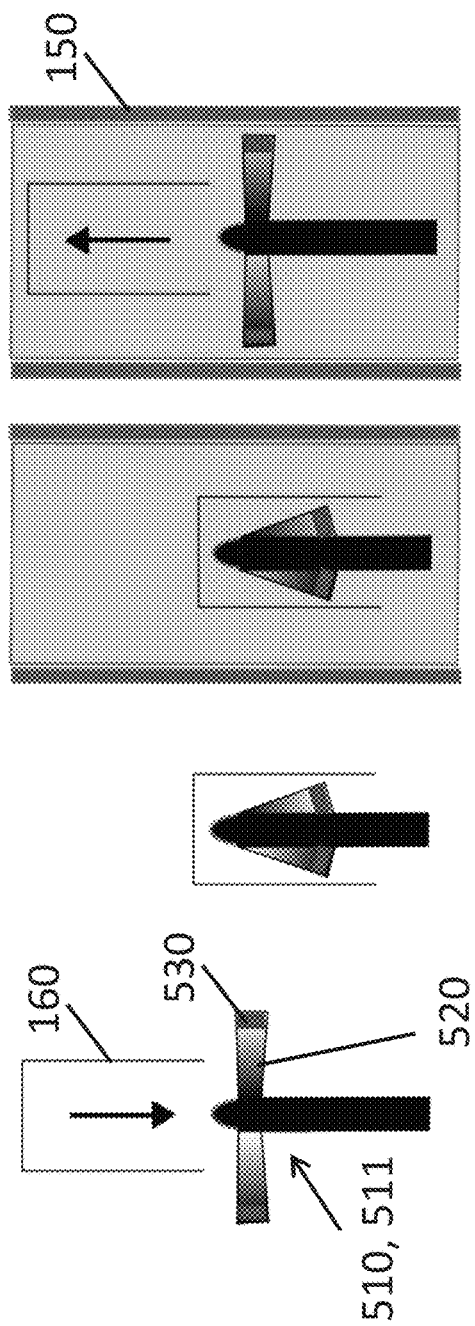
FIG. 49 schematically illustrates consecutive steps for the deployment of a sprung blade propeller.

In some embodiments, the propeller blades 520 may be formed as an integral part of the shaft 610 such that the shaft 610 and the blades 520 comprise a single monolithic component. The unit may be formed from an elastic material and/or a thermo-mechanical material, in which the material displays temperature-dependent dynamic mechanical properties, such that the blades 520 are deformable relative to the shaft 610 and able to bend towards the shaft 610. The unit may be formed of a biocompatible material. The blades 520 may be deformable into a folded or collapsed configuration for deployment and may be configured to spring-out into an unbiased operative position. The propeller 511 may comprise any suitable number of blades 520 (e.g., 2, 3, 4, etc.). FIG. 49 schematically illustrates consecutive steps for the deployment of a sprung blade 520. A deployment sheath 160 may be positioned over the rotor 510. The sheath 160 may have an internal diameter that is smaller than the outer diameter of the rotor 510 formed by the radial tips 521 of the blade 520. Prior to delivery, the sheath 160 may be centered over the rotor 510 and pressed against the blades 520 causing the blades 520 to deform and fold against the shaft 610. The blades 520 may be configured to be deformable in only one direction (e.g., a proximal direction or distal direction) and the sheath 160 may be introduced over the rotor 510 such that it promotes deformation in the deformable direction. For example, in some embodiments, the blades 520 may be foldable such that the blade radial tips 521 extend toward the proximal direction. The MCS device 500 may be delivered in some implementations to the descending aorta via the femoral artery such that the proximal end of the device, from which the device is deployed, is downstream of the distal end of the device. The direction of the blood flow toward the proximal end of the device may facilitate maintaining the blades 520 in an expanded configuration when uncovered by a sheath 160. The rotor 510 may be introduced into the blood vessel in a folded configuration within the sheath 160. The sheath 160 may be removed from the rotor 610 when positioned within the blood vessel 150 allowing the blades 520 to expand into their operative and unbiased configuration. In some implementations, the process may be reversed for removing the rotor 510 from the body. Embodiments comprising sprung blades 520 may advantageously require minimal parts and mechanical components. Such embodiments may be suitable for short-term and/or long-term use.

Figure 50A:
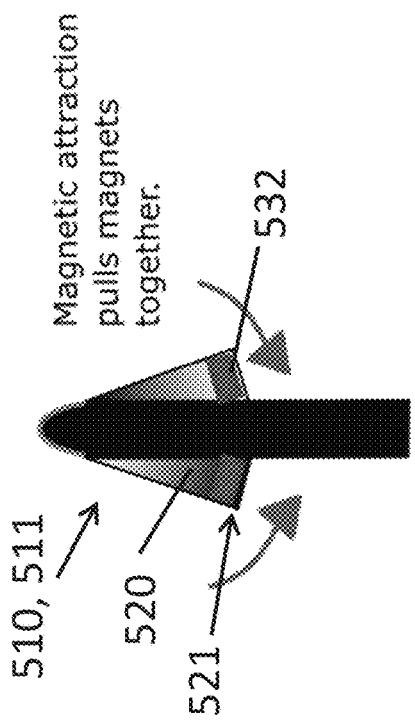
Figure 50B:
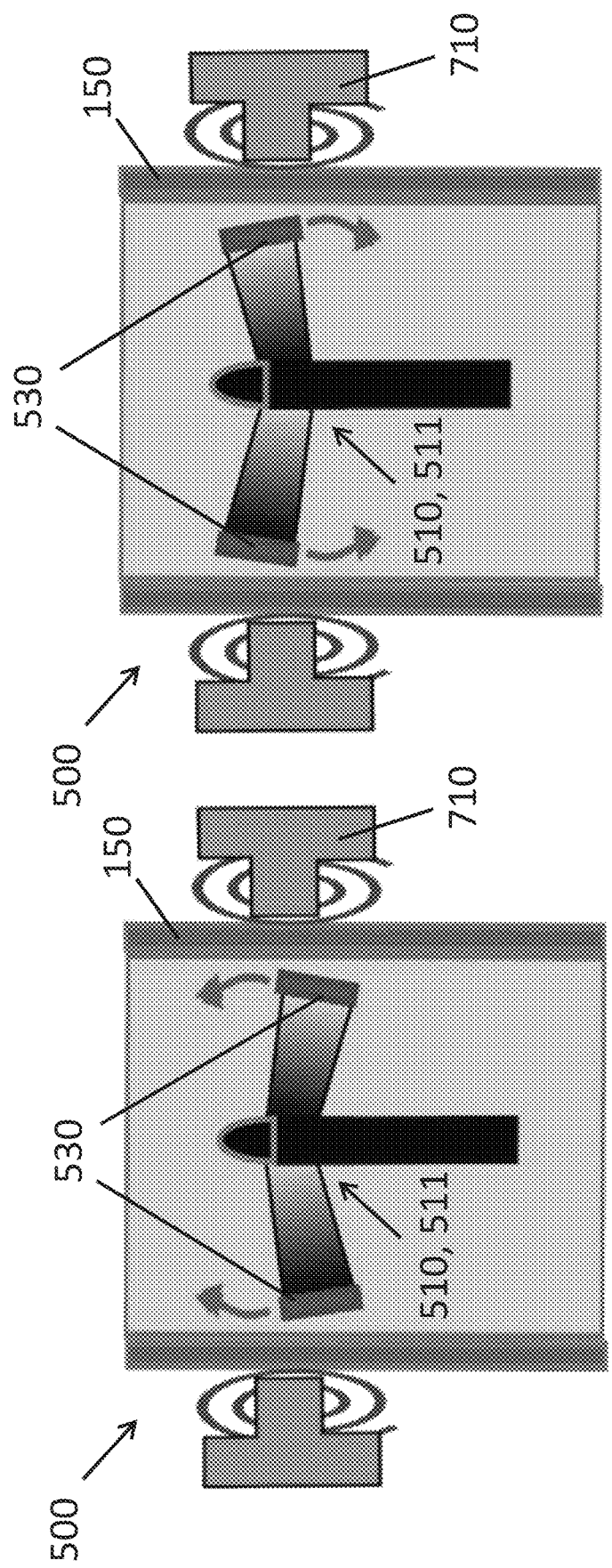

The blade radial tips 521 of a single propeller 511 may comprise magnets 530 of opposite polarity for being driven by a stator 710. For example, a rotor 510 comprising two blades 520 may incorporate a magnet 530 of opposite polarity in each blade 520 and may be configured to be driven by a six pole three phase stator 710. Some embodiments may comprise rotors 510 having more than two blades 520. In some embodiments having more than two blades 520, the polarity of the blades may circumferentially alternate. In some embodiments having more than two blades 520, only some of the blades 520 may comprise magnets 530. For example, in some embodiments, only two blades 520 may comprise magnets 530 which may be of opposite polarity. In some embodiments, blades 520 comprising magnets 530 of opposite polarity may be circumferentially positioned substantially opposite of each other. In embodiments comprising foldable blades 520, particularly embodiments comprising propellers 511 having only two blades 520, blades 520 having opposite polarities may promote a folded configuration, as the blades 520 will experience attraction toward one another. Blades 520 having higher magnetic density in the blade radial tips 521 may especially bias the blades 520 into a folded configuration, as schematically illustrated in FIG. 50A. In some embodiments, particularly in embodiments comprising propellers 511 having more than two blades 520, the attraction of blades 520 having opposite polarity may be mitigated by the repulsion between blades 520 having the same polarity. Magnetic attraction between magnets 530 in the blades 520 and stator coils 710 of opposite polarity may promote self-alignment of the blades 520 or blade radial tips 521 along the axial direction with the stator 710. For instance, as schematically illustrated in FIG. 50B, in embodiments in which the blades 520 are foldable and/or deformable the magnetic attraction between the blades 520 and the stator 710 may promote alignment of the blade radial tips 521 with the stator 710. Self-alignment of the blades 520 may be particularly useful in embodiments in which the blades 520 are foldable and/or deformable in both a proximal and distal direction. In some embodiments comprising multiple propellers 511 or rows of blades 520, the blades 520 between different rows may be circumferentially aligned. The magnetic polarity of circumferentially aligned blades 520 may be the same such that the blades 520, particularly the blade radial tips 521, repel one another. As schematically illustrated in FIG. 50C, magnetic repulsion between the blade radial tips 521 may facilitate self-alignment of the blade radial tips 521 with the one or more stators 710. The magnetic repulsion may be particularly useful in embodiments in which the blades 520 of different rows may be foldable toward each other.

Figure 52B:
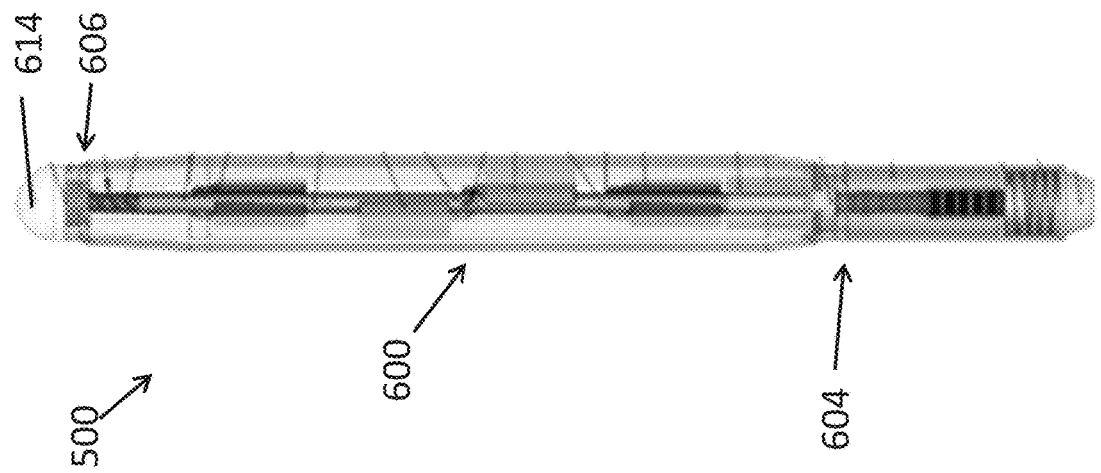
FIGS. 52A-52E schematically illustrate an example of a foldable MCS device having rows of magnetic and non-magnetic blades.
Figure 52A:
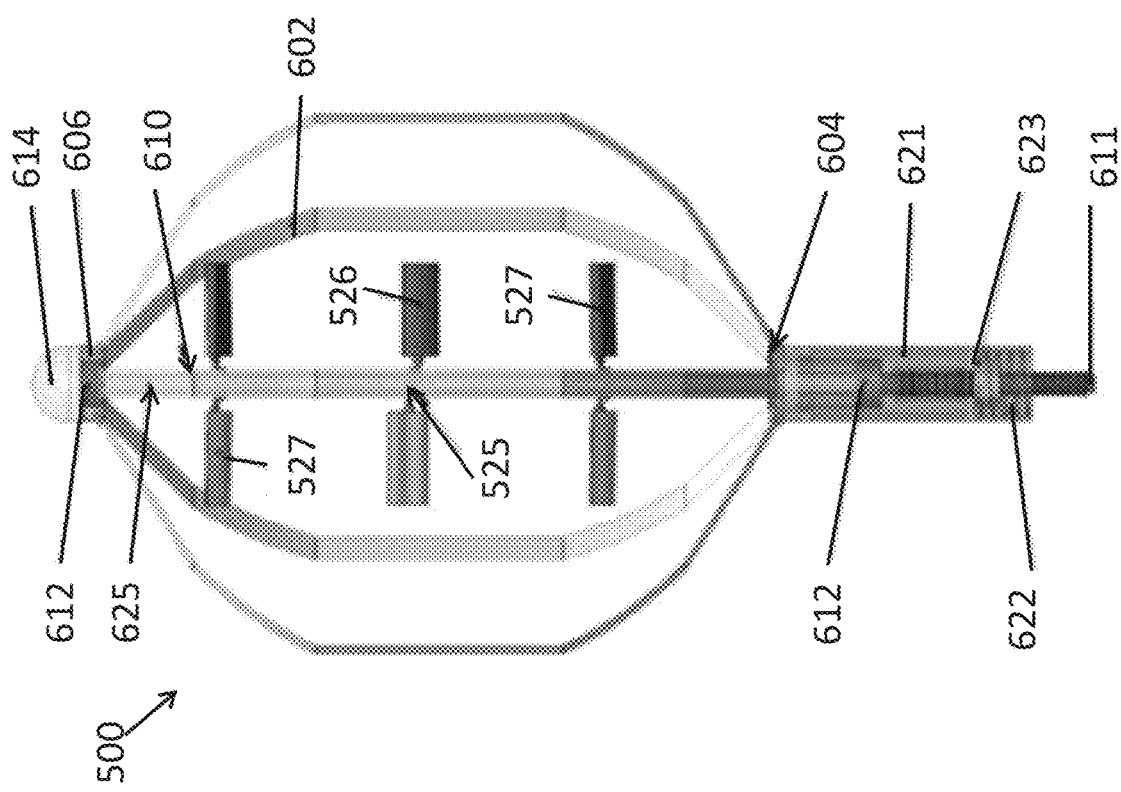
Figures 52C, 52D, 52E:
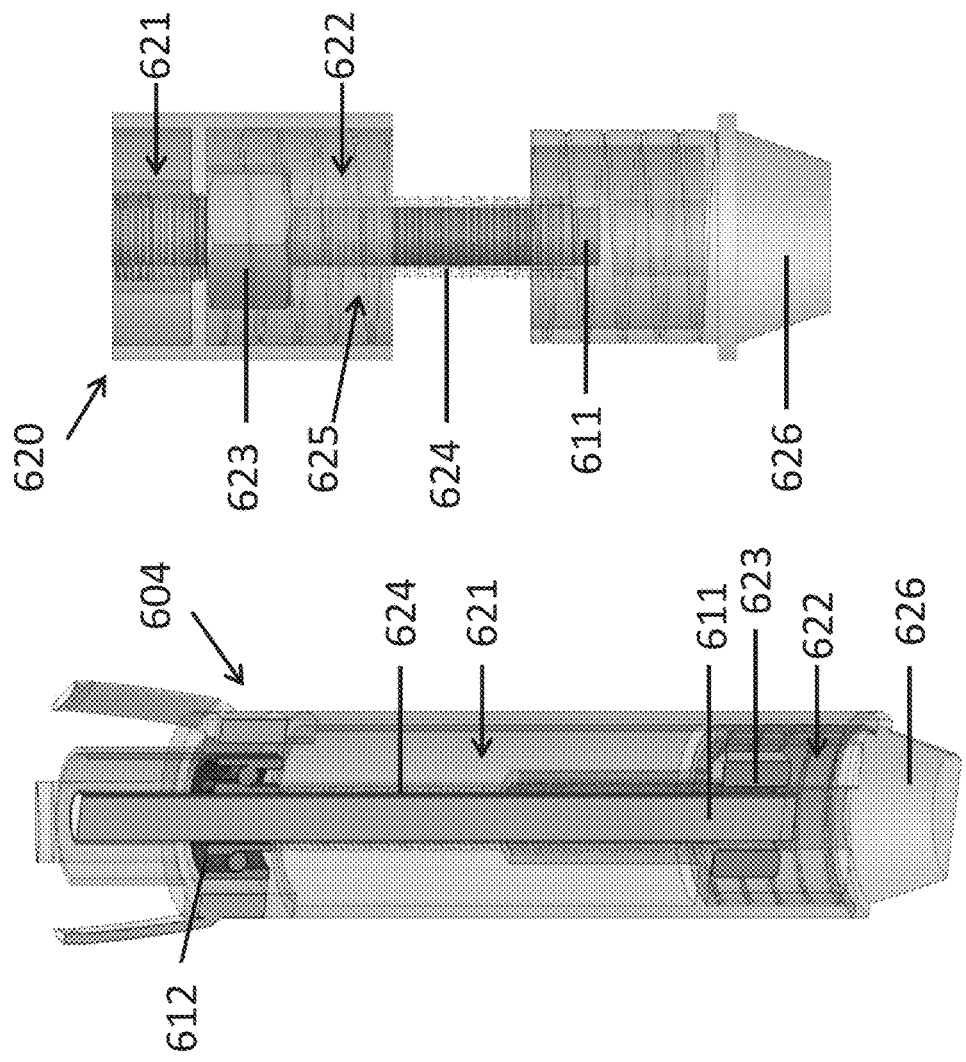

In some embodiments, the MCS device 500 may be delivered to the blood vessel with the rotor partially disassembled. The rotor 510 may be fully assembled within the blood vessel in a manner similar to construction a "ship in a bottle." FIGS. 51A-51E schematically illustrate an MCS device 500 having a partially disassembled configuration for delivery and an operative fully assembled configuration. FIG. 51A schematically illustrates various components of the rotor 510 in a disassembled configuration. FIG. 51B schematically illustrates the same components in a fully assembled configuration. The rotor 510 may comprise an upper hub and a lower hub. The upper hub may be the distal hub 606 and the lower hub may be the proximal hub 604, the delivery device being positioned at the proximal end of the MCS device 500. The proximal hub 604 may be fixedly coupled to the shaft 610. The distal hub 606 may comprise a recess 615 for receiving the shaft 610. The distal end of the shaft 610 may comprise an insert 616 configured to be received within the recess 615 of the distal hub 606 and to fixedly secure the shaft 610 to the distal hub 606, such as frictionally secure the shaft 610 to the hub 606 by an interference fit. The propeller 611 may comprise a channel 516 for receiving the shaft 610 and allowing the shaft 610 to extend through the propeller 510. A floating shim 617 may be coupled around the shaft 610 along a central portion of the shaft 610. The floating shim 617 may be configured to be received within the propeller channel 516 and act as a bearing 612 that allows the propeller 611 to rotate around the shaft 610, which may remain fixed in place. The floating shim 617 may be surrounded on the lower side of the propeller 611 by a fixed shim 618 which is fixedly coupled to or integral with the proximal hub 605. Thus, the rotor 510 and floating shim 617 may be configured to rotate around the fixed shaft 610. FIGS. 51C-51E schematically illustrates the assembly of the partially disassembled MCS device 500. The distal hub 606, rotor 510, and proximal hub 604 may be initially disassembled. FIG. 51C illustrates substantially orthogonal views of the partially disassembled device. The distal hub 606 may be joined to the proximal hub 605 by the anchoring mechanism 600 (e.g., the struts 602 of an anchoring mechanism 600 described elsewhere herein). The unbiased configuration of the anchoring mechanism 600 may be a collapsed configuration, such that the outer diameter of the anchoring mechanism 600 is minimized. A tensioning line 619 may be fixed to the distal hub 606 and may pass through the propeller channel 516. In some embodiments, the tensioning line 619 may pass through the proximal hub 604. For example, the tensioning line 619 may extend through an internal lumen in the shaft 610. The tensioning line 619 may extend proximally through the delivery device. The propeller 511 may initially be oriented in an axial direction, such that the blades 520 extend parallel to the central axis rather than perpendicular to the central axis as in an operative configuration, substantially minimizing the outer diameter of the rotor 510 assembly. The MCS device 500 may be delivered to the blood vessel in the collapsed configuration depicted in FIG. 51C. Upon positioning the device in the blood vessel, the tensioning line 619 may be tensioned (e.g., retracted in the proximal direction) as depicted in FIG. 51D. The tension line may be tensioned via actuation outside the body. Tensioning of the tension line 519 may bring the distal hub 606, propeller 511, and proximal hub 604 together causing the shaft 610 to extend through the propeller channel 516 and into the recess 615 of the distal hub 606. Placement of the shaft 610 through the propeller channel 516 causes the propeller 511 to assume an operative configuration in which the propeller blades 520 extend in a radial direction, substantially perpendicular to the central axis, increasing the outer diameter of the rotor 510. Bringing together the distal hub 606 and the proximal hub 604 causes expansion of the anchoring mechanism 600. For example, the struts 602 may be flexed in a radially outward direction. Securing the distal hub 606 to the shaft 610 may secure the anchoring mechanism 600 in an expanded configuration. Upon fully assembling the rotor 510 of the MCS device 500, the delivery device may be removed. FIG. 51E depicts the MCS device 500 in a fully assembled operative configuration FIGS. 52A-52E schematically illustrate another example of an MCS device 500. FIG. 52A depicts the device in an expanded operative configuration. FIG. 52B depicts the device in a folded configuration for delivery. The MCS device 500 may comprise features substantially the same or similar to other examples of MCS devices disclosed herein. The MCS device 500 may comprise a rotor 510 having three propellers 511. Each propeller 511 may comprise a pair of diametrically positioned blades 520. In some embodiments, only the middle propeller 511 comprises magnetic blades 526. The non-magnetic blades 527 may be driven by rotation of the rotor via the magnetic blades 526. In some embodiments, the magnetic blades 526 may be foldable in opposite directions, as described elsewhere herein, and as depicted in FIG. 52C. In some embodiments, the non-magnetic blades may be foldable in the same direction, as described elsewhere herein and as depicted in FIG. 48C, which may minimize the overall axial length of the device. The blades 520 may be coupled via handles 523 to a rotatable shaft 610. In some embodiments, the rotatable shaft 610 may comprise an inner sleeve. The rotatable shaft may be coupled via bearings 612 at a proximal hub 605 and a distal hub 606 to the anchoring mechanism 600. The distal hub 606 may comprise a dome cap 614. The proximal hub 604 may be translatable along the central axis toward the distal hub 606, such as through an adjustment mechanism 620, such as a threaded screw mechanism, which may lock the anchoring mechanism 600 in an expanded configuration. FIG. 52D schematically depicts a cross section of the proximal hub 604. FIG. 52E schematically depicts a close up of the threaded screw adjustment mechanism 620. The adjustment mechanism 620 may comprise an upper chamber 621 and a lower chamber 622. The mechanism may use a screw 623 (e.g. a hex nut) which is positioned in the lower chamber 622 around a threaded shaft 624. The threaded shaft 624 may be concentrically arranged around the rotating shaft 610 such that the threaded shaft 624 does not rotate. A tool may be insertable into the lower chamber for adjusting the screw mechanism 620. Screwing the hex nut 623 in one direction may advance the proximal hub 604 toward the distal hub 606, while screwing the hex nut 623 in the opposite direction may retract the proximal hub 604 from the distal hub 606. In some embodiments, springs 625 positioned in or coupled to the proximal hub 604 and/or the distal hub 606 may bias the anchoring mechanism 600 into a folded configuration. FIG. 31B depicts a perspective view of the MCS device 500 positioned within a stator 710 (which may not be to scale). For example, a proximal spring 625 may link the proximal hub 605 to a linking unit 626 which is configured to be coupled to the delivery device. In some embodiments, the MCS device 500 may comprise substantially the same or similar features as disclosed in U.S. Pat. No. 5,749,85, filed on Feb. 27, 1995, which is hereby incorporated by reference in its entirety.

Figures 53A, 53B:
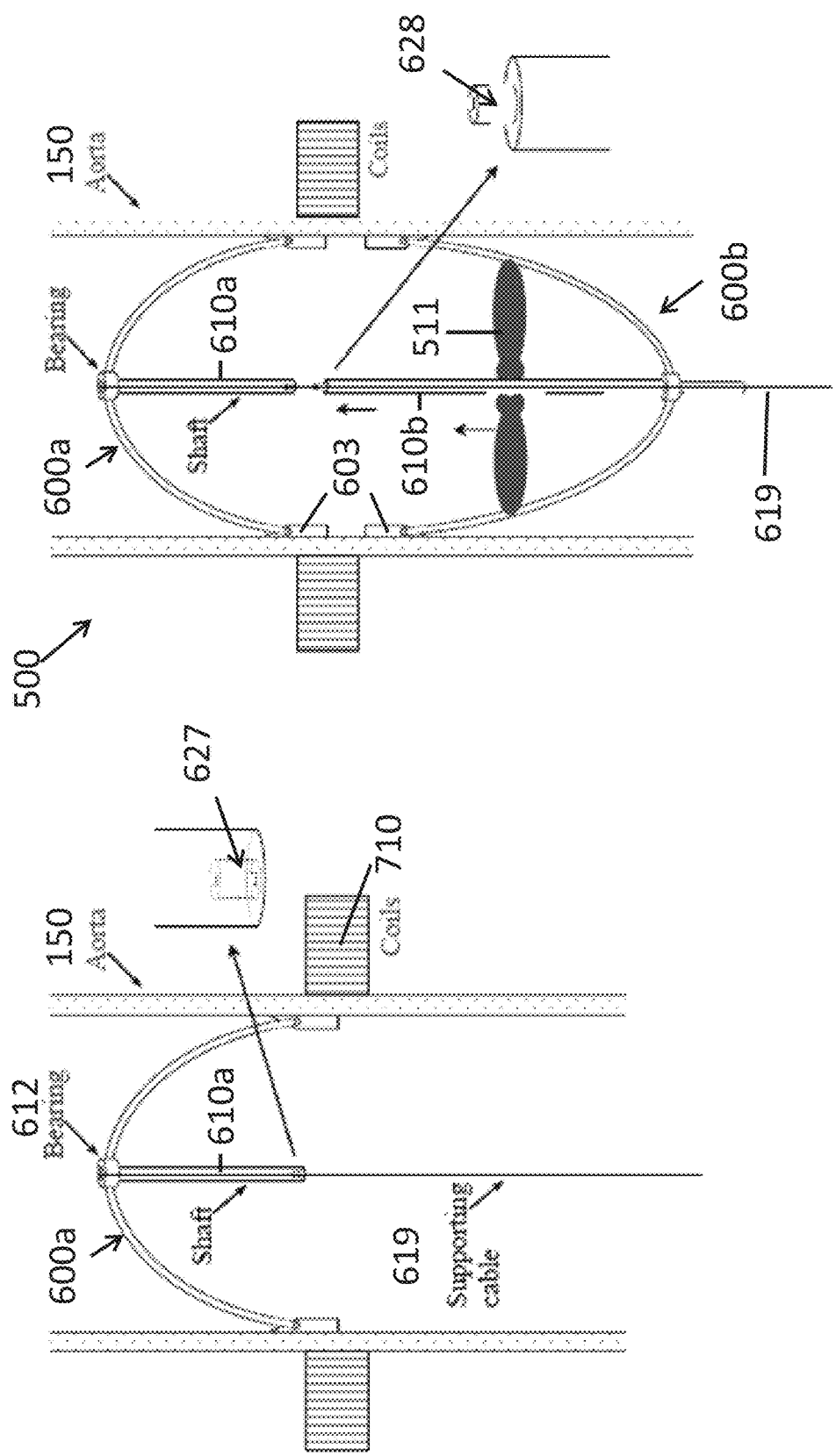
FIGS. 53A-53B schematically illustrate the intravascular coupling of a distal half and proximal half of a divisible MCS device.

In some embodiments, the rotor 510 and the anchoring mechanism 600 may be divided into two discrete components. FIGS. 53A and 53B schematically illustrate the intravascular coupling of a distal half and proximal half of an example of an MCS device 500 comprising a rotor 510 and anchoring mechanism 600 complex. The anchoring mechanism 600 may comprise a distal cage portion 600a and a proximal cage portion 600b. In some embodiments, the distal and proximal cage portions 600a, 600b may resemble two halves of an egg shell. The distal cage portion 600a may be installed first, as depicted in FIG. 53A, followed by the proximal cage portion 600b, as depicted in FIG. 53B. Each cage portion of the anchoring mechanism 600 may comprise a portion of the shaft 610. In some embodiments the proximal cage portion 600b may be approximately half the length of the anchoring mechanism 600. In some embodiments, the proximal cage portion 600b and the distal cage portion 600a may each comprise substantially half the shaft 610. The propeller 511 may be fixedly coupled to the shaft 610. In some embodiments, the propeller 511 is coupled to the proximal portion of the shaft 610b as illustrated in FIG. 49B. In some embodiments, the propeller 511 may be coupled to the distal cage portion 600a. In some embodiments, the MCS device 500 may comprise multiple propellers 511. In embodiments comprising multiple propellers 511, the propellers 511 may be coupled to the same or to different portions of the shaft 610. The shaft 610 may be configured to rotate with respect to the anchoring mechanism 600 via bearings 612, such as ball bearings, positioned at the proximal and distal hubs 605, 606 of the anchoring mechanism 600. The proximal and distal portions 610a, 610b of the shaft 610 may be configured to be joined together. For example, the distal portion 610a of the shaft 610 may have a recess 627 configured to mate with a projection 628 on the proximal portion 610b of the shaft 610 or vice-versa. The MCS device 500 may comprise a locking mechanism for locking the proximal and distal portions of the shaft together. The distal cage portion 600a and the proximal cage portion 600b may or may not be configured to be joined along their struts 602 upon assembly of the shaft 610. A supporting cable 619 may extend from the distal shaft 610a to the proximal shaft 610b. The support cable 619 may extend through the proximal shaft 610b such that when tensioned it may bring the distal cage portion 600a and distal shaft portion 610a together with the proximal cage portion 600b and proximal shaft portion 600b. In some implementations, the propeller 511 may be configured to be aligned with an extravascular stator 710 upon assembly of the lower and upper portions 600a, 600b.

Figure 54B:
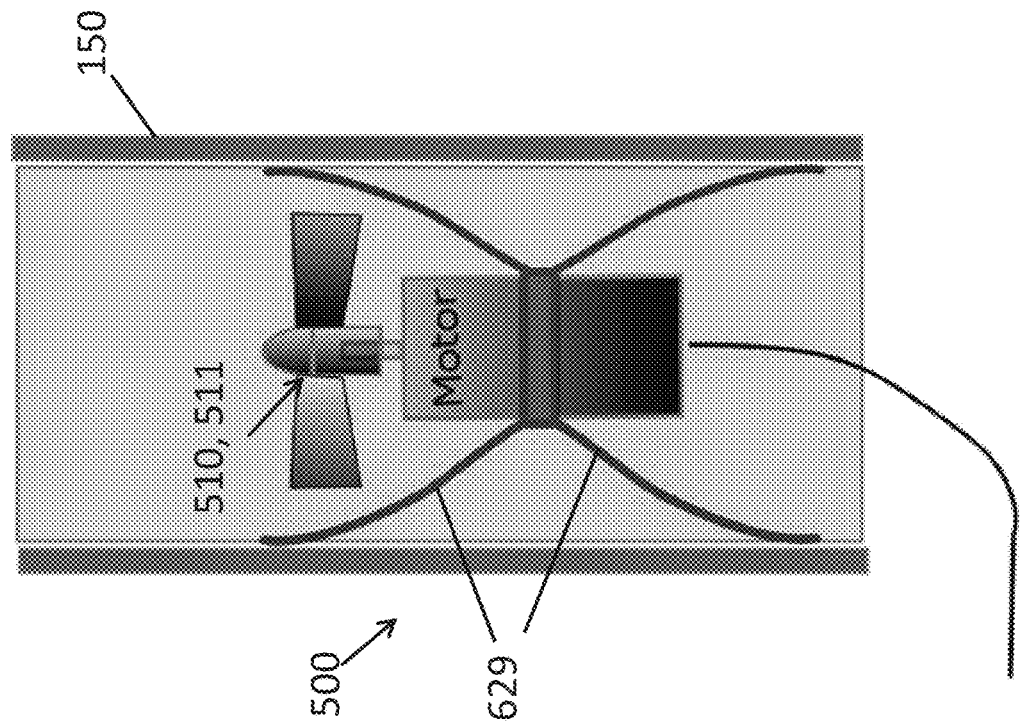
FIGS. 54A-54B schematically illustrate the deployment of an MCS device comprising a leaf spring anchoring mechanism.
Figure 54A:
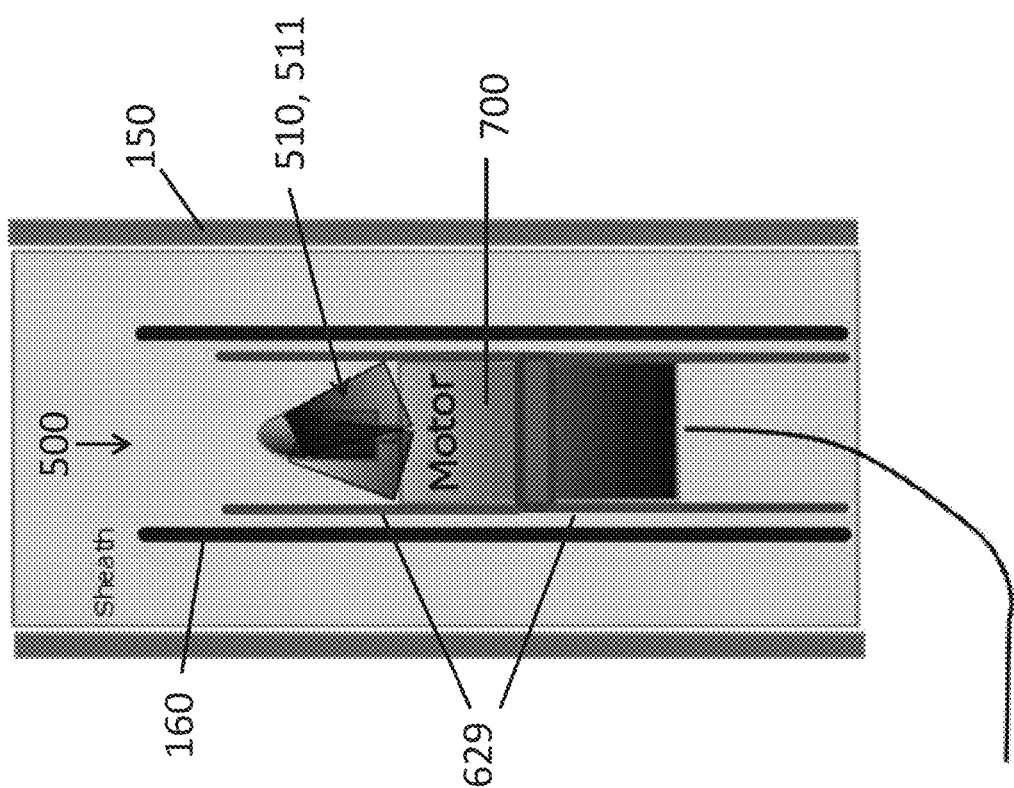

In some embodiments, the anchoring mechanism 600 may be configured to naturally self-expand. For instance, the anchoring mechanism 600 may comprise leaf springs 629 which are biased radially outward. In some embodiments, one or more leaf springs 629 may be coupled to the rotor 510 (via a stator) or coupled to an intravascular motor 700. FIGS. 54A and 54B schematically illustrate the deployment of an MCS device 500 comprising a leaf spring anchoring mechanism 600. As depicted in FIG. 54A, the leaf springs may be biased in a radially inward direction by a delivery sheath 160. As depicted in FIG. 54B, upon removal of the delivery sheath from the MCS device 500 the leaf springs 629 may naturally self-expand in a radially outward direction anchoring the MCS device 500 to the internal lumen of the blood vessel 150. The leaf springs 629 may be connected to a central point along the axial direction of the MCS device 500. In some embodiments, as illustrated in FIGS. 54A and 54B, the leaf springs 629 may have free ends which extend radially outward. In some embodiments, the leaf springs 629 may form an hour-glass shape anchoring mechanism 600. The leaf-spring anchoring mechanism 600 may comprise the same or similar features as disclosed in U.S. Pat. No. 9,572,915, filed on Mar. 26, 2013, hereby incorporated by reference in its entirety.

Figure 55B:
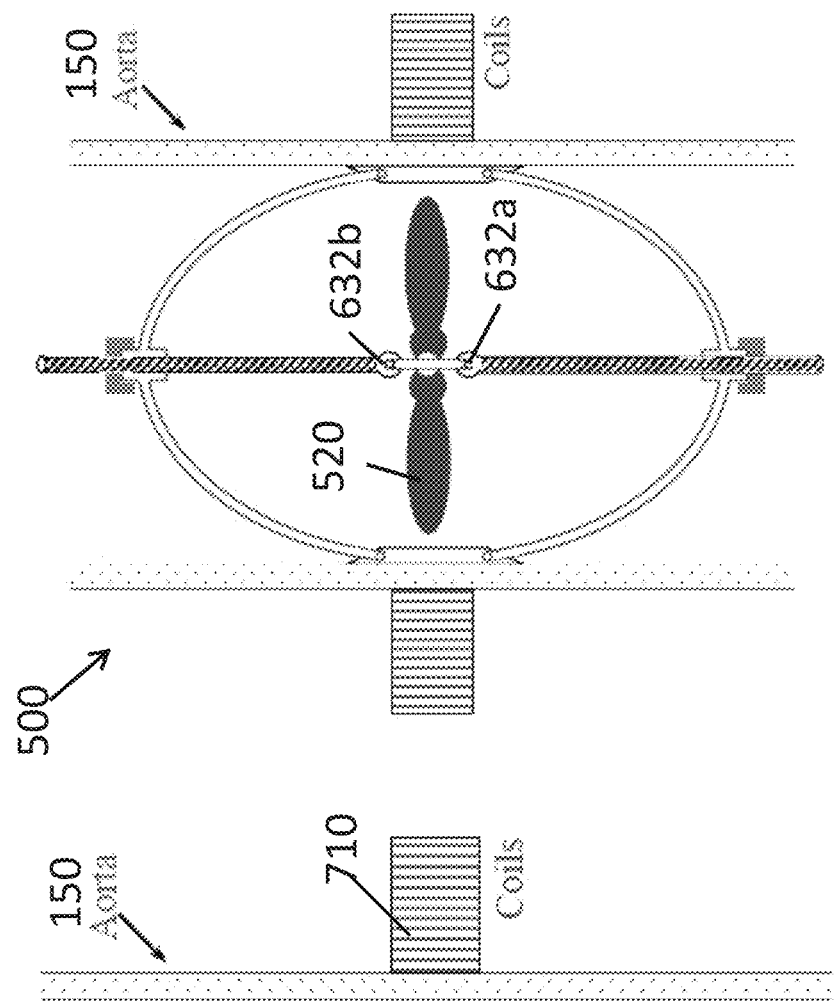
Figure 55A:
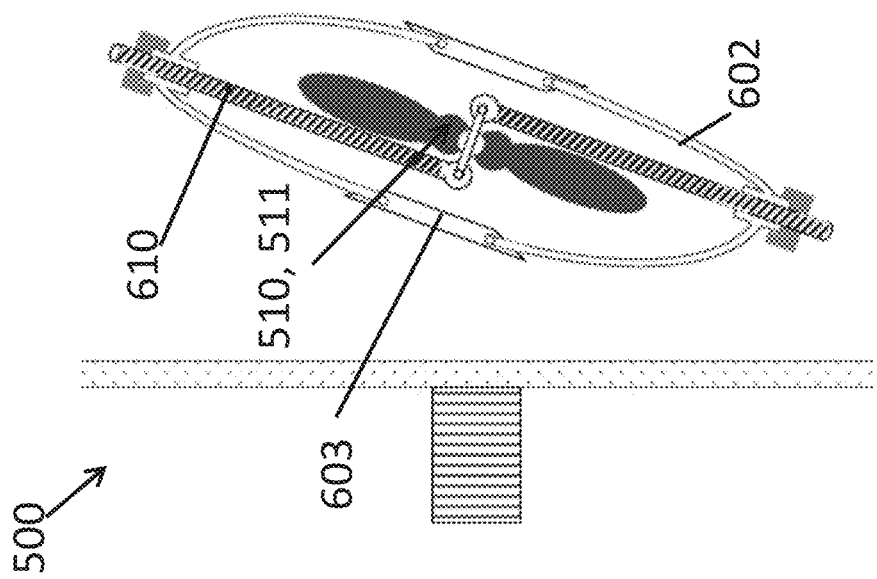
Figure 55C:
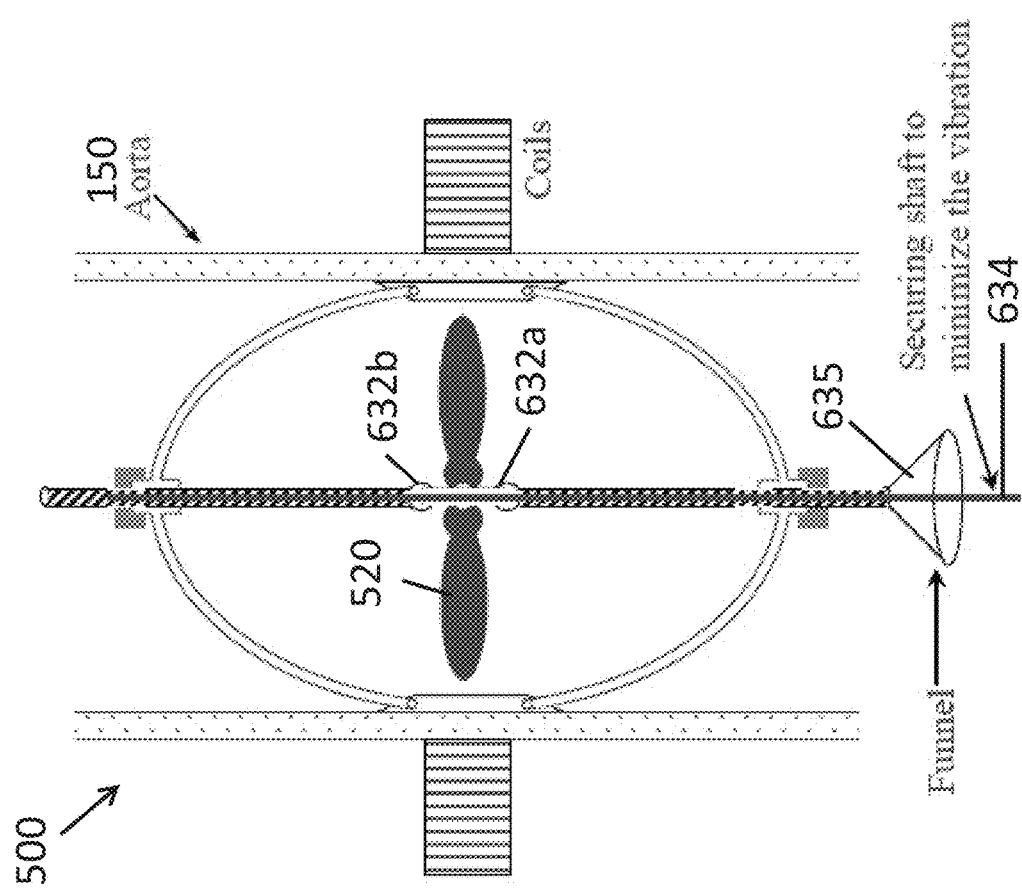

In some embodiments, the shaft 610 of the MCS device 500 may be jointed. FIGS. 55A-55E depict examples of an MCS device 500 comprising a z-shape folding mechanism. In some embodiments, the shaft 610 may be double jointed such that a first joint 632a is positioned proximally of the propeller 511 and a second joint 632b is positioned distally of the propeller 511. The double-jointed shaft 610 may allow the shaft 610 to assume a substantially z-shaped configuration. FIG. 55A schematically illustrates an MCS device 500 comprising a shaft 610 in a folded z-shape configuration. The propeller 511 may be positioned around an intermediate portion of the jointed shaft 610, which may extend through a channel in the propeller 516. The z-shape configuration may allow the propeller 511 to be oriented such that the propeller blades 520 extend substantially parallel to the central axis, substantially minimizing the outer diameter of the rotor 500. In some embodiments, the propeller 511 may be configured to rotate around the shaft such that the shaft 610 remains fixed with respect to the anchoring mechanism 600. Embodiments comprising a rotatable propeller 511 around a fixed shaft 610 may only require one mechanical bearing 612 (e.g., a ball bearing) between the rotor 510 and the shaft 610, as opposed to two bearings 612 between the proximal and distal ends of the shaft 610 and the anchoring mechanism 600, which reduces the number of bearings and can increase the mechanical efficiency of the rotor 510. After the rotor 510 is deployed, the shaft 610 may be fully extended such that the proximal portion, intermediate portion, and distal portion of the shaft are substantially collinear. For example, in some embodiments, the distal end and/or the proximal end of the shaft 610 may be further extended beyond the distal hub 606 or the proximal hub 605, respectively, which will decrease the axial separation between the proximal hub 605 and the distal hub 606. The MCS device 500 may use a threaded screw mechanism or any other suitable means for translating the shaft relative to the proximal hub 604 and/or the distal hub 606. The decreasing distance between the proximal hub 604 and the distal hub 606 cause the jointed portions of the shaft 610 to straighten into alignment. FIG. 55B schematically depicts the z-shaped device in an expanded configuration anchored within a blood vessel 150. The expansion may be actuated by a shaft mechanism secured to the proximal end of the MCS device 500, which can be removed after expansion of the device and anchoring the device in the blood vessel. In some embodiments, the shaft 610 may comprise an internal lumen extending from its proximal end to its distal end or to some point in the distal portion of the shaft 610. A rigid securing shaft 634 may be inserted through the internal lumen to secure or lock the shaft 610 in a straightened/expanded configuration. FIG. 55C schematically illustrates the insertion of a securing shaft 634. The securing shaft 634 may reduce the wobbling and vibration of the z-shape shaft 610. In some implementations, insertion of the securing shaft 634 may be used to facilitate straightening of the z-shape shaft 610 into an operative configuration. In some embodiments, securing the shaft in an operative configuration can be accomplished with a snapping mechanism, a compass mechanism, and/or a double securing nut or similar mechanism. Any suitable locking mechanisms well-known in the art can be used. In some implementations, a funnel shaped receptacle 635 may be coupled to the bottom of the device, as depicted in FIG. 55C. The funnel shaped receptacle 635 can be used to help center a removal tool for removal procedures. FIG. 55D illustrates a perspective view of a z-shape MCS device 500 in a folded configuration. FIG. 55E illustrates a close up perspective view of the joints 632a, 632b in the z-shape shaft 610 and the bearing 612 between the propeller 511 and the intermediate portion of the shaft 610.

In some embodiments, the anchoring mechanism 600 may comprise one or more securing bands 603 joining proximal and distal struts or bands 602. The securing bands 603 may be approximately centered along the longitudinal axis of the MCS device 500. The securing bands 603 may be axially aligned with a propeller 511 in the device's operative configuration. In some embodiments, a securing band 603 may be configured to extend around the entire circumference of the MCS device 500. The securing band may be coupled to multiple struts 602 extending in a substantially perpendicular direction to the securing band 603. In some embodiments the securing bands 603 may serve as a shroud for the propeller 511. The securing band or bands 603 may prevent contact between the propeller blades 520 and the blood vessel wall.

Figure 56A:
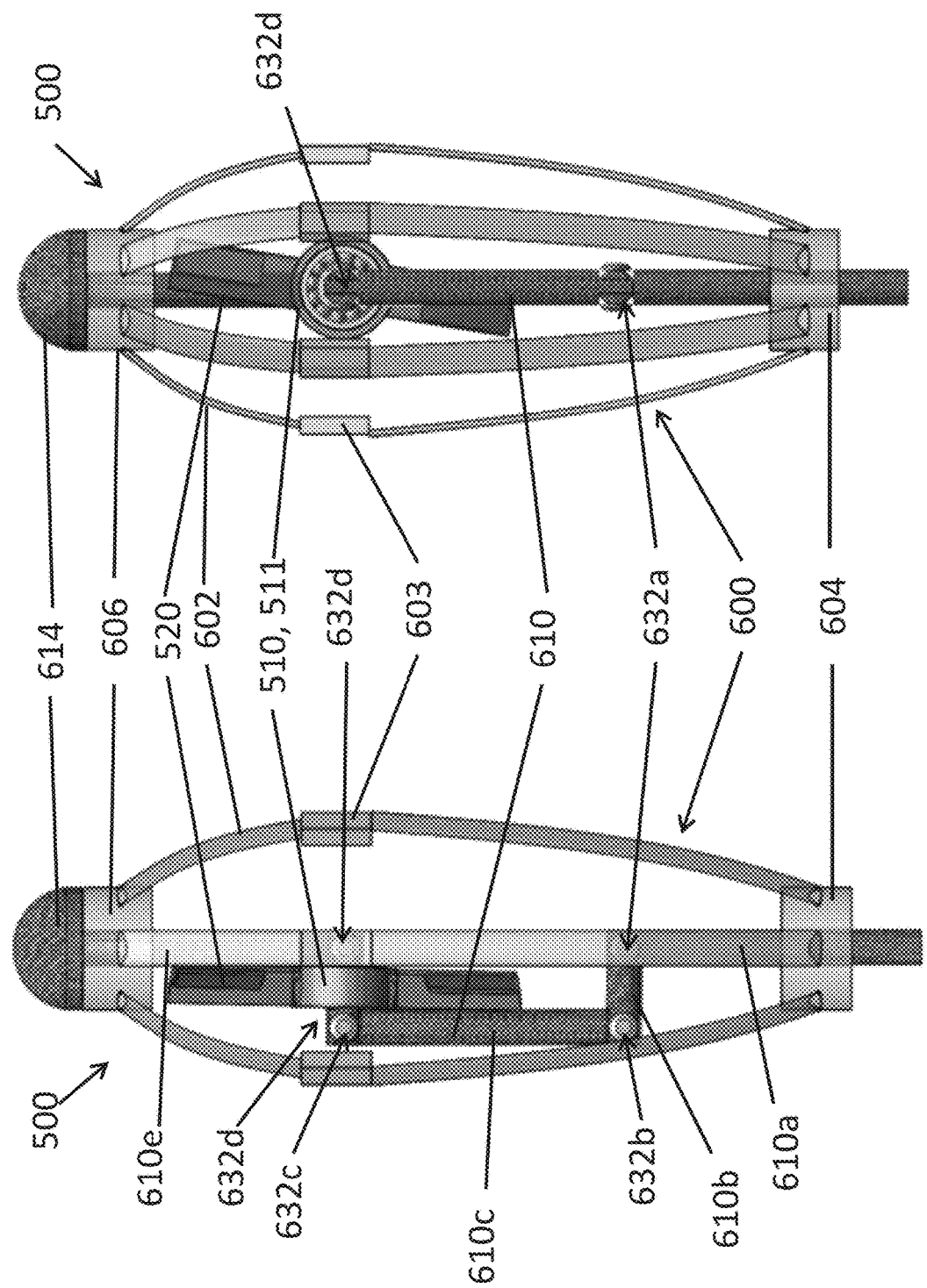
FIGS. 56A-56C schematically illustrate an example of an MCS device comprising a c-shape folding mechanism.
Figures 56B, 56C:
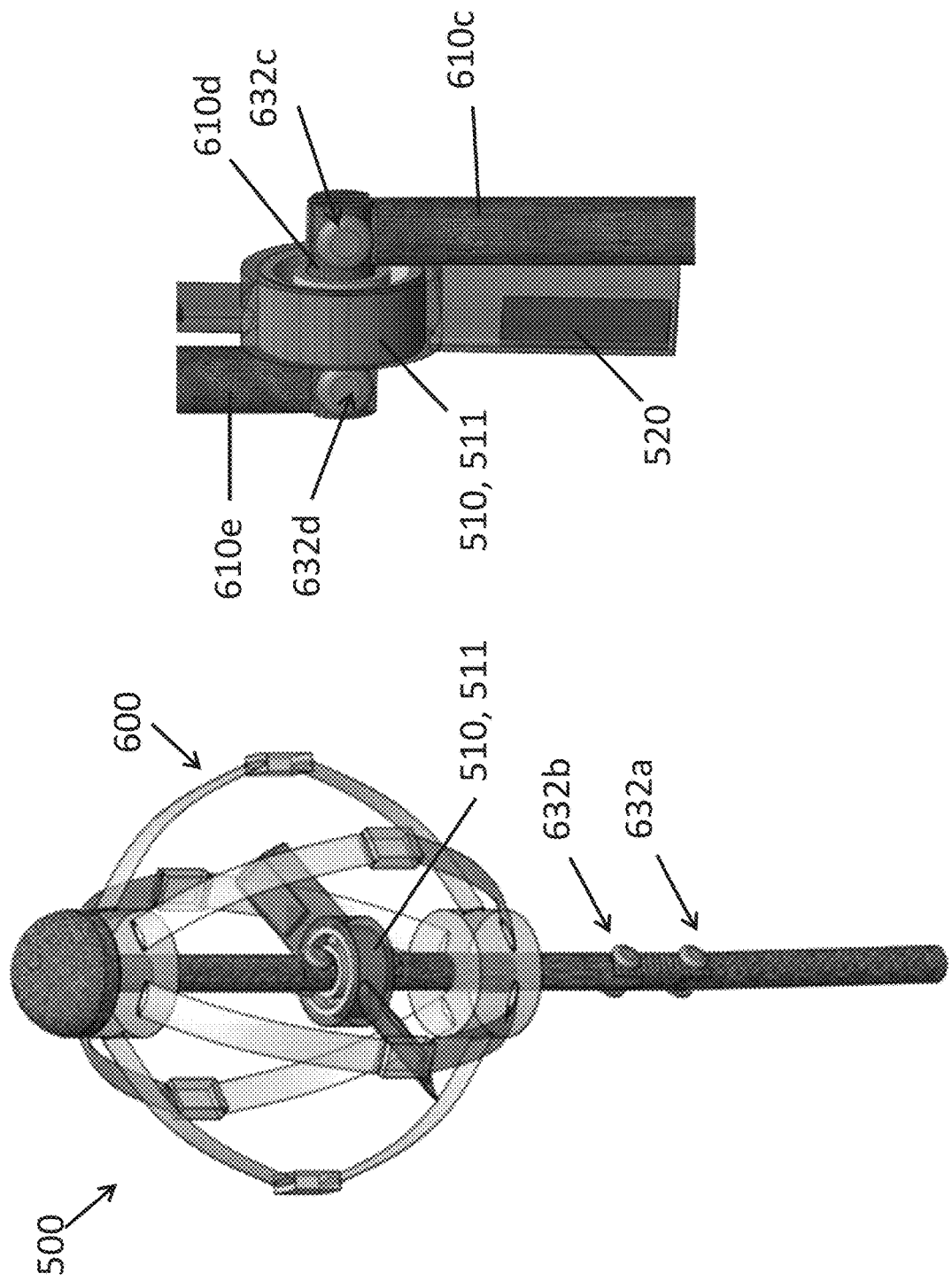

FIGS. 56A-56C schematically illustrate another example of an MCS device 500 comprising a jointed shaft 610 comprising a c-shape folding mechanism. The MCS device depicted in FIGS. 56A-56C may comprise substantially similar features to that depicted in FIGS. 55A-55E. In some embodiments, the MCS device 500 may comprise a shaft 610 with four joints 632a, 632b, 632c, 632d configured to place the shaft 610 into a c-shape configuration. The shaft 610 may comprise a proximal portion 610a, an intermediate proximal portion 610b, a central portion 610c, an intermediate distal portion 610d, and a distal portion 610e. The propeller 511 may be positioned around either the intermediate proximal portion 610b or the intermediate distal portion 610d such that it may extend in a direction substantially parallel to the central axis when in a c-shape configuration, reducing the outer diameter of the rotor 510. The c-shape folding mechanism may advantageously allow collinear alignment of the proximal hub 604 and the distal hub 606. FIG. 56A depicts substantially orthogonal views of the MCS device 500 having a c-shape folding mechanism in a folded configuration. FIG. 56B depicts the MCS device 500 in an expanded configuration. FIG. 56C depicts a close up view of the propeller 511 and two surrounding joints 632 in the folded configuration.

In some embodiments, the MCS devices disclosed herein may include multiple rotors 510 which are configured to be independently driven by separate motors 700. For instance, the MCS device 500 may comprise contra-rotating propellers 512, 514, each of which are driven by a separate stator 710. In some embodiments, the propellers may be configured to rotate around a fixed shaft 610. Bearings 612 may be positioned between each propeller 511 and the fixed shaft 610. In some embodiments, the propellers 511 are fixedly coupled to a portion of the shaft 610 such that the shaft 610 rotates. The shaft 610 may be divided into multiple portions which are capable of rotating independently of one another. Bearings 612 may be positioned between independently rotatable portions of the shaft 610.

Figure 57C:
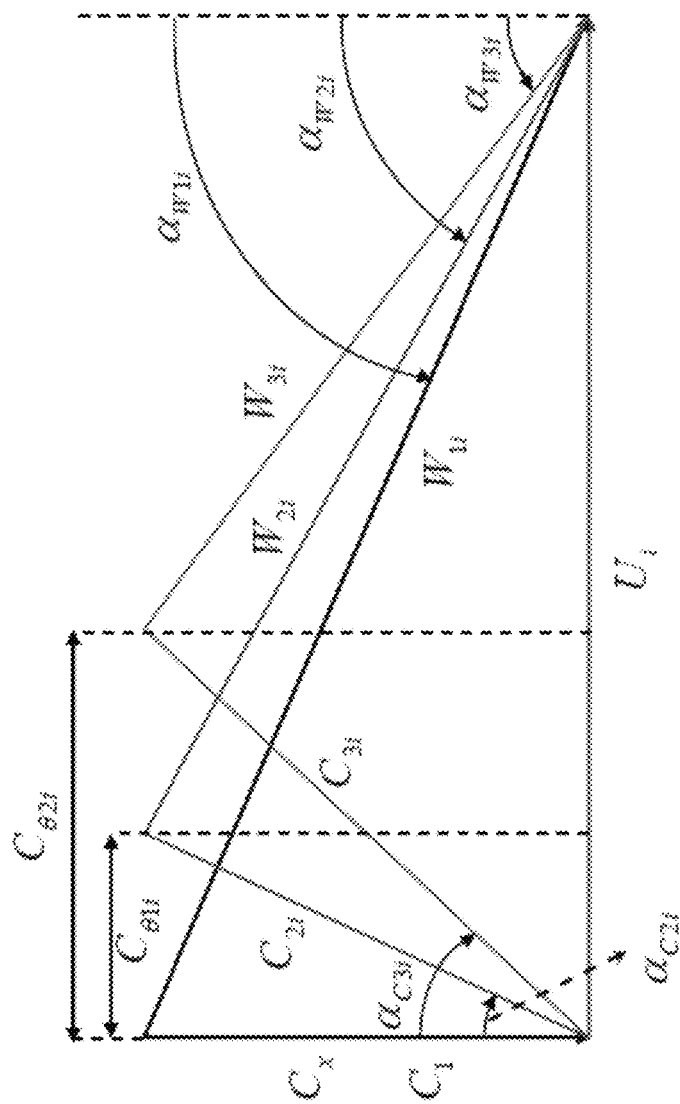
Figure 57D:
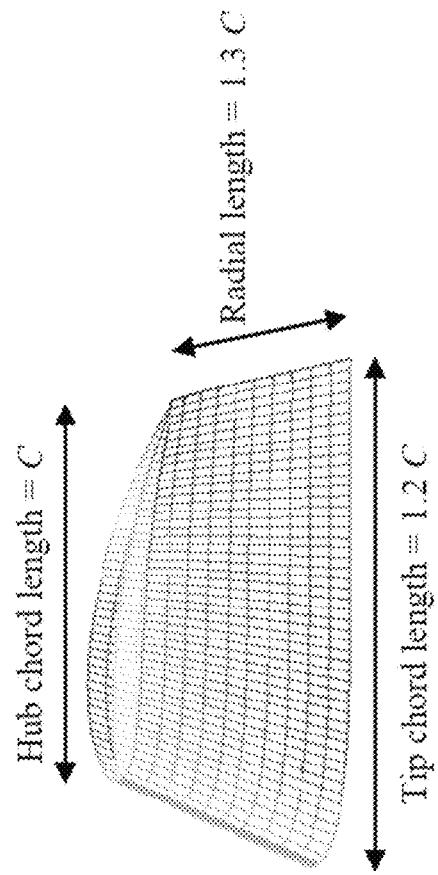

The design of the propeller blades 620 may affect the efficiency, noise, vibration, aerodynamics, and cost of the MCS device 500. Blade design parameters may include blade number, chord, thickness distribution, twist distribution, and blade material. Thinner airfoils may advantageously increase the lift-to-drag ratio. Thicker airfoils may advantageously provide a higher stiffness. FIG. 57A depicts a table of examples of input parameters that may be used in designing the blades. FIG. 57B depicts a table of parameters that may be mathematically calculated based on the input parameters. FIG. 57C schematically illustrates geometric representations of blade angles. FIG. 57D illustrates a three-dimensional blade 520 and examples of relative dimensions of the hub chord length, the tip chord length, and the radial length. The tip (as opposed to the radial tip) may form a front edge of the blade 620 as it rotates and the hub may form a back edge. The blades 620 may radially extend to form the outer diameter of the rotor 510. The diameter of the rotor 510 may be configured to span a significant proportion of the blood vessel diameter. In some embodiments, the inner blood vessel wall may be secured from the radial tips 521 of the blades 520 via the anchoring mechanisms 600. Minimizing the gap between the radial tips 521 of the rotor 510 and the blood vessel wall reduces back flow, which may improve the efficiency of the MCS device 500.

Figure 58A:
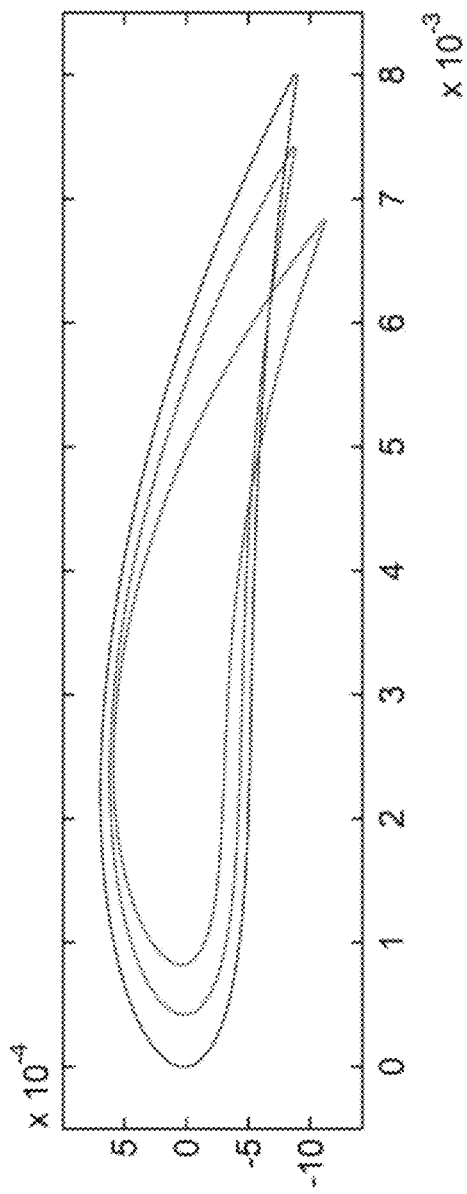
FIGS. 58A-58I schematically illustrate various examples of blade geometries.
Figure 58B:
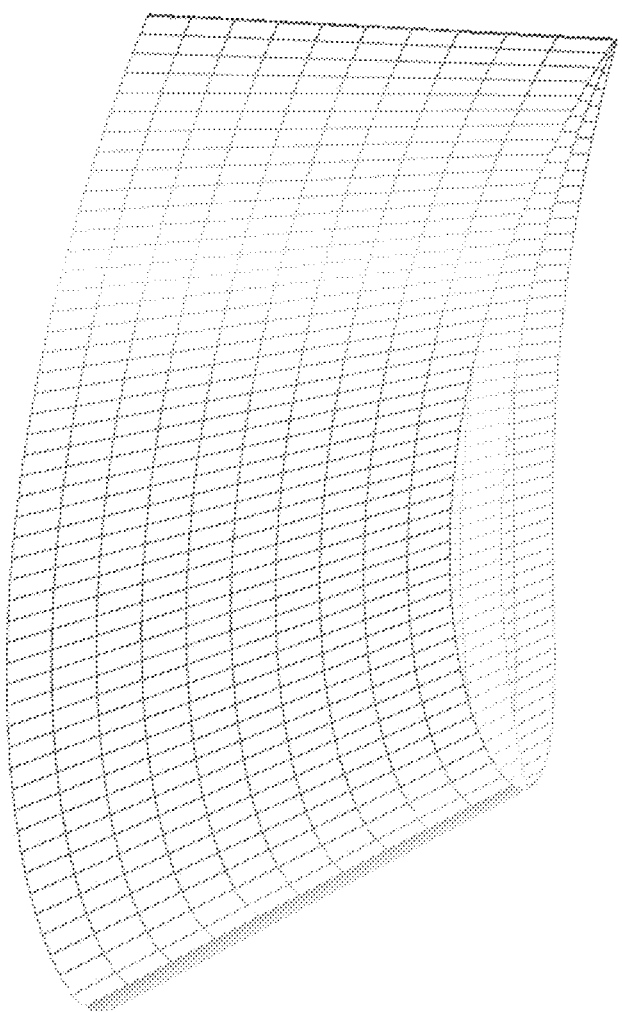
Figure 58C:
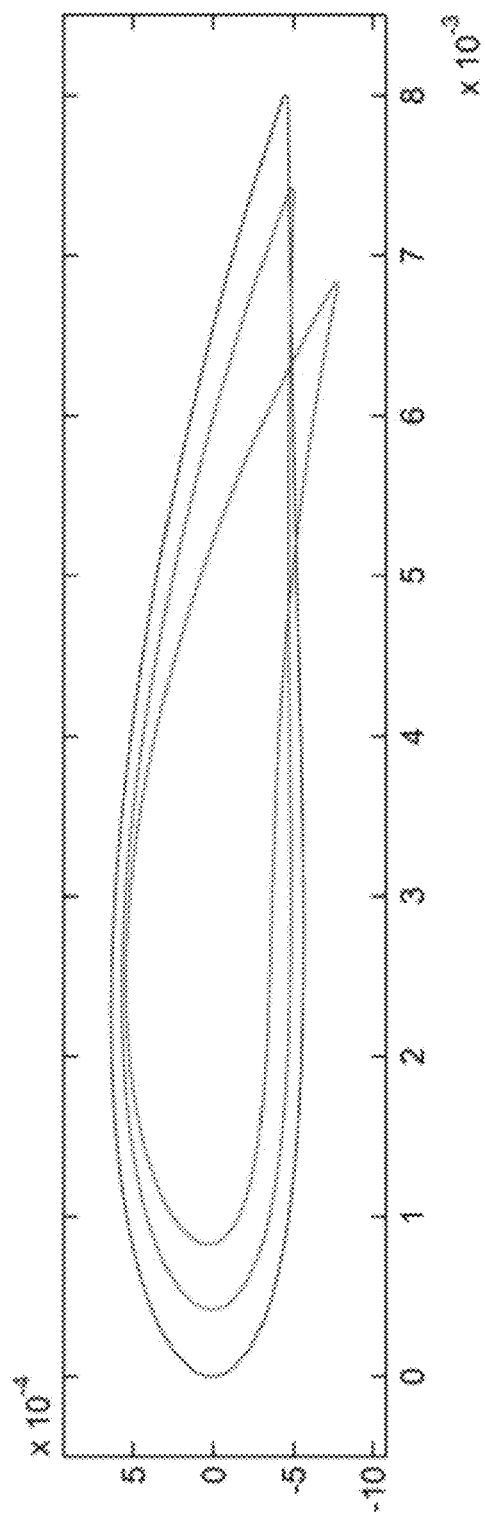
Figure 58D:
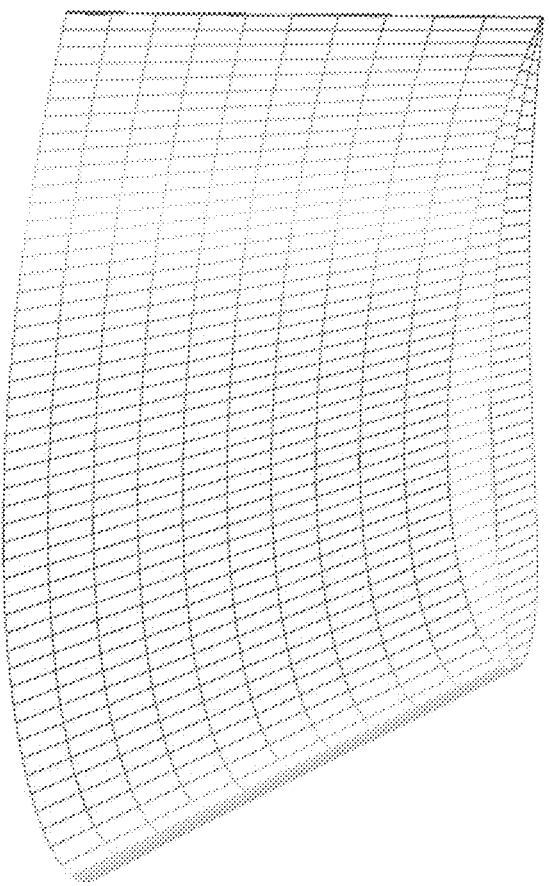
Figure 58E:
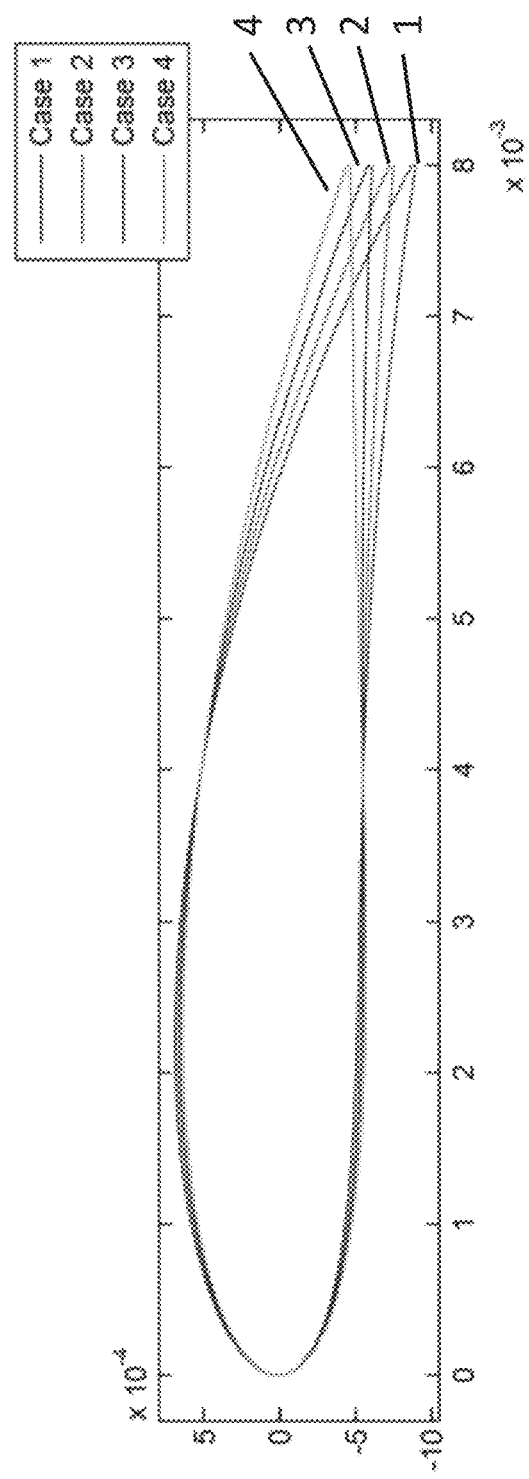
Figure 58F:
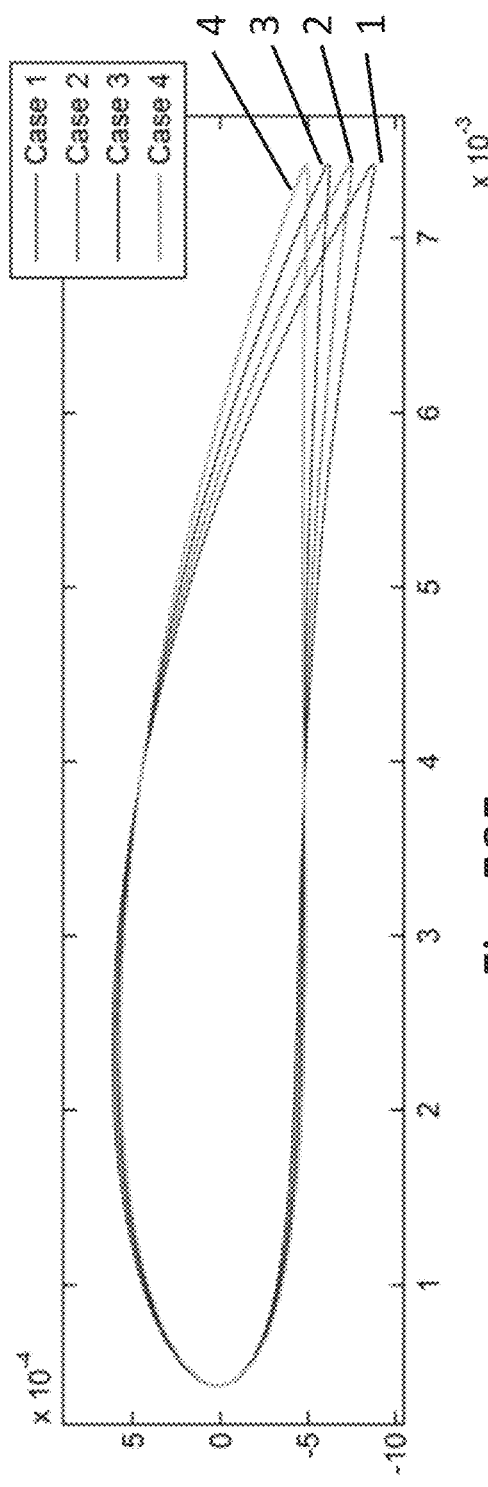
Figure 58G:
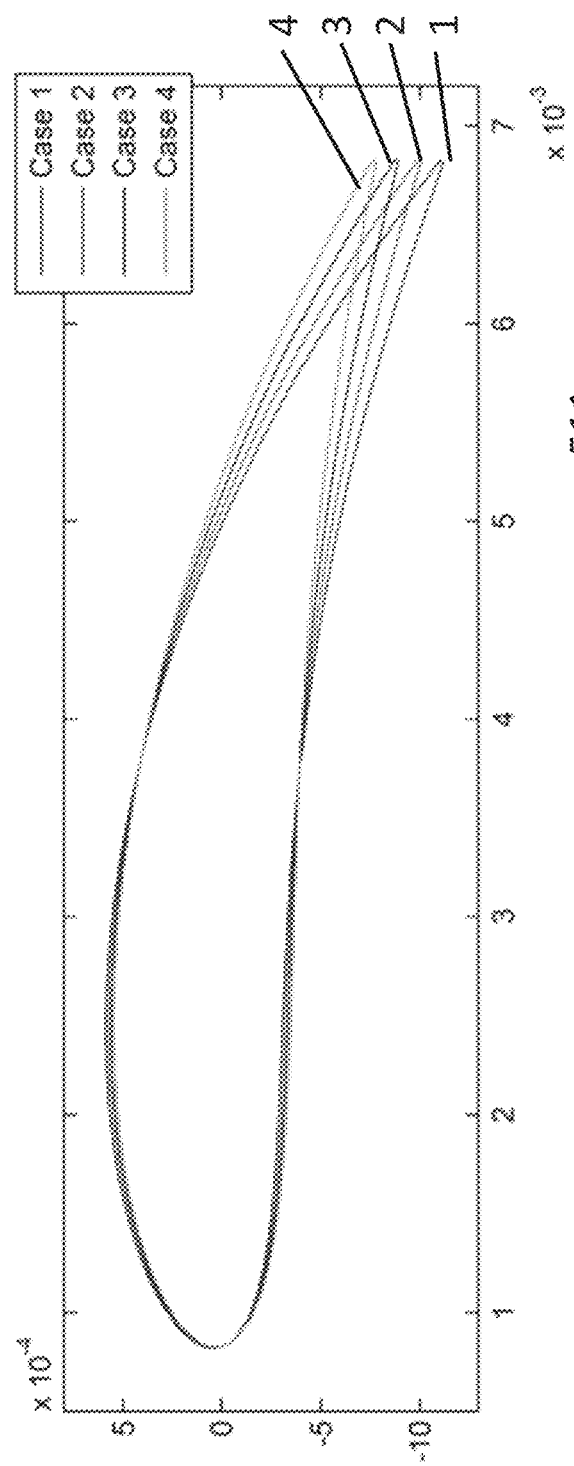
Figure 58I:
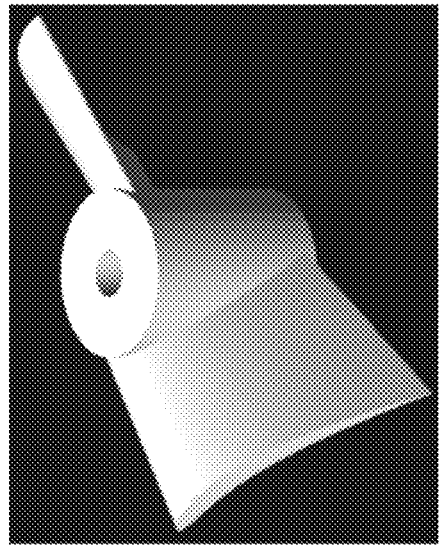
Figure 58H:
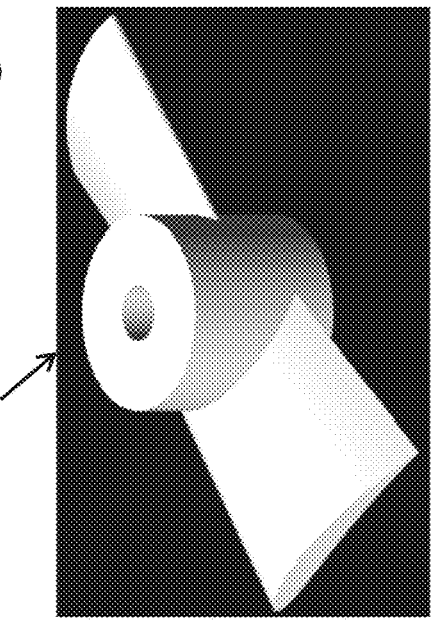

FIGS. 58A-58I schematically illustrate various examples of blade geometries. Blades 520 may comprise a stagger angle defined as the angle between the chord line and the rotor's axial direction or central axis of the MCS device (also known as the setting angle). The blades 520 may comprise a stagger angle between 0 degrees and 90 degrees. In some embodiments, the stagger angle may be between 0 degrees and 5 degrees, between 5 degrees and 10 degrees, between 10 degrees and 40 degrees, or more than 40 degrees. The blade 520 may be modeled by dividing the blade 520 into three sections, such as profiles of a front edge or tip section, a back edge or hub section, and a mean profile, as depicted in the sectional views of FIGS. 58A-58K. FIGS. 58A and 58B illustrate sectional views and three-dimensional views, respectively, of a blade comprising 5 degree inlet, outlet, and stagger angles. FIGS. 58C and 58D illustrate sectional views and three-dimensional views, respectively, of a blade comprising 2 degree inlet, outlet, and stagger angles. FIG. 58E-58G illustrate sectional views of the tip sections, mean sections, and hub sections, respectively, for 5 degree (case 1), 4 degree (case 2), 3 degree (case 3), and 2 degree (case 1) stagger angles. FIGS. 58H and 58I illustrate perspective views of propeller geometries comprising stagger angles of 10 degrees and 40 degrees, respectively.

Figure 59A:
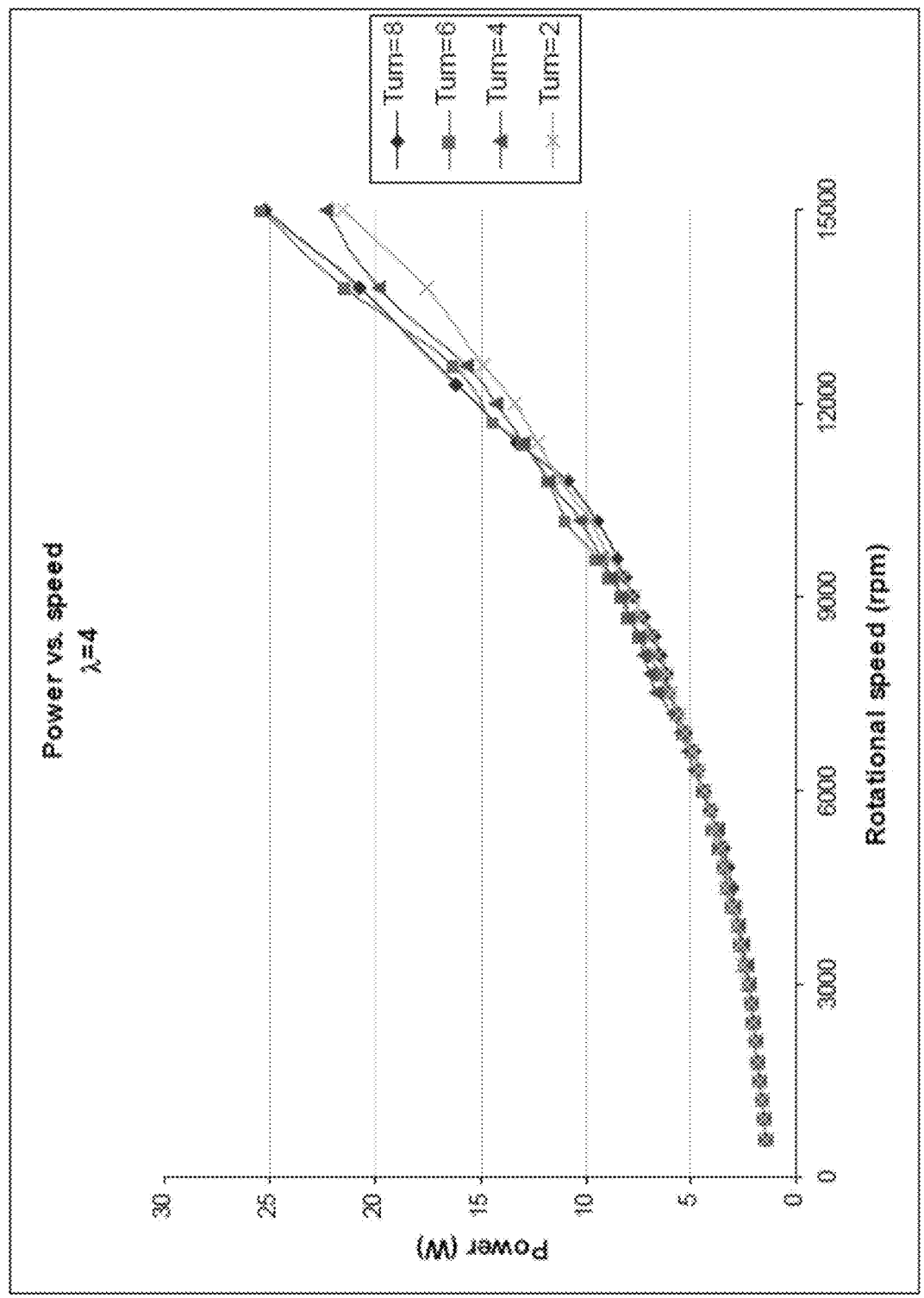
FIGS. 59A-59M depict experimental results for blades having various stagger degrees.
Figure 59B:
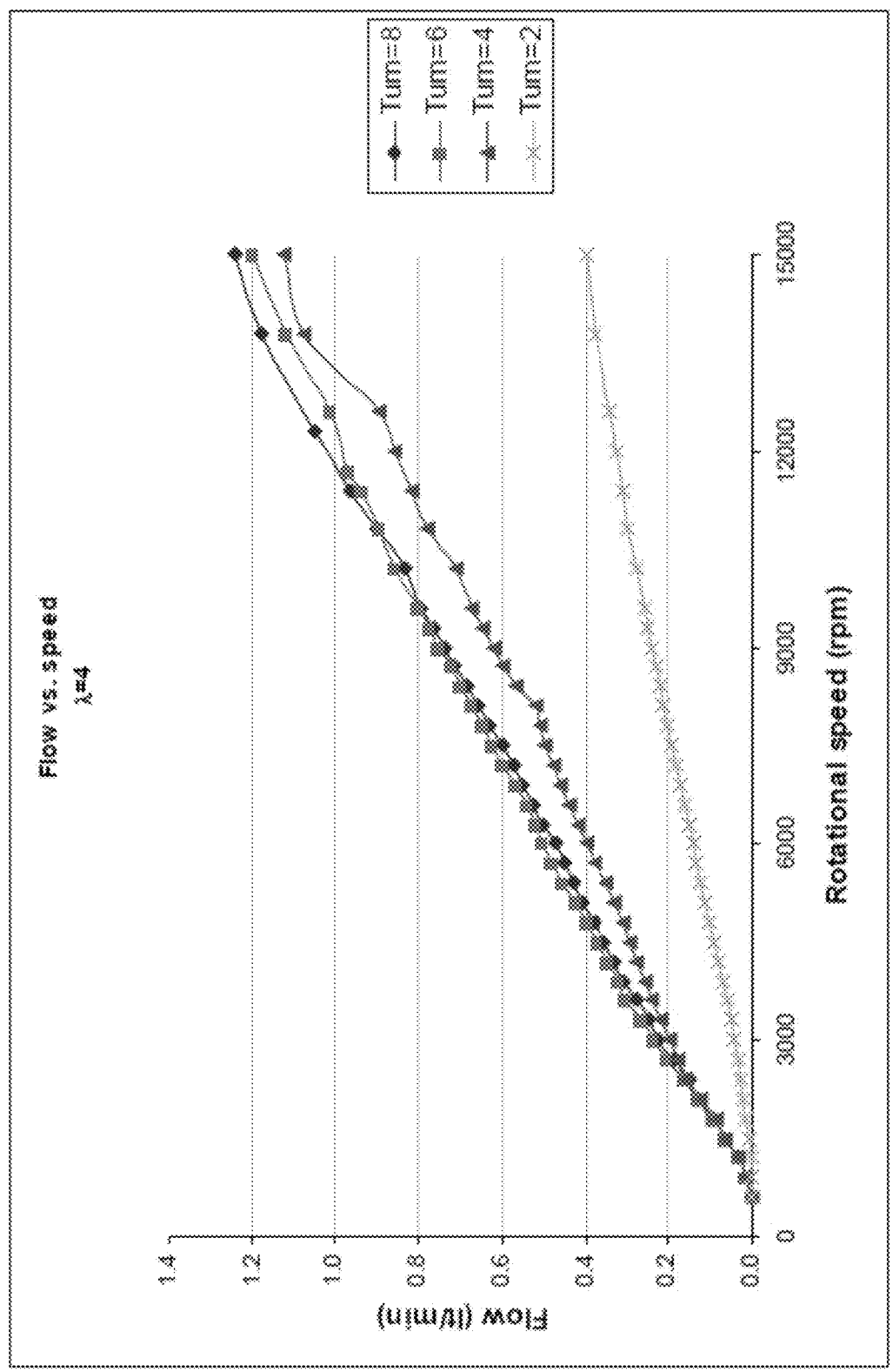
Figure 59C:
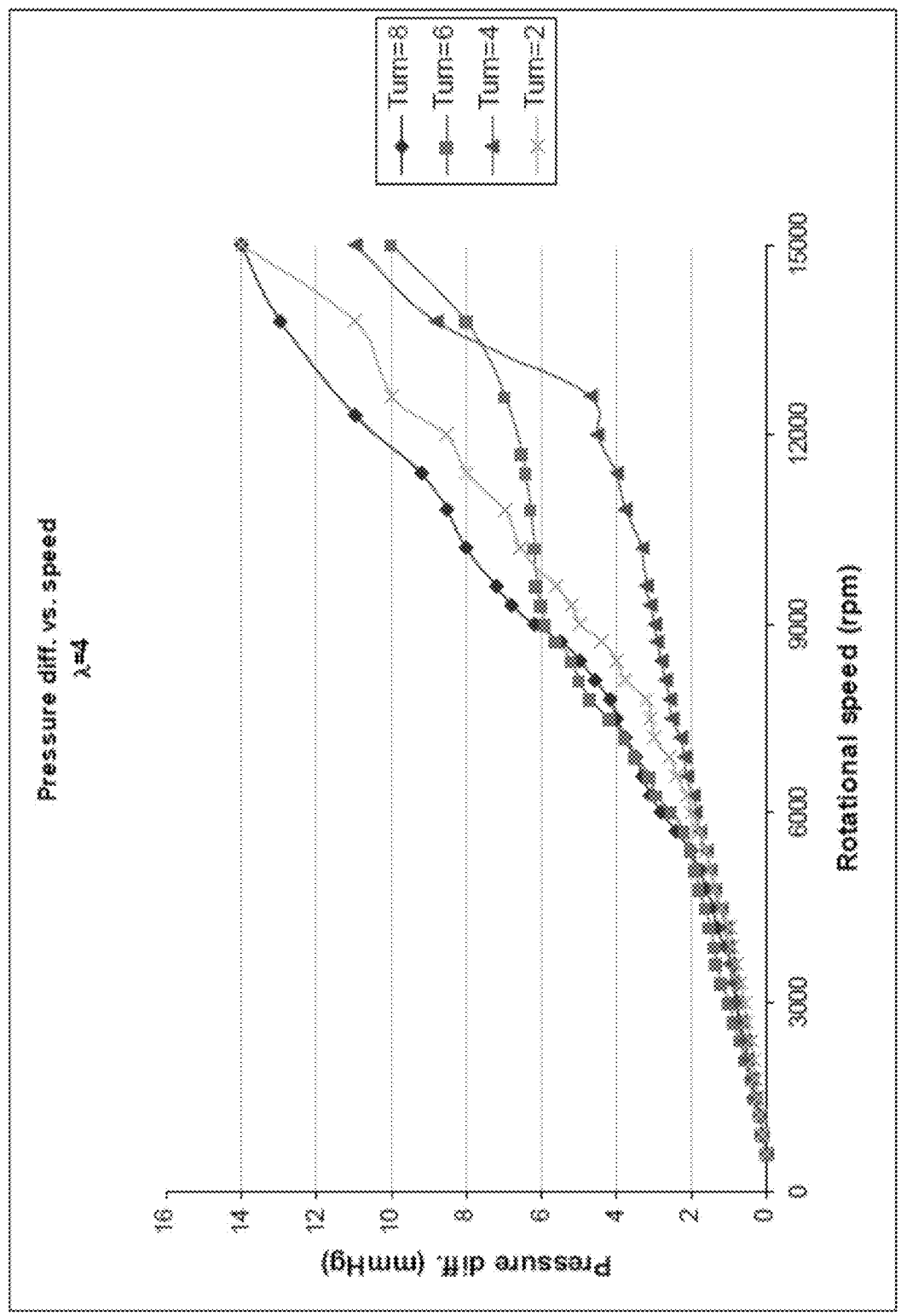
Figure 59D:
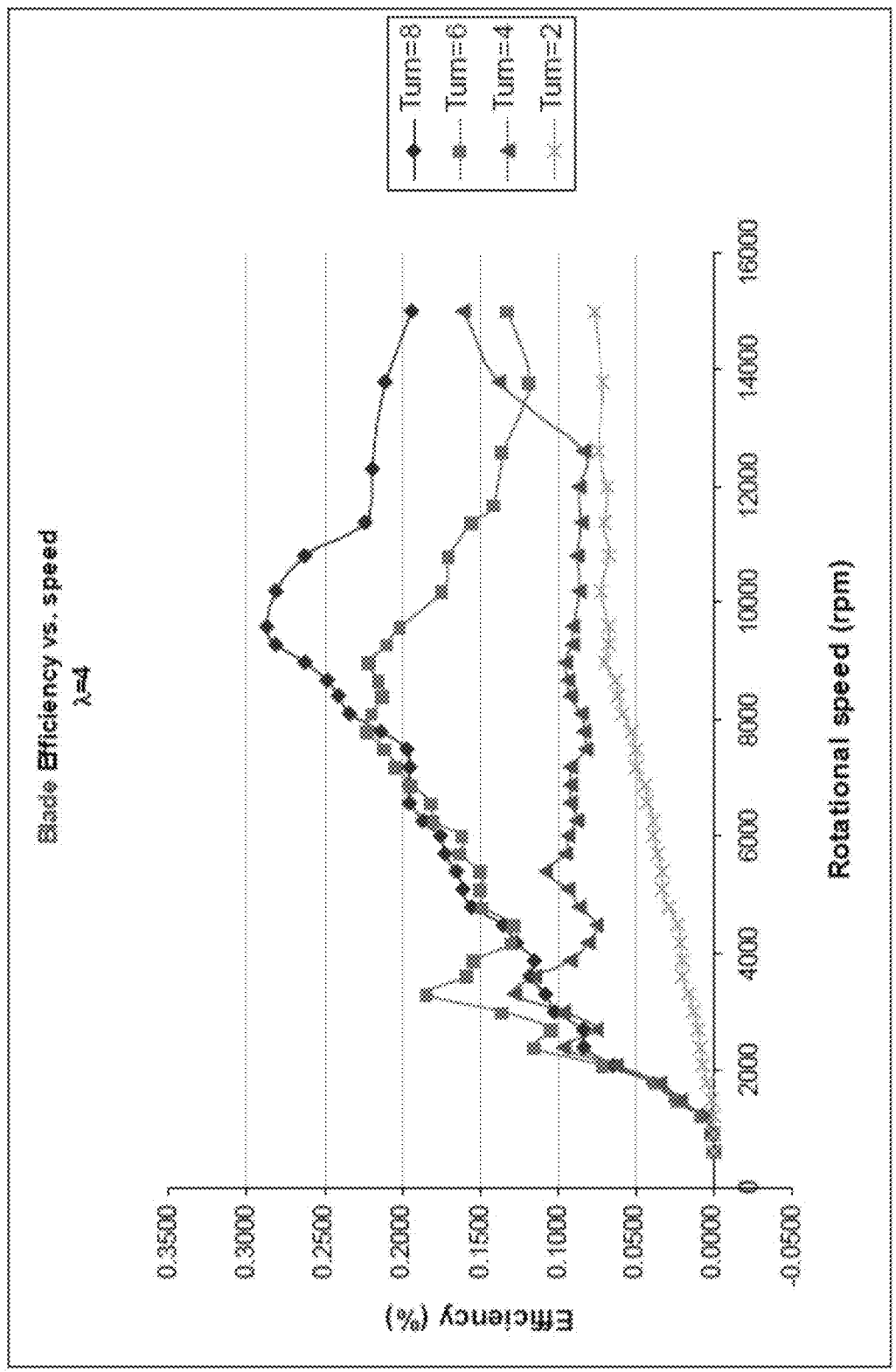
Figure 59E:
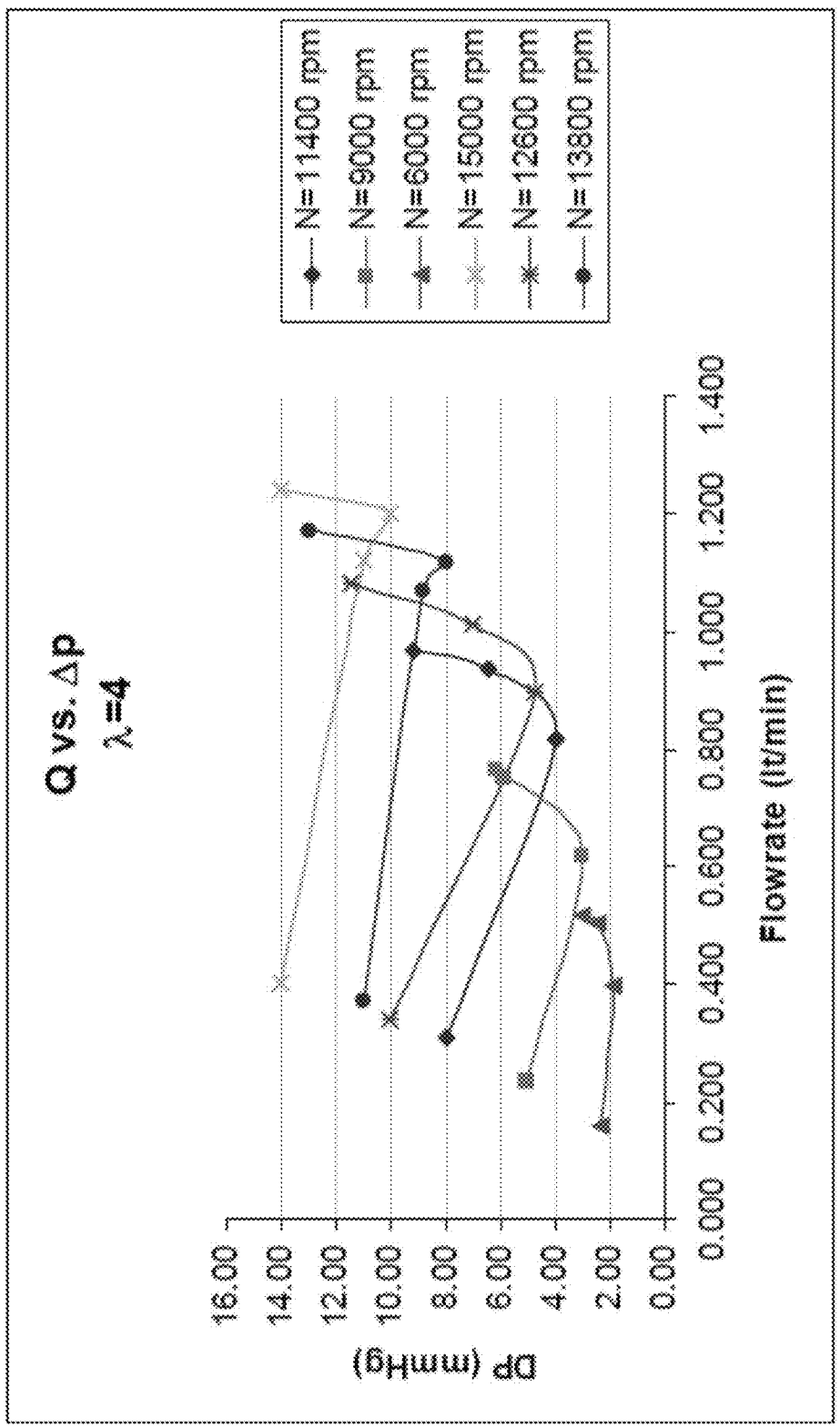
Figure 59F:
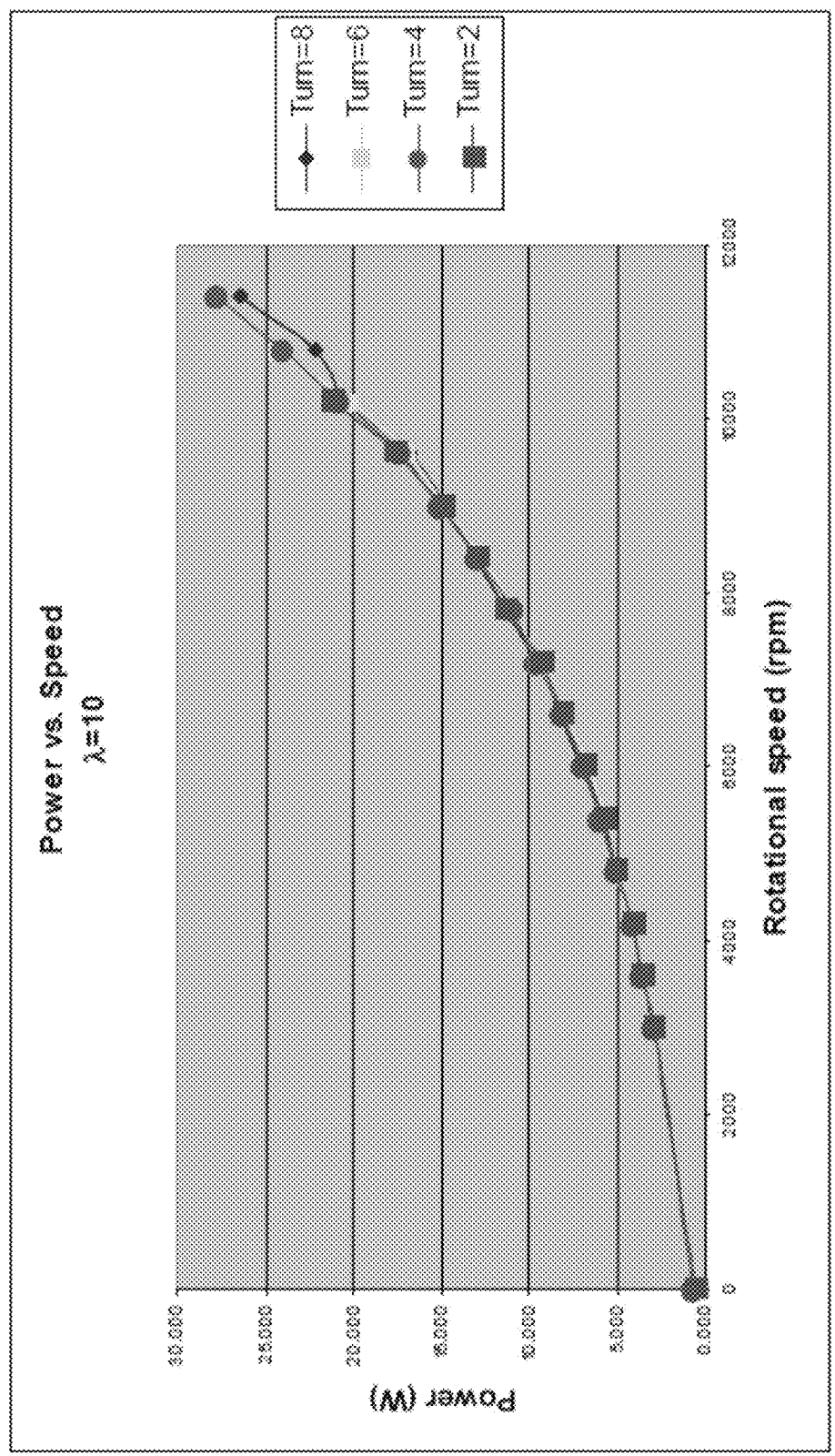
Figure 59G:
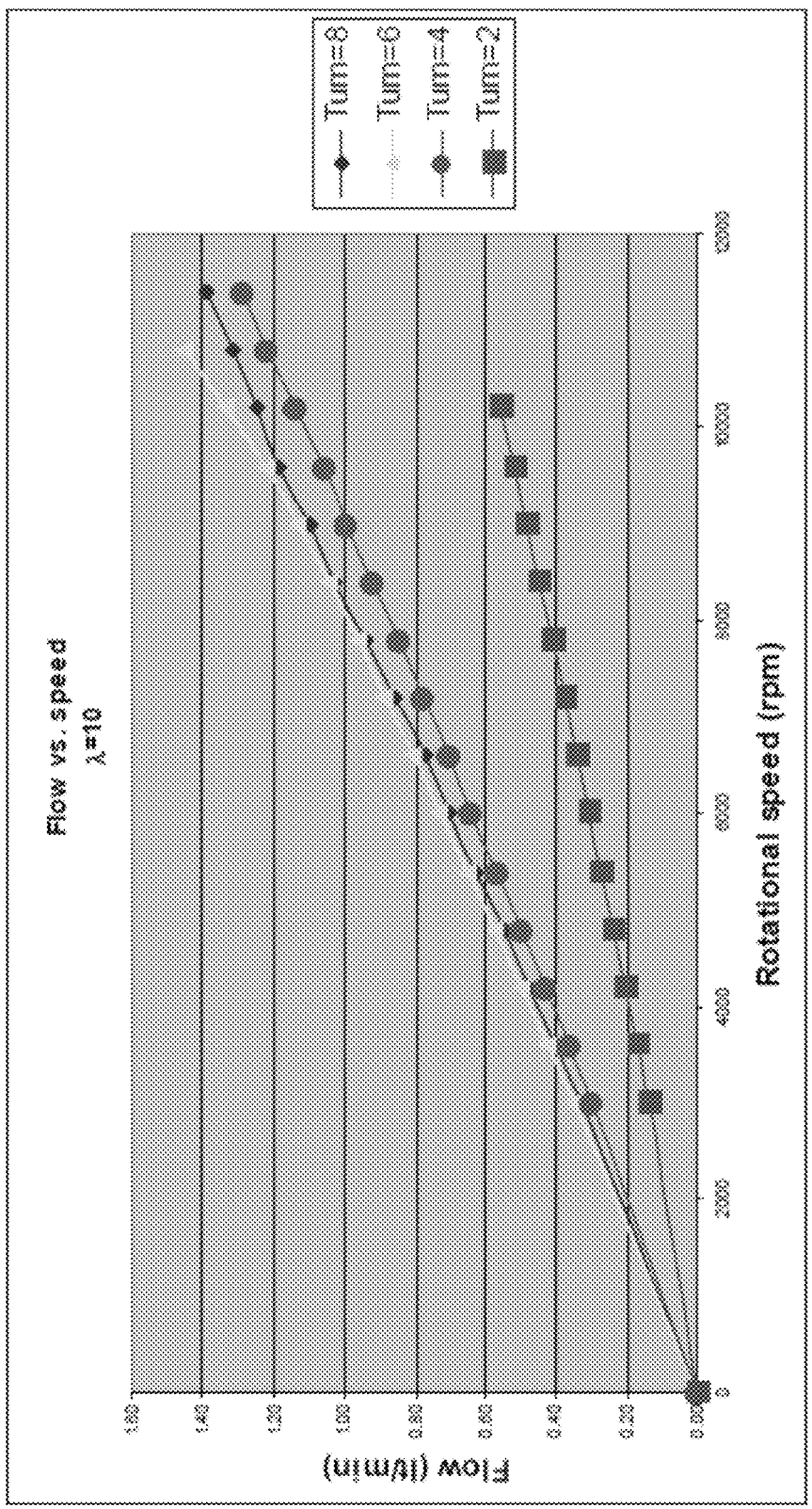
Figure 59H:
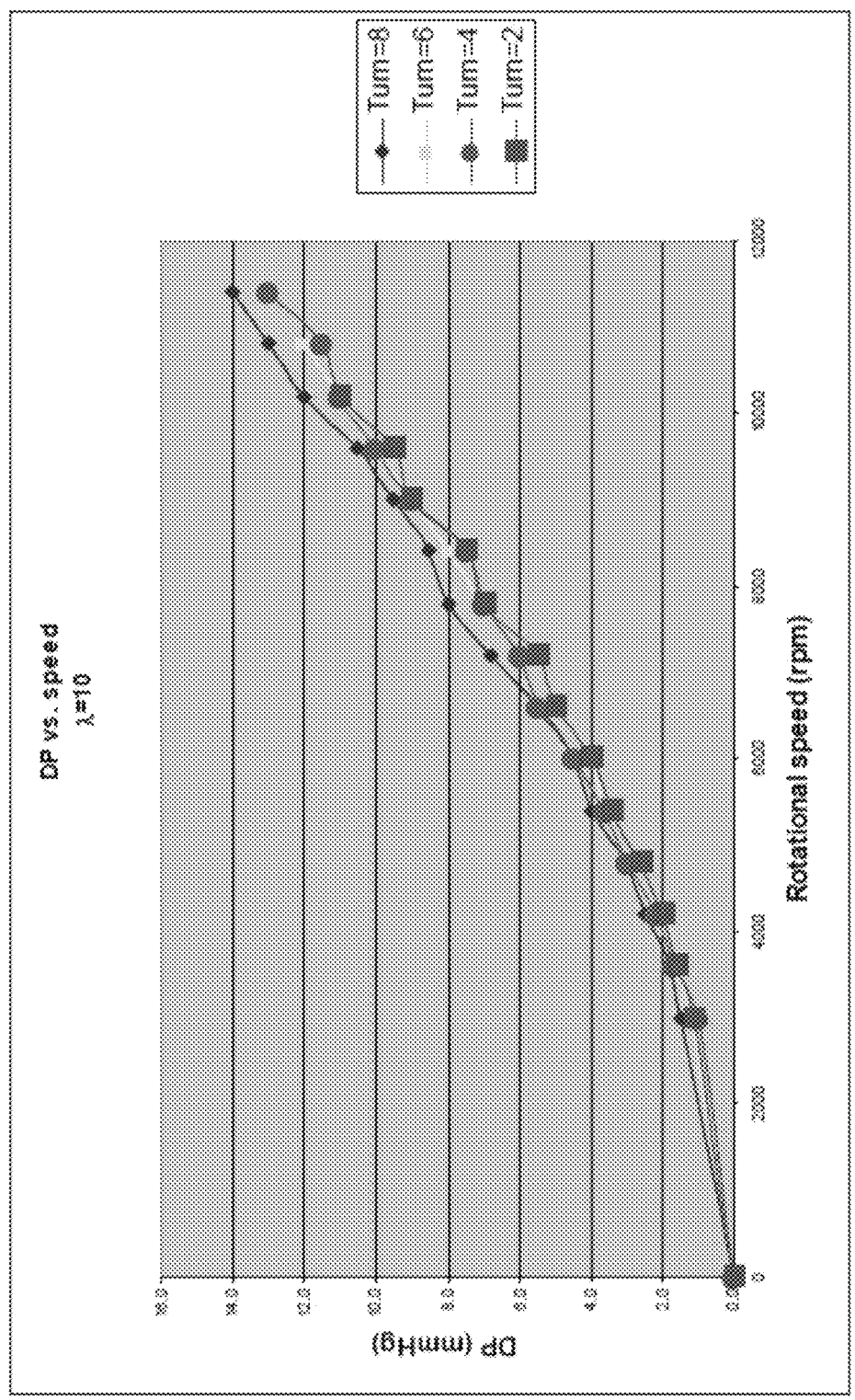
Figure 59I:
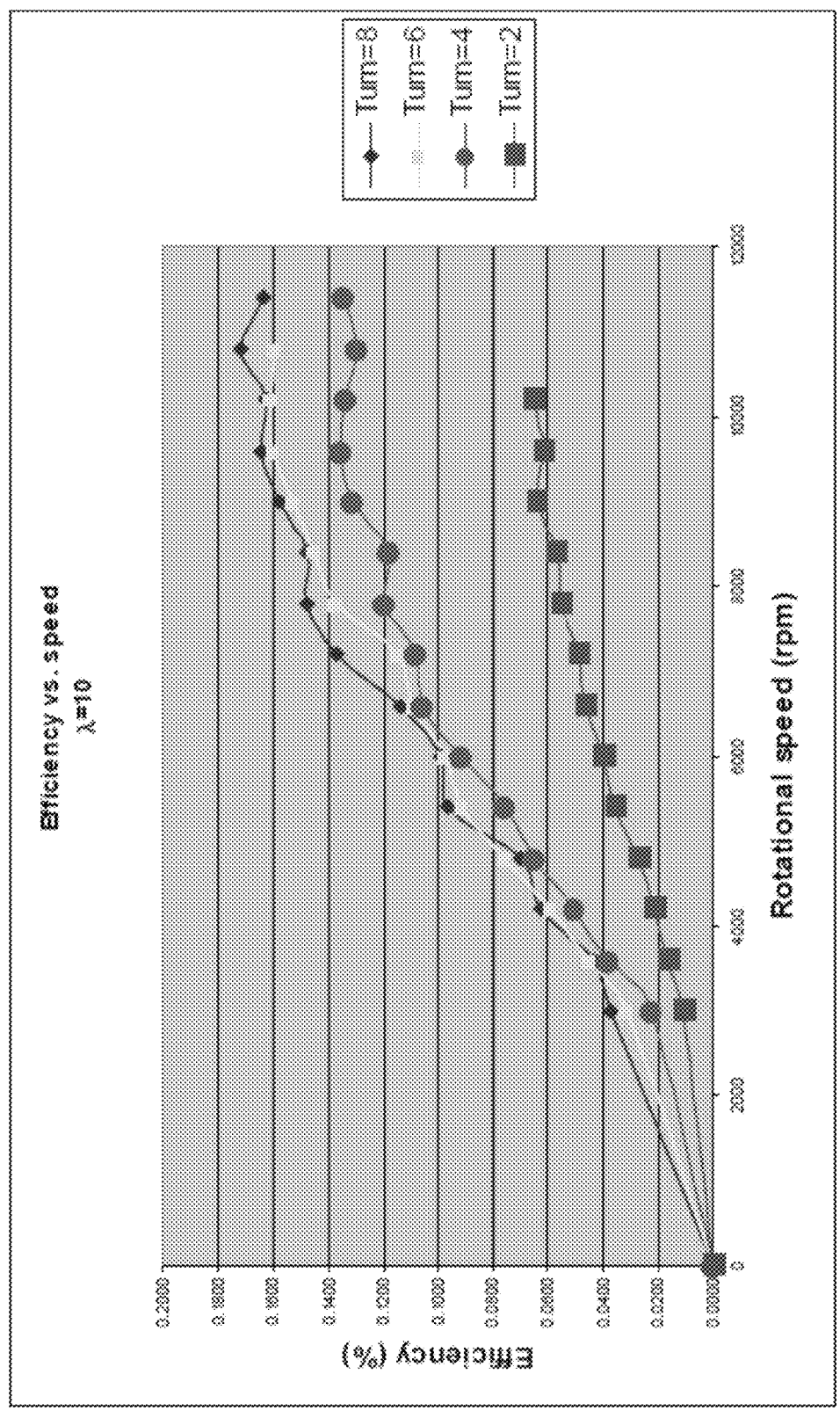
Figure 59J:
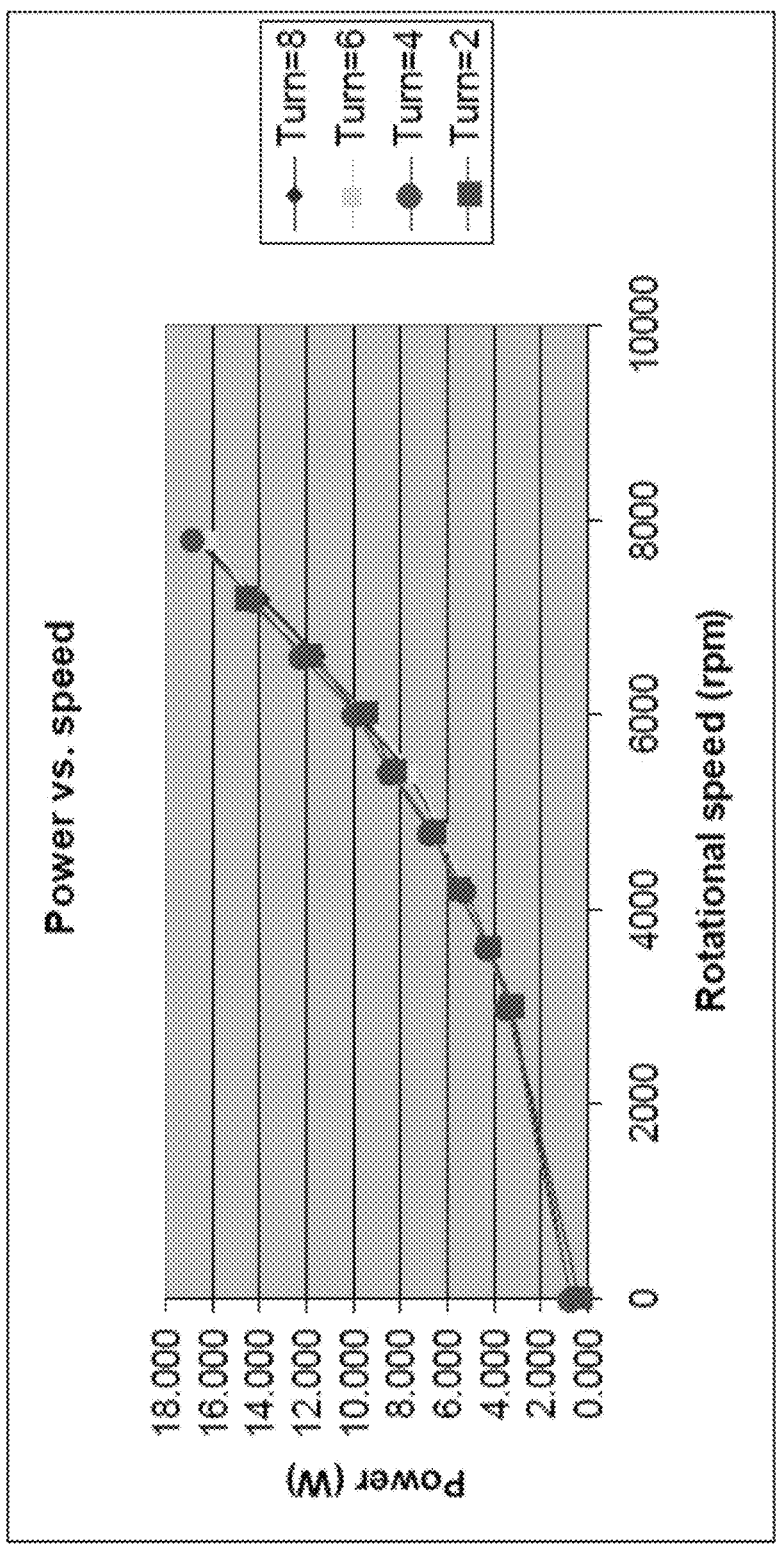
Figure 59K:
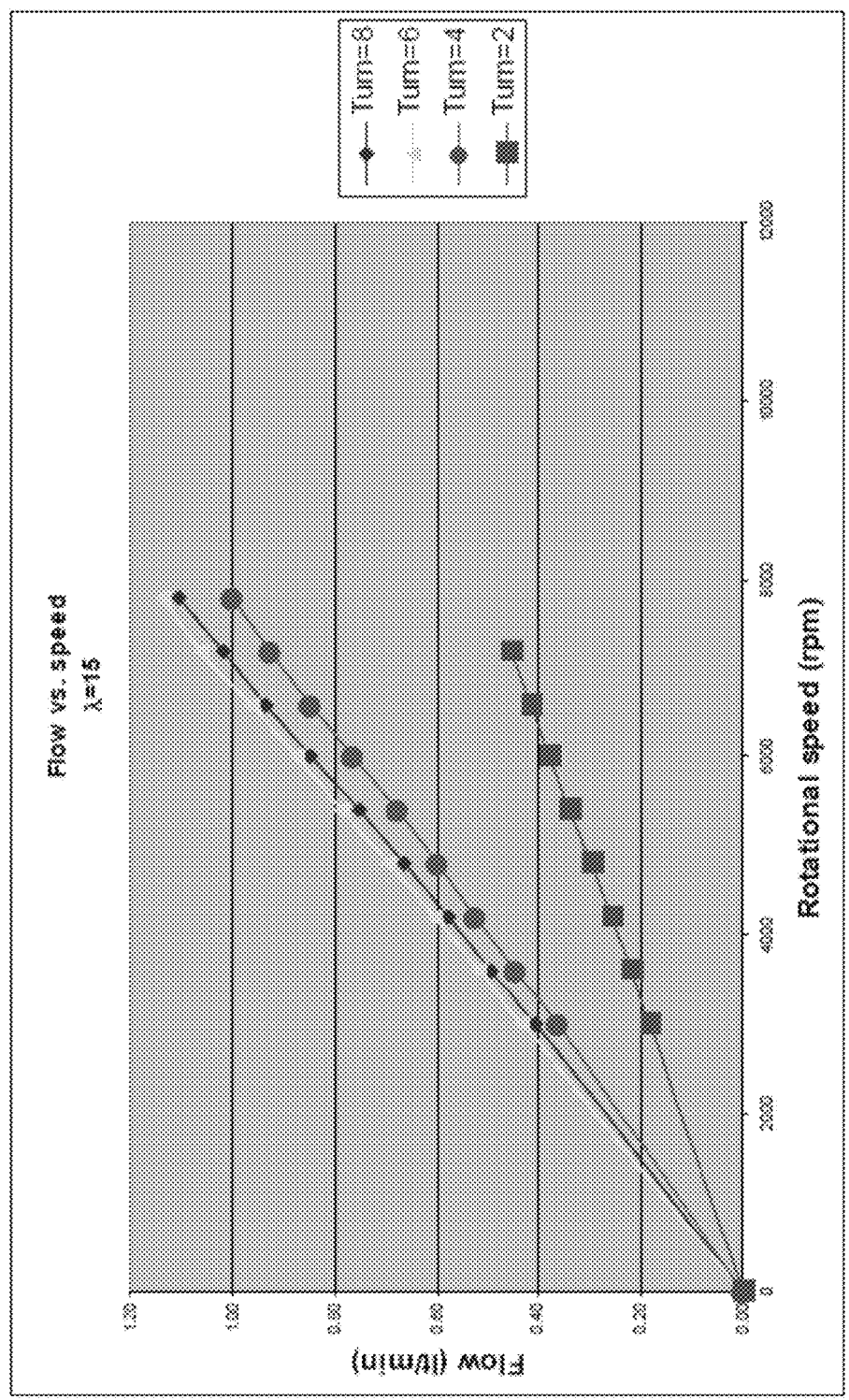
Figure 59L:
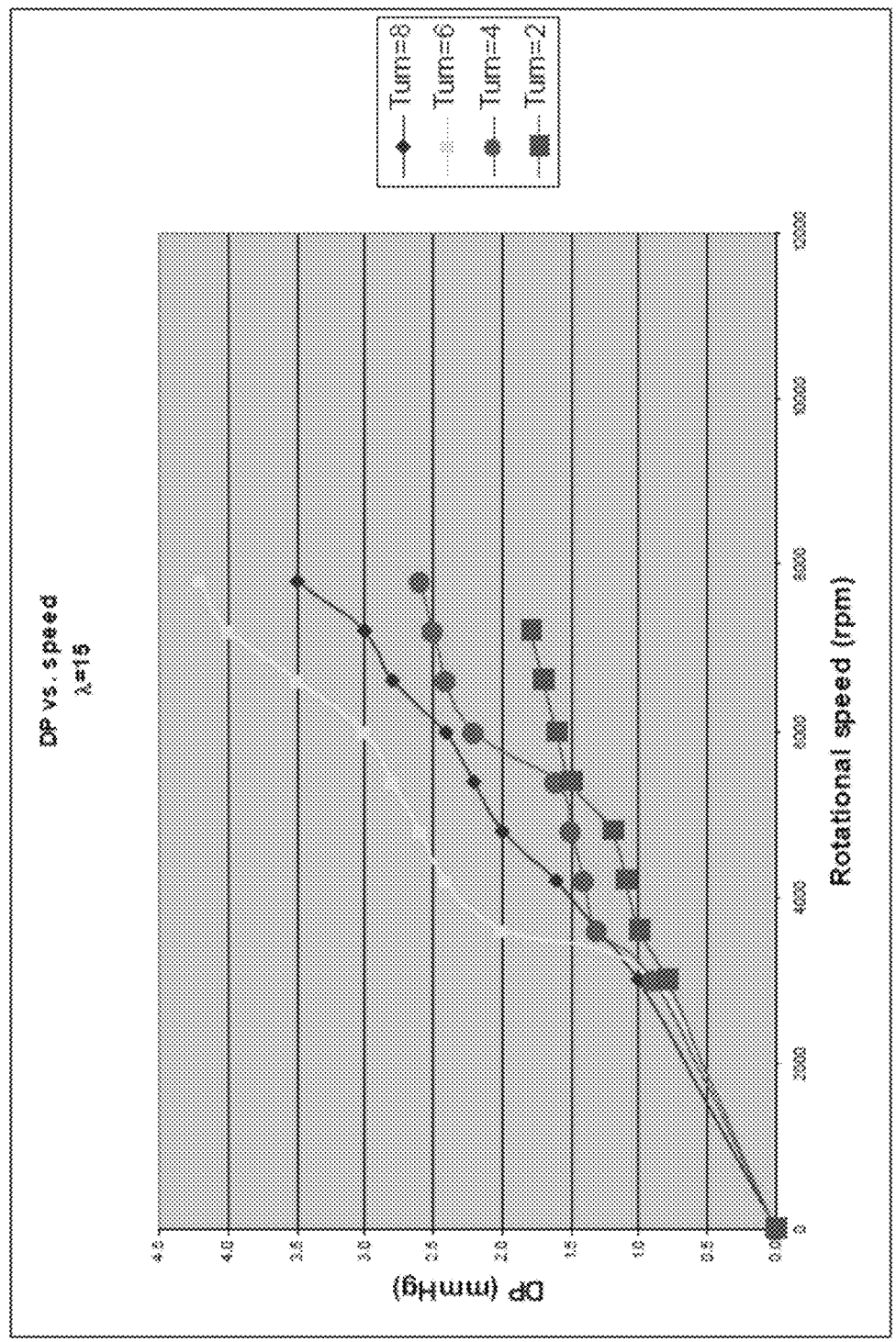
Figure 59M:
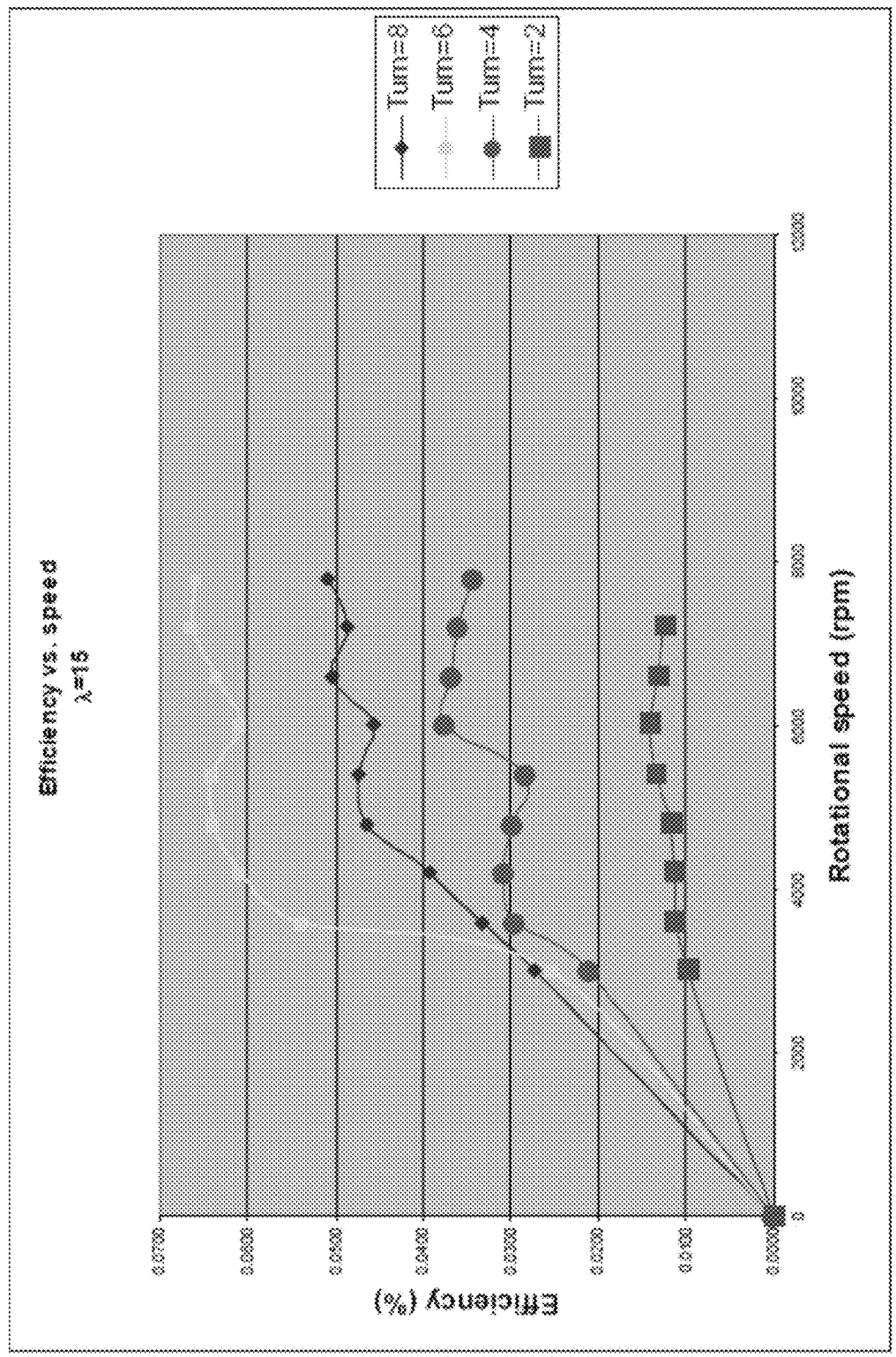

FIGS. 59A-59M depict experimental results for blades having various stagger degrees. The results were contained for various degrees of resistance which were emulated by a multi-turn valve, in which a higher number of turns applies higher resistance to rotation. FIGS. 59A-59E depict results for blades 520 having a 4 degree stagger angle. FIGS. 59F-59I depict results for blades 520 having a 10 degree stagger angle. FIGS. 59J-59M depict results for blades 520 having a 15 degree stagger angle. FIGS. 59A, 59F, and 59J depict the electrical power consumed (W) as measured by current drawn at 24 V for various rotational speeds (rpm). FIGS. 59B, 59G, and 59K depict the flow rate (L/min) for various rotational speeds (rpm). FIGS. 59C, 59H, and 59L depict the pressure difference or pressure rise (mmHg) before and after the blade 520 as measured by pressure transducers for various rotational speeds (rpm). FIGS. 59D, 59I, and 59M depict the efficiency (%) of the blade 520 for various rotational speeds (rpm). FIG. 59E depicts the correlation between pressure differential (mmHg) and flow rate (L/min).

This invention relates in some aspects to various embodiments of percutaneously implantable cardiovascular support (PICS) devices. PICS devices can include percutaneously implantable Mechanical Circulatory Support Devices (MCSD). In some embodiments, PICS may be configured for implantation in the aorta via the femoral artery. In some methods of use, PICS may be intended for implantation percutaneously. In some methods of use, PICS may be intended for implantation with minimally invasive surgery. Cardiovascular support devices can be configured for either long-term implantation or short-term (e.g., temporary)

implantation. Some embodiments may be designed for early New York Heart Association (NYHA) class III CHF (before Interagency Registry for Mechanically Assisted Circulator Support (INTERMACS level 7) and more severe conditions. In some embodiments, devices may be configured for in-series implantation in the aorta. Thus, in some embodiments, the adult specification can include about a 5 L/min flow rate and from about 20 to about 40 mm Hg pressure rise, where the remaining pressure rise is given by the diseased native heart.

Some embodiments may be designed with operating conditions specifically configured for particular state of the patient, including the stage of disease. For instance, a MCS designed for late stage II or early stage III CHF may provide a lesser pressure rise, while a MCS designed for late stage III or early stage IV CHF may provide a greater pressure rise, to better supplant the failing heart. In some embodiments, devices be configured to provide a flow rate of about, at least about, or no more than about 1 L/min, 2 L/min, 3 L/min, 4 L/min, 5 L/min, 6 L/min, 7 L/min, 8 L/min, 9 L/min, 10 L/min, or any ranges including two of the foregoing values. In some embodiments, the devices be configured to provide a flow rate of about, at least about, or no more than about 5 mm Hg, 10 mm Hg, 15 mm Hg, 20 mm Hg, 25 mm Hg, 30 mm Hg, 35 mm Hg, 40 mm Hg, 45 mm Hg, 50 mm Hg, 55 mm, Hg 60 mm Hg, 65 mm Hg, 70 mm Hg, 75 mm Hg, 80 mm Hg, 85 mm Hg, 90 mm Hg, 95 mm Hg, 100 mm Hg, or any ranges including two of the foregoing values. In some embodiments, devices can be configured with operating conditions to replicate the conditions of a healthy patient.

Some devices may be designed to be implanted in-series with the heart. As described herein, such arrangements may effectively reduce the load on the heart. Some devices may be configured to lower the resistance to blood flow. As described herein, such arrangements provide the heart increased potential for regeneration of diseased tissue. Devices may be configured to require less power, and therefore be lighter in weight and more compact. Devices may be configured to pump blood at a continuous flow. Devices may be configured to pump blood at a pulsated flow. Devices may be configured to pump blood at a flow rate advantageous to complement the pulsing heart.

Ventricular Assist Devices (VAD) are heart assist pumps that can include an inlet anastomosed to one of the four chambers of the native diseased heart. In some methods of use, the VAD device is anastomosed to the left ventricle. This configuration is more common. In some methods of use, the VAD device is anastomosed to the right ventricle. In some methods of use, the VAD device is anastomosed to one of the atria. Mechanical circulatory support devices (MCSD) are also heart assist pumps. MCSDs, in contrast to VADs, are typically installed in the vasculature. MCSDs, in contrast to VADs, are not typically attached to any part of the diseased native heart. Usually the MCSDs are designed for a less invasive implantation procedure than the VADs.

Permanent MCSDs are devices that may be used over a short or over a long period of time. Due to their design, permanent MCSDs have some components that once installed in the human body, these components are configured to stay in the patient's body, even if some other parts of the MCSD are later removed. In some embodiments, a cage or support structure stays within the body after removal of other components. In some embodiments, a motor or power source stays within the body after removal of other components. In some embodiments, one or more components is permanently coupled to a structure within the body of the patient.

Temporary MCSDs can be specifically configured for short-term use with the intent that after the temporary use all components of the device will be fully removed from the patient's body. Thus a key characteristic of a temporary MCSD in some embodiments is that no part of the device will stay in the patient's body after use. In some embodiments, the Temporary MCSD is configured to be removed as a unit. In some embodiments, two or more components of the Temporary MCSD are configured to be removed separately or independently. In some methods of use, the Temporary MCSD is removed in a single surgical procedure. In some methods of use, the Temporary MCSD may be configured for removal via the femoral artery. In some methods of use, the Temporary MCSD may be configured for removal percutaneously. In some methods of use, the Temporary MCSD may be configured for removal with minimally invasive surgery.

Some devices indicated for at least class III CHF (INTERMACS levels 5, 6, 7) may be designed with the rotor of the turbomachine and electric motor being designed for implantation, periodic removal and re-implantation. In some methods of use, the devices may be configured for periodic removal via the femoral artery. In some methods of use, the devices may be configured for periodic removal percutaneously. In some methods of use, the devices may be configured for periodic removal with minimally invasive surgery. In some methods of use, the devices may be configured for re-implantation via the femoral artery. In some methods of use, the devices may be configured for re-implantation percutaneously. In some methods of use, the devices may be configured for re-implantation with minimally invasive surgery. In some methods of use, the devices can be implanted and re-implanted via the same type of procedure. In some methods of use, the devices can be implanted and re-implanted via different types of procedures. As an example, the devices may be configured for implantation, periodic removal and re-implantation via the femoral artery in the aorta.

As described herein, devices may be Permanent MCSDs such that one or more components are permanently installed. In some embodiments, the stator of the motor may be permanently installed. In some methods of use, the stator of the motor may be permanently installed around and outside the aorta, surrounding the location of the rotor. In some methods of use, the stator may be configured to be positioned around an outer circumference of the blood vessel. In some methods of use, the stator may be configured to be positioned around another structure of the patient. The stator may include a hinge or other mechanical feature to allow the stator to be positioned there around. The stator may include an anchoring structure to permanently attach to the patient. As described herein, the stator can include one or more electromagnets positioned around the circumference of the stator. The stator is configured to be positioned concentrically around the blades of a propeller or impeller to electromagnetically drive rotation of the at least one magnetic blade.

However, other components may be removed after use, or intermediately removed during use. As one example, the rotor of the turbomachine and/or electric motor may be designed to be removed. In some embodiments, all components of some devices are configured to be permanently installed.

Some devices with the above flow rate and pressure rise specifications may be configured for short term use. In some embodiments, the device is configured to be used for a few hours, e.g., about, at least about, or no more than about 1 hour, 2 hours, 4 hours, 8 hours, 12 hours, 16 hours, 20 hours, 24 hours, or a few days, e.g., 1 day, 2 days, 3 days, 4 days, 5 days, 6 days, 7 days, or any range including any two of the foregoing values. In some embodiments, the device is configured to be used less than a week, less than 5 days, less than 3 days, less than 1 day, less than 12 hours, more than 1 hour, more than 4 hours, more than 12 hours, more than 1 day, more than 3 days, more than 5 days, or any range of the foregoing values. In some embodiments, the device is configured to be used between a few hours and up to about 5 days. Devices may be configured for implantation and then complete removal of all components from the human body. Devices may be configured to address Acute Cardiogenic Shock (CGS). Devices may be configured to address Percutaneous Coronary Intervention (PCI). Devices may be configured to address acute decompensated heart failure (ADHF). Devices may be configured to address Cardio Renal Syndrome (CRS). Devices may be configured to provide temporary relief of the native heart in very early stages of CHF. Other uses of the devices are contemplated.

Some embodiments include percutaneously implantable Temporary MCSDs configured for implantation. In some methods of use, the device may be configured for implantation in the aorta via the femoral artery. In some methods of use, the device may be configured for implantation in the aorta percutaneously. In some methods of use, the device may be configured for implantation in the aorta with minimally invasive surgery. The device may be intended for short term, temporary use, ranging from a few hours to up to about five days. At the end of use, all components of the device are removed from the patient's body.

In some embodiments, a device could include axial, and/or centrifugal impellers. Some devices may be configured to provide support during Percutaneous Coronary Intervention (PCI) for those who are hemodynamically unstable after acute heart attack, for acute decompensated heart failure (ADHF), for cardio-renal syndrome (CRS) patients and acute cardiogenic shock (ACS), as well as for early NYHA class II CHF (before INTERMACS level 7) and more-severe conditions. Some devices may be configured for in-series implantation in the aorta.

Some devices can be a temporary MCSD as described herein. Devices can provide any flow rate and pressure rise described herein. However, some devices may be configured for short term use, typically varying between a few hours and up to about 5 days. All components of temporary devices can be configured to be removed after the short term use. For instance, in some embodiments, no component is configured to be permanently attached to the body of the patient. Unlike some permanently implantable devices, temporary MCSDs can be configured for implantation and then complete removal of all components from the human body. In this way, temporary devices may be configured to addresses PCI, ADHF, CRS, ACS, and temporary relief of the native heart in very early stages of CHF.

Clinical experience performed by an inventor suggests that a device with the specifications as disclosed elsewhere herein can be used effectively as an alternative to other percutaneous systems during percutaneous coronary intervention (PCI). Clinical experience performed by an inventor also suggests that the implantation location of the device (e.g., in the descending aorta) can also provide additional but substantial therapeutic advantages due to increasing perfusion to the kidneys. Other clinical advantages are contemplated.

Some illustrations of devices are included in FIGS. 60A-72. In some embodiments, features described as related to temporary devices may be incorporated into permanently implantable devices and features described as related to permanently implantable devices may be incorporated into temporary devices. Temporary devices may include any feature of any device described herein. Permanent devices may include any feature of any device described herein.

in some embodiments, devices may include two or more foldable impellers or propellers rotating in opposite directions, e.g., contra-rotation with respect to each other. In some embodiments, contra-rotating blades rotate with equal and opposite rpm. In some embodiments, contra-rotating blades rotate with unequal rpm. The impellers, and surrounding support, are placed in the folded position via a catheter in the aorta upstream of the kidneys. In some methods of use, this may be in the descending aorta, or further upstream in the aorta, anywhere up to the aortic valve. Once the catheter is removed the blades and surrounding support spring into the unfolded position. In some methods of use, the temporary device is removed via the reverse procedure by folding it and capturing it into a catheter.

Some devices may be connected to a motor, which may have its own internal speed-reducing gearbox. The motor may be integrally connected to the devices intra-corporeally, or connected via a short bending shaft to the devices intra-corporeally. In some embodiments, power will be delivered to the motor via an electric cable. In some embodiments, the impellers and gearbox achieving contra-rotation are placed intra-corporeally in the descending aorta, and they are connected to an extra-corporeal motor or gear motor via a flexible drive shaft. The contra-rotating blades may have unequal rpm or equal rpm, based in part on the associated gearboxes. The electric motor may have integral with it an epicyclic gearbox reducing motor rpm the first time, e.g., a gear motor, then additional gearboxes reduce the motor rpm a second time before the impellers. In some embodiments, rotation of the two impellers in opposite directions is achieved via a gearbox. This gearbox may be just upstream of the impellers, just downstream of the impellers, or between the impellers. The gearbox receives input power and rotation from one shaft, and provides output via one or more two contra-rotating shafts to the two impellers.

The input to the gearboxes can be via sun gears, both driven by one center shaft. For instance, the downstream impeller may be driven by the planet carrier of the downstream epicyclic gearbox (ring fixed), and the upstream impeller may be driven by the ring of the upstream epicyclic gearbox (planet carrier fixed to nose cone, and via struts to stationary motor casing) to achieve contra rotation. The gear ratios can be adjusted by the diameters of their internal components to achieve exact contra-rotation, i.e. the rpm of the two rotors is equal and opposite. Alternatively, the diameters of internal gear components can be used to make the rpm of the downstream rotor higher or lower than the rpm of the upstream rotor, to accommodate contra-rotation at different impeller rpm, for example for optimal flow dynamics or for balancing reasons.

FIGS. 60A-60G schematically illustrate examples of MCS devices 500 configured for installation in the lumen of a blood vessel. MCS devices 500 can be permanent or temporary implantable devices. In some embodiments, the MCS 500 may comprise one or more rotors 510. The rotor 510 can have any configuration of rotors described herein. In some embodiment, the rotor 510 may be designed to operate with a stator. The rotors 510 may comprise one, two, or more propellers 511. The propeller 511 can have any configuration of propellers described herein. The propellers 511 may comprise one or more radially extending blades 520 configured to transfer force to the blood flowing through the vasculature. The blades 520 can have any configuration of blades described herein. In some embodiments, the MCS 500 may comprise one or more impellers 200 described herein. The impellers 200 can have any configuration of impellers described herein.

FIGS. 60A and 60B illustrate an example of a MCS device 500 with two rotors 510. In some embodiments, the MCS devices 500 can include any number of rotors, e.g., one rotor, two rotors, three rotors, etc. In some embodiments, the MCS device 500 may comprise more than one rotor 510. In some embodiments, each rotor 510 may comprise a propeller 511 configured to rotate independently of the propellers of other rotors. In some embodiments, each rotor 510 may comprise a propeller 511 configured to rotate simultaneously with the propeller of another rotor.

Each propeller 511 includes a number of blades. In the illustrated example, each propeller 511 may include four blades 520. The propeller 511 may have two pairs of diametrically opposed blades 520. The four blades 520 may be circumferentially spaced, e.g., spaced apart by approximately 90 degrees. The four blades 520 may be unevenly spaced apart. In the illustrated example, each propeller 511 includes one row of blades. In some embodiments, the propeller 511 can include two or more rows of blades.

The propeller 511 may be comprised of one or more radially extending blades 520. In some embodiments, the blades 520 may be aligned at a given axial position of the MCS device 500. In some embodiments, the blades 520 may be axially spaced along the axis of the MCS device 500. In some embodiments, one or more rotors 510 may comprise more than one propeller 511. In some embodiments, one or more rotors 510 may comprise more than one row of blades 520. In some embodiments, the propellers 511 of the same rotor 510 may be configured to rotate simultaneously. The propellers 511 may impart a velocity on blood flowing through the vasculature in which the MCS device 500 is installed. The one or more rotors 510 may be aligned along an axial dimension of the blood vessel. The axial dimension may extend parallel to the overall direction of blood flow within the vessel (upstream to downstream) and define a central axis of the MCS device 500. The axis of rotation of the one or more rotors 510 may be aligned substantially along the central axis of the MCS device 500. The axis of rotation of each of the rotors 510 may be aligned such that they are coaxial.

In some embodiments, magnetic elements may be used in the blades. In some embodiments, the whole blades may be magnetic. In some embodiments, the blades can be driven by a coil outside of the blades. For example, the coil may be outside of the blood vessel or aorta for permanent implantation. For example, the coil may be located inside the vessel, for instance in a support structure. Because axial blades are smaller than helical blades, most of the blade (e.g., a majority of the blade) may be a magnet.

In some embodiments, the blades may be made of shape memory materials. The material of the blades may enable folding into or against the hub for implantation and/or removal. In some embodiments, the components of the MCS device must be able to carry the fluid and magnetic forces exerted on them. If the blades are too pliable, the blades will be unable to carry the fluid forces. For example, if blades can twist to become axial, centrifugal, or helical they may not be able to carry the fluid or magnetic force necessary to generate mixed axial and centrifugal flow characteristics, wherein centrifugal would be pure losses.

In some embodiments, the optimal number of blades may be 2, 3, 4, 5, or 6 blades per rotating blade row. In some embodiments, the propeller or impeller has 1 blade in a single blade row, 2 blades in a single blade row, 3 blades in a single blade row, 4 blades in a single blade row, 5 blades in a single blade row, or 6 blades in a single blade row, one row, two rows, or three rows, or any combination of the foregoing configurations. In some embodiments, the rotor may include 1, 2, 3, 4, 5, or 6 blade rows. Each blade row may be rotated by the same rotor.

In some embodiments, the optimum stagger angle may be between approximately 40 and 90 degrees from the hub direction. In some embodiments, the optimum stagger angle is between 40 and 50 degrees, between 50 and 60 degrees, between 60 and 70 degrees, between 70 and 80 degrees, between 80 and 90 degrees, between 40 and 60 degrees, between 50 and 70 degrees, between 60 and 80 degrees, between 70 and 90 degrees, between 40 and 70 degrees, between 50 and 80 degrees, between 60 and 90 degrees, or any range including any two of the foregoing values. In some embodiments, the MCS device may comprise an optimized number of blades. In some embodiments, the MCS device may comprise an optimized stagger angle of the blades.

MCS devices may include axial propeller type blades, as described elsewhere herein. Axial propeller type blades are generally distinct from helical screws, in that they comprise distinct turbomachine geometries. Cutting azimuthal segments of helical devices does in some cases not result in as efficient 3D axial turbomachines as turbomachines comprising axial propeller type blades.

The MCS device 500 may comprise an anchoring mechanism 600 for anchoring the turbomachinery within the aorta or blood vessel. The anchoring mechanism 600 may be a cage, circumferential band, or other support structure configured to surround the turbomachinery and to allow blood flow to pass through. In some embodiments, the cage structure may comprise upstream and downstream points substantially aligned with the axis of rotation of the one or more rotors 510. The anchoring mechanisms 600 may be configured to hold the MCS device 500 in place within the blood vessel through pressure exerted on the blood vessel wall at points where the anchoring mechanism 600 contacts the blood vessel. The anchoring mechanism 600 may be expandable as described elsewhere herein.

For temporary devices, the anchoring mechanism 600 may be designed to temporary anchor the device within the aorta or blood vessel. The anchoring mechanism 600 may be atraumatic to rest against the vessel wall. For permanent devices, the anchoring mechanism 600 may be designed to permanently engage the tissue of the patient. The anchoring mechanism 600 may take on various forms to achieve the desired level of fixation.

FIG. 60A illustrates a collapsed configuration. FIG. 60B illustrates an expanded configuration. The MCS devices 500 may have one or more intermediate configurations between the collapsed configuration and the expanded configuration. In the collapsed configuration, the one, two, or more blades are configured to collapse to a low profile configuration. In the expanded configuration, the one or more blades are moved laterally outward. In some embodiments, the MCS device may be implanted in a collapsed state and deployed inside descending aorta, ascending aorta, or left ventricle via the aortic valve.

FIGS. 60C and 60D illustrate the MCS devices 500 within a blood vessel 150. FIGS. 60C and 60D schematically illustrate the surgical installation of the MCS device 500. In FIG. 60C, the anchoring mechanism 600 is removed, showing the rotors.

FIG. 60E illustrate a perspective view of the MCS devices 500 with two rotors 510. Each rotor 510 includes a propeller 511 that includes three blades 520. The three blades 520 may be circumferentially spaced, e.g., spaced apart by approximately 120 degrees. In some embodiments, one or more propellers 511 include a single blade. In some embodiments, one or more propellers 511 include two blades. The two blades 520 can be circumferentially spaced, e.g., spaced apart by approximately 180 degrees, or unevenly space. In some embodiments, the two or more propellers 511 have the same number of blades. In some embodiments, the two or more propellers 511 have the same configuration of blades, such as the same spacing between blades. In some embodiments, the two or more propellers 511 have a different number of blades. In some embodiments, the two or more propellers 511 have a different configuration of blades, such as different spacing between blades.

In some embodiments, the anchoring mechanism 600 may have a barrel-shape configuration as shown in FIG. 60E. In some embodiments, the anchoring mechanism 600 can be designed to minimize contact with the vessel wall. In some embodiments, the anchoring mechanism 600 is the point or points of contact with the vessel wall. In some embodiments, the anchoring mechanism 600 may act as a centering mechanism for the rotors.

FIG. 60F illustrates an example of a contra rotors device including a pair of contra-rotating propellers 512, 514. In some embodiments, the second propeller 514 may reverse the direction of the tangential velocity component. In some embodiments, the second propeller 514 may add to the axial velocity component of the blood flow such that the axial velocity of the blood is continually increased as it passes through the MCS device 500. In some embodiments, MCS devices 500 may include contra-rotating blades. Contra-rotating blades may be highly beneficial to minimize hemolysis. Contra-rotating blades may be able to operate efficiently at a lower rpm than devices without contra-rotating blades. The MCS devices 500 can include any number of propellers, including any number of contra-rotating propellers. The MCS devices 500 can include any arrangement of propellers, including any arrangement of contra-rotating propellers. In the illustrated embodiment, the pair of contra-rotating propellers 512, 514 are axially aligned. In the illustrated embodiment, the pair of contra-rotating propellers 512, 514 have the same number of blades. In the illustrated embodiment, the pair of contra-rotating propellers 512, 514 have blades that are equally spaced around the circumference.

In some embodiments, the magnitude of angular velocities of two propellers within a pair of contra-rotating propellers 512, 514 may be equal. Contra-rotating propellers 512, 514 with equal angular velocity magnitudes may result in output velocity vectors comprising small tangential velocity components, such as that necessary to replicate natural helical blood flow in the aorta. In some embodiments, the magnitude of angular velocities of two propellers within a pair of contra-rotating propellers 512, 514 may be unequal.

The final velocity vector at the output of the MCS device 500 may be modulated by the blade geometry. The blades of the propeller 511 and/or the contra-rotating propellers 512, 514 can be selected to have the desired flow characteristics. The blades of the propeller 511 and/or the contra-rotating propellers 512, 514 can be selected based on the size of the blades. The blades of the propeller 511 and/or the contra-rotating propellers 512, 514 can be selected based on the tilt of the blades. The blades of the propeller 511 and/or the contra-rotating propellers 512, 514 can be selected based on the total number of blades of the propeller. The blades of the propeller 511 and/or the contra-rotating propellers 512, 514 can be selected based on the direction of rotation of the propeller 511 and/or the contra-rotating propellers 512, 514.

The blades of the propeller 511 and/or the contra-rotating propellers 512, 514 can be selected based on the desired distance between the two or more propellers 511 and/or contra-rotating propellers 512, 514 in the MCS device 500. The blades of the propeller 511 and/or the contra-rotating propellers 512, 514 can be selected based on the ordering of the propellers in an axial direction in the MCS device 500. The blades of the propeller 511 and/or the contra-rotating propellers 512, 514 can be selected based on the desired number of propellers to achieve a blood flow characteristic. The blades of the propeller 511 and/or the contra-rotating propellers 512, 514 can be selected based on the desired angular velocities of the propeller 511 and/or the contra-rotating propellers 512, 514 to achieve a blood flow characteristic.

In some embodiments, the propellers 511, the contra-rotating propellers 512, 514, impellers, or contra-rotating impellers may have a diameter taking most of the available blood vessel diameter. This configuration can have advantages. The RPM of the one or more propellers or impellers may be minimized for the pressure rise and flow rate specification, thus minimizing blood trauma. In some embodiments, the propellers 511, the contra-rotating propellers 512, 514, impellers, or contra-rotating impellers may have a diameter less than the available blood vessel diameter. In some embodiments, one or more support structures have a diameter that fills a portion of the available blood vessel diameter.

In some embodiments, the propellers 511, the contra-rotating propellers 512, 514, impellers, or contra-rotating impellers are coupled to a motor. The motor can have any features of motors described herein. MCS device 500 can include any structure or hub to contain or house the motor. In some embodiments, one or more contra-rotating motors may be located in the hub of propellers or impellers. MCS device 500 can include any structure to deliver power to the motor. MCS device 500 can include any structure to deliver control signals to the motor. In some embodiments, one or more catheter based conduits are provided for carrying conductors for power delivery and control signals.

FIG. 60G illustrates an example of a single rotor with a pre-swirler 540 and a de-swirler 542. The MCS device 500 can include one or more pre-swirlers. The MCS device 500 can include one or more de-swirlers. The pre-swirlers and de-swirlers may comprise 3D conformations. The blades may include a complex 3D configuration. This configuration of the pre-swirlers may impart a desired flow characteristic on the blood prior to entry into the propeller. This configuration of the de-swirlers may impart a desired flow characteristic on the blood after engagement with the propeller.

The pre-swirlers and de-swirlers may provide improved hydrodynamics over simple 2D struts. For example, 2D struts may not be able to impart the desired flow characteristics. In some embodiments, the pre-swirlers and/or de-swirlers are compared to those which are 2D in shape. These 2D struts may be extruded from a tube. These 2D struts may have poor flow characteristics. In contrast, the 3D pre-swirl and de-swirl vanes may be configured to have vane-angle changes from hub to tip. This configuration can impart better flow characteristics on the blood. In some embodiments, the 3D pre-swirl and de-swirl vanes are not planar. In some embodiments, the 3D pre-swirl and de-swirl vanes extend in three planes. In some embodiments, the 3D pre-swirl and de-swirl vanes extend in multiple directional vectors in a thickness dimension. In some embodiments, the 3D pre-swirl and de-swirl vanes have a longitudinal twist. In some embodiments, the 3D pre-swirl and de-swirl vanes have a longitudinal curvature.

The pre-swirlers and de-swirlers may have a compressed configuration and an expanded configuration, similar to the blades. The pre-swirlers and de-swirlers may be foldable against a hub or other structure of the MCS device 500. In some embodiments, the pre-swirlers and de-swirlers may be removable from the remainder of the device. In some embodiments, the pre-swirlers and de-swirlers may be permanently coupled to the device.

Figure 61C:
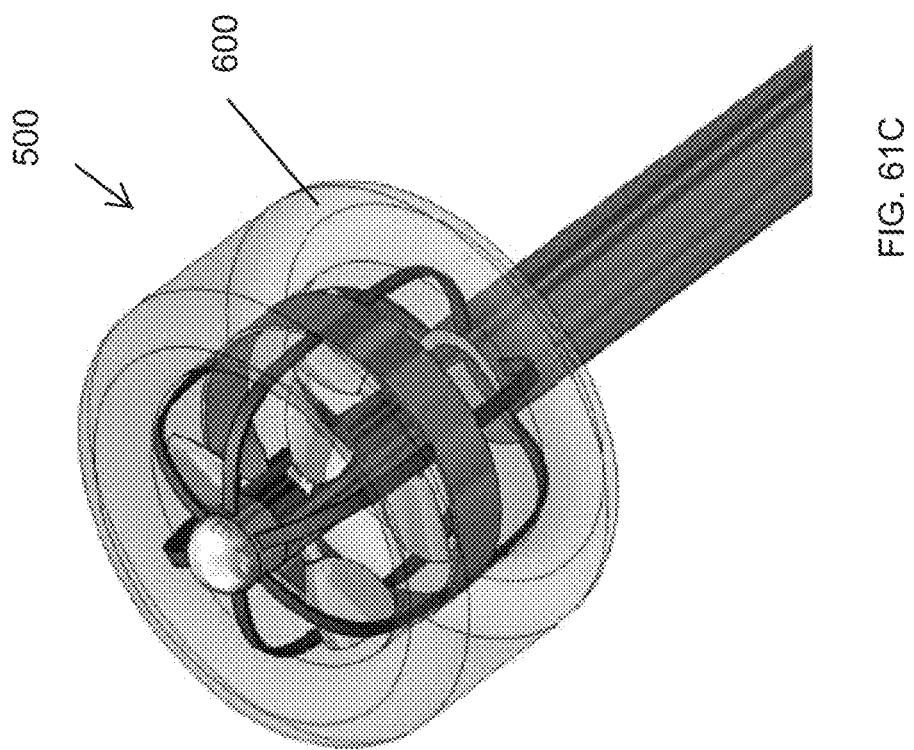
FIGS. 61A-61C schematically illustrate operating configurations of the MCS device comprising a balloon.
Figure 61B:
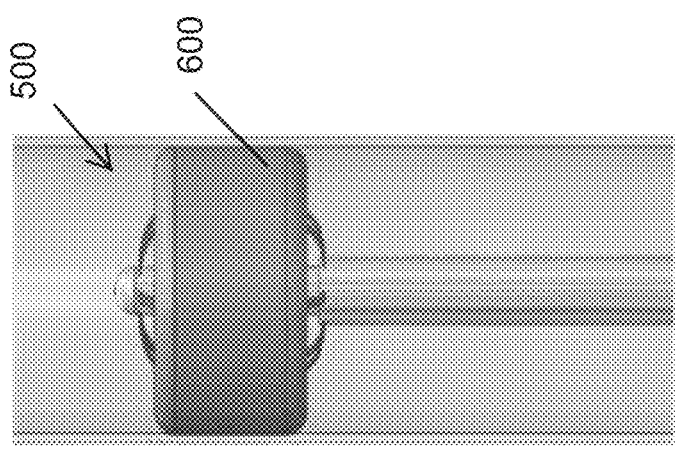
Figure 61A:
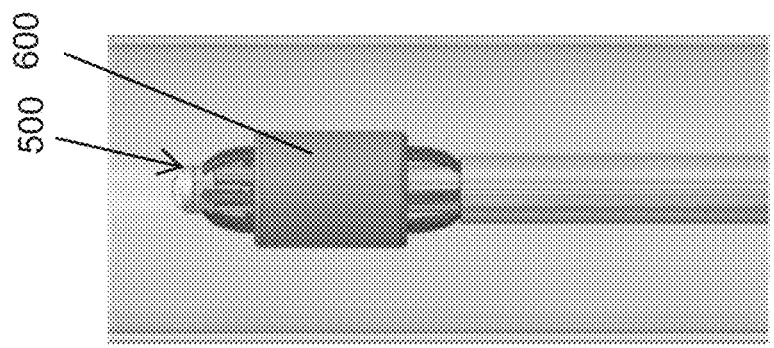

FIGS. 61A-61C illustrate an anchoring mechanism 600 for anchoring the turbomachinery within the blood vessel. FIG. 61A illustrates a folded device 500 with a deflated balloon. FIGS. 60B and 60C illustrate an unfolded device 500 with an inflated balloon. The anchoring mechanism 600 may include a balloon configured to surround the turbomachinery and to allow blood flow to pass through. The balloon can be selectively inflated within the blood vessel or aorta. In some embodiments, the balloon fills a portion of the diameter of the blood vessel. In some embodiments, the balloon is designed to rest against the blood vessel and be a point of contact with the blood vessel. The anchoring mechanism 600 may also include one or more struts. The struts can rest against the inside diameter of the balloon. The struts can center the turbomachinery within the lumen of the balloon.

In some embodiments, the balloon may have a tube configuration as shown in FIG. 61C. In some embodiments, the balloon may comprise an upstream and downstream periphery substantially offset from the axis of rotation of the one or more rotors 510. The balloon may be configured to hold the MCS device 500 in place within the blood vessel through pressure exerted on the blood vessel wall at the side surface where the balloon contacts the blood vessel. The balloon may be expandable such as through inflation medium. In some methods of use, the balloon is inflated when within the blood vessel or aorta. The inflation medium can be delivered through one or more conduits to the balloon. The inflation medium can be a biocompatible material such as saline. In some embodiments, the inflation medium is a gas. In some embodiments, the inflation medium is a liquid. In some embodiments, the inflation medium is a solid, solid-forming, or curable material. The balloon may be expandable by absorption of liquid, such as blood. In some embodiments, the balloon is permeable to liquid allowing the balloon to expand. In some embodiments, the balloon can be deflated. In some embodiments, the balloon is configured to be a permanent structure within the body of the patient.

FIGS. 62A-62B illustrate intra-corporeal motors. The MCS device 500 may comprise one or more motors 700 coupled to the one or more rotors 510 to provide rotational force to the one or more rotors 510. In embodiments comprising more than one rotor 510, some or all of the rotors 510 may be driven by different motors. FIG. 62B illustrate a plurality, e.g., two intra-corporeal motors 700 positioned back to back. Each intra-corporeal motor 700 provides rotational force to an independent rotor. The two intra-corporeal motors 700 are positioned within a sealed capsule 550 to prevent the passage of blood into the motors 700. FIG. 62A illustrates the assembled device with the sealed capsule. For TAD, the motor can be easily removed with the removal of the device.

FIG. 62C illustrates a magnetic coupling 552. The magnetic coupling is illustrated between the rotor 510 and the motor 700. The rotor is the hub of the propeller and provides a location for coupling to the motor. The coupling can be any mechanical couple to transmit rotational movement from the motor to the rotor. In some embodiments, the rotor and/or propeller may be coupled to the motor by any magnetic means. In the illustrated embodiment, magnets are provided on the rotor and the motor. In some embodiments, the rotor and/or propeller may be directly rotated by the motor stator and may be referred to as part of the motor 700. For instance, magnets driven by the electromagnetic stator of the motor may be coupled to or installed within the rotor or rotors 510. Other configurations of coupling are contemplated. In some embodiments, the coupling of the turbomachine to the motor may be accomplished via a shaft. In some embodiments, the coupling of the turbomachine to the motor may be accomplished via magnetic coupling.

In some embodiments, there is provided one or more couplings between the motors, where multiple motors are provided. The coupling between the motors may be via magnetic coupling, connectors, and/or bearings. In some embodiments, bearings at the proximal and distal end of the MCS device may be hydrodynamic. In some embodiments, bearings at the proximal and distal end of the MCS device may be magnetic. In some embodiments, bearings at the proximal and distal end of the MCS device may be self-lubricating using circulating blood.

FIG. 62D illustrates another embodiment of a motor. One or more epicyclic gears 554 (also known as planetary gears) may be used to achieve contra-rotation between the two rotors. Other configurations of motors are contemplated.

FIG. 62E illustrates lubrication channels 556. In some embodiments, a lubricating fluid may be provided through the catheter to lubricate the driveline. For example, a lubricating fluid may be transported through small channels in the catheter to a proximal bearing of the rotor 510 and returned through a line comprising the driveline. In some embodiments, the distal bearing of the rotor 510 may be lubricated by blood flow.

Figure 63C:
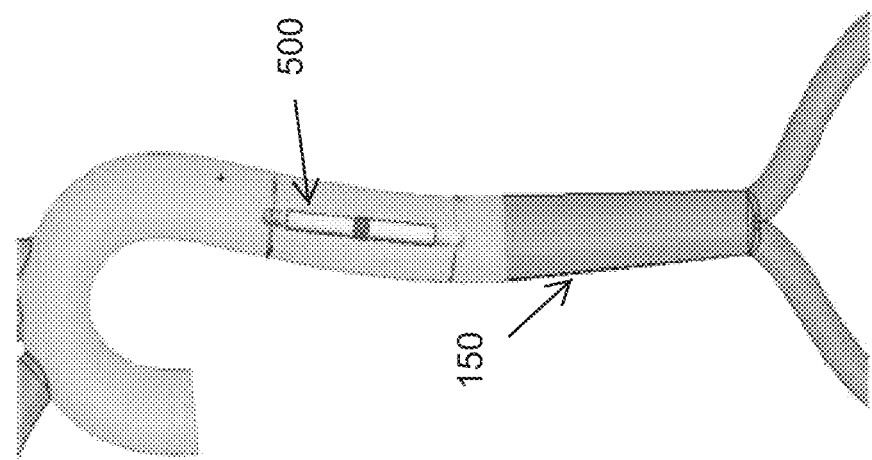
FIGS. 63A-63C schematically illustrate examples of MCS devices configured for installation in the lumen of a blood vessel.
Figure 63B:
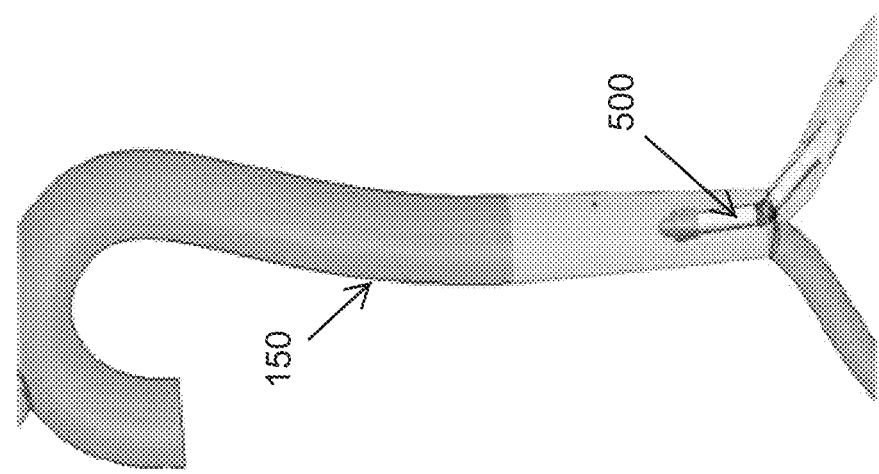
Figure 63A:
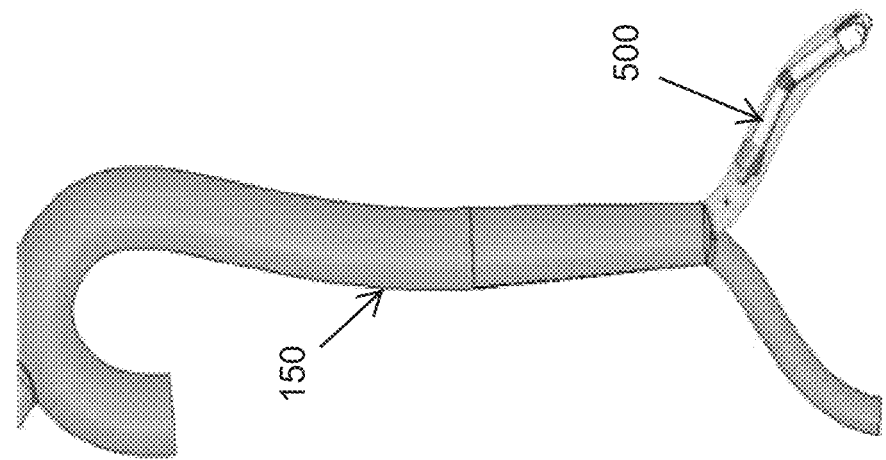

FIGS. 63A-63C illustrate the MCS device 500 positioned within a blood vessel 150. The MCS device 500 can be inserted in a low profile configuration until the MCS device 500 reaches a target vessel. The MCS device 500 can be unfolded or deployed to expand the one or more blades 520. In embodiments comprising an intra-corporeal motor, the motor or motors may be positioned within the lumen of the blood vessel (intravascular).

FIG. 64A illustrates articulated sleeves for insertion 560. The articulated sleeves can allow the MCS device 500 to bend as the MCS device 500 travels to the target vessel. FIG. 64B illustrates tail to tail motors 700 within the articulate sleeve 560. The motors 700 can be positioned tail to tail to operate rotors at each end of the sleeve. FIG. 64C illustrates head to tail motors 700 within the articulate sleeve. The motors 700 can be positioned in any configurations within the articulate sleeve or other capsule. The motors can be easily removed with the removal of the device.

Figure 65B:
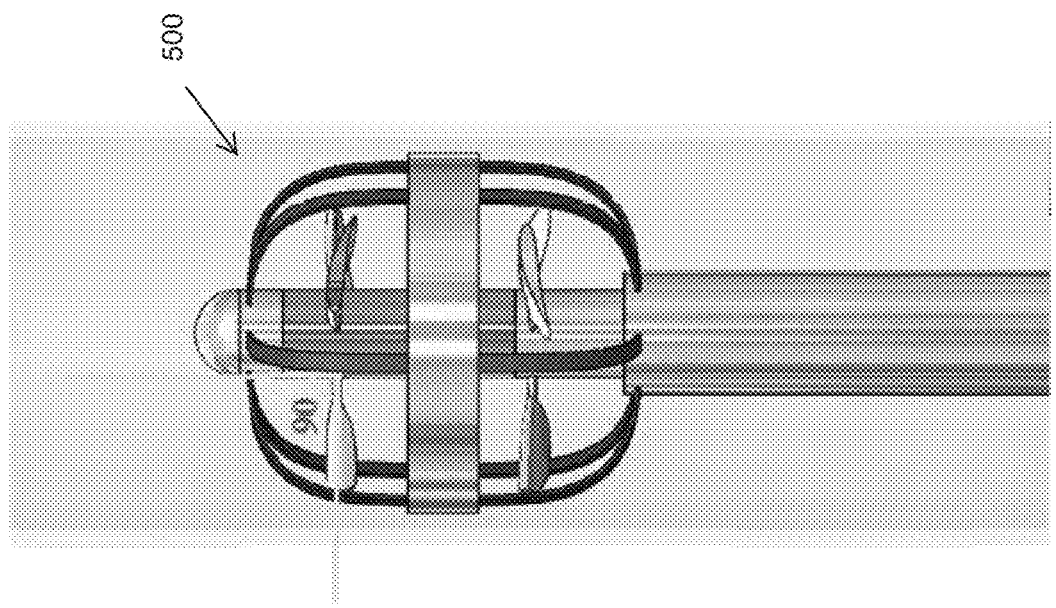
FIGS. 65A-65B schematically illustrate operating configurations of the MCS device opening in an umbrella-like fashion.
Figure 65A:
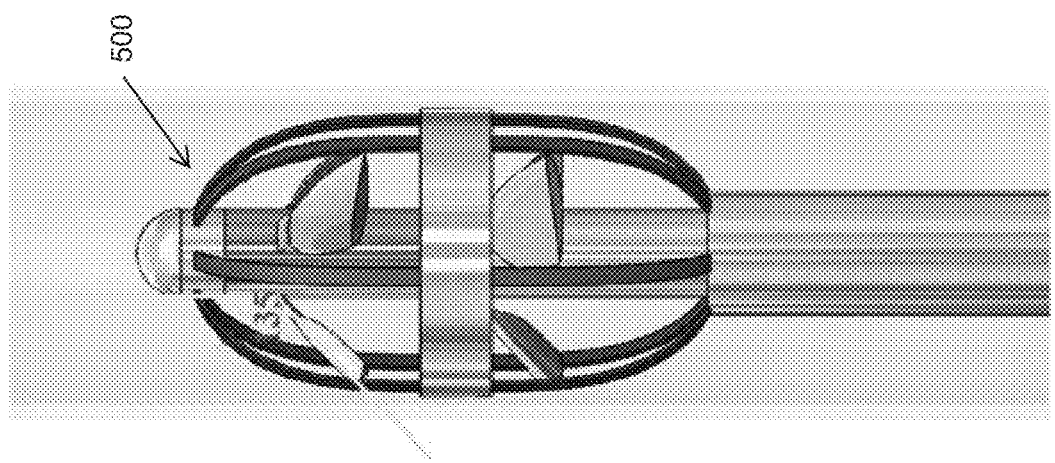

FIGS. 65A-65B illustrate the opening of blades in an umbrella-like fashion. FIG. 65A illustrates partial opening in a smaller aorta. The blades form an angle of about 135 degrees with the longitudinal axis of the MCS device 500. FIG. 65B illustrates full opening in a larger aorta. The blades form an angle of 90 degrees with the longitudinal axis of the MCS device 500. The tip diameter of the propeller is smaller in FIG. 65A than in FIG. 65B. The MCS device may be configured to maintain a substantially constant gap size between the blade tips and the anchoring mechanism regardless of size of the aorta. In some embodiments, the MCS device 500 can include an impeller designed to open in an umbrella-like fashion.

In some embodiments, the MCS device 500 may include one or more foldable propellers and/or impellers. The foldable impellers may be inserted collapsed against the hub of the device, and then opened in an umbrella-like fashion at the desired aortic location to various degrees. The tip diameter of the impeller or propeller varies by the amount of opening of the umbrella. The propellers or impellers may be enclosed within a cage or other anchoring mechanism 600. The propellers or impellers may open partially to a variable umbrella opening, resulting in variable tip diameter. The umbrella design may keep the turbomachine tip-to-cage gap at optimum levels as described herein. The MCS device 500 may comprise an adjustable operating impeller or propeller diameter configured to maintain a substantially constant gap size between the blade tips and the anchoring mechanism. The MCS device 500 may comprise an adjustable operating impeller or propeller diameter configured to maintain a substantially constant gap size between the blade tips and the blood vessel wall. In some embodiments, the MCS device 500 has a variable impeller diameter to maintain the desired gap with a one size impeller.

In some embodiments, the impellers or propellers of the MCS device 500 may be intended to be either fully open or fully closed. The impellers or propellers of the MCS device 500 possess a fixed tip diameter in the open position. This embodiment can be an alternative to the umbrella-like opening described above. The diameter of the fixed diameter propellers or impellers may be set, for example, at approximately 10 mm, 12 mm, 14 mm, 16 mm, 18 mm, 20 mm, 22 mm, 24 mm, 26 mm, 28 mm, 30 mm, 32 mm, between 10 mm and 20 mm, between 20 mm and 30 mm, less than 30 mm, less than 22 mm, less than 20 mm, less than 18 mm, more than 10 mm, more than 14 mm, more than 16 mm, or any range including two of the foregoing values.

In some embodiments, the blades may be inserted in a collapsed state whether designed to partially open or fully open. The blades can be loaded into one or more sleeves for delivery. The blades may be spring-loaded and ready to expand upon removal of the sleeves. Once expanded to the full extent or to a partial extent, as described herein, the centrifugal action of rotation may keep the blades in an open configuration. In the case of partial opening, the blades may be locked in position. In some embodiments, the blades are locked from the hub side.

MCS devices may include a tip-diameter dimension. The interior diameter of the aorta at the implantation location varies from patient to patient, for instance, between approximately 20 mm and 32 mm. This varying dimension may present a series of problems, as there is generally a desire to limit the gap between the propeller or impeller tip and the surrounding device or blood vessel structure. Optimal gaps, balancing requirements between hydraulic efficiency and hemolysis, may be between approximately 0.2 and 2 mm, e.g., 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 2 mm or any range including two of the foregoing values. For example, in some embodiments, the preferred or nominal gap size may be approximately 0.5 mm. Larger gaps may result in regurgitant flow from the device outlet to the device inlet, and thus reduced hydraulic efficiency, as well as increased mixing and hemolysis. However, providing a device with a fixed large diameter to reduce the gap may make the device unsuitable (too large) to be accommodated in specific patient anatomies. In some embodiments, there is provided a customized device. In some embodiments, there is provided an adjustable size device. In some embodiments, the MCS device accommodates variable sized blood vessels using adjustability. In some embodiments, the MCS device is available in a potential matrix of device sizes, from smaller to larger diameters. In some embodiments, there is the ability to select a device from a range of device sizes from smaller diameters to larger diameters, to accommodate the desirable gaps in each case. In some embodiments, the MCS device is available in a variety of dimeter sizes in the fully open position to accommodate varying aorta sizes.

In some embodiments, the propeller or impeller can be designed to operate in conjunction with an expandable member, e.g., a balloon. FIGS. 61A-61C provide an example balloon. The MCS device may include a cylindrical-sleeve shaped balloon. The balloon may include an open center to accommodate along its axis the open (unfolded) propeller or impeller. The balloon can be used to adjust the size of the gap between the blade tips and the balloon. The internal diameter of the balloon can be varied via a level of inflation to adjust for the desired gap size as well as accommodate the propeller or impeller blades and balloon in the blood vessel.

In some embodiments, the balloon may serve as the anchoring mechanism for the MCS device. In some embodiments, the balloon may be coupled to an outer diameter of the cage or struts. In some embodiments, the balloon may be coupled to an inner diameter of the cage or struts. In some embodiments, two balloons may be used, one coupled to each side (internal, external) of the cage or struts. The MCS device may comprise an impeller or propeller having a fixed operative diameter as described herein. The impeller or propeller having a fixed operative diameter may be surrounded by a balloon that inflatable to various sizes such that the gap between the propeller or impeller tip and the inner diameter of the balloon is adjustable. In some embodiments, the inner diameter of the balloon is adjustable, such as the central lumen through which the turbomachinery passes. In some embodiments, the outer diameter of the balloon may be adjustable. The outer diameter may be advantageously adjusted to fit against the wall of the vessel.

By utilizing a cylindrical-sleeve type balloon with an open center to accommodate in its axis the open propeller or impeller, the balloon internal diameter can be varied to adjust for the desired gap size. By utilizing a cylindrical-sleeve type balloon, the balloon external diameter can be varied to fit the impeller plus balloon into the blood vessel. In some embodiments, the MCS device may have a variable impeller tip diameter and variable balloon inflation to accommodate blood vessel diameter while keeping tip-to-balloon gap at optimum levels balancing hemolysis with tip leakage. In some embodiments, the MCS device may have a few impeller size devices and variable balloon inflation to fit desired gap in varying blood-vessel diameters.

In some embodiments, the balloon may comprise an axial length configured to extend axially beyond the one or more propellers or impellers. In some embodiments, the balloon may comprise an axial length configured to extend distally beyond the one or more propellers or impellers. In some embodiments, the balloon may comprise an axial length configured to extend proximally beyond the one or more propellers or impellers. In some embodiments, the balloon may comprise an axial length configured to extend both proximally and distally beyond the one or more propellers or impellers. Extending the length of the balloon may optimize blood flow through the MCS device. This increased axial length can have many advantages including reducing hemolysis, protecting against backflow, optimizing fluid dynamics, and/or avoiding vortices.

The balloon may be a generally cylindrical tube like structure as illustrated herein. In some embodiments, the balloon is spherical. In some embodiments, the balloon is conical. In some embodiments, the balloon comprises two or more balloons. In some embodiments, the balloon comprises two or more axial balloons. In some embodiments, the balloon comprises two or more circumferential balloons. In some embodiments, the balloon comprises two or more circumferential lobes. For example, the balloon can include a cloverleaf design with four lobes. Other configurations are contemplated.

The balloon can include one or more surfaces configured to contact the blood vessel. The balloon can include one or more rounded edges. The balloon may comprise shaped inlet and/or outlet regions. For example, the inlet and/or outlet regions may be shaped as smooth-shaped bodies of revolution above and/or below the propeller or impeller structure. The inlet and/or outlet regions may be designed to smooth the inflow into the propeller/impellers and outflow out of the propeller or impellers. The inlet and/or outlet regions may be designed in a manner minimizing recirculating flow patterns, dead-flow regions, and/or minimizing losses. The inlet and/or outlet regions may be shaped with optimization techniques similar to aircraft inlets and diffusers. In some embodiments, the MCS device may include shaped balloon inlets and/or outlets.

The MCS device can include the cage or anchoring mechanism 600. The cage or anchoring mechanism 600 can be deployed in embodiments with or without a balloon. The cage or anchoring mechanism 600 can be deployed in embodiments with one or more rotors/propellers. The cage or anchoring mechanism 600 can be deployed in embodiments with one or more contra-rotating rotors/propellers. In some embodiments, the structures of the perimeter struts forming the cage or anchoring mechanism 600 may be shaped to open into 3D blades directing the flow in the desired direction. For example, the struts may form blades that extend in an axial and circumferential direction from proximal to distal ends. The blades may extend radially inward in a proximal to distal direction. The blades may extend radially outward in a proximal to distal direction. The blades may have a uniform thickness as they extend along the proximal to distal direction. The blades may have a variable thickness as they extend along the proximal to distal direction. The blades may have the same or similar features as pre-swirler and/or de-swirler blades described herein.

The MCS device can include one or more coils. The coils may be used in an addition to or alternatively to the balloon. In some embodiments, the coils can be used to form funnels (3D bodies of revolution) at the inlet and/or outlet of the MCS device. In some embodiments, the coils can provide strength to the balloon. In some embodiments, the coils can improve flow characteristics. In some embodiments, the coils can be provide at the inlet, the outlet, or both the inlet and the outlet. In some embodiments, the coils can serve the function as pre-swirlers and/or de-swirlers. In some embodiments, the coils can accommodate the differences in blood-vessel diameter from the tip and cage diameter. In some embodiments, the coils can be expanded and uncoiled, as well as compressed and stretched to change shape. In some embodiments, the coils can form the desired gap between the blade tips and the coils.

Figure 66D:
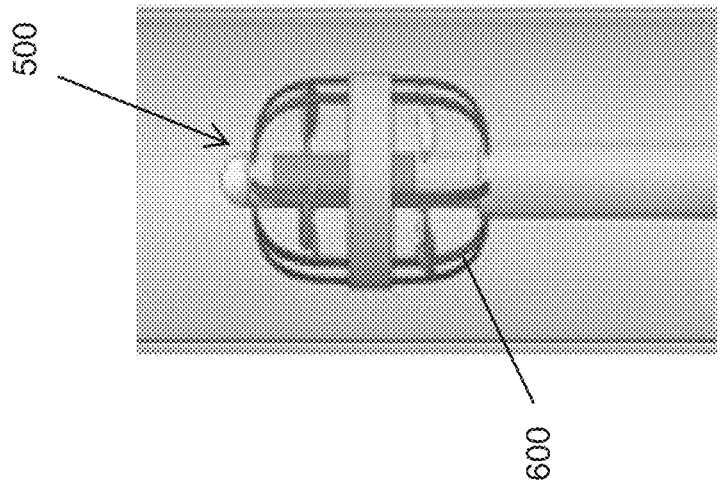
FIGS. 66A-66D schematically illustrate operating configurations of the MCS device comprising various motor and support configurations.
Figure 66C:
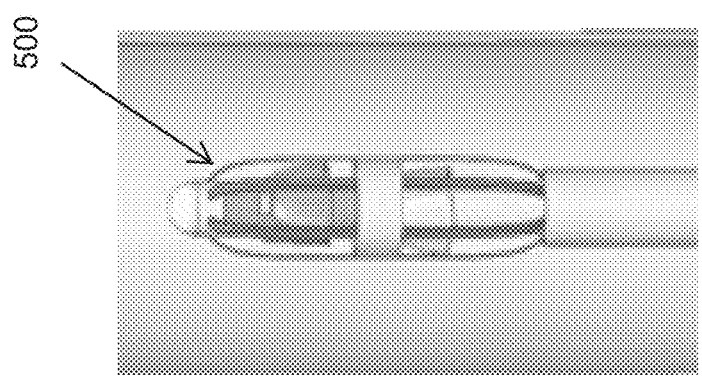
Figure 66B:
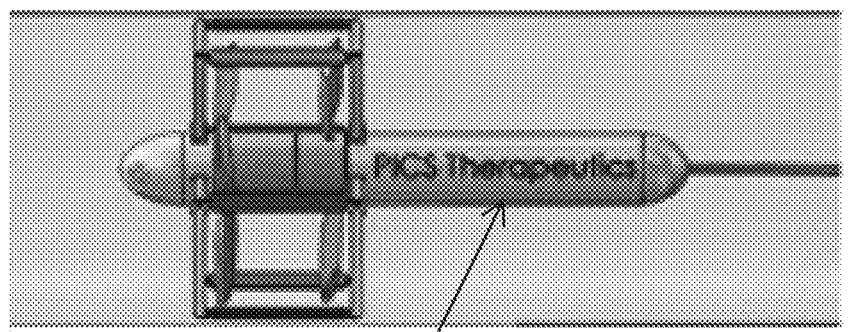
Figure 66A:
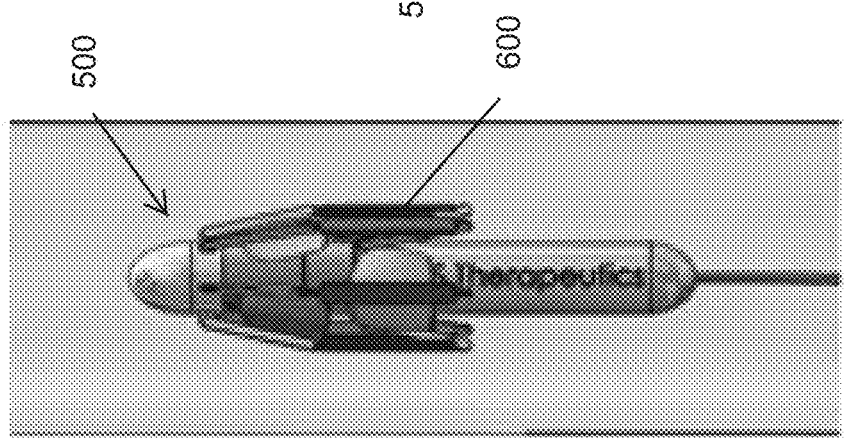

FIGS. 66A-66D illustrate an example of perimeter struts forming the cage or anchoring mechanism 600. In some embodiments, the impellers or propellers of the MCS device may be intended to be either fully open and possess a fixed tip diameter in the open position. In some embodiments, the impellers or propellers of the MCS device may be intended to be opened in an umbrella like fashion. FIG. 66A illustrates an embodiment of a collapsed configuration. The blades of the propeller are against the hub of the device. The anchoring mechanism 600 extends distally along the hub of the device. The anchoring mechanism 600 can include one or more hinges or other mechanical structures that enable the anchoring mechanism 600 to fold. FIG. 66B illustrates an embodiment of an expanded configuration of the embodiment of FIG. 66A. The blades of the propeller are laterally extended from the rotor. The anchoring mechanism 600 is also laterally extended. The propellers of the MCS device 500 may have a fixed tip diameter in the open position between the blade tips and the struts of the anchoring mechanism 600. In the illustrated embodiment, each strut of the anchoring mechanism 600 extends laterally away, then distally, then laterally toward the device. The strut forms two 90 degree angles or similar angles when expanded. Other configurations are contemplated. FIGS. 66A-66B illustrate an intra-corporeal motor with folding cage support.

FIG. 66C illustrates an embodiment of a collapsed configuration. The blades of the propeller are in a low profile, insertion, and/or removal configuration. FIG. 66D illustrates an embodiment of an expanded configuration of the embodiment of FIG. 66C. The blades of the propeller and the anchoring mechanism 600 are laterally extended. The propellers of the MCS device 500 may have a fixed tip diameter in the open position between the blade tips and the struts of the anchoring mechanism 600. The propellers of the MCS device 500 may have a variable tip diameter in the open position between the blade tips and the struts of the anchoring mechanism 600. In the illustrated embodiment, each strut of the anchoring mechanism 600 curves or forms an arch in the proximal-distal direction. Other configurations are contemplated. FIGS. 66C-66D illustrate an extra-corporeal motor with a thicker drive shaft. FIGS. 66A-66D illustrate the MCS device deployed in a blood vessel. FIGS. 66A-66D illustrate an intra-corporeal motor with folding cage support, and extra-corporeal motor (thicker drive shaft), both in a blood vessel.

In some embodiments, the MCS device may comprise pre-swirler and/or de-swirler stationary vanes. The pre-swirler and/or de-swirler stationary vanes may also serve as the support structures of the hub of the turbomachine. In some embodiments, the pre-swirler and/or de-swirler stationary vanes may form the cage or anchoring mechanism surrounding the one or more rotors. In some embodiments, the MCS device may comprise struts opening in blade shapes. The struts may function as the pre-swirler and/or de-swirler. The struts functioning as a pre-swirler and/or a de-swirler can have a 3D configuration when expanded.

In some embodiments, more than one impeller or propeller may be positioned between pre-swirler and de-swirler stationary vanes (e.g., 2, 3, 4, 5, or more impellers or propellers). In some embodiments, one impeller or propeller may be positioned between pre-swirler and de-swirler stationary vanes. In some embodiments two or more contra-rotating impellers or propeller may be positioned between pre-swirler and de-swirler stationary vanes. In some embodiments, the stationary vanes may only serve the function of the pre-swirler. In some embodiments, the stationary vanes may only serve the function of the de-swirler.

Whether with one rotor or a pair of contra-rotating rotors, the structures of the perimeter struts forming the cage may be shaped to open into 3D blades. The 3D blades may be designed for directing the flow in the desired direction. In some embodiments, the MCS device may comprise pre-swirler and/or de-swirler struts to optimize flow angles and turbomachinery efficiency. The 3D blades can be pre-formed to have the desired configuration when expanded. The 3D blades can be formed of a shape memory material.

In some embodiments, the cage or anchoring mechanism 600 may be a solid cylinder. The cage or anchoring mechanism 600 may comprise one or more supporting rings at the proximal and distal end. The cage or anchoring mechanism 600 may comprise one or more supporting rings located at the axial location of the propeller or impeller tips. The cage or anchoring mechanism 600 may comprise axial elements between the supporting rings that expand to fit inside the blood vessel. The axial elements may be 3D blades. The cage or anchoring mechanism 600 may be made of flexible materials that expand to the required shape. In some embodiments, the MCS device may comprise a cage and/or supporting structure. In some embodiments, the MCS device may comprise an installation procedure including the deployment of a cage or anchoring mechanism 600.

In some methods of use, the cage or anchoring mechanism 600 may be implanted separately from the impeller device or other turbomachinery. In some methods of use, the cage or anchoring mechanism 600 can be implanted similar to a stent cage. The cage or anchoring mechanism 600 may comprise a balloon or other space-occupying feature. In some methods of use, the cage or anchoring mechanism 600 is expanded prior to insertion of the turbomachinery. The cage or anchoring mechanism 600 expands against the wall of the vessel. In some embodiments, the cage or anchoring mechanism 600 may include a central lumen for insertion of the turbomachinery. In some embodiments, the cage or anchoring mechanism 600 is designed to ensure the central lumen of the cage or anchoring mechanism 600 matches the diameter of the propeller or impeller with the appropriate gap. In some embodiments, the design ensures that there is not an excessive gap between the tip of propeller or impeller blades and the wall of vessel. In some embodiments, the design ensures that there is not an excessive gap between the tip of propeller or impeller blades and the wall of anchoring mechanism or cage in the stent tube configuration.

In some embodiments, MCS devices may include interior sleeves or stents. The sleeves or stents may be in one piece or multi-pieces. The sleeves or stents may be implanted against the interior blood vessel wall. The sleeves or stents may be implanted such that a supporting structure can be attached to hold the bearings and main shaft of the propellers or impellers. Other configurations of support structures are contemplated.

In some embodiments, if the stent cage is delivered independently, the impeller device may have pre-swirlers and/or post-swirlers. The pre-swirlers and/or post-swirlers may be self-expanding. The pre-swirlers and/or post-swirlers may be mechanically expanded disks. In some embodiments, the pre-swirlers and/or post-swirlers may function to centralize the propeller or impeller and prevent collision with vessel wall. In some embodiments, the pre-swirlers and/or post-swirlers may be collapsible for when removal is required. Variable diameters of blood vessel may be accommodated using different openings comprising 3D pre-swirlers and/or de-swirlers.

In some methods of use, the cage or anchoring mechanism 600 may be implanted simultaneously with the impeller device or other turbomachinery. In some methods of use, the cage or anchoring mechanism 600 and the blades can be expanded simultaneously. In some methods of use, the cage or anchoring mechanism 600 and the blades can be expanded independently and/or sequentially. In some methods of use, the cage or anchoring mechanism 600 and the blades can be expanded to varying degrees. In some embodiments, the design ensures that there is not an excessive gap between the tip of propeller or impeller blades and the wall of vessel and/or the wall of anchoring mechanism or cage.

In some embodiments, the MCS device may comprise two contra-rotating propellers or impellers. In some embodiments, such a configuration may result in maximum hydraulic efficiency. In some embodiments, such a configuration may result in minimum rotor RPM. In some embodiments, such a configuration may result in minimum hemolysis. In some embodiments, the MCS device may include a pair of contra-rotating impellers maximizing efficiency and minimizing hemolysis.

Figure 67C:
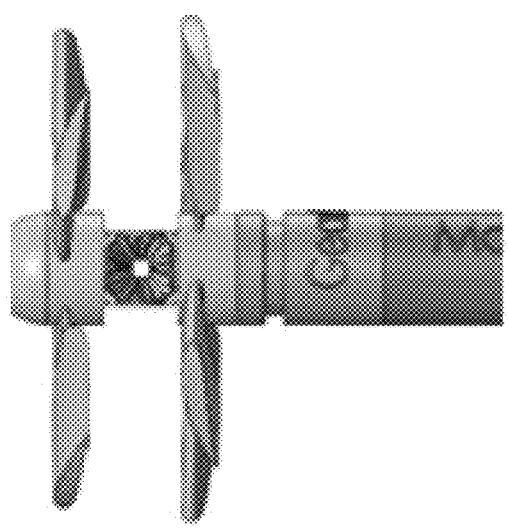
FIGS. 67A-67C schematically illustrate operating configurations of the MCS device comprising a bevel gearbox for contra-rotation.
Figure 67B:
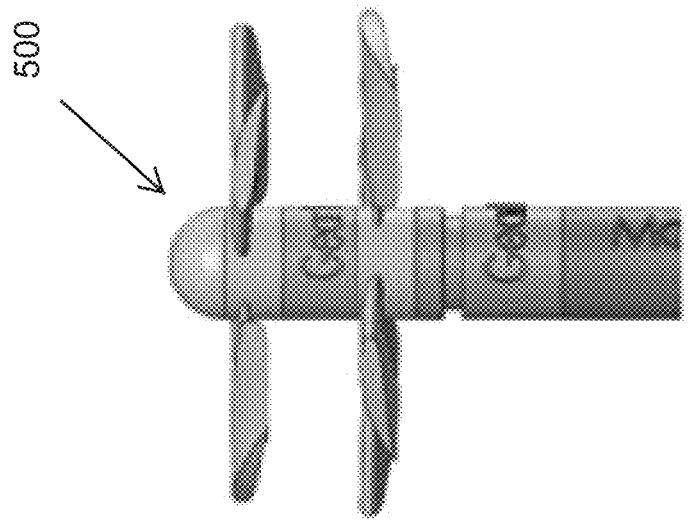
Figure 67A:
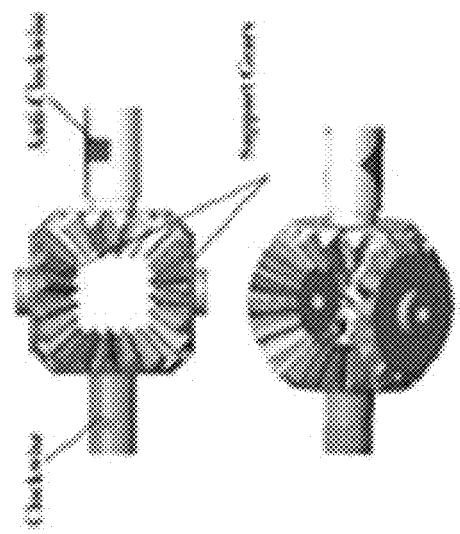

FIGS. 67A-67C illustrate a configuration comprising two contra-rotating propellers. FIG. 67A illustrates the bevel gearbox achieving contra-rotation. The first shaft moves clockwise and the second shaft moves counter clockwise. The support gears are also illustrated. The MCS device is shown in FIG. 67B. The positioning of the bevel gearbox is shown in FIG. 67C. FIGS. 67A-67C illustrate an intracorporeal motor, a first gearbox reducing the shaft speed, a first rotor, a bevel gearbox achieving a contra-rotation from the first rotor, and then the second rotor. The bevel gearbox achieving a contra-rotation from the first rotor is illustrated in FIGS. 67A and 67C.

In some embodiments, power may be delivered to blades by a miniature electric motor (or motors). The motor, controller, and power supply may be extra-corporeal, as described elsewhere herein. The motor may be extra-corporeal and catheters may serve as drive shafts. The motor may be intra-corporeal. The motor may be located in the hub of turbomachines. The catheter in the installed and operating condition may be an electric cable delivering power from outside the body to the motor location in the aorta. The motor may be intra-corporeal with the controller and power supply being located extra-corporeally.

In some embodiments, a gearing mechanism may be needed between the motor and the rotating impeller or propeller. The gearing mechanism may be located next to the motor. The gearing mechanism may be located next to the one or more impellers. The gearing mechanism may be intra-corporeal or extra-corporeal. In some embodiments, the motor, gearing mechanism, and propeller/impeller are all intra-corporeal, and only the electric cable goes through the rotor. In some embodiments, one or more of the motor, gearing mechanism and propeller/impeller are intra-corporeal. In some embodiments, one or more of the motor, gearing mechanism and propeller/impeller are extra-corporeal.

One or more epicyclic gears (also known as planetary gears) may be used to achieve contra-rotation between the two rotors. Epicyclic gears have four main elements: a sun; planets; a planet carrier; and a ring. One of three components is held stationary: the planet carrier and planets; or the ring; or rarely the sun. Depending on which component is held stationary different gear ratios are achieved, and concurrently the output shaft may be co-rotating or contra-rotating from the input shaft to the gearbox. The epicyclic gearbox or boxes may be intra- or extra-corporeal.

FIG. 68A-68D illustrate a configuration with two gearboxes or gearing mechanisms 554. The first gear 554 and the motor 770 are within a sealed capsule. The second gear 554 is located between the rotors 510. The ring of the second gear is connected to the second rotor 510. FIG. 68A illustrates the two gearboxes. FIG. 68B illustrates the external view of the MCS device 500. FIGS. 68C and 68D illustrate the location of the two gear boxes within the device. This is one example of several arrangements of planetary gearboxes, other configurations are contemplated. The planetary gearboxes achieve contra-rotation. The MCS device comprises an intra-corporeal motor with two planetary gearboxes in series. The motor shaft is driving the sun of the first gearbox. The ring is stationary. The planet carrier is the output shaft for the first rotor and is connected to the sun of the second gearbox. The planets of the second gearbox are stationary and connected to the front stationary hub. The rotating ring of the second gearbox is the output. In this arrangement, the first rotor is contra-rotating from the motor shaft. In this arrangement, the second rotor is co-rotating with the rotor shaft. The size of the gear teeth can be used to modify the gear ratios as needed. The cage may be supported by the stationary motor. FIG. 68A-68D illustrate gear 1 and motor inside the sealed capsule and gear 2 with the ring connected to the second rotor. While the motor 700 is illustrated as having a 5W (watt) power, other configurations are contemplated, e.g., 1 W, 2 W, 5 W, 10 W, 15 W, 20 W, 25 W, 30 W, or any range of the foregoing values.

Figure 69:
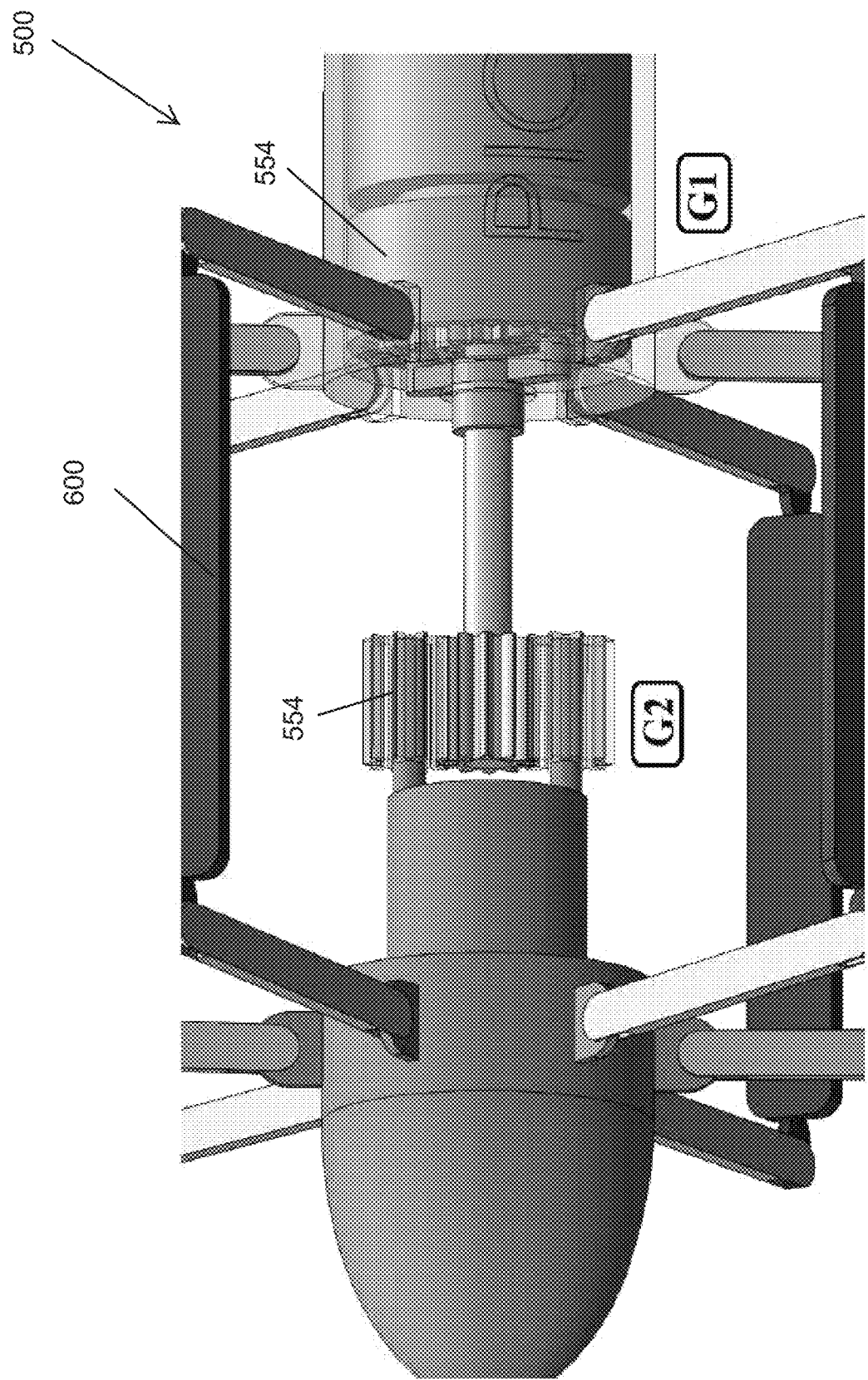
FIG. 69 schematically illustrates an operating configuration of the MCS device comprising two gearboxes.

FIG. 69 illustrates another configuration with two gearboxes 554. The rotors are omitted from the figures. The cage 600 is shown. The first gear G1 and the motor are within a sealed capsule. The ring is fixed with the first gear. In some embodiments, the first gear will operate the first rotor. In some embodiments, the second gear G2 is located between the rotors. The planets are fixed with the second gear. The cage may be supported by the stationary ring of the first gearbox and by the stationary hub. FIG. 69 illustrates G1 wherein the ring is fixed and G2 wherein the planets are fixed.

In some embodiments, in a contra-rotating configuration, there may be one motor with a differential-type gearing device. In some embodiments, bevel gears are provided. The bevel gears may provide contra-rotation to two shafts from one motor. This gearing may be intra-corporeal or extra-corporeal. If in this arrangement the motor is extracorporeal, then there may be one shaft from the motor to the intra-corporeal gearing. In this arrangement, there can be two contra-rotating shafts on the outlet of the bevel gearing, at the same axial end of the bevel gear, or in the opposite ends of the bevel gear. In some embodiments, the bevel gearing may be extra-corporeal, located next to the extra-corporeal motor. In this arrangement, two concentric shafts may be placed along the blood vessel to the contra-rotating impellers. Other configurations of intra-corporeal and extra-corporeal gearing mechanisms are contemplated.

In some embodiments, intra-corporeal motors may be configured tail-to-tail. In some embodiments, intra-corporeal motors may be configured head-to-tail. In some embodiments, intra-corporeal motors may be arranged in the axial direction. In some embodiments, intra-corporeal motors may be configured to articulate for installation. The intra-corporeal motors may be articulated, for example, by being located in an articulating sleeve.

In embodiments comprising one or more intra-corporeal motors in one or more turbomachine hubs, the electric cables may be installed around the perimeter of the cage or anchoring mechanism 600. In some embodiments, the electric cables may be installed along the hub of the device.

FIGS. 70A-70B illustrate an embodiment of the MCS device 500. In some embodiments, the MCS device 500 may comprise a nose propeller 570. The MCS device 500 may include foldable caging, forming a support structure 600. The MCS device 500 may include one or more hydrodynamic bearings 572. The MCS device 500 may include one or more blades 520. The MCS device 500 may include one or more gearboxes 554. The MCS device 500 may include a motor 700. The MCS device 500 may include a sealed capsule 550 for the motor 700. The MCS device 500 may include a cord 574 extending from the sealed capsule. The foldable cage 600 extends from the nose propeller and the sealed capsule. The nose propeller and the sealed capsule include hubs that allow the foldable cage 600 to connect thereto.

Figure 71:
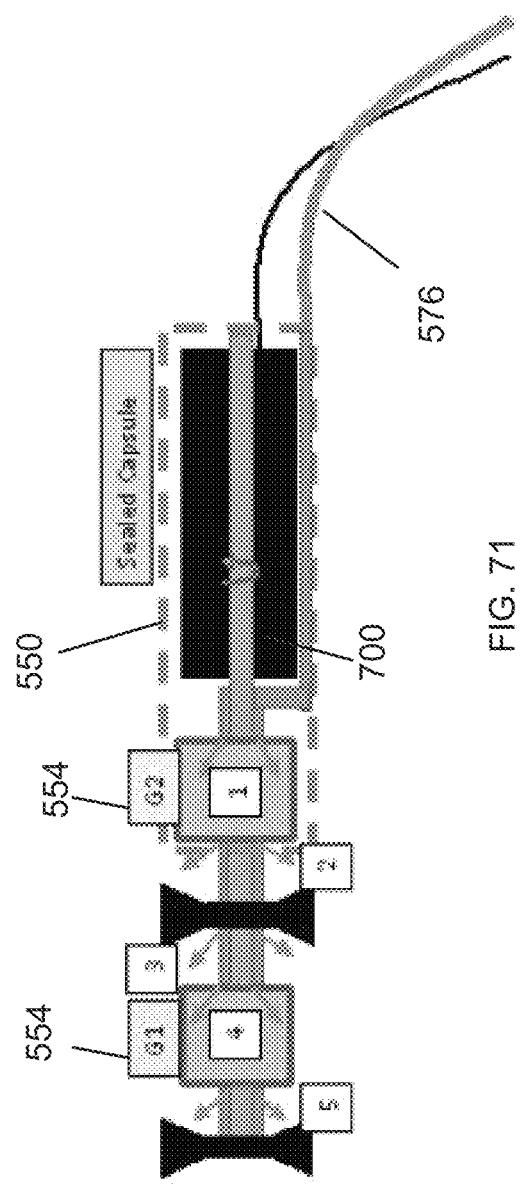
FIG. 71 schematically illustrates an operating configuration of the MCS device comprising a lubrication path.

FIG. 71 illustrates an example of lubrication path 576. The lubrication path extends through the sealed capsule 550. The lubrication path extends through the gearboxes 554 G1, 554 G2. A biocompatible lubricant may be pumped through the motor 700 and/or gearbox or gearboxes 554. One example, in which the lubricant is diffused in the blood stream, is shown in the figures. The lubricant may be returned outside the body.

Figure 72:
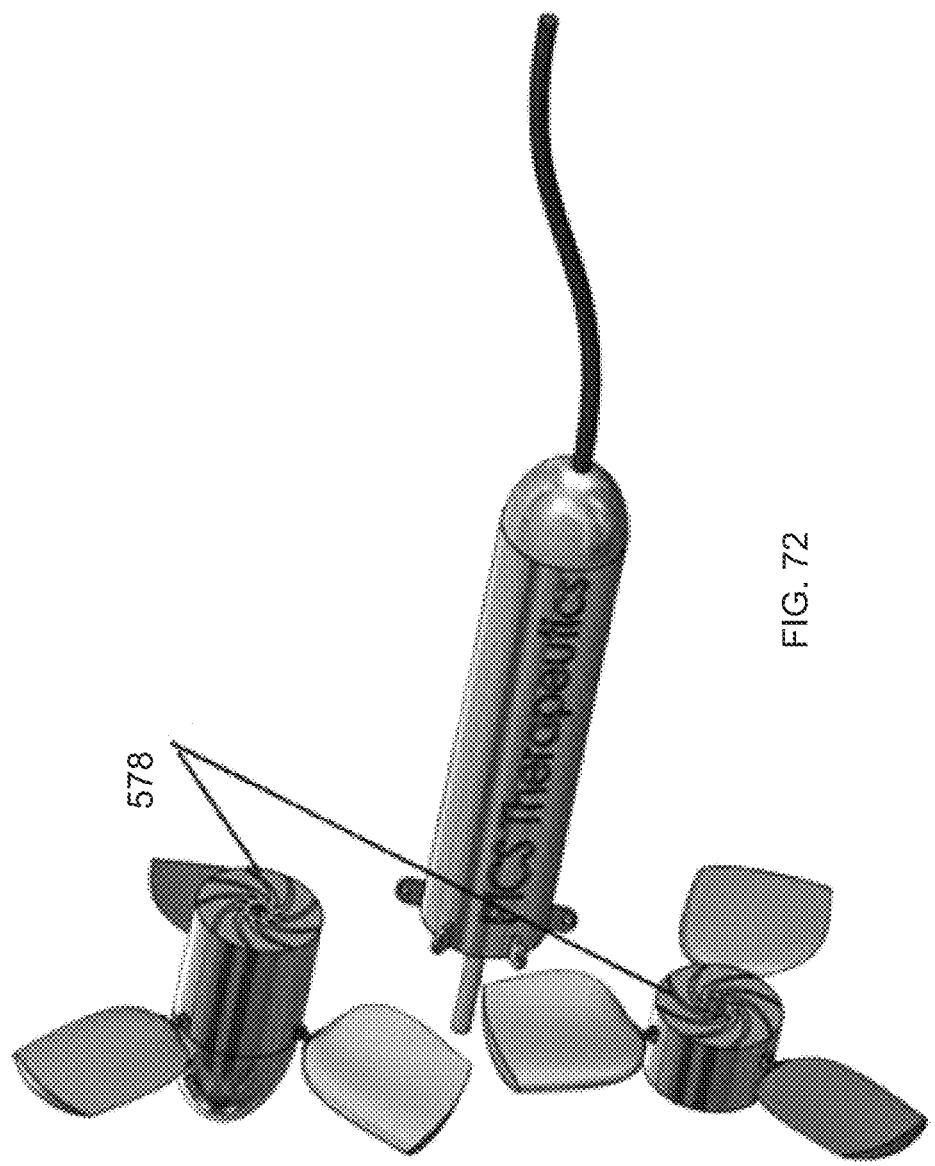
FIG. 72 schematically illustrates an operating configuration of the MCS device comprising spiral grooves.

FIG. 72 illustrates spiral grooves 578. The pump-out spiral grooves may improve the wash-out flow in the critical regions. Spiral grooves may be used between rotating and stationary elements in the pump head to remove stagnant blood flow between rotating and stationary components. FIG. 72 illustrates pump-out spiral grooves to improve the wash-out flow in the critical regions.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims. It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A temporary, removable mechanical circulatory support heart-assist device, the device comprising:
   at least two propellers or impellers, each propeller or impeller comprising a plurality of blades arranged around an axis of rotation, the blades being configured to pump blood; and
   a gearbox,
   wherein the gearbox is configured to receive input power and rotation from one input shaft, and provide output via two contra-rotating output shafts, the two contra-rotating output shafts configured to drive two propellers or impellers of the at least two propellers or impellers to rotate in opposite directions,
   wherein the two propellers or impellers of the at least two propellers or impellers that rotate in opposite directions are both configured to pump blood in a first direction,
   wherein the two propellers or impellers are shaped to reduce the vorticity of the flow downstream of the device when the two propellers or impellers rotate in opposite directions.

2. The device of claim 1, wherein the gearbox is placed between a motor and a downstream propeller or impeller of the at least two propellers or impellers, and further comprising a second gearbox between the upstream and downstream propeller or impeller of the at least two propellers or impellers.

3. The device of claim 2, wherein diameters of the gears in the gearbox and the second gearbox are configured to achieve equal rpm between the at least two propellers or impellers.

4. The device of claim 2, wherein diameters of the gears in the gearbox and the second gearbox are configured to achieve different rpm between the at least two propellers or impellers.

5. The device of claim 1, further comprising a balloon, wherein the balloon is configured to expand to fill the difference between minimum and maximum aorta sizes.

6. The device of claim 1, wherein the one input shaft is connected via a flexible shaft to an electric motor or gearmotor.

7. The device of claim 1, wherein the gearbox is an epicyclic-type gearbox and further comprising a second epicyclic-type gearbox.

8. The device of claim 7, wherein suns of both epicyclic gearboxes are driven by sun gears connected via an input shaft to an electric motor.

9. The device of claim 1, where the blades of the two propellers or impellers of the at least two propellers or impellers rotating in opposite directions comprise flexible connections to impeller hubs to accommodate insertion and removal with folded blades, and operation with unfolded blades.

10. The device of claim 1, further comprising an anchoring mechanism, the anchoring mechanism being configured to anchor the at least one propeller within a lumen of a blood vessel, the anchoring mechanism comprising:
    a collapsed configuration for installing the anchoring mechanism in the blood vessel; and
    an expanded configuration wherein at least a portion of the anchoring mechanism is configured to be pressed against a wall of the lumen of the blood vessel.

11. The device of claim 1, further comprising a pre-swirler configured to increase a tangential velocity component of blood flow entering the support.

12. The device of claim 1, wherein the plurality of blades of a propeller or an impeller of the at least two propellers or impellers have a fixed open diameter.

13. The support of claim 1, wherein the plurality of blades of a propeller or an impeller of the at least two propellers or impellers have a variable open diameter.

14. A method of treating congestive heart failure in a patient, the method comprising:
    installing a mechanical circulation support within a lumen of a descending aorta of the patient, wherein the mechanical circulation heart-assist device comprises:
       at least two propellers or impellers, each propeller or impeller comprising a plurality of blades arranged around an axis of rotation, the blades being configured to pump blood, wherein two propellers or impellers of the at least two propellers or impellers rotate in opposite directions,
       a gearbox configured to receive input power and rotation from one input shaft and provide output via two contra-rotating output shafts, the two contra-rotating output shafts configured to drive two propellers or impellers of the at least two propellers or impellers to rotate in opposite directions,
       wherein the two propellers or impellers of the at least two propellers or impellers that rotate in opposite directions are both configured to pump blood in a first direction, wherein the two propellers are shaped to reduce the vorticity of the flow downstream of the device when the two propellers rotate in opposite directions.

15. The method of claim 14, wherein the device is configured to provide a pressure rise between about 20 mmHg and about 40 mmHg in the blood flow and to maintain a flow rate of about 5 L/min.

16. The method of claim 14, further comprising expanding the plurality of blades to a fixed diameter.

17. The method of claim 14, further comprising expanding the plurality of blades to a variable diameter.

18. The method of claim 14, wherein the gearbox is placed between a motor and a downstream propeller or impeller of the at least two propellers or impellers to provide contra-rotation of the at least two propellers or impellers.

19. The method of claim 14, wherein the at least two propellers or impellers rotate at equal rpm.

20. The method of claim 14, wherein the at least two propellers or impellers rotate at different rpm.

* * * * *